(12) United States Patent
Hirai et al.

(10) Patent No.: US 7,388,010 B2
(45) Date of Patent: Jun. 17, 2008

(54) QUINOXALINONE DERIVATIVES

(75) Inventors: Hiroshi Hirai, Tsukuba (JP); Nobuhiko Kawanishi, Tsukuba (JP); Masaaki Hirose, Tsukuba (JP); Tetsuya Sugimoto, Tsukuba (JP); Kaori Kamijyo, Tsukuba (JP); Jun Shibata, Tsukuba (JP); Kouta Masutani, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/532,677

(22) PCT Filed: Oct. 27, 2003

(86) PCT No.: PCT/JP03/13707

§ 371 (c)(1),
(2), (4) Date: Jun. 15, 2005

(87) PCT Pub. No.: WO2004/039809

PCT Pub. Date: May 13, 2004

(65) Prior Publication Data

US 2006/0019959 A1    Jan. 26, 2006

(30) Foreign Application Priority Data

Oct. 29, 2002 (JP) ............................. 2002-313588

(51) Int. Cl.
*A61K 31/498* (2006.01)
*A61P 35/00* (2006.01)
*C07D 487/00* (2006.01)

(52) U.S. Cl. ..................................... 514/249; 544/338
(58) Field of Classification Search ................ 514/249; 540/469
See application file for complete search history.

(56) References Cited

FOREIGN PATENT DOCUMENTS

| JP | 2002-220338 | 8/2002 |
|---|---|---|
| WO | 98/33798 | 8/1998 |
| WO | 02/02550 | 1/2002 |

OTHER PUBLICATIONS

Malumbres et al. Nature Reviews: Cancer, 2001, 1(3), 222-231.*
Fischer et al. Expert Opinion on Investigational Drugs, 2003, 12(6), 955-970.*

* cited by examiner

*Primary Examiner*—James O. Wilson
*Assistant Examiner*—Noble Jarrell
(74) *Attorney, Agent, or Firm*—Wenderoth, Lind & Ponack, L.L.P.

(57) ABSTRACT

A quinoxalinone derivative of the formula (I):

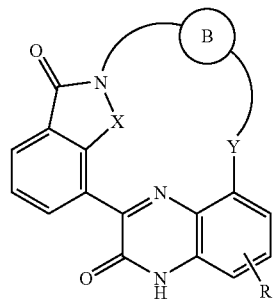

(I)

or a pharmaceutically acceptable salt or ester thereof, wherein;
X is NH, S or the like;
Y is O or the like;
the partial structure

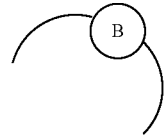

is, for example, the formula:

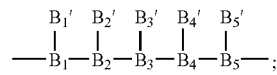

$B_1, B_2, \ldots, B_{n-1}$ and $B_n$, (in which n is 4, 5 or 6) are each independently CH, N or the like;
$B'_1, B'_2, \ldots, B'_{n-1}$ and $B'_n$ (in which n is 4, 5 or 6) are each independently hydrogen or the like; and
R is hydrogen, lower alkyl or the like.

14 Claims, No Drawings ly have a family, and each Cdk
QUINOXALINONE DERIVATIVES

This application is a U.S. national stage of International Application No. PCT/JP2003/013707 filed Oct. 27, 2003.

TECHNICAL FIELD

The present invention relates to a novel quinoxalinone derivative which is useful as pharmaceuticals, a process for preparing the same and a composition containing the same as an active ingredient.

BACKGROUND ART

In the process of normal cell proliferation, cell division and its pause occur orderly in accordance with cell cycle, while cancer cell proliferation is characterized by disorder. For this reason, abnormality in the cell cycle control mechanism is supposed to have a direct relation with oncogenesis or malignant alteration of cancer. The cell cycle of a mammalian cell is regulated by a serine/threonine kinase called cyclin-dependent kinase (hereinafter abbreviated as Cdk) family, and Cdk needs to form a complex with the regulatory subunit called cyclin in order to exhibit its enzymatic activity. A cyclin itself also have a family, and each Cdk molecule is considered to regulate the progression of a certain cell cycle by forming a complex with a cyclin molecule which is expressed specifically at the corresponding stage of the cell cycle. For example, D type cyclin, in combination with Cdk4 or Cdk6, regulates the progression of G1 phase, cyclin E-Cdk2 regulates G1/S boundary, cyclin A-Cdk2 regulates the progression of S phase, and cyclin B-cdc2 regulates the progression of G2/M, respectively. In addition, three sub-types D1, D2 and D3 are known as a D type cyclin, and moreover the activity of Cdk is considered to be regulated not only by its association with cyclins but also by phosphorylation/dephosphorylation of Cdk molecules, degradation of cyclin molecules and binding with Cdk inhibitor proteins (Advanced Cancer Research, Vol. 66, pp 181-212(1995); Current Opinion in Cell Biology, Vol. 7, pp 773-780(1995): Nature, Vol. 374, pp 131-134 (1995)).

Cdk inhibitor proteins in a mammalian cell are classified roughly into two kinds due to the differences in structure and property; Cip/Kip family and INK4 family. The former inhibits cyclin-Cdk complex widely, while the latter binds with Cdk4 or Cdk6, thereby specifically inhibiting cyclin-Cdk complex (Nature, vol. 366, pp 704-707(1993); Molecular and Cellular Biology, vol. 15, pp 2627-2681(1995): Genes and Development, vol. 9, pp 1149-1163 (1995)).

For example, P21(Sdi1/Cip1/Waf1) is nominated for a representative example of the former, of which RNA transcription is induced by a cancer repressor gene product, p53.

On the other hand, for example, p16 (INK4a/MTS1/CDK4I/CDKN2) is one of the Cdk inhibitor proteins belonging to the latter. The P16 gene is located on the human chromosome 9p21 which are found to be abnormal with a high frequency in human cancer cells. Actually, many cases of deletion of the p16 gene have been reported in clinical patients. Also, high-frequency of tumorigenesis in a p16 knockout-mouse has been reported (Nature Genetics, vol. 8, pp 27-32(1994); Trends in Genetics, vol. 11, pp 136-140 (1995); Cell, vol. 85, pp 27-37(1996)).

Each Cdk regulates the progression of cell cycle by phosphorylation of a certain target protein in a specific phase of cell cycle, and above all, the retinoblastoma (RB) protein is considered to be one of the most important target proteins. The RB protein plays an important role in progression from G1 phase to S phase and is rapidly phosphorylated during the term from late G1 phase to initial S phase. It is considered that this phosphorylation is carried out by cyclin D-Cdk4/Cdk6 complex followed by cyclin E-Cdk2 complex, following progression of cell cycle. The complex composed of hypophosphorylated RB and transcription factor E2F in early G1 phase dissociates when the RB protein becomes hyperphosphorylated. As a result, E2F becomes a transcriptional activator, and at the same time, the suppression of the promoter activity by RB-E2F complex is removed, thus leading to the activation of E2F dependent transcription. At present, the Cdk-RB pathway consisting of E2F, its suppressor RB protein, Cdk4/Cdk6 which repressively regulates the function of RB protein, Cdk inhibitory protein which controls the kinase activity of Cdk4/Cdk6, and D-type cyclin is thought to be an important mechanism to regulate the progression from G1 phase to S phase (Cell, vol. 58, pp 1097-1105(1989); Cell, vol. 65, pp 1053-1061 (1991); Oncogene, vol. 7, pp 1067-1074(1992); Current Opinion in Cell Biology, Vol. 8, pp 805-814(1996); Molecular and Cellular Biology, vol. 18, pp 753-761(1998)). In fact, E2F-binding DNA sequence is located, for example, upstream of the sequence of many cell growth-related genes which are important in S phase, and it is reported that in several genes among them the transcription is activated in an E2F-dependent manner during the term from late G1 phase to initial S phase (The EMBO Journal, vol. 9, pp 2179-2184, (1990); Molecular and Cellular Biology, vol. 13, pp 1610-1618 (1993)).

Abnormalities of any factors which relates to in the Cdk-RB pathway such as, for example, deletion of functional p16, high expression of cyclin D1, high expression of Cdk4 and deletion of functional RB protein are frequently found in human cancer cells (Science, vol. 254, pp 1138-1146(1991); Cancer Research, Vol. 53, pp 5535-5541 (1993); Current Opinion in Cell Biology, Vol. 8, pp 805-814(1996). These are abnormal to such an extent that they tend to promote the progression from G1 phase to S phase, and thus it is obvious that this pathway plays an important role in malignant alteration or abnormal growth of cancer cells.

Previously, as known compounds having an inhibitory activity on Cdk family, a series of chromone derivatives represented, for example, by flavopiridol are known (WO 97/16447, 98/13344); however, the inhibitory activity of those chromone derivatives is not sufficient.

DISCLOSURE OF THE INVENTION

The present inventors previously prepared a novel pyrazinone derivative having inhibitory activity against Cdk, and filed a PCT international application (PCT/JP01/05545; WO 02/02550).

Although the above pyrazinone derivative showed Cdk inhibitory activity, its cell growth-inhibitory activity was not sufficient.

Therefore, a compound with a novel basic structure having an excellent cell growth-inhibitory activity as well as inhibitory activity against CdK is now desired.

The present inventors conducted intensive studies in order to provide a novel compound having an excellent cell growth-inhibitory activity as well as CdK inhibitory activity. As a result, we found that a novel quinoxalinone derivative has both an inhibitory activity against Cdk and cell growth-inhibitory activity, and thus completed the present invention. It is obvious that the quinoxalinone derivative of the present invention has completely structural originality as compared to the above pyrazinone derivative in light of its cyclic structure containing a quinoxalinone core structure.

Thus, the present invention relates to a quinoxalinone derivative of the formula (I):

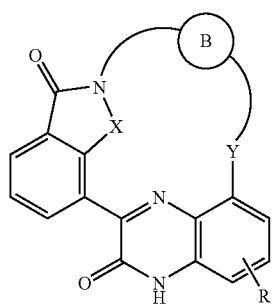

or a pharmaceutically acceptable salt or ester thereof, wherein;

X is NH, S, O or $CH_2$;

Y is O or NR', wherein R' is hydrogen or lower alkyl;

the partial structure

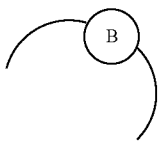

is selected from the following formula:

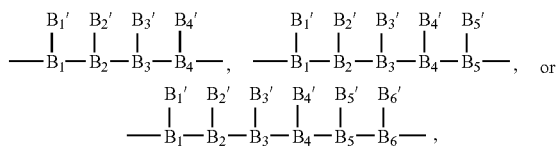

wherein $B_1, B_2, \ldots, B_{n-1}$ and $B_n$, and $B'_1, B'_2, \ldots, B'_{n-1}$ and $B'_n$ (in which n is 4, 5 or 6) are each defined as follows:

$B_1, B_2, \ldots, B_{n-1}$ and $B_n$ are each independently C, CH, $CR_0$, N or O (wherein when $B_1, B_2, \ldots, B_{n-1}$ and $B_n$ are each independently C, then $B'_1, B'_2, \ldots, B'_{n-1}$ and $B'_n$ are oxo, respectively;

when $B_1, B_2, \ldots, B_{n-1}$ and $B_n$ are each independently O, then $B'_1, B'_2, \ldots, B'_{n-1}$ and $B'_n$ are each taken together with $B_1, B_2, \ldots, B_{n-1}$ and $B_n$, respectively, to form O, with the proviso that two or more members of $B_1, B_2 \ldots, B_{n-1}$ and $B_n$, at the same time, are not taken together with $B'_1, B'_2, \ldots, B'_{n-1}$ and $B'_n$, respectively, to form O; and $R_0$ is lower alkyl), and $B'_1, B'_2, \ldots, B'_{n-1}$ and $B'_n$ are each independently hydrogen, halogen, hydroxy, oxo, lower alkoxy, amino, lower alkylamino, di-lower alkylamino, lower alkyl or lower alkenyl (wherein said lower alkyl and said lower alkenyl may be substituted with one or more, same or different substituents selected from the group consisting of hydroxy, lower alkoxy, amino and lower alkylamino, and among $B'_1, B'_2, \ldots, B'_{n-1}$ and $B'_n$, $B'_i$ and $B'_{i+2}$ (in which i is 1, 2 or 3) taken together with $B_i$, $B_{i+1}$ and $B_{i+2}$, or $B'_i$ and $B'_{i+3}$ (in which i is 1 or 2) taken together with $B_i$, $B_{i+1}$, $B_{i+2}$ and $B_{i+3}$, may form a cycloalkyl having five to six carbon atoms or an aliphatic heterocyclic group selected from <substituent group $\beta_1$>, and said cycloalkyl and said aliphatic heterocyclic group may be substituted with one or more, same or different substituents selected from lower alkyl and <substituent group $\alpha$>);

R is hydrogen, lower alkyl, lower alkenyl, amino of which nitrogen is di-substituted with $R_a$ and $R_b$, amino-lower alkyl of which nitrogen is di-substituted with $R_a$ and $R_b$, or L, wherein $R_a$ and $R_b$ are each independently hydrogen, lower alkyl, lower alkoxyalkyl or halogenated lower alkyl, and L is $L_1$-$L_2$-$L_3$ (wherein $L_1$ is a single bond, —$(CH_2)_{k1}$—, —$(CH_2)_{k1}$—O— or —$(CH_2)_{k1}$—NH— (in which k1 is an integer of 1 to 3); $L_2$ is a single bond or —$(CH_2)_{k2}$— (in which k2 is an integer of 1 to 3); and $L_3$ is lower alkyl, lower alkoxy, cycloalkyl having three to six carbon atoms, phenyl, pyridyl, pyrrolidinyl or piperidinyl, said lower alkyl, lower alkoxy, cycloalkyl having three to six carbon atoms, phenyl, pyridyl, pyrrolidinyl or piperidinyl being optionally substituted with one or more fluorine atoms); or a substituent selected from <substituent group $\alpha$>, which may be substituted with one or more, same or different substituents selected from <substituent group $\gamma$>, or lower alkyl substituted with said substituent; or a cyclic group selected from <substituent group $\beta_2$>, which may be substituted with one or more, same or different substituents selected from a lower alkyl, <substituent group $\alpha$> and <substituent group $\gamma$>, and also may be substituted with J (wherein J is $J_1$-$J_2$-$J_3$; $J_1$ is a single bond, —C(=O)—, —O—, —NH—, —NHCO—, —$(CH_2)_{k3}$— or —$(CH_2)_{k3}$—O— (in which k3 is an integer of 1 to 3); $J_2$ is a single bond or —$(CH_2)_{k4}$— (in which k4 is an integer of 1 to 3); and $J_3$ is lower alkyl, lower alkoxy, —$CONR_aR_b$ (wherein $R_a$ and $R_b$ each have the same meaning as defined above), phenyl, pyridyl, pyrrolidinyl or piperidinyl, said lower alkyl, lower alkoxy, phenyl, pyridyl, pyrrolidinyl or piperidinyl being optionally substituted with one or more fluorine atoms), or lower alkyl substituted with said cyclic group, and in the above, <substituent group $\alpha$>, <substituent group $\beta_1$>, <substituent group $\beta_2$> and <substituent group $\gamma$> each have the meaning shown below:

<Substituent Group $\alpha$> hydroxy, hydroxy-lower alkyl, cyano, halogen, carboxyl, lower alkanoyl, loweralkoxycarbonyl, loweralkoxy, loweralkoxyalkyl, amino, lower alkylamino, lower alkylsulfonyl, halogenated lower alkyl, halogenatedlower alkoxy, halogenatedlower alkylamino, nitro and lower alkanoylamino, <Substituent Group $\beta_1$>

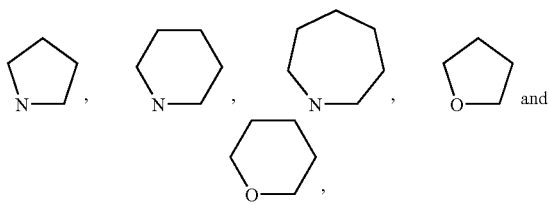

<Substituent Group β₂>

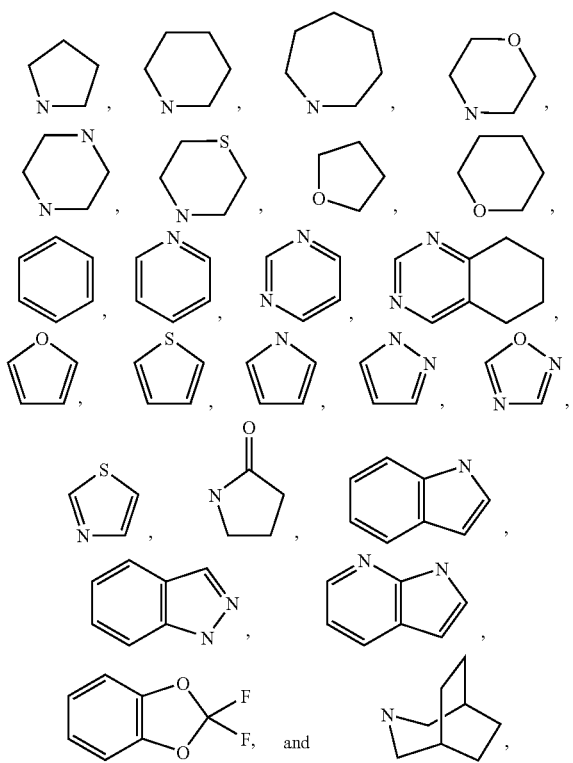

<Substituent Group γ> cycloalkyl having three to six carbon atoms, lower alkyl substituted with cycloalkyl having three to six carbon atoms, phenyl, lower alkyl substituted with phenyl, pyridyl, pyrrolidinyl and piperidinyl, wherein said cycloalkyl having three to six carbon atoms, phenyl, pyridyl, pyrrolidinyl and piperidinyl may be substituted with one or more fluorine atoms.

The symbols and terms described in the present specification are hereinafter explained.

The term "lower alkyl" in the above formula (I) refers to a straight- or branched-chain alkyl group having one to six carbon atoms; for example, methyl, ethyl, propyl, isopropyl, butyl, isobutyl, sec-butyl, tert-butyl, pentyl, hexyl or the like; preferably methyl, ethyl, propyl, isopropyl, tert-butyl or pentyl; particularly preferably methyl.

The term "lower alkenyl" in the above formula (I) refers to a straight- or branched-chain alkenyl group having two to six carbon atoms; for example, vinyl, 1-propenyl, allyl, isopropenyl, 1-butenyl, 3-butenyl, 1,3-butanedienyl, 2-pentenyl, 4-pentenyl, 1-hexenyl, 3-hexenyl, 5-hexenyl or the like; preferably 1-propenyl.

The term "halogen" in the above formula (I) refers to, for example, fluorine atom, chlorine atom, bromine atom, iodine atom or the like; preferably fluorine atom, chlorine atom or bromine atom; more preferably fluorine atom.

The term "lower alkoxy" in the above formula (I) refers to a group in which oxygen atom is substituted with "lower alkyl"; concretely for example, methoxy, ethoxy, propoxy, isopropoxy, butoxy, isobutoxy, sec-butoxy, tert-butoxy, pentyloxy, neopentyloxy, hexyloxy, isohexyloxy or the like; preferably methoxy, ethoxy, isopropyloxy or tert-butoxy; more preferably methoxy or ethoxy, particularly preferably methoxy.

The term "lower alkoxyalkyl" in the above formula (I) refers to the above "lower alkyl" substituted with the above "lower alkoxy"; for example, methoxymethyl, ethoxymethyl, isopropoxymethyl, butoxymethyl, isobutoxymethyl, sec-butoxymethyl, tert-butoxymethyl, pentyloxymethyl, neopentyloxymethyl, hexyloxymethyl, isohexyloxymethyl, 1-methoxyethyl, 1-ethoxyethyl, 1-isopropoxyethyl, 1-butoxyethyl, 1-isobutoxyethyl, 1-sec-butoxyethyl, 1-tert-butoxyethyl, 1-pentyloxyethyl, 1-neopentyloxyethyl, 1-hexyloxyethyl, 1-isohexyloxyethyl, 2-methoxyethyl, 2-ethoxyethyl, 2-isopropoxyethyl, 2-butoxyethyl, 2-isobutoxyethyl, 2-sec-butoxyethyl, 2-tert-butoxyethyl, 2-pentyloxyethyl, 2-neopentyloxyethyl, 2-hexyloxyethyl, 2-isohexyloxyethyl, 1-methoxy-1-methylethyl, 1-ethoxy-1-methylethyl, 1-isopropoxy-1-methylethyl, 1-butoxy-1-methylethyl, 1-isobutoxy-1-methylethyl, 1-sec-butoxy-1-methylethyl, 1-tert-butoxy-1-methylethyl, 1-pentyloxy-1-methylethyl, 1-neopentyloxy-1-methylethyl, 1-hexyloxy-1-methylethyl, 1-isohexyloxy-1-methylethyl or the like; preferably, for example, methoxymethyl, ethoxymethyl or isopropoxymethyl; particularly preferably methoxymethyl.

The term "halogenated lower alkyl" in the above formula (I) refers to "lower alkyl" substituted with "halogen"; preferably "lower alkyl" substituted with one to three fluorine atoms; more preferably "lower alkyl" substituted with three fluorine atoms. Concrete examples thereof include trifluoromethyl, difluoromethyl, 2,2,2-trifluoroethyl, pentafluoroethyl and the like; preferably trifluoromethyl.

The term "halogenated lower alkoxy" in the above formula (I) refers to "lower alkoxy" substituted with "halogen"; preferably "lower alkoxy" substituted with one to three fluorine atoms; more preferably "lower alkoxy" substituted with three fluorine atoms. Concrete examples thereof include trifluoromethoxy, difluoromethoxy, 2,2,2-trifluoroethoxy, pentafluoroethoxy and the like; preferably trifluoromethoxy.

The term "lower alkoxycarbonyl" in the above formula (I) refers to a carbonyl group substituted with the above "lower alkoxy"; concretely for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, neopentyloxycarbonyl, hexyloxycarbonyl, isohexyloxycarbonyl or the like, preferably methoxycarbonyl, ethoxycarbonyl, isopropoxycarbonyl or tert-butoxycarbonyl; more preferably methoxycarbonyl or ethoxycarbonyl; particularly preferably methoxycarbonyl.

The term "lower alkanoyl" in the above formula (I) refers to a carbonyl group substituted with the above "lower alkyl"; for example, acetyl, propionyl, butyryl, isobutyryl, pivaloyl or the like; preferably acetyl.

The term "lower alkylamino" in the above formula (I) refers to an amino group which is N-substituted with the above "lower alkyl"; for example, N-methylamino, N-ethylamino, N-propylamino, N-isopropylamino, N-butylamino, N-isobutylamino, N-tert-butylamino, N-pentylamino, N-hexylamino or the like; preferably, for example, N-methylamino, N-ethylamino, N-butylamino or N-tert-butylamino, particularly preferably N-tert-butylamino.

The term "halogenated lower alkylamino" in the above formula (I) refers to "lower alkylamino" substituted with "halogen"; preferably "lower alkylamino" substituted with one to three fluorine atoms; more preferably "lower alkylamino" substituted with three fluorine atoms. Concrete examples thereof include 2,2,2-trichloroethyl, 2,2,2-trifluoroethyl and the like; particularly preferably 2,2,2-trifluoroethyl.

The term "di-lower alkylamino" in the above formula (I) refers to an amino group which is N,N-disubstituted with the above "lower alkyl"; for example, N,N-dimethylamino, N,N-diethylamino, N,N-dipropylamino, N,N-diisopropylamino, N,N-dibutylamino, N,N-diisobutylamino, N,N-di-tert-butylamino, N,N-dipentylamino, N,N-dihexylamino, N-ethyl-N-methylamino, N-methyl-N-propylamino or the like; preferably, for example, N,N-dimethylamino, N,N-diethylamino, N,N-dibutylamino, N-ethyl-N-methylamino or N-methyl-N-propylamino.

The term "lower alkylsulfonyl" in the above formula (I) refers to a sulfonyl group substituted with the above "lower alkyl"; for example, methylsulfonyl, ethylsulfonyl, butylsulfonyl or the like; preferably, for example, methylsulfonyl or ethylsulfonyl; particularly preferably methylsulfonyl.

The term "cycloalkyl having three to six carbon atoms" in the above formula (I) refers to cyclopropyl, cyclobutyl, cyclopentyl or cyclohexyl, preferably cyclopropyl or cyclopentyl. The term "cycloalkyl having five to six carbon atoms" in the above formula (I) refers to cyclopentyl or cyclohexyl, preferably cyclopentyl.

The term "hydroxy-lower alkyl" in the above formula (I) refers to the above "lower alkyl" substituted with a hydroxy group; preferably "lower alkyl" substituted with one to three hydroxy groups; particularly preferably "lower alkyl" substituted with one hydroxy group. Concrete examples thereof include hydroxymethyl, 1-hydroxyethyl, 2-hydroxyethyl, 1-hydroxypropyl, 2-hydroxypropyl, 3-hydroxypropyl, 1-hydroxy-2-methylethyl, 1-hydroxybutyl, 1-hydroxy-2-methylpropyl, 1-hydroxy-2,2-dimethylethyl, 1-hydroxypentyl, 1-hydroxy-2-methylbutyl, 1-hydroxyhexyl, 1-hydroxy-2-methylpentyl and the like; preferably hydroxymethyl, 1-hydroxyethyl, 2-hydroxyethyl and 1-hydroxy-2-methylethyl.

The term "amino-lower alkyl" in the above formula (I) refers to the above "lower alkyl" substituted with an amino group; concretely for example, aminomethyl, 1-amino, 2-aminoethyl, 1-aminopropyl, 2-aminopropyl, 3-aminopropyl, 1-amino-2-methylethyl, 1-aminobutyl, 1-amino-2-methylpropyl, 1-amino-2,2-dimethylethyl, 1-aminopentyl, 1-amino-2-methylbutyl, 1-aminohexyl, 1-amino-2-methylpentyl or the like, preferably aminomethyl, 1-aminoethyl, 2-aminoethyl, or 1-amino-2-methylethyl.

The term "lower alkanoyl" in the above formula (I) refers to a carbonyl group substituted with the above "lower alkyl"; preferably a carbonyl group substituted with an alkyl group having one to five carbon atoms. Concrete examples thereof include acetyl, propionyl, butyryl, isobutyryl, valeryl, isovaleryl, pivaloyl, pentanoyl and the like; preferably acetyl, propionyl and pivaloyl; particularly preferably acetyl.

The term "lower alkanoylamino" in the above formula (I) refers to an amino group substituted with the above "lower alkanoyl"; for example, N-acetylamino, N-propionylamino, N-butyrylamino or the like; preferably, for example, N-acetylamino or N-propionylamino.

"Cdk" refers to a cyclin-dependent kinase including Cdk2, Cdc2(=Cdk1), Cdk4, Cdk6, Cdk7 and the like. Here, Cdk2 is cyclin-dependent kinase 2, Cdc2 is a cell division cycle 2, Cdk1 is a cyclin-dependent kinase 1, Cdk4 is a cyclin-dependent kinase 4, Cdk6 is a cyclin-dependent kinase 6, and Cdk7 is a cyclin-dependent kinase 7. The term "Cdk inhibitor" means an inhibitor against a cyclin-dependent kinase including Cdk2, Cdc2, Cdk4, Cdk6, Cdk7 and the like.

The aforementioned term "pharmaceutically acceptable salt or ester thereof" is explained later.

BEST MODE FOR CARRYING OUT THE INVENTION

The embodiments of the compound of the formula (I) will be described in more detail below.

X is NH, S, O or $CH_2$; preferably NH or S; particularly preferably NH.

Y is O or NR' (wherein R' is hydrogen or lower alkyl), preferably O.

The partial structure

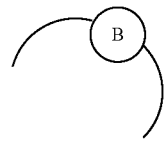

is selected from the following formula:

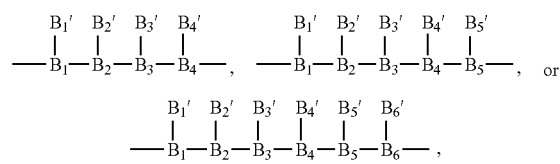

preferably the following formula:

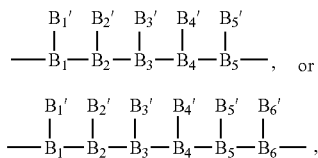

more preferably the following formula:

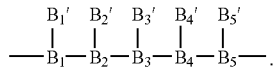

The above $B_1, B_2, \ldots, B_{n-1}$ and $B_n$, and $B'_1, B'_2, \ldots, B'_{n-1}$ and $B'_n$ (in which n is 4, 5 or 6) are explained below. In the above formula (I), $B_1, B_2, \ldots, B_{n-1}$ and $B_n$, and $B'_1, B'_2, \ldots, B'_{n-1}$ and $B'_n$ (in which n is 4, 5 or 6) mean $B_1, B_2, B_3$ and $B_4$, and $B'_1, B'_2, B'_3$ and $B'_4$ when n=4; $B_1, B_2, B_3, B_4$ and $B_5$, and $B'_1, B'_2, B'_3, B'_4$ and $B'_5$ when n=5; $B_1, B_2, B_3, B_4, B_5$ and $B_6$, and $B'_1, B'_2, B'_3, B'_4, B'_5$ and $B'6$ when n=6, respectively.

$B_1, B_2, \ldots, B_{n-1}$ and $B_n$ are each independently C, CH, $CR_0$, N or O, wherein $R_0$ is lower alkyl, and when the partial structure

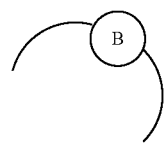

is the formula:

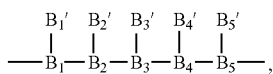

then preferably $B_1$, $B_2$, $B_3$, $B_4$ and $B_5$ are each independently CH; or $B_1$, $B_2$, $B_4$ and $B_5$ are each independently CH and $B_3$ is N or O; particularly preferably, $B_1$, $B_2$, $B_4$ and $B_5$ are each independently CH and $B_3$ is N, and when the partial structure

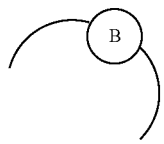

is the formula:

then preferably $B_1$, $B_2$, $B_3$, $B_5$ and $B_6$ are each independently CH and $B_4$ is N.

Also, when at least one carbon atom of $B_1$, $B_2$, $B_3$, $B_4$ and $B_5$ is an asymmetric carbon, a compound of the above formula (I) includes any optical isomer thereof as well as a racemate thereof.

In the above $B_1$, $B_2$, ..., $B_{n-1}$ and $B_n$, when $B_1$, $B_2$, ..., $B_{n-1}$ and $B_n$ are each independently C, then $B'_1$, $B'_2$, ..., $B'_{n-1}$ and $B'_n$ are oxo, respectively;

when $B_1$, $B_2$, ..., $B_{n-1}$ and $B_n$ are each independently O, then $B'_1$, $B'_2$, ..., $B'_{n-1}$ and $B'_n$ are each taken together with $B_1$, $B_2$, ..., $B_{n-1}$ and $B_n$, respectively, to form O, with the proviso that two or more members of $B_1$, $B_2$, ..., $B_{n-1}$ and $B_n$, at the same time, are not taken together with $B'_1$, $B'_2$, ..., $B'_{n-1}$ and $B'_n$, respectively, to form O.

$B'_1$, $B'_2$, ..., $B'_{n-1}$ and $B'_n$ are each independently hydrogen, halogen, hydroxy, oxo, lower alkoxy, amino, lower-alkyl amino, di-lower-alkylamino, lower alkyl or lower alkenyl, wherein $B'_1$, $B'_2$, ..., $B'_{n-1}$ and $B'_n$ are each independently taken together with $B_1$, $B_2$, ... $B_{n-1}$ and $B_n$, respectively, to form O, with the proviso that two or more members of $B'_1$, $B'_2$, ..., $B'_{n-1}$ and $B'_n$, at the same time, are not taken together with $B_1$, $B_2$, ..., $B_{n-1}$ and $B_n$, respectively, to form O.

In the above $B'_1$, $B'_2$, ..., $B'_{n-1}$ and $B'_n$, said lower alkyl and said lower alkenyl may be substituted with one or more, same or different substituents selected from the group consisting of hydroxy, lower alkoxy, amino and lower alkylamino.

Also, among the above $B'_1$, $B'_2$, ..., $B'_{n-1}$ and $B'_n$, $B'_i$ and $B'_{i+2}$ (in which i is 1, 2 or 3) taken together with $B_i$, $B_{i+1}$ and $B_{i+2}$, or $B'_i$ and $B'_{i+3}$ (in which i is 1 or 2) taken together with $B_i$, $B_{i+1}$, $B_{i+2}$ and $B_{i+3}$, may form a cycloalkyl having five to six carbon atoms or an aliphatic heterocyclic group selected from the group consisting of

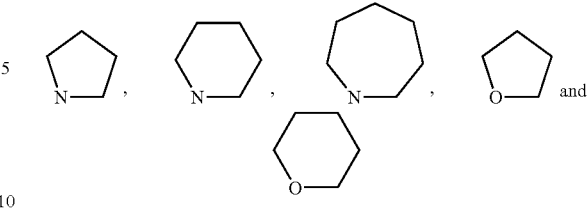

(hereinafter referred to as <substituent group $\beta_1$>), and said cycloalkyl and said aliphatic heterocycle may be substituted with one or more, same or different substituents selected from the group consisting of hydroxy, hydroxy-lower alkyl, cyano, halogen, carboxyl, lower alkanoyl, lower alkoxycarbonyl, lower alkoxy, lower alkoxyalkyl, amino, lower alkylamino, lower alkylsulfonyl, halogenated lower alkyl, halogenated lower alkoxy, halogenated lower alkylamino, nitro and lower alkanoylamino (hereinafter referred to as <substituent group $\alpha$>) and lower alkyl.

Moreover, in the above $B'_1$, $B'_2$, ..., $B'_{n-1}$ and $B'_n$, when the partial structure

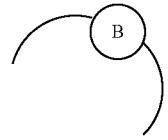

is the formula:

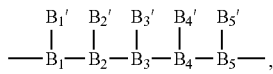

then preferably
all of $B'_1$, $B'_2$, $B'_3$, $B'_4$ and $B'_5$ are hydrogen; or
one of $B'_1$, $B'_2$, $B'_3$, $B'_4$ and $B'_5$ is lower alkyl or lower alkenyl, and all the others are hydrogen; or
at least two of $B'_1$, $B'_2$, $B'_3$, $B'_4$ and $B'_5$ are each independently lower alkyl or lower alkenyl, and all the others are hydrogen; or
among $B'_1$, $B'_2$, $B'_3$, $B'_4$ and $B'_5$, $B'_i$ and $B'_{i+2}$ (in which i is 1, 2 or 3) taken together with $B_i$, $B_{i+1}$ and $B_{i+2}$, form an aliphatic heterocycle selected from the group of

(hereinafter referred to as <substituent group $\beta_{1a}$>), wherein said aliphatic heterocycle may be substituted with one or more, same or different substituents selected from the group consisting of hydroxy, hydroxy-lower alkyl, halogen, lower alkoxycarbonyl, lower alkoxy, lower alkoxyalkyl, lower alkylamino, methyl substituted with one to three fluorine atoms, methoxy substituted with one to three fluorine atoms and lower alkylamino substituted with one to three fluorine atoms (hereinafter referred to as <substituent group $\alpha_a$>) and lower alkyl, and the others are hydrogen, lower alkyl or lower alkenyl;

more preferably, $B_1$, $B_2$, $B_4$ and $B_5$ are each independently CH, $B_3$ is N, and all of $B'_1$, $B'_2$, $B'_3$, $B'_4$ and $B'_5$ are hydrogen; or one of $B'_1$, $B'_2$, $B'_3$, $B'_4$ and $B'_5$ is lower alkyl or lower alkenyl, and all the others are hydrogen; or at least two of $B'_1$, $B'_2$, $B'_3$, $B'_4$ and $B'_5$ are each independently lower alkyl or lower alkenyl, and all the others are hydrogen; or among $B'_1$, $B'_2$, $B'_3$, $B'_4$ and $B'_5$, $B'_i$ and $B'_{i+2}$ (in which i is 1, 2 or 3) taken together with $B_i$, $B_{i+1}$ and $B_{i+2}$, form an aliphatic heterocycle selected from <substituent group $\beta_{1a}$>, wherein said aliphatic heterocycle may be substituted with one or more, same or different substituents selected from lower alkyl and <substituent group $\alpha_a$>, and the others are hydrogen, lower alkyl or lower alkenyl;

particularly preferably,

X is NH;

$B_1$, $B_2$, $B_4$ and $B_5$ are each independently CH and $B_3$ is N;

among $B'_1$, $B'_2$, $B'_3$, $B'_4$ and $B'_5$, $B'_i$ and $B'_{i+2}$ (in which i is 1) taken together with $B_i$, $B_{i+1}$ and $B_{i+2}$ form an aliphatic heterocycle selected from <substituent group $\beta_{1a}$>, wherein said aliphatic heterocycle may be substituted with lower alkyl, and the others are hydrogen.

Furthermore, in the above $B'_1$, $B'_2$, ..., $B'_{n-1}$ and $B'_n$, when the partial structure

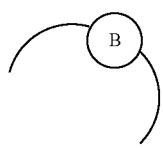

is the formula:

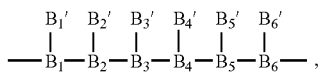

then preferably $B'_i$ and $B'_{i+3}$ (in which i is 1 or 2) among $B'_1$, $B'_2$, $B'_3$, $B'_4$, $B'_5$ and $B'_6$, taken together with $B_i$, $B_{i+1}$, $B_{i+2}$ and $B_{i+3}$, form

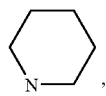

and all the others are hydrogen;

more preferably $B'_1$, $B'_2$, $B'_3$, $B'_5$ and $B'_6$ are each independently CH, $B_4$ is N, and $B'_i$ and $B'_{i+3}$ (in which i is 1 or 2) among $B'_1$, $B'_2$, $B'_3$, $B'_4$, $B'_5$ and $B'_6$, taken together with $B_i$, $B_{i+1}$, $B_{i+2}$ and $B_{i+3}$, form

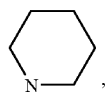

and all the others are hydrogen.

The partial structure

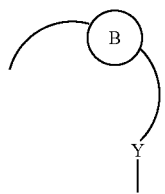

includes, for example,

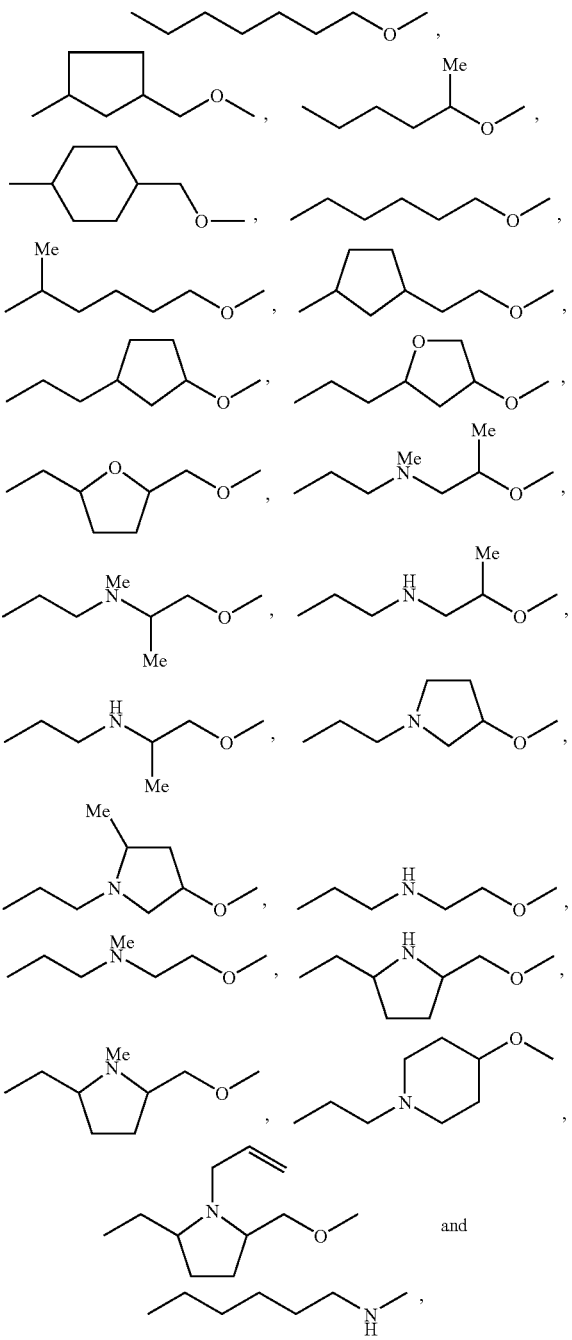

-continued preferably

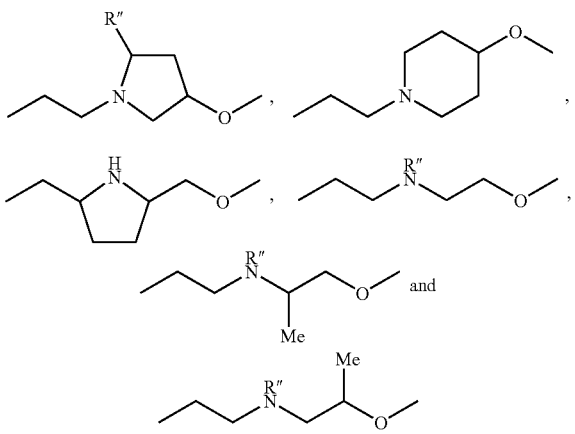

wherein R" is hydrogen or methyl, more preferably

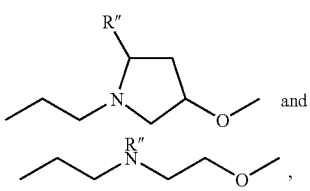

particularly preferably

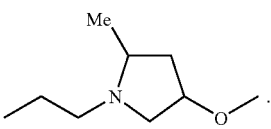

As mentioned above, in terms of improvement in solubility of compounds of the formula (I), it is preferable that any one of $B_1, B_2, \ldots, B_{n-1}$ and $B_n$ is a nitrogen atom.

R is hydrogen, lower alkyl, lower alkenyl, amino of which nitrogen is di-substituted with $R_a$ and $R_b$, amino-lower alkyl of which nitrogen is di-substituted with $R_a$ and $R_b$, or L, wherein $R_a$ and $R_b$ are each independently hydrogen, lower alkyl, lower alkoxyalkyl or halogenated lower alkyl; and L is $L_1$-$L_2$-$L_3$ (wherein $L_1$ is a single bond, —$(CH_2)_{k1}$—, —$(CH_2)_{k1}$—O— or —$(CH_2)_{k1}$—NH— (in which k1 is an integer of 1 to 3); $L_2$ is a single bond or —$(CH_2)_{k2}$— (in which k2 is an integer of 1 to 3); and $L_3$ is lower alkyl, lower alkoxy, cycloalkyl having three to six carbon atoms, phenyl, pyridyl, pyrrolidinyl or piperidinyl, said $L_3$ is lower alkyl, lower alkoxy, cycloalkyl having three to six carbon atoms, phenyl, pyridyl, pyrrolidinyl or piperidinyl being optionally substituted with one or more fluorine atoms); or a substituent selected from <substituent group α> which may be substituted with one or more, same or different substituents selected from the group consisting of cycloalkyl having three to six carbon atoms, lower alkyl substituted with cycloalkyl having three to six carbon atoms, phenyl, lower alkyl substituted with phenyl, pyridyl, pyrrolidinyl and piperidinyl, said cycloalkyl having three to six carbon atoms, phenyl, pyridyl, pyrrolidinyl and piperidinyl being optionally substituted with one or more fluorine atoms (hereinafter referred to as <substituent group γ>, or lower alkyl substituted with said substituent; or a cyclic group selected from the group consisting of

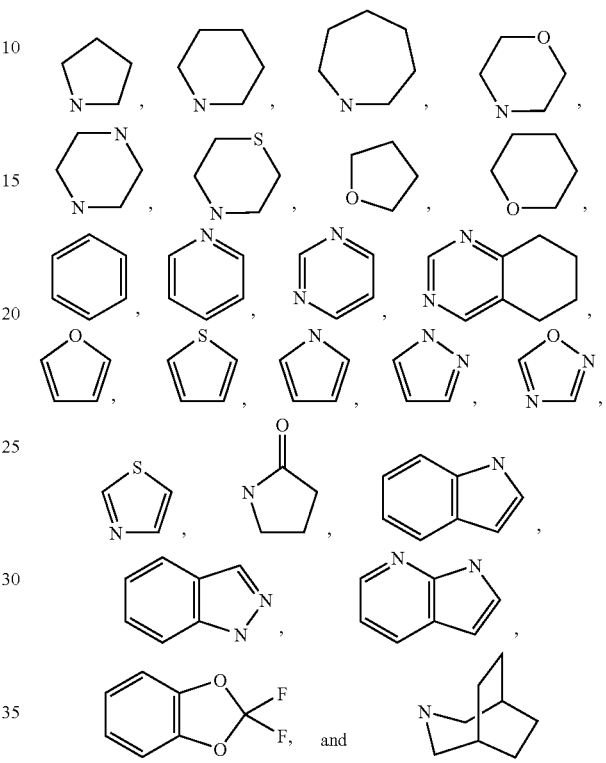

(hereinafter referred to as <substituent group $\beta_2$>), wherein said cyclic group may be substituted with one or more, same or different substituents selected from lower alkyl, <substituent group α> and <substituent group γ>, and also may be substituted with J. Here, J is $J_1$-$J_2$-$J_3$, wherein $J_1$ is a single bond, —C(=O)—, —O—, —NH—, —NHCO—, —$(CH_2)_{k3}$— or —$(CH_2)_{k3}$—O— (in which k3 is an integer of 1 to 3); $J_2$ is a single bond or —$(CH_2)_{k4}$— (in which k4 is an integer of 1 to 3); and $J_3$ is lower alkyl, lower alkoxy, —CONR$_a$R$_b$ (wherein $R_a$ and $R_b$ each has the same meaning as defined above), phenyl, pyridyl, pyrrolidinyl or piperidinyl, said lower alkyl, lower alkoxy, phenyl, pyridyl, pyrrolidinyl or piperidinyl being optionally substituted with one or more fluorine atoms, or lower alkyl substituted with said cyclic group.

In addition, R is preferably hydrogen, amino-lower alkyl of which nitrogen is di-substituted with $R_a$ and $R_b$, or L, wherein $R_a$ and $R_b$ are each independently lower alkyl, and L is $L_1$-$L_2$-$L_3$ (wherein $L_1$ is a single bond, —$(CH_2)_{k1}$—, —$(CH_2)_{k1}$—O— or —$(CH_2)_{k1}$—NH— (in which k1 is 1 or 2); $L_2$ is a single bond or —$(CH_2)_n$— (in which k2 is 1 or 2); and $L_3$ is lower alkoxy or cycloalkyl having three to six carbon atoms); or a cyclic group selected from <substituent group $\beta_2$> which may be substituted with one or more, same or different substituents selected from lower alkyl and <substituent group α>, or lower alkyl substituted with said cyclic group, wherein <substituent group $\beta_2$> is selected from

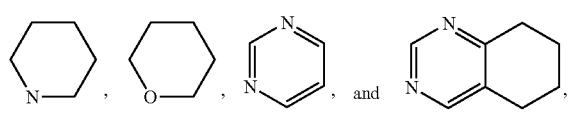

and <substituent group α> is selected from halogen, lower alkoxy, lower alkoxyalkyl, methyl substituted with one to three fluorine atoms and methoxy substituted with one to three fluorine atoms; or lower alkyl substituted with a substituent selected from the group consisting of lower alkylamino and lower alkylamino substituted with one to three fluorine atoms.

The above R binds to the quinoxalinone structure preferably as described in the following formula:

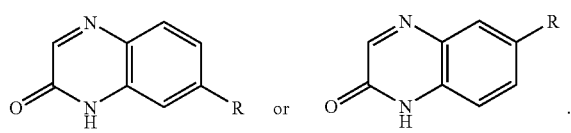

The above R includes, for example,

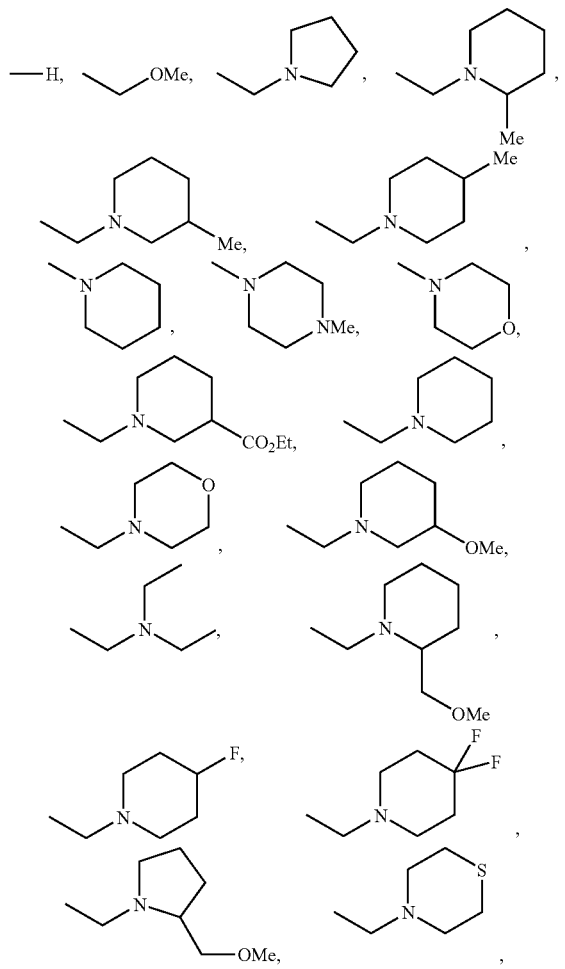

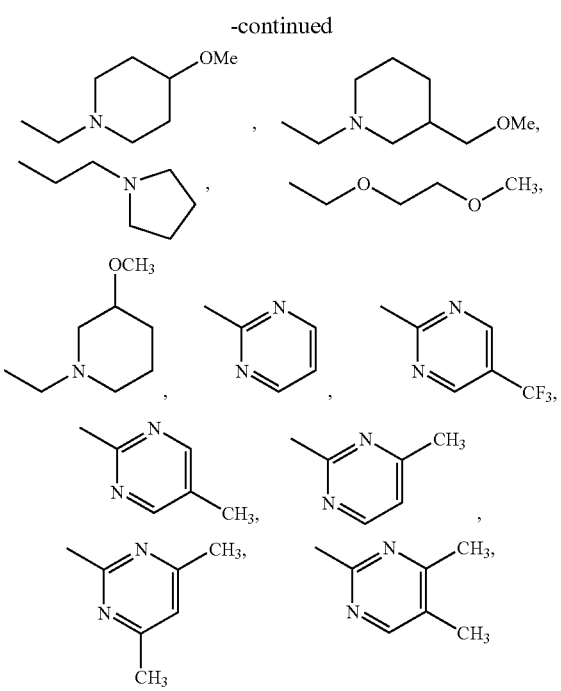

and the like; preferably includes

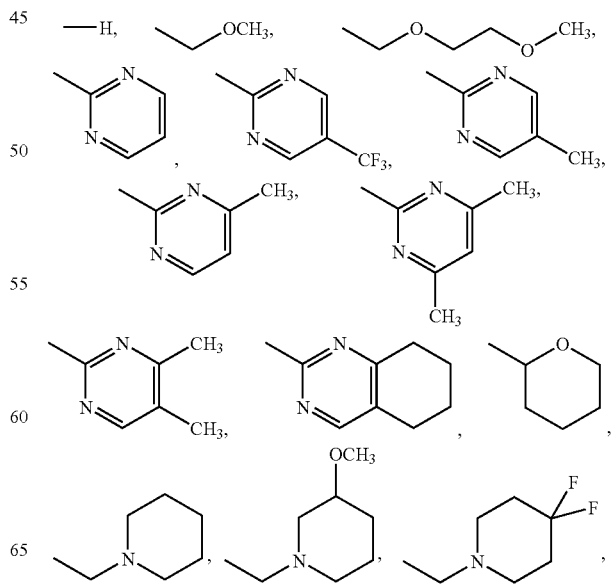

-continued

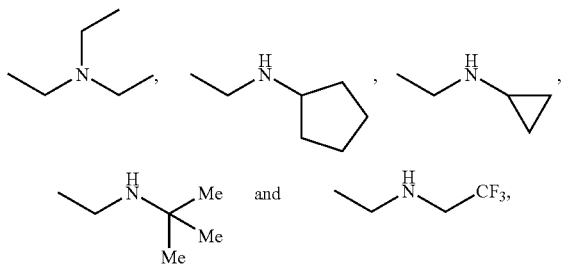

more preferably includes

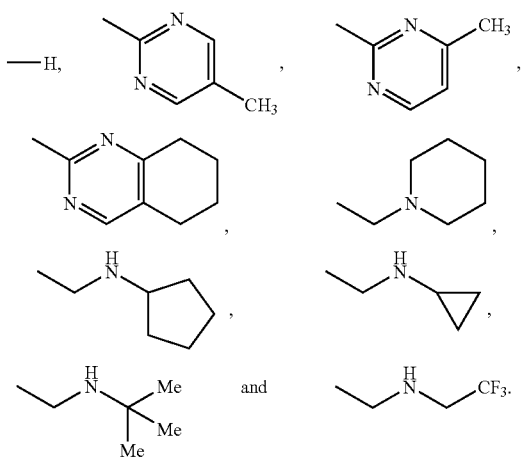

The present invention relating to a compound of the formula (I), including a pharmaceutically acceptable salt or ester thereof, may also be described as follows.

(i) A quinoxalinone derivative of the formula (I):

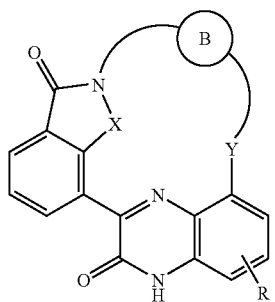

(I)

or a pharmaceutically acceptable salt or ester thereof, wherein;

X is NH, S, O or $CH_2$;

Y is O or NR', wherein R' is hydrogen or lower alkyl;

the partial structure

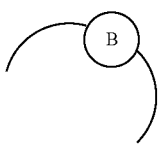

is selected from the following formula:

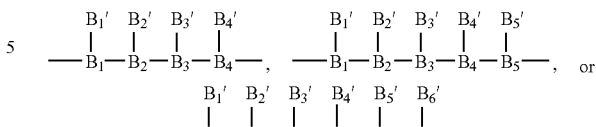

wherein $B_1, B_2, \ldots, B_{n-1}$ and $B_n$, and $B'_1, B'_2, \ldots, B'_{n-1}$ and $B'_n$ (in which n is 4, 5 or 6) are each defined as follows:

$B_1, B_2, \ldots, B_{n-1}$ and $B_n$ are each independently C, CH, $CR_0$, N or O (wherein when $B_1, B_2, \ldots, B_{n-1}$ and $B_n$ are each independently C, then $B'_1, B'_2, \ldots, B'_{n-1}$ and $B'_n$ are oxo, respectively;

when $B_1, B_2, \ldots, B_{n-1}$ and $B_n$ are each independently O, then $B'_1, B'_2, \ldots, B'_{n-1}$ and $B'_n$ are each taken together with $B_1, B_2, \ldots, B_{n-1}$ and $B_n$, respectively, to form O, with the proviso that two or more members of $B_1, B_2, \ldots, B_{n-1}$ and $B_n$, at the same time, are not taken together with $B'_1, B'_2, \ldots, B'_{n-1}$ and $B'_n$, respectively, to form O; and $R_0$ is lower alkyl), and $B'_1, B'_2, \ldots, B'_{n-1}$ and $B'_n$ are each independently hydrogen, halogen, hydroxy, oxo, lower alkoxy, amino, lower alkylamino, di-lower alkylamino, lower alkyl or lower alkenyl (wherein said lower alkyl and said lower alkenyl may be substituted with one or more, same or different substituents selected from the group consisting of hydroxy, lower alkoxy, amino and lower alkylamino, and among $B'_1, B'_2, \ldots, B'_{n-1}$ and $B'_n$, $B'_i$ and $B'_{i+2}$ (in which i is 1, 2 or 3) taken together with $B_i$, $B_{i+1}$ and $B_{i+2}$, or $B'_i$ and $B'_{i+3}$ (in which i is 1 or 2) taken together with $B_i$, $B_{i+1}$, $B_{i+2}$ and $B_{i+3}$, may form a cycloalkyl having five to six carbon atoms or an aliphatic heterocyclic group selected from <substituent group $\beta_1$>, and said cycloalkyl and said aliphatic heterocyclic group may be substituted with one or more, same or different substituents selected from lower alkyl and <substituent group $\alpha$>);

R is hydrogen, lower alkyl, lower alkenyl, amino in which the nitrogen atom is di-substituted with $R_a$ and $R_b$, aminolower alkyl in which the nitrogen atom is di-substituted with $R_a$ and $R_b$, or L, wherein $R_a$ and $R_b$ are each independently hydrogen, lower alkyl, lower alkoxyalkyl or halogenated lower alkyl, and L is $L_1$-$L_2$-$L_3$ (wherein $L_1$ is a single bond, —$(CH_2)_{k1}$—, —$(CH_2)_{k1}$—O— or —$(CH_2)_{k1}$—NH— (in which k1 is an integer of 1 to 3); $L_2$ is a single bond or —$(CH_2)_{k2}$— (in which k2 is an integer of 1 to 3); and $L_3$ is lower alkyl, lower alkoxy, cycloalkyl having three to six carbon atoms, phenyl, pyridyl, pyrrolidinylorpiperidinyl, said lower alkyl, lower alkoxy, cycloalkyl having three to six carbon atoms, phenyl, pyridyl, pyrrolidinyl or piperidinyl being optionally substituted with one or more fluorine atoms); or a substituent selected from <substituent group $\alpha$>, which may be substituted with one or more, same or different substituents selected from <substituent group $\gamma$>, or lower alkyl substituted with said substituent; or a cyclic group selected from <substituent group $\beta_2$>, which may be substituted with one or more, same or different substituents selected from a lower alkyl, <substituent group $\alpha$> and <substituent group $\gamma$>, and also may be substituted with J (wherein J is $J_1$-$J_2$-$J_3$; $J_1$ is a single bond, —C(=O)—, —O—, —NH—, —NHCO—, —$(CH_2)_{k3}$— or —$(CH_2)_{k3}$—O— (in which k3 is an integer 1 to 3); $J_2$ is a single bond or —$(CH_2)_{k4}$— (in which k4 is an integer of 1 to 3); and $J_3$ is lower alkyl, lower alkoxy, —$CONR_aR_b$ (wherein $R_a$ and $R_b$ each have the same meaning as defined above), phenyl, pyridyl, pyrrolidinyl or piperidinyl, said lower alkyl, lower alkoxy, phenyl, pyridyl, pyrrolidinyl or piperidinyl being optionally substituted with one or more fluorine atoms), or lower alkyl substituted with said cyclic group, and in the above, <substituent group α>, <substituent group $β_1$>, <substituent group $β_2$> and <substituent group γ> each have the meaning shown below:

<Substituent Group α> hydroxy, hydroxy-lower alkyl, cyano, halogen, carboxyl, lower alkanoyl, lower alkoxycarbonyl, lower alkoxy, lower alkoxyalkyl, amino, lower alkylamino, lower alkyl sulfonyl, halogenated lower alkyl, halogenated lower alkoxy, halogenated lower alkylamino, nitro and lower alkanoylamino, <Substituent Group $β_1$>

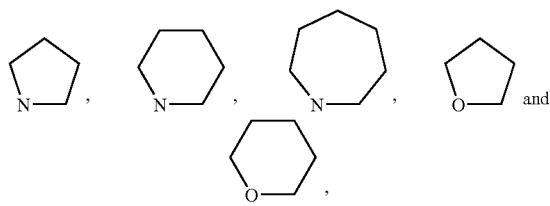

<Substituent Group $β_2$>

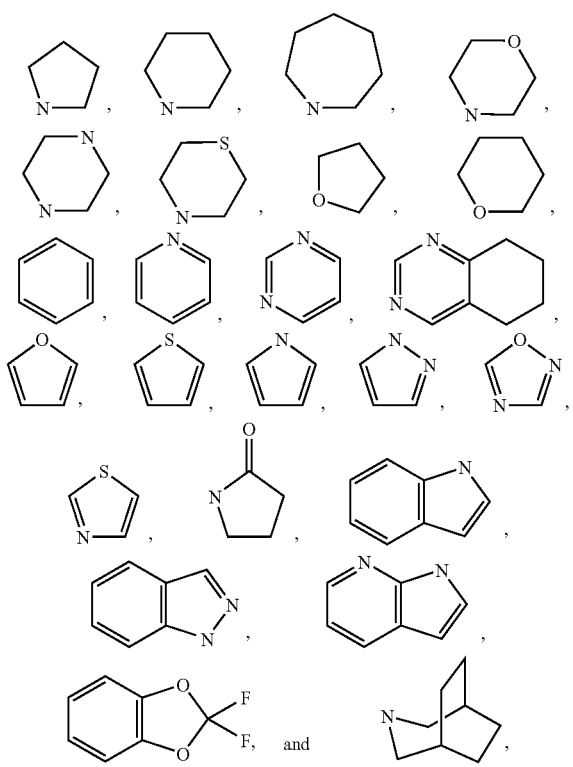

<Substituent Group γ> cycloalkyl having three to six carbon atoms, lower alkyl substituted with cycloalkyl having three to six carbon atoms, phenyl, lower alkyl substituted with phenyl, pyridyl, pyrrolidinyl and piperidinyl, wherein said cycloalkyl having three to six carbon atoms, phenyl, pyridyl, pyrrolidinyl and piperidinyl may be substituted with one or more fluorine atoms; or (ii) The compound according to the above (i) or a pharmaceutically acceptable salt or ester thereof, wherein;

X is NH or S; and

Y is O; or (iii) The compound according to the above (ii) or a pharmaceutically acceptable salt or ester thereof, wherein;

the partial structure

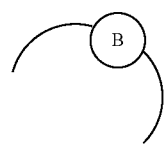

is the formula:

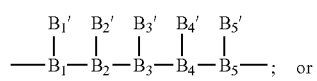

(iv) The compound according to the above (iii) or a pharmaceutically acceptable salt or ester thereof, wherein;

$B_1$, $B_2$, $B_3$, $B_4$ and $B_5$ are each independently CH; or $B_1$, $B_2$, $B_4$ and $B_5$ are each independently CH, and $B_3$ is N or O; or (v) The compound according to the above (iv) or a pharmaceutically acceptable salt or ester thereof, wherein;

the <substituent group α> is selected from hydroxy, hydroxy-lower alkyl, halogen, lower alkoxycarbonyl, lower alkoxy, lower alkoxyalkyl, lower alkylamino, methyl substituted with one to three fluorine atoms, methoxy substituted with one to three fluorine atoms and lower alkylamino substituted with one to three fluorine atoms, and the <substituent group $β_1$> is

(vi) The compound according to the above (v) or a pharmaceutically acceptable salt or ester thereof, wherein;

$B_1$, $B_2$, $B_4$ and $B_5$ are each independently CH, $B_3$ is N, and all of $B'_1$, $B'_2$, $B'_3$, $B'_4$ and $B'_5$ are hydrogen; or one of $B'_1$, $B'_2$, $B'_3$, $B'_4$ and $B'_5$ is lower alkyl or lower alkenyl, and all the others are hydrogen; or at least two of $B'_1$, $B'_2$, $B'_3$, $B'_4$ and $B'_5$ are each independently lower alkyl or lower alkenyl, and all the others are hydrogen; or among $B'_1$, $B'_2$, $B'_3$, $B'_4$ and $B'_5$, $B'_i$ and $B'_{i+2}$ (in which i is 1, 2 or 3) taken together with $B_i$, $B_{i+1}$ and $B_{i+2}$ form an aliphatic heterocycle selected from <substituent group $β_1$> (wherein said aliphatic heterocycle may be substituted with one or more, same or different substituents selected from lower alkyl and <substituent group α>), and the others are hydrogen, lower alkyl or lower alkenyl; or (vii) The compound according to the above (vi) or a pharmaceutically acceptable salt or ester thereof, wherein;

X is NH;

$B_1$, $B_2$, $B_4$ and $B_5$ are each independently CH, and $B_3$ is N;

among $B'_1$, $B'_2$, $B'_3$, $B'_4$ and $B'_5$, $B'_i$ and $B'_{i+2}$ (in which i is 1) taken together with $B_i$, $B_{i+1}$ and $B_{i+2}$ form an aliphatic heterocycle selected from <substituent group $\beta_1$> (wherein said aliphatic heterocycle may be substituted with lower alkyl), and the others are hydrogen; or (viii) The compound according to the above (ii) or a pharmaceutically acceptable salt or ester thereof, wherein;

the partial structure

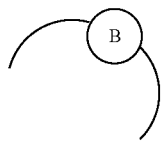

is the formula:

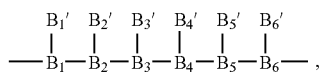

wherein $B_1$, $B_2$, $B_3$, $B_5$ and $B_6$ are each independently CH, and $B_4$ is N; among $B'_1$, $B'_2$, $B'_3$, $B'_4$, $B'_5$ and $B'_6$, $B'_i$ and $B'_{i+3}$ (in which i is 1 or 2) taken together with $B_i$, $B_{i+1}$, $B_{i+2}$ and $B_{i+3}$ form

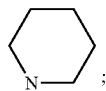

and all the others are hydrogen; or (ix) The compound according to any one of the above (vi) to (viii) or a pharmaceutically acceptable salt or ester thereof, wherein the R binds to quinoxalinone as described in the following formula:

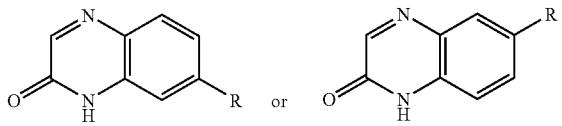

(x) The compound according to the above (ix) or a pharmaceutically acceptable salt or ester thereof, wherein;

R is hydrogen, amino-lower alkyl in which the nitrogen atom is di-substituted with $R_a$ and $R_b$, or L, wherein $R_a$ and $R_b$ are each independently lower alkyl, and L is $L_1$-$L_2$-$L_3$ (wherein $L_1$ is a single bond, —$(CH_2)_{k1}$—, —$(CH_2)_{k1}$—O— or —$(CH_2)_{k1}$—NH— (in which k1 is an integer of 1 or 2; $L_2$ is a single bond or —$(CH_2)_{k2}$— (in which k2 is an integer of 1 or 2); and $L_3$ is lower alkoxy or cycloalkyl having three to six carbon atoms); or a cyclic group selected from <substituent group $\beta_2$>, which may be substituted with one or more, same or different substituents selected from lower alkyl and <substituent group $\alpha$>, or lower alkyl substituted with said cyclic group, wherein the <substituent group $\beta_2$> is selected from

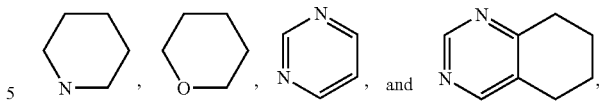

and the <substituent group $\alpha$> is selected from halogen, lower alkoxy, lower alkoxyalkyl, methyl substituted with one to three fluorine atoms, and methoxy substituted with one to three fluorine atoms; or lower alkyl substituted with a substituent selected from the group consisting of lower alkylamino and lower alkylamino substituted with one to three fluorine atoms; or (xi) The compound according to the above (ii) or a pharmaceutically acceptable salt or ester thereof, wherein;

the partial structure

is selected from the group consisting of

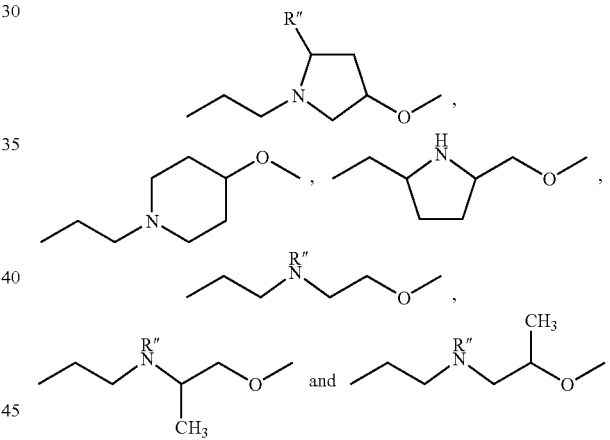

wherein R'' is hydrogen or methyl; and

R is selected from the group consisting of

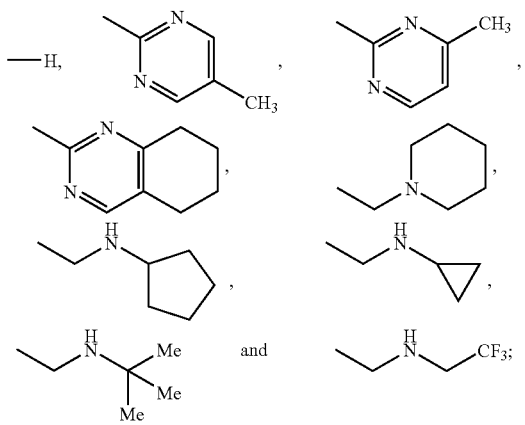

or
(xii) The compound according to the above (xi) or a pharmaceutically acceptable salt or ester thereof, wherein;
X is NH; and
the partial structure
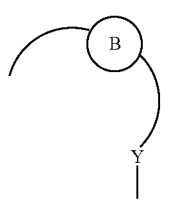
is the formula:
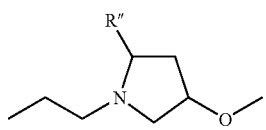
wherein R" is methyl; or
(xiii) The compound according to the above (i) or a pharmaceutically acceptable salt or ester thereof, wherein;
the quinoxalinone derivative is
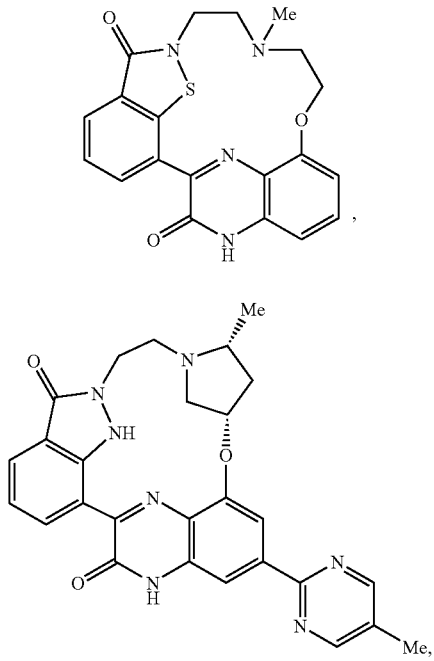
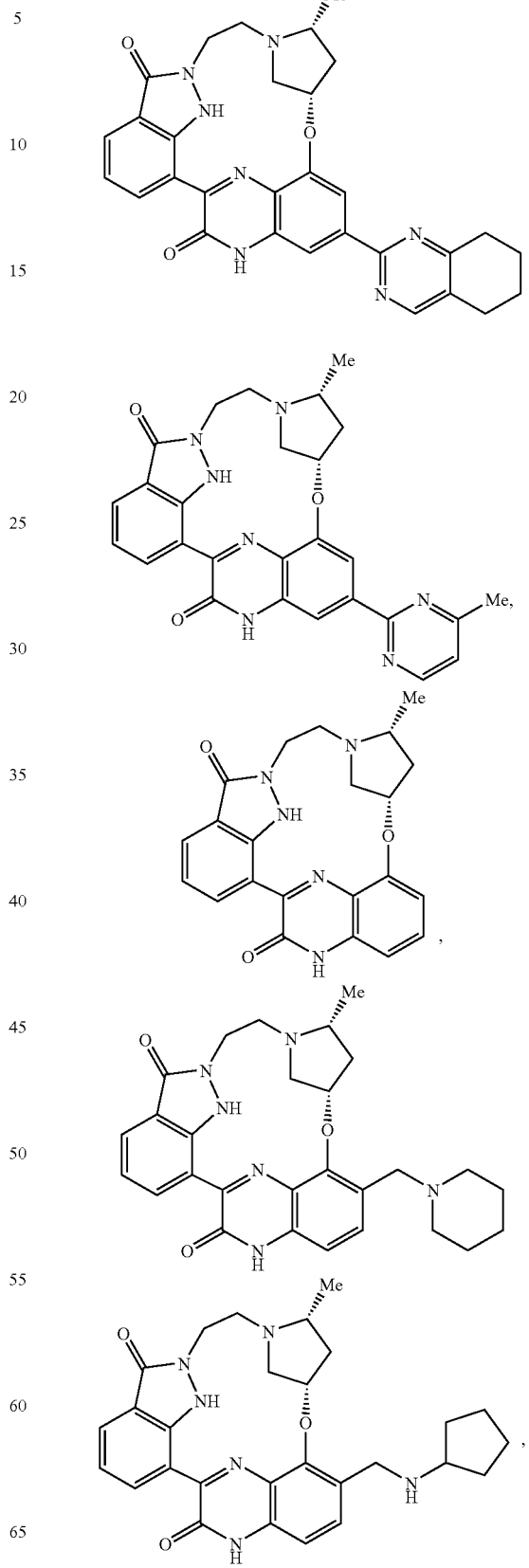

-continued

[Chemical structures shown]

(xiv) A pharmaceutical composition comprising one or more kinds of the quinoxalinone derivative according to the above (i) as an active ingredient, together with a pharmaceutically acceptable carrier or diluent; or (xv) A Cdk inhibitor comprising one or more kinds of the quinoxalinone derivative according to the above (i) as an active ingredient, together with a pharmaceutically acceptable carrier or diluent; or (xvi) An anti-cancer agent comprising one or more kinds of the quinoxalinone derivative according to the above (i) as an active ingredient, together with a pharmaceutically acceptable carrier or diluent.

As mentioned above, in the compound of the formula (I):

(I)
[Chemical structure]

wherein X, Y, n; the partial structure

[Partial structure diagram]

$B_1, B_2, \ldots, B_{n-1}$ and $B_n$; $B'_1, B'_2, \ldots, B'_{n-1}$ and $B'_n$; R, <substituent group α>, <substituent group $β_1$>, <substituent group $β_2$> and <substituent group γ> each have the same meaning as defined above, the partial structure

[Partial structure diagram]

is selected from the following formula:

[Chemical formulas with $B_1, B_2, B_3, B_4$ / $B'_1, B'_2, B'_3, B'_4$ etc.]

Therefore, the compound of the formula (I) may also be defined as the compound of the formula (I):

(I)
[Chemical structure]

wherein X, Y, n; $B_1, B_2, \ldots, B_{n-1}$ and $B_n$; $B'_1, B'_2, \ldots, B'_{n-1}$ and $B'_n$; R, <substituent group α>, <substituent group $β_1$>, <substituent group β2> and <substituent group γ> each have the same meaning as defined above.

On the basis of the above newly defined formula (I), a preparation method of the compound of the formula (I) is hereinafter described.

The compound of the formula (I):

(I)

wherein X, Y, n; $B_1, B_2, \ldots, B_{n-1}$ and $B_n$; $B'_1, B'_2, \ldots, B'_{n-1}$ and $B'_n$; R, <substituent group α>, <substituent group $β_1$>, <substituent group $β_2$> and <substituent group γ> each have the same meaning as defined above, can be prepared by removing a protecting group from the compound of the below-mentioned formula (II) or (III):

(II)

(III)

wherein X, Y, n; $B_1, B_2, \ldots, B_{n-1}$ and $B_n$; $B'_1, B'_2, \ldots, B'_{n-1}$ and $B'_n$; R, <substituent group α>, <substituent group $β_1$>, <substituent group β2> and <substituent group γ> each have the same meaning as defined above, and PG is 4-methoxybenzyl, 2,4-dimethoxybenzyl, benzyl, t-butyl, methyl, ethyl, methoxymethyl, 2-(trimethylsilylethoxy)methyl or the like, preferably, methyl or 2-(trimethylsilylethoxy)methyl, methoxymethyl. Removal of the protecting group can be carried out according to the method described in Protective Groups in Organic Synthesis (T. W. Greene, John Wiley & Sons, Inc, 1981) or its analogous methods, such as solvolysis using an acid, though it depends on the kind of protecting groups and the stability of compounds used.

The preparation methods of the compounds of the formula (II) or (III):

(II)

(III)

are hereinafter described.

Preparation Method A:

The compound of the above formula (II) or (III) wherein Y is an oxygen atom can be prepared by subjecting the compound of the below formula (IV) or (V):

(IV)

-continued

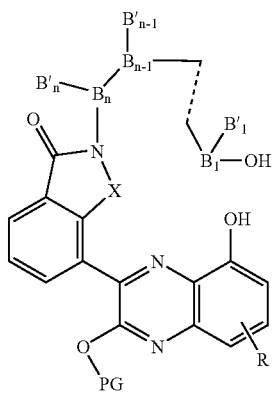
(V)

wherein X, Y, n; $B_1, B_2, \ldots, B_{n-1}$ and $B_n$; $B'_1, B'_2, \ldots, B'_{n-1}$ and $B'_n$; R, <substituent group α>, <substituent group $β_1$>, <substituent group $β_2$>, <substituent group γ> and PG each have the same meaning as defined above, to the Mitsunobu reaction for intramolecular cyclization (Synthesis, 1981, 1). For example, the compound of the above formula (II) or (III) can be prepared by reacting the compound of the above formula (IV) or (V) with triphenylphosphine and diethyl azodicarboxylate in a solvent such as tetrahydrofuran, 1,4-dioxan, methylene chloride, chloroform, toluene or the like. In this reaction, the reaction temperature is usually 0° C. to room temperature, although it may be appropriately chosen depending on the starting material or the reaction solvent to be used. Further, the reaction is usually completed within 1 to 24 hours, but the reaction time may be appropriately adjusted to make it longer or shorter.

The compound of the above formula (IV) can be prepared by removing the protecting group represented by $PG_2$ or $PG_3$ from the compound of the formula (VI):

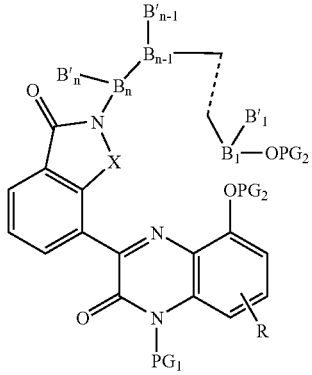
(VI)

wherein n; $B_1, B_2, \ldots, B_{-1}$ and $B_n$; $B'_1, B'_2, \ldots, B'_{n-1}$ and $B'_n$; R, <substituent group α>, <substituent group $β_1$>, <substituent group $β_2$> and <substituent group γ> each have the same meaning as defined above; $PG_1$, $PG_2$ and $PG_3$ are each a protecting group; $PG_1$ and $PG_2$ are the same or different and are each 4-methoxybenzyl, 2,4-dimethoxybenzyl, benzyl, t-butyl, methyl, ethyl, methoxymethyl, 2-(trimethylsilylethoxy)methyl, t-butyldimethylsilyl, t-butyldiphenylsilyl, acetyl, benzoyl, or the like, preferably methyl, 2-(trimethylsilylethoxy)methyl or methoxymethyl; and $PG_3$ is hydrogen, 4-methoxcybenzyl, 2,4-dimethoxybenzyl, benzyl, methoxymethyl, 2-(trimethylsilylethoxy)methyl, t-butyldimethylsilyl, t-butyldiphenylsilyl, acetyl, benzoyl or the like, preferably t-butyldimethylsilyl, t-butyldiphenylsilyl, acetyl or benzoyl.

Removal of the protecting group can be carried out according to the method described in Protective Groups in Organic Synthesis (T. W. Greene, John Wiley & Sons, Inc, 1981) or its analogous methods such as solvolysis using an acid or a base, chemical reduction using a metal complex hydride, and catalytic reduction using a palladium carbon catalyst or Raney nickel catalyst, though it depends on the kind of protecting groups and the stability of compounds used.

The compounds of the above formula (VI) wherein X is S can be prepared by reacting the compound of the formula (VII) or (VIII):

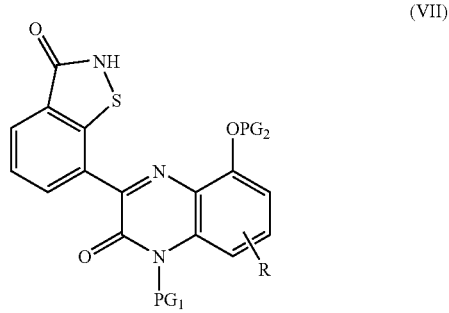
(VII)

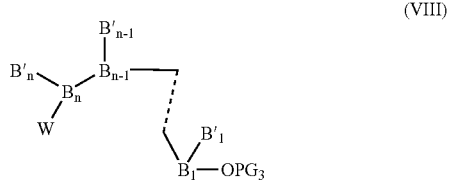
(VIII)

wherein n; $B_1, B_2, \ldots, B_{n-1}$ and $B_n$; $B'_1, B'_2, \ldots, B'_{n-1}$ and $B'_n$; R, <substituent group α>, <substituent group $β_1$>, <substituent group $β_2$> and <substituent group γ>, $PG_1$, $PG_2$ and $PG_3$ each have the same meaning as defined above; and W is a leaving group such as methanesulfonyloxy, with a base such as sodium hydroxide, lithium hydroxide or the like in a solvent such as 1,4-dioxan or the like. In this reaction, the reaction temperature is usually room temperature to the boiling point of the solvent used, preferably 100° C., though it may be appropriately chosen depending on the starting material or the reaction solvent used. Further, the reaction is usually completed within 1 to 24 hours, but the reaction time may be appropriately adjusted to make it longer or shorter.

The compound of the above formula (VII) can be prepared by reacting the compound of the formula (IX):

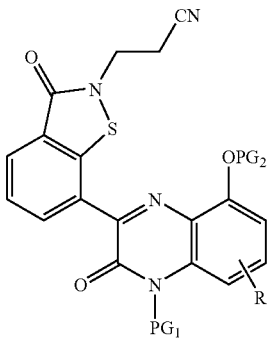

wherein R, <substituent group α>, <substituent group $β_1$>, <substituent group $β_2$>, <substituent group γ>, $PG_1$ and $PG_2$ each have the same meaning as defined above, with a base such as lithium hexamethyldisilazide or the like in a solvent such as tetrahydrofuran or the like. In this reaction, the reaction temperature is usually 0° C. to the boiling point of the solvent used, preferably room temperature, though it maybe appropriately chosen depending on the starting material or the reaction solvent to be used. Further, the reaction is usually completed within 1 to 24 hours, preferably for 1 hour, but the reaction time may be appropriately adjusted to make it longer or shorter.

The compound of the above formula (IX) can be prepared from the compound of the formula (X):

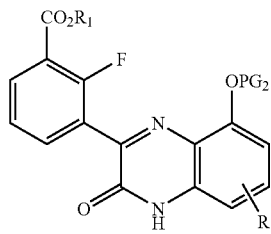

wherein $R_1$ is lower alkyl such as methyl, ethyl or the like; R, <substituent group α>, <substituent group $β_1$>, <substituent group $β_2$>, <substituent group γ> and $PG_2$ each have the same meaning as defined above, and 2-cyanoethylamine, according to a method similar to the Preparation Method B-1 described in WO 02/02550.

The compound of the above formula (X) can be prepared from the compound of the formula (XI):

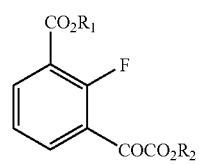

wherein $R_1$ and $R_2$ are the same or different and are each lower alkyl such as methyl, ethyl or the like, according to a method similar to the Preparation Method A described in WO 02/02550.

The compound of the above formula (XI) can be prepared by reacting a corresponding (2-fluoro-3-iodophenyl)oxoacetic acid ester with carbon monoxide in a mixed solvent of a solvent such as N,N-dimethylacetamide, N-methylpyrrolidone, N,N-dimethylformamide or the like, and an alcohol such as methanol, ethanol or the like, in the presence of a ligand such as 1,1'-bis (diphenylphosphino)ferrocene or the like, a palladium catalyst such as palladium(II) acetate or the like, and a base such as triethylamine or the like. In this reaction, the reaction temperature is usually 50° C. to the boiling point of the solvent to be used, though it may be appropriately chosen depending on the starting material or the reaction solvent to be used. Further, the reaction is usually completed within 1 to 24 hours, but the reaction time may be appropriately adjusted to make it longer or shorter.

In addition to the aforementioned method, the compound of the above formula (VI) wherein X is S can be prepared from the compound of the above formula (X) and the compound of the below formula (XII):

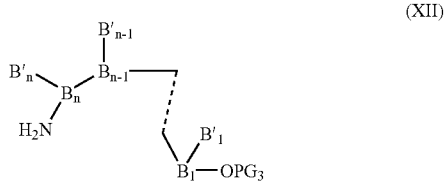

wherein n; $B_1, B_2, \ldots, B_{n-1}$ and $B_n$; $B'_1, B'_2, \ldots, B'_{n-1}$ and $B'_n$; <substituent group α>, <substituent group $β_1$>, <substituent group $β_2$>, <substituent group γ> and $PG_3$ each have the same meaning as defined above, according to a method similar to the Preparation Method B-1 described in WO 02/02550.

The compound of the above formula (VI) wherein X is NH can be prepared from the compound of the above formula (X) and the compound of the below formula (XIII):

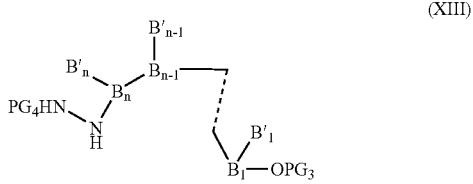

wherein n; $B_1, B_2, \ldots, B_{n-1}$ and $B_n$; $B'_1, B'_2, \ldots, B'_{n-1}$ and $B'_n$; <substituent group α>, <substituent group $β_1$>, <substituent group $β_2$>, <substituent group γ> and $PG_3$ each have the same meaning as defined above; and $PG_4$ is t-butoxycarbonyl, benzyloxycarbonyl, allyloxycarbonyl, formyl, acetyl, trifluoroacetyl or the like, preferably t-butoxycarbonyl, allyloxycarbonyl or the like, according to a method similar to the Preparation Method B-2b described in WO 02/02550.

The compound of the above formula (VI) wherein X is O can be prepared from the compound of the above formula (X) and the compound of the below formula (XIV):

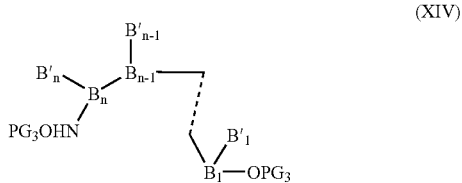

(XIV)

wherein n; $B_1, B_2, \ldots, B_{n-1}$ and $B_n$; $B'_1, B'_2, \ldots, B'_{n-1}$ and $B'_n$; <substituent group α>, <substituent group $β_1$>, <substituent group $β_2$>, <substituent group γ> and $PG_3$ each have the same meaning as defined above, according to a method similar to the Preparation Method B-3 described in WO 02/02550.

The compound of the above formula (V) wherein X is S can be prepared from the compound of the below formula (XV):

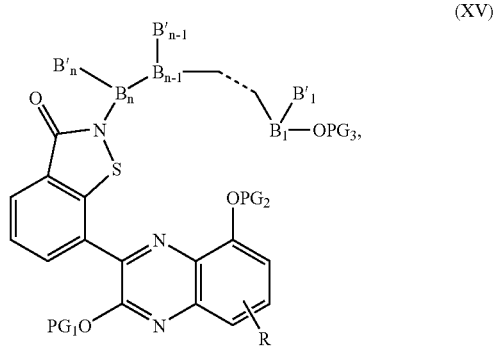

(XV)

wherein n; $B_1, B_2, \ldots, B_{n-1}$ and $B_n$; $B'_1, B'_2, \ldots, B'_{n-1}$ and $B'_n$; R, <substituent group α>, <substituent group $β_1$>, <substituent group $β_2$>, <substituent group γ>, $PG_1$, $PG_2$ and $PG_3$ each have the same meaning as defined above, according to a method similar to the Preparation Method B-1 described in WO 02/02550.

The compound of the above formula (XV) can be prepared from the compound of the below formula (XVI):

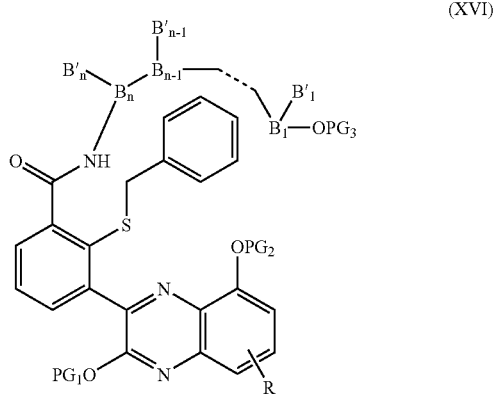

(XVI)

wherein n; $B_1, B_2, \ldots, B_{n-1}$ and $B_n$; $B'_1, B'_2, \ldots, B'_{n-1}$ and $B'_n$; R, <substituent group α>, <substituent group $β_1$>, <substituent group $β_2$>, <substituent group γ>, $PG_1$, $PG_2$ and $PG_3$ each have the same meaning as defined above, according to the Preparation Method B-1 described in WO 02/02550. Alternatively, the compound of the above formula (XV) can be prepared by an improved version of the Preparation Method B-1 described in WO 02/02550. That is, the compound of the above formula (XV) can also be prepared by reacting the compound of the above formula (XVI) with sulfuryl chloride in a solvent such as methylene chloride or the like in the presence of an organic base such as N-methylpyrrolidine, triethylamine or the like. In this reaction, the reaction temperature is usually −78° C. to −50° C., though it may be appropriately chosen depending on the starting material or the reaction solvent to be used. The reaction is usually completed within 10 to 60 minutes, but the reaction time maybe appropriately adjusted to make it longer or shorter.

The compound of the above formula (XVI) can be prepared from the compound of the below formula (XVII):

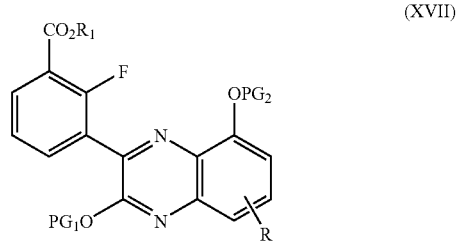

(XVII)

wherein R, <substituent group α>, <substituent group $β_1$>, <substituent group $β_2$>, <substituent group γ>, $R_1$, $PG_1$ and $PG_2$ each have the same meaning as defined above, according to a method similar to the Preparation Method B-1 described in WO 02/02550.

The compound of the above formula (XVII) can be prepared by reacting the compound of the below formula (XVIII):

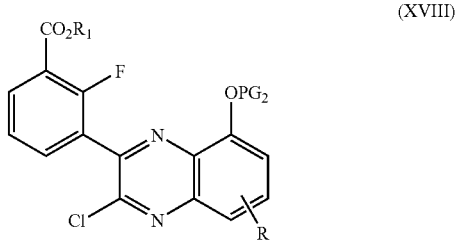

(XVIII)

wherein R, <substituent group α>, <substituent group $β_1$>, <substituent group $β_2$>, <substituent group γ>, $R_1$ and $PG_2$ each have the same meaning as defined above, with an alkali metal alkoxide such as sodium methoxide or the like in a solvent such as tetrahydrofuran, methanol or the like. In this reaction, the reaction temperature is usually room temperature to 50° C., preferably room temperature, though it may be appropriately chosen depending on the starting material or the reaction solvent to be used. Further, the reaction is usually completed within 1 to 24 hours, but the reaction time maybe appropriately adjusted to make it longer or shorter.

The compound of the above formula (XVIII) can be prepared by reacting the compound of the above formula (X) with thionyl chloride and N,N-dimethylformamide. In this reaction, the reaction temperature is usually room temperature to the boiling point of the solvent to be used, preferably the boiling point, although it may be appropriately chosen depending on the starting material to be used. Further, the reaction is usually completed within 10 to 60 minutes, but the reaction time may be appropriately adjusted to make it longer or shorter.

The compound of the above formula (V) wherein X is NH can be prepared from the compound of the below formula (XIX):

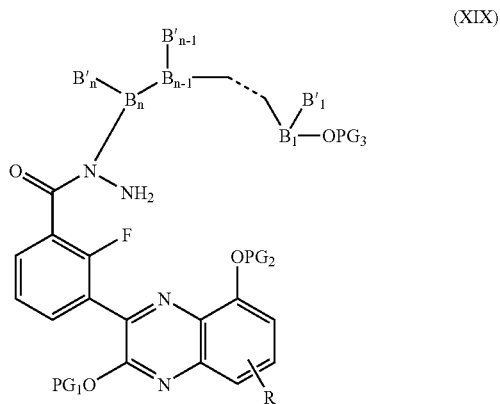

(XIX)

wherein n; $B_1, B_2, \ldots, B_{n-1}$ and $B_n$; $B'_1, B'_2, \ldots, B'_{n-1}$ and $B'_n$; R, <substituent group α>, <substituent group $β_1$>, <substituent group $β_2$>, <substituent group γ>, $PG_1$, $PG_2$ and $PG_3$ each have the same meaning as defined above, according to a method similar to the Preparation Method B-2b described in WO 02/02550.

The compound of the above formula (XIX) can be prepared from the compound of the above formula (XVII) and the compound of the above formula (XIII) according to a method similar to the Preparation Method B-2b described in WO 02/02550. Alternatively, the compound of the above formula (XIX) can also be prepared from the compound of the below formula (XX):

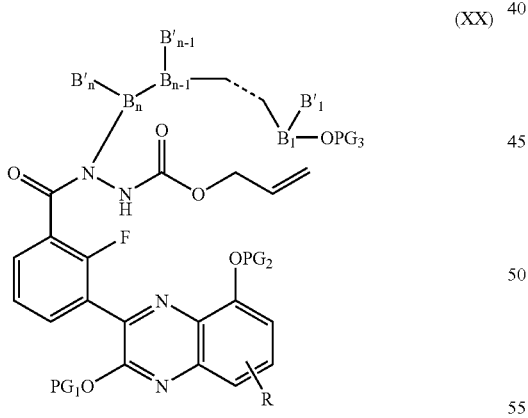

(XX)

wherein n; $B_1, B_2, \ldots B_n$ and $B_n$; $B'_1, B'_2, \ldots, B'_{n-1}$ and $B'_n$; R, <substituent group α>, <substituent group $β_1$>, <substituent group $β_2$>, <substituent group γ>, $PG_1$, $PG_2$ and $PG_3$ each have the same meaning as defined above, with a nucleophile such as diethylamine, formic acid or the like in a solvent such as tetrahydrofuran or the like in the presence of a palladium catalyst such as tetrakis(triphenylphosphine) palladium(0) or the like. In this reaction, the reaction temperature is usually 0° C. to room temperature, although it may be appropriately chosen depending on the starting materials and the reaction solvent to be used. Further, the reaction is usually completed within 1 to 24 hours, but the reaction time may be appropriately adjusted to make it longer or shorter.

The compound of the above formula (XX) can be prepared from the compound of the above formula (XVII) and the compound of the above formula (XIII) wherein $PG_4$ is allyloxycarbonyl, according to a method similar to the Preparation Method B-2b described in WO 02/02550.

Preparation Method B:

The compound of the above formula (II) or (III) wherein Y is an oxygen atom can be prepared by reacting the compound of the below formula (XXI) or (XXII):

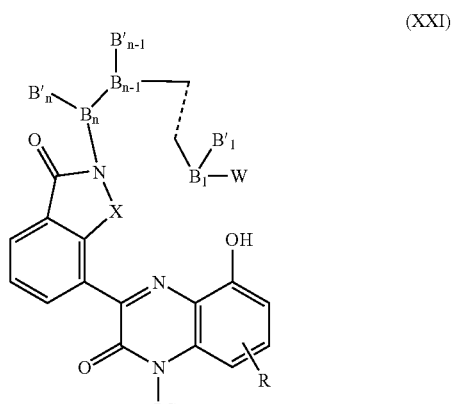

(XXI)

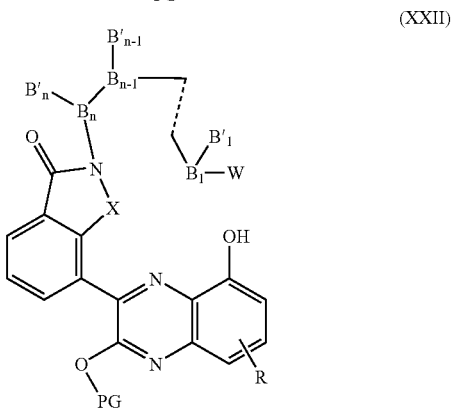

(XXII)

wherein X, n; $B_1, B_2, \ldots, B_{n-1}$ and $B_n$; $B'_1, B'_2, \ldots, B'_{n-1}$ and $B'_n$; R, <substituent group α>, <substituent group $β_1$>, <substituent group $β_2$>, <substituent group γ> and PG each have the same meaning as defined above; and W is a leaving group such as a iodine atom, a bromine atom, a methanesulfonyloxy group or the like, with a base such as potassium carbonate or the like in an aprotic polar solvent such as N,N-dimethylformamide or the like. In this reaction, the reaction temperature is usually room temperature to 100° C., preferably 60° C. to 80° C., although it may be appropriately chosen depending on the starting material and the reaction solvent to be used. Further, the reaction is usually completed within 1 to 24 hours, but the reaction time may be appropriately adjusted to make it longer or shorter.

The compound of the above formula (XXI) or (XXII) can be prepared according to a method similar to the Preparation Method A as mentioned above.

Preparation Method C:

The compound of the above formula (II) or (III) wherein X is NH and Y is a nitrogen atom can be prepared by reacting the compound of the below formula (XXIII) or (XXIV) with the compound of the below formula (XXV):

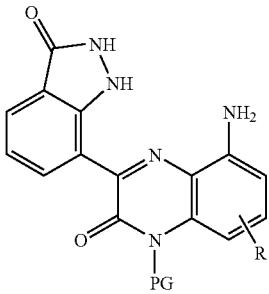
(XXIII)

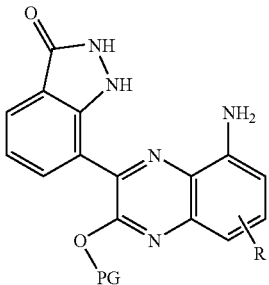
(XXIV)

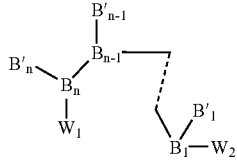
(XXV)

wherein X, n; $B_1, B_2, \ldots, B_{n-1}$ and $B_n$; $B'_1, B'_2, \ldots, B'_{n-1}$ and $B'_n$; R, <substituent group α>, <substituent group $β_1$>, <substituent group $β_2$>, <substituent group γ> and PG each have the same meaning as defined above; and $W_1$ and $W_2$ are each independently a leaving group such as a iodine atom, a bromine atom, a methanesulfonyloxy group or the like, in an aprotic polar solvent such as N,N-dimethylformamide or the like. In this reaction, the reaction temperature is usually room temperature to the boiling point of the solvent used, preferably 60° C. to 80° C., although it may be appropriately chosen depending on the starting materials and the reaction solvent to be used. Further, the reaction is usually completed within 10 to 60 minutes, but the reaction time may be appropriately adjusted to make it longer or shorter.

The compound of the above formula (XXIII) or (XXIV) can be prepared according to a method similar to the above Preparation Method A and the methods described in WO 02/02550.

The introduction or conversion of R may be carried out at any one of steps in the preparation of the above synthetic intermediates. Hereinafter, such introduction or conversion of R in the compound of the above formula (II) or (III) is described.

The compound of the above formula (II) or (III) wherein R is methyl can be prepared from the corresponding compound of the above formula (II) or (III) wherein R is hydroxymethyl. That is, the compound of the above formula (II) or (III) wherein R is methyl can be prepared by converting said hydroxymethyl group into methanesulfonyloxymethyl group, chloromethyl group or the like, followed by catalytic hydrogenation using a transition metal catalyst.

Also, the compound of the above formula (II) or (III) wherein R is methanesulfonyloxymethyl is reacted in a solvent such as tetrahydrofuran, methanol, 1,4-dioxane or the like, or a mixed solvent thereof in the presence of a transition metal catalyst such as 10% palladium-carbon catalyst or the like under a hydrogen atmosphere, thereby to produce the compound of the above formula (II) or (III) wherein R is methyl. In this reaction, the reaction temperature is usually 0° C. to the boiling point of the solvent used, although it may be appropriately chosen depending on the starting material and the solvent to be used in the reaction. Further, the reaction is usually completed within 1 to 24 hours, but the reaction time may be appropriately adjusted to make it longer or shorter.

Also, the compound of the above formula (II) or (III) wherein R is vinyl can be prepared from the corresponding compound of the above formula (II) or (III) wherein R is a bromine atom. For example, the compound of the above formula (II) or (III) wherein R is a bromine atom is reacted with tributylvinyltin in a solvent such as toluene, 1,4-dioxane, N,N-dimethylformamide or the like, preferably toluene, in the presence of a palladium catalyst such as tetrakis(triphenylphosphine)palladium(0) or the like, thereby to produce the compound of the above formula (II) or (III) wherein R is vinyl. In this reaction, the reaction temperature is usually room temperature to the boiling point of the solvent used, preferably 80° C. to 100° C., although it may be appropriately chosen depending on the starting material and the reaction solvent to be used. Further, the reaction is usually completed within 1 to 24 hours, but the reaction time may be appropriately adjusted to make it longer or shorter.

The compound of the above formula (II) or (III) wherein R is N-alkyl-lower alkanoylamino can be prepared from the corresponding compound of the above formula (II) or (III) wherein R is a bromine atom. For example, the compound of the above formula (II) or (III) wherein R is a bromine atom is reacted with an amide such as 2-pyrrolidinone or the like, in a solvent such as toluene, 1,4-dioxane, N,N-dimethylformamide or the like, preferably 1,4-dioxane, in the presence of a phosphine such as 4,5-bis(diphenylphosphino)-9,9-dimethylxanthene or the like, a palladium catalyst such as tris(benzylideneacetone)dipalladium(0)-chloroform adduct or the like, and a base such as cesium carbonate or the like, thereby to produce the compound of the above formula (II) or (III) wherein R is N-alkyl-lower alkanoylamino. In this reaction, the reaction temperature is usually room temperature to the boiling point of the solvent used, preferably 60° C. to 120° C., though it may be appropriately chosen depending on the starting material and the reaction solvent to be used. Further, the reaction is usually completed within 1 to 24 hours, but the reaction time may be appropriately adjusted to make it longer or shorter.

The compound of the above formula (II) or (III) wherein R is (dialkyl)aminomethyl or (monoalkyl)aminomethyl can be prepared from the compound of the above formula (II) or (III) wherein R is hydroxymethyl. That is, the hydroxymethyl of the compound of the above formula (II) or (III) wherein R is (dialkyl)aminomethyl or (monoalkyl)aminomethyl is converted into the methanesulfonyloxymethyl thereof, the chloromethyl thereof or the like, followed by alkylation of the resulting product with dialkylamine or (monoalkyl)amine, or alkylation of the resulting product with dialkylamine in the presence of an acid catalyst.

According to the former method, the compound of the above formula (II) or (III) wherein R is methanesulfonyloxymethyl can be prepared by reacting the compound of the above formula (II) or (III) wherein R is hydroxymethyl, with methanesulfonyl chloride in a solvent such as chloroform, methylene chloride, tetrahydrofuran, N,N-dimethylformamide, diethyl ether, ethyl acetate or the like, in the presence of an organic base such as triethylamine, diisopropylethylamine or the like. In this reaction, the reaction temperature is usually 0° C. to room temperature, although it may be appropriately chosen depending on the starting material to be used, and the reaction is usually completed within 1 to 2 hours, but the reaction time may be appropriately adjusted to make it longer or shorter. Further, the compound of the above formula (II) or (III) wherein R is methanesulfonyloxymethyl is reacted with a dialkylamine such as piperidine, morpholine, N-methylpiperazine, diethylamine or the like, or (monoalkyl)amine such as cyclopentylamine, t-butylamine or the like in a solvent such as chloroform, methylene chloride, tetrahydrofuran, N,N-dimethylformamide or the like in the presence of an inorganc base such as potassium carbonate or the like, thereby to produce the compound of the above formula (II) or (III) wherein R is (dialkyl) aminomethyl or (monoalkyl)aminomethyl. In this reaction, the reaction temperature is usually 0° C. to the boiling point of the reaction solvent used, although it may be appropriately chosen depending on the starting material and the reaction solvent to be used, and the reaction is usually completed within 1 to 24 hours, but the reaction time may be appropriately adjusted to make it longer or shorter. According to the latter method, the compound of the above formula (II) or (III) wherein R is hydroxymethyl is reacted with a dialkylamine such as piperidine, morpholine, N-methylpiperazine, diethylamine or the like in a solvent such as chloroform, methylene chloride, tetrahydrofuran, N,N-dimethylformamide, diethyl ether, ethyl acetate, toluene or the like in the presence of an acid catalyst such as acetic acid, hydrochloric acid, sulfuric acid, 4-toluenesulfonic acid or the like, thereby to produce the compound of the above formula (II) or (III) wherein R is (dialkyl)aminomethyl. In this reaction, the reaction temperature is usually room temperature to the boiling point of the solvent used for the reaction, although it may be appropriately chosen depending on the starting material and the reaction solvent to be used, and the reaction is usually completed within 1 to 3 days, but the reaction time may be appropriately adjusted to make it longer or shorter.

Further, the compound of the above formula (II) or (III) wherein R is 2-[(dialkyl) amino] ethyl can be prepared by addition reaction of the dialkylamino to the corresponding compound of the above formula (II) or (III) wherein R is vinyl, and the production is mentioned above. For example, the compound of the above formula (II) or (III) wherein R is vinyl is reacted in a sealed tube using a dialkylamine such as pyrrolidine or the like as a solvent usually at 100° C. to 150° C., preferably 120° C., although the reaction temperature may be appropriately chosen depending on the starting material and the reaction solvent to be used, thereby to produce the compound of the above formula (II) or (III) wherein R is 2-[(dialkyl)amino]ethyl. The reaction is completed within 1 to 24 hours, but the reaction time may be appropriately adjusted to make it longer or shorter.

Also, the compound of the above formula (II) or (III) wherein R is alkoxycarbonyl can be prepared from the corresponding compound of the above formula (II) or (III) wherein R is a bromine atom. For example, the compound of the above formula (II) or (III) wherein R is a bromine atom is reacted with carbon monooxide in a solvent including a mixture of a solvent such as N,N-dimethylacetamide, N-methylpyrrolidone, N,N-dimethylacetamide or the like, and an alcohol such as methanol, ethanol or the like, in the presence of a ligand such as 1,1'-bis(diphenylphosphino) ferrocene or the like, a palladium catalyst such as palladium (II) acetate or the like, and a base such as sodium hydrogencarbonate or the like, thereby to produce the compound of the above formula (II) or (III) wherein R is an alkoxycarbonyl group. In this reaction, the reaction temperature is usually 50° C. to the boiling point of the solvent used in the reaction, though it may be appropriately chosen depending on the starting material and the reaction solvent to be used, and the reaction is usually completed within 1 to 24 hours, but the reaction time may be appropriately adjusted to make it longer or shorter.

The compound of the above formula (II) or (III) wherein R is amino can be prepared from the compound of the above formula (II) or (III) wherein R is a bromine atom. For example, the compound of the above formula (II) or (III) wherein R is a bromine atom is reacted with a dialkylamine such as N-methylpiperazine, piperidine, morpholine or the like in a solvent such as toluene, 1,4-dioxane, N,N-dimethylformamide or the like, preferably toluene, in the presence of a palladium catalyst such as tris(benzylideneacetone) dipalladium-chloroform adduct or the like, a phosphine such as (R)-(+)-2,2'-bis(di-4-tolylphosphino)-1,1'-binaphthyl or the like and a base such as sodium t-butoxide or the like, thereby to propduce the compound of the above formula (II) or (III) wherein R is a dialkylamino group. In this reaction, the reaction temperature is usually room temperature to the boiling point of the solvent used in the reaction, preferably 60° C. to 120° C., though it may be appropriately chosen depending on the starting material and the reaction solvent to be used, and the reaction is usually completed within 1 to 24 hours, but the reaction time may be appropriately adjusted to make it longer or shorter.

The compound of the above formula (II) or (III) wherein R is hydroxycarbonyl can be prepared by reacting the corresponding compound of the above formula (II) or (III) wherein R is alkoxycarbonyl, with an aqueous solution of sodium hydroxide, potassium hydroxide, lithium hydroxide or the like in a solvent such as tetrahydrofuran, 1,4-dioxane, methanol, ethanol or the like. In this reaction, the reaction temperature is usually 0° C. to the boiling point of the solvent used in the reaction, preferably room temperature, though it may be appropriately chosen depending on the starting material and the reaction solvent to be used, and the reaction is usually completed within 1 to 24 hours, but the reaction time may be appropriately adjusted to make it longer or shorter.

Further, the compound of the above formula (II) or (III) wherein R is hydroxymethyl can be prepared by reducing the corresponding compound of the above formula (II) or (III) wherein R is hydroxycarbonyl. For example, the compound of the above formula (II) or (III) wherein R is hydroxycarbonyl is reacted with a condensing agent such as benzotriazol-1-yloxytripyrrolidinophosphonium hexafluorophosphate or the like in a solvent such as tetrahydrofuran or the like in the presence of an organic base such as N,N-diisopropylethylamine or the like at 0° C. to room temperature for 5 minutes to 1 hour, followed by reaction with a reducing agent such as lithium tetrahydroborate or the like, thereby to produce the compound of the above formula (II) or (III) wherein R is hydroxymethyl. In this reaction, the reaction temperature is usually 0° C. to room temperature, though it may be appropriately chosen depending on the starting material and the reaction solvent to be used, and the reaction is usually completed within 10 minutes to 24 hours, but the reaction time may be appropriately adjusted to make it longer or shorter.

In addition, the compound of the above formula (II) or (III) wherein R is alkoxymethyl can be prepared by alkylation of the corresponding compound of the above formula (II) or (III) wherein R is hydroxymethyl. For example, the compound of the above formula (II) or (III) wherein R is hydroxymethyl is reacted with an alkylating agent such as methyl iodide, dimethyl sulfate or the like in a solvent such as N,N-dimethylformamide, 1,4-dioxane, tetrahydrofuran or the like in the presence of an inorganic base such as sodium hydride, potassium, t-butoxide or the like, thereby to produce the compound of the above formula (II) or (III) wherein R is alkoxymethyl. In this reaction, the reaction temperature is usually 0° C. to the boiling point of the solvent used in the reaction, preferably room temperature, though it may be appropriately chosen depending on the starting material and the reaction solvent to be used, and the reaction is usually completed within 1 to 24 hours, but the reaction time may be appropriately adjusted to make it longer or shorter.

The compound of the above formula (II) or (III) wherein R is an aromatic cyclic group or an aromatic heterocyclic group attached via the carbon atom to the quinoxalinone core structure can be prepared from the corresponding compound of the above formula (II) or (III) wherein R is a bromine atom. For example, the compound of the above formula (II) or (III) wherein R is a bromine atom is reacted with a boronic acid such as pyrimidine-5-boronic acid or the like in a solvent such as 1,2-dimethoxyethane-water, toluene-water, 1,4-dioxane-water, N,N-dimethylamide or the like in the presence of a palladium catalyst such as tetrakis(triphenylphosphine)palladium or the like, and a base such as potassium carbonate or the like, thereby to produce the compound of the above formula (II) or (III) wherein R is an aromatic cyclic group or an aromatic heterocyclic groups attached via the carbon atom to the quinoxalinone core structure. In this reaction, the reaction temperature is usually room temperature to the boiling point of the solvent used in the reaction, preferably 60° C. to 120° C., though it maybe appropriately chosen depending on the starting material and the reaction solvent to be used, and the reaction is usually completed within 1 to 24 hours, but the reaction time may be appropriately adjusted to make it longer or shorter.

The compound of the above formula (II) or (III) wherein R is an aromatic heterocyclic group attached via the nitrogen atom to the quinoxalinone core structure can be prepared from the corresponding compound of the above formula (II) or (III) wherein R is a bromine atom. For example, the compound of the above formula (II) or (III) wherein R is a bromine atom is reacted with an aromatic heterocyclic compound such as indole or the like in a solvent such as toluene, 1,4-dioxane, N,N-dimethylformamide or the like, preferably 1,4-dioxane, in the presence of a phosphine such as 4,5-bis(diphenylphosphino)-9,9-dimethylxanthene or the like, a palladium catalyst such as tris(benzylideneacetone)dipalladium(0)-chloroform adduct or the like and a base such as cesium carbonate or the like, thereby to produce the compound of the above formula (II) or (III) wherein R is an aromatic heterocyclic group attached via the nitrogen atom to the quinoxalinone core structure. In this reaction, the reaction temperature is usually room temperature to the boiling point of the solvent used in the reaction, preferably 60° C. to 120° C., though it may be appropriately chosen depending on the starting material and the reaction solvent to be used, and the reaction is usually completed within 1 to 24 hours, but the reaction time may be appropriately adjusted to make it longer or shorter.

Further, the compounds having other groups represented by R, such as lower alkyl such as ethyl or the like; lower alkyl substituted by aliphatic heterocyclic group; and aliphatic heterocyclic group bonded via the nitrogen atom to the quinoxaline core structure, may be prepared according to the aforementioned methods.

The starting materials, reagents, (2-fluoro-3-iodophenyl)oxoacetic acid ester, and the compounds of the above formulae (VIII), (XII), (XIII), (XIV) and (XXV) used in the preparation of the compounds of the formula (I) are all known, or they can be prepared by the per se known method utilizing the known compounds.

Hereinafter, (2-fluoro-3-iodophenyl)oxoacetic acid ester, and the compounds of the above formulae (VIII), (XII), (XIII), (XIV) and (XXV) are described.

The (2-fluoro-3-iodophenyl)oxoacetic acid ester can be prepared by reacting a commercially available 2-fluoro-1-iodobenzene with a strong base such as lithium diisopropylamide, or the like in an ether solvent such as tetrahydrofuran or the like at a low temperature and then reacting the resultant lithio compound with a chlorooxoacetate derivative or an oxalic acid diester.

The compound of the above formula (VIII) can be prepared from the diol compound of the following formula (XXVI):

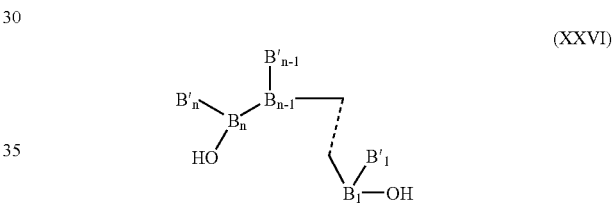

(XXVI)

wherein n; $B_1, B_2, \ldots, B_{n-1}$ and $B_n$; $B'_1, B'_2, \ldots, B'_{n-1}$ and $B'_n$; <substituent group α>, <substituent group $β_1$>, <substituent group $β_2$> and <substituent group γ> each have the same meaning as defined above, and the diol compound is commercially available or can be prepared from the known compounds such as corresponding diesters, dicarboxylic acids or the like by the known method such as reduction with lithium aluminum hydride. That is, the compound of the above formula (VIII) can be prepared by introducing a protecting group into one of the hydroxy groups in the diol compound of the above formula (XXVI) to convert into the compound of the formula (XXVII):

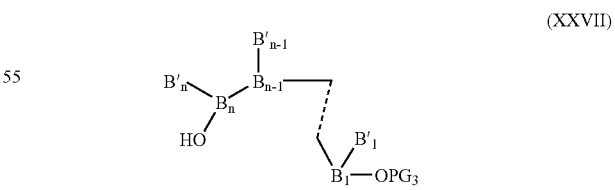

(XXVII)

wherein n; $B_1, B_2, \ldots, B_{n-1}$ and $B_n$; $B'_1, B'_2, \ldots, B'_{n-1}$ and $B'_n$; <substituent group α>, <substituent group $β_1$>, <substituent group $β_2$>, <substituent group γ> and $PG_3$ each have the same meaning as defined above, and then reacting the other hydroxy group with methanesulfonyl chloride or the like in the presence of a base such as triethylamine or the like.

The aminoalcohol derivative of the above formula (XII) is commercially available, or can be prepared by introducing a protecting group into the hydroxy group of the commercially available aminoalcohol. Alternatively, the aminoalcohol derivative of the above formula (XII) can be prepared by substituting the leaving group W of the compound of the above formula (VIII) with an azido group using sodium azide or the like in a polar solvent such as dimethylformamide or the like and then subjecting the resulting product to catalytic hydrogenation using a palladium catalyst, thereby to reduce the azide group into the amino group.

The hydrazine derivative of the above formula (XIII) can be prepared by oxidizing a commercially available aldehyde or ketone or the hydroxy group of the compound of the above formula (XXVII) with a sulfur trioxide-pyridine complex and then obtaining the objective compound from the resultant aldehyde or ketone. That is, the carbonyl group of these compounds is converted into the hydrazide group, and then the resultant compound is reacted with a reducing agent such as sodium tetrahydroborate, sodium cyanotrihydroborate, sodium triacetoxyhydroborate or the like in the presence of an acid such as acetic acid, trifluoroacetic acid, hydrochloric acid, 4-toluenesulfonic acid, zinc chloride or the like, thereby to give the compound of the above formula (XIII).

The hydroxylamine derivatives of the above formula (XIV) can be prepared by introducing a protecting group into the two hydroxy groups of a hydroxylamine obtained by the reduction of a commercially available oxime according to a method similar to the aforementioned method.

The dihalogenated alkyl derivative or disulfonic acid ester derivative of the above formula (XXV) is commercially available, or can be prepared by converting the two hydroxy groups of the compound of the above formula (XXVI) into the disulfonic acid ester with methanesulfonyl chloride or the like. Further, the disulfonic acid ester is reacted with sodium iodide in a polar solvent such as dimethylformamide or the like to produce the corresponding dihalogenated alkyl derivative.

With respect to the novel quinoxalinone compounds prepared by the above methods, Cdk inhibitory activity (cyclin D2-Cdk4 inhibitory activity and cyclin D2-Cdk6 inhibitory activity are described as examples) and inhibitory activity of 5-bromo-2'-deoxyuridine:BrdU) uptake are shown below.

Cdk4 Inhibitory Activities (1) Purification of Cyclin D2-Cdk4 cDNAs of Cdk4 and its activating factor cyclin D2 were each introduced into a baculovirus expression vector to obtain a recombinant baculovirus; it was then co-infected to an insect cell Sf9 to highly express active cyclin D2/Cdk4 complexes. The cells were recovered, solubilized and the enzymes were purified by HPLC column chromatography (The Embo Journal, vol. 15, 7060-7069 (1996)).

(2) Determination of Cyclin D2-Cdk4 Activity

In the determination of cyclin D2-Cdk4 activity, a synthetic peptide Arg-Pro-Pro-Thr-Leu-Ser-Pro-Ile-Pro-His-Ile-Pro-Arg corresponding to the amino acid number 775-787 of RB protein was used as a substrate [The EMBO Journal, vol. 15, 7060-7069 (1996)].

The reaction was carried out according to a method partially modifying Kitagawa et al. (Oncogene, vol. 7, 1067-1074 (1992)). Purified cyclin D2-Cdk4, 100 µM substrate peptide, 50 µM non-labeled adenosine triphosphate (ATP) and 1 µCi [γ-33P]-labeled ATP (2000-4000 Ci/mmole) were added to a reaction buffer (referred to as R buffer) consisting of 20 mM Tris-HCl buffer (pH 7.4), 10 mM magnesium chloride, 4.5 mM 2-mercaptoethanol and 1 mM ethylene glycol bis(β-aminoethyl ether)-N,N,N',N'-tetraacetic acid (EGTA) to make a total volume of 21.1 µl. The mixture was incubated at 30° C. for 45 minutes. After that, 350 mM phosphate buffer (10 µl) was added to the reaction solution to stop the reaction. The peptide substrate was adsorbed on a P81 paper filter in a 96-well plate, and the plate was washed several times with 75 mM phosphate buffer, and then its radioactivity was measured by a liquid scintillation counter. The [γ-33P]-labeled ATP was purchased from Daiichi Pure Chemicals.

Addition of test compounds to the reaction system was carried out in such a manner that the compounds were dissolved in dimethyl sulfoxide to prepare a series of diluted solutions, and then each aliquot (1.1 µl) was added to the reaction system. A control group was prepared by addition of only dimethyl sulfoxide (1.1 µl) to the reaction system.

The compounds in the following Working Examples were chosen as typical compounds of the present invention, and $IC_{50}$ values against cyclin D2-Cdk4 activity of those compounds were determined. The results are shown in the table below.

TABLE 1

| Compound of Working Example (shown by the number only) | $IC_{50}$ (nM) |
|---|---|
| [1] | 3.6 |
| [4] | 2.5 |
| [5] | 4.3 |
| [6] | 2.9 |
| [7] | 3.5 |
| [8] | 6.1 |
| [9] | 11 |
| [10] | 6.3 |
| [11] | 12 |
| [12] | 11 |
| [14] | 2.2 |
| [20] | 1.6 |
| [23] | 2.1 |
| [25] | 8.2 |
| [28] | 16 |
| [31] | 6.4 |
| [32] | 9 |
| [34] | 12 |
| [35] | 12 |
| [36] | 34 |
| [37] | 17 |
| [38] | 12 |
| [39] | 6.9 |
| [45] | 14 |
| [46] | 3.1 |
| [48] | 3.6 |
| [51] | 6.1 |
| [54] | 8.5 |
| [55] | 7.9 |
| [56] | 9.2 |
| [65] | 6.9 |
| [71] | 13 |
| [80] | 1.7 |
| [83] | 2 |
| [84] | 6.2 |
| [85] | 6.7 |
| [86] | 2.7 |
| [87] | 2.6 |
| [89] | 2.7 |
| [90] | 3.7 |
| [91] | 3.2 |
| [92] | 2.8 |
| [94] | 3.6 |
| [95] | 4.1 |
| [99] | 5.2 |
| [100] | 2.4 |
| [102] | 1.4 |

TABLE 1-continued

| Compound of Working Example (shown by the number only) | IC$_{50}$ (nM) |
|---|---|
| [104] | 1.6 |
| [107] | 7.7 |
| [111] | 5.5 |
| [118] | 14 |
| [122] | 2.5 |
| [123] | 9.6 |
| [124] | 8.2 |
| [125] | 15 |
| [126] | 9.4 |
| [127] | 11 |
| [128] | 3.5 |
| [129] | 4.9 |
| [130] | 6.5 |
| [131] | 8.2 |
| [134] | 6.4 |
| [135] | 2.5 |
| [136] | 3.2 |
| [137] | 3.4 |
| [138] | 4.2 |
| [139] | 3 |
| [140] | 3 |
| [141] | 26 |
| [142] | 15 |
| [143] | 2.2 |
| [144] | 2.9 |
| [145] | 2.7 |
| [146] | 5.2 |

These results clearly show that the compounds of the present invention exhibit strong inhibitory activities against cyclin D2-Cdk4.

Cdk6 Inhibitory Activities (1) Purification of Cyclin D2-Cdk6

In the same manner as with cyclin D2-Cdk4, cDNAs of Cdk6 and its activating factor cyclin D2 were each introduced into a baculovirus expression vector to obtain a recombinant vaculovirus; it was then co-infected to an insect cell Sf9 to highly express active cyclin D2/Cdk6 complexes. The cells were recovered, solubilized and the enzymes were purified by a HPLC column chromatography.

(2) Determination of Cyclin D2-Cdk6 Activity

In the determination of cyclin D2-Cdk6 activity, a synthetic peptide Arg-Pro-Pro-Thr-Leu-Ser-Pro-Ile-Pro-His-Ile-Pro-Arg was used.

The reaction was carried out according to a method partially modifying Kitagawa et al. (Oncogene, vol. 7, 1067-1074 (1992)). Purified cyclin D2-Cdk6, 100 µM substrate peptide, 50 µM non-labeled ATP and 1.5 µCi [γ-33P]-labeledATP (2000-4000 Ci/mmole) were added to R buffer to make a total volume of 21.1 µl. The mixture was reacted at 30° C. for 40 minutes, and then 350 mM phosphate buffer (10 µl) was added to the reaction solution to stop the reaction. The peptide substrate was adsorbed on a P81 paper in a 96-well plate, and the plate was washed with 75 mM phosphate buffer, and then its radioactivity was measured by a liquid scintillation counter.

Addition of test compounds to the reaction system was carried out in such a manner that the compounds were dissolved in DMSO to prepare a series of diluted solutions, and then each aliquot (1.1 µl) was added to the reaction system. A control group was prepared by addition of only dimethyl sulfoxide (1.1 µl) to the reaction system.

The compounds of [11], [51] and [134] were chosen as typical compounds of the present invention, and IC$_{50}$ values against cyclin D2-Cdk6 activity of those compounds were determined. The results are shown in the table below.

TABLE 2

| Compound of Working Example (shown by the number only) | IC$_{50}$ (nM) |
|---|---|
| [11] | 24 |
| [51] | 25 |
| [134] | 12 |

These results clearly show that the compounds of the present invention exhibit strong inhibitory activities against cyclin D2-Cdk6.

As mentioned above, since the compounds of the present invention have strong Cdk inhibitory activities, they are useful as a Cdk inhibitory agent. Further, the Cdk inhibitory agent may contain a pharmaceutically acceptable carrier or diluent.

Inhibitory Activities of 5-bromo-2'-deoxyuridinee (BrdU) Uptake

Growing cells perform DNA duplication in the S phase of the cell cycle, and divide into daughter cells in the M phase via the G2 phase. As an index for the cell growth, there is a method to determine the amount of BrdU taken into newly synthesized DNAs in the DNA duplicating cells ((J. Immunol Methods, vol. 82, p. 169-179 (1985); J. Immunolog. Methods, vol. 106, p. 95-100 (1988); Cytometry, vol. 14, p. 640-648 (1993)). Inhibitory activities of BrdU uptake was determined in order to investigate the effect of the compounds of the present invention against cancer cells.

(1) Method for Cell Culture

HCT116 cells derived from human colon cancer were cultured in Dulbecco's modified Eagle's medium containing 10% fetal bovine serum at 37° C. in the presence of 5% carbon dioxide under an atmosphere of saturated steam.

(2) Determination of Inhibitory Activities of BrdU Uptake

Cell culture medium (100 µl each) containing $2.5 \times 10^3$ of HCT116 cells was dispensed into each well of a 96-well cell culture dish, and then the cells were pre-cultured overnight. On the next day, a series of diluted solutions was prepared with DMSO from a DMSO solution containing the compounds of the present invention. Then, a series of diluted solutions, or DMSO only as a control without addition of the compound, was added in an amount of 1% to the cell culture medium. Finally, 100 µl of culture medium containing the above diluted solution containing the compounds or DMSO only were each added to the cells which had been pre-cultured in the 96-well dish, and then the cells were cultured for 12 hours.

Quantitative determination of BrdU uptake was performed using the Cell Proliferation ELISA, BrdU (chemiluminescence)(Roche Diagnostics). Each 20 µL of 10× concentrated BrdU labeling reagent was added to the cells which had been cultured together with the compound for 12 hours, which were subjected to pulse labeling at 37° C. for 1 hour, and then the culture solution was removed. Then, after addition of a FixDenat solution to the cells, the cells were incubated at room temperature for 30 minutes for fixation of cells and denaturation of DNA. After removal of the FixDenat solution, anti-BrdU antibody labeled with peroxidase was added to the cells, and then the cells were incubated at room temperature for 90 minutes. The cells were washed four times with a washing solution, and a substrate was added thereto. The cells were incubated at room temperature for 10 minutes and chemical luminescence was determined with a luminometer.

As typical compounds of the present invention, the compounds [11], [12], [39], [51], [71], [83], [85], [134] and [141] were chosen, and IC50 values of these compounds on BrdU uptake were determined. The results are shown in table 3.

TABLE 3

| Compounds of Working Examples (hereinafter shown by the number only) | $IC_{50}$ (nM) |
|---|---|
| [11] | 16 |
| [12] | 9.7 |
| [39] | 9.4 |
| [51] | 23 |
| [71] | 75 |
| [83] | 30 |
| [85] | 20 |
| [134] | 7.8 |
| [141] | 20 |

The compounds of the present invention are useful as anti-cancer agents (cancer remedies) for treatment of cancers, because they strongly inhibit BrdU uptake and thus apparently have cell growth-inhibitory activity. That is, a pharmaceutical composition containing a novel quinoxalinone derivative or a pharmaceutically acceptable salt or ester thereof according to the present invention, or an anti-cancer agent containing a novel quinoxalinone derivative or a pharmaceutically acceptable salt or ester thereof according to the present invention are effective for the treatment of cancer patients. Also, said pharmaceutical composition and anti-cancer agent may contain a pharmaceutically acceptable carrier or diluent. In the above description, "pharmaceutically acceptable carrier or diluent" means excipients (e.g. fat, bees wax, semi-solid or liquid polyol, natural or hydrogenated (hardened) oil); water (e.g. distilled water, especially distilled water for injection); physiological saline, alcohols (e.g. ethanol), glycerol, polyol, aqueous glucose, mannitol, vegetable oil or the like; and additives (e.g. fillers, disintegrating agents, binders, lubricants, wetting agents, stabilizers, emulsifiers, dispersing agents, preservatives, sweeteners, pigments, condiments or perfumes, thickening agents, diluting agents, buffers, solvents or solubilizers, agents for attaining storage effect, salts for adjusting osmotic pressure, coating agents or anti-oxidants).

Suitable tumors against which the compounds of the present invention are expected to exhibit a therapeutic effect are, for example, human solid cancers. Examples of the human solid cancers are brain cancer, head and neck cancer, esophagus cancer, thyroid cancer, small cell cancer, non-small cell cancer, breast cancer, stomach cancer, gallbladder/bile duct cancer, hepatic cancer, pancreatic cancer, colon cancer, rectal cancer, ovarian cancer, chorioepithelioma, uterine cancer, cervical cancer, renal pelvic/ureteral cancer, bladder cancer, prostate cancer, penile cancer, testicular cancer, embryonal cancer, Wilms cancer, skin cancer, malignant melanoma, neuroblastoma, osteosarcoma, Ewing's sarcoma and soft tissue sarcoma.

The aforementioned "a pharmaceutically acceptable salt or ester" is described below.

When the compounds of the present invention are used as an anti-cancer agent, they may be used as a pharmaceutically acceptable salt thereof. Typical examples of such pharmaceutically acceptable salt are a salt with an alkali metal such as sodium, potassium or the like, hydrochloride, and trifluoroacetate.

A pharmaceutically, if desired, acceptable salt of the present invention may be prepared by combination of conventional methods employed in the field of synthetic organic chemistry. A specific example includes neutralization of a free-form solution of the compounds of the present invention with an alkali solution or an acidic solution.

The esters of the compounds of the present invention include, for example, methyl ester and ethyl ester. These esters can be prepared by esterification of a free carboxyl group of the compounds according to a conventional method.

The dosage form of the compounds of the present invention can be chosen from a variety of forms, and include, for example, oral formulations such as tablets, capsules, powders, granules, solution or the like, and sterilized liquid parenteral formulations such as solutions, suspensions or the like.

Here, the solid pharmaceutical preparations may be manufactured as tablets, capsules, granules or powders, with or without a suitable additive according to a conventional method. Such additive includes, for example, sugars such as lactose and glucose; starches such as corn starch, wheat., and rice; fatty acids such as stearic acid; inorganic salts such as sodium metasilicate, magnesium aluminate, and anhydrous calcium phosphate; synthetic polymers such as polyvinylpyrrolidone, and polyalkylene glycol; fatty acid salts such as calcium stearate, and magnesium stearate; alcohols such as stearyl alcohol, and benzyl alcohol; synthetic cellulose derivatives such as methylcellulose, carboxymethyl cellulose, ethyl cellulose, and hydroxypropylmethyl cellulose; and other additives commonly used such as water, gelatin, talc, vegetable oil, gum arabic or the like.

These solid preparations such as tablets, capsules, granules or powders may generally contain 0.1 to 100%, preferably 5 to 100%, more preferably 5 to 85%, particularly preferably 5 to 30%, by weight, of an active ingredient.

The liquid preparations such as suspensions, syrups or injections can be prepared by using a suitable additive (e.g. water, alcohols, or plant-derived oils such as soy bean oil, peanut oil or sesame oil) commonly used for the preparation of liquid preparations.

Especially, examples of suitable solutions or diluents for parenteral administration such as intramuscular, intravenous, or subcutaneous injection are distilled water for injection, aqueous solution of lidocaine hydrochloride (for intramuscular injection), physiological saline, aqueous glucose solution, ethanol, intravenous injection solutions (e.g. aqueous solutions of citric acid or sodium citrate), electrolytic solutions (e.g. intravenous drip infusion, intravenous injection) and a mixed solution thereof.

Further, these injection preparations can be in a previously-dissolved form as well as a powder itself with or without additives which are to be dissolved when used. These injection solutions usually may contain 0.1 to 10%, preferably 1 to 5%, by weight, of an active ingredient.

The preferred practical dosage of the compounds of the present invention may be properly determined depending on the kind of compounds to be used, the kind of compositions to be combined, administration frequency, a specific part of human body to be treated, and the conditions of patients. For example, a daily dose per adult is: in the case of oral administration, 10 to 500 mg, preferably 10 to 200 mg; in the case of parenteral administration, preferably intravenous injection, 10 to 100 mg, preferably 10 to 30 mg. Although administration frequency varies depending on the administration route and the diseases of patients, it can be administered in single or two to five divisions, preferably two to three divisions.

EXAMPLES

The present invention will be described in more detail in conjunction with Working Examples hereinafter, but it is to be construed that the present invention is not limited thereto.

For example, when a racemate is described in Working Examples, chiral compounds thereof should be included in the present invention. Also, preparation methods of the compounds represented by the formulae [A-1] to [A-34] are described in Reference Examples 1 to 34.

Thin-layer chromatography in Working Examples and Reference Examples was carried out using silica gel $_{60}F_{254}$ (Merck) as a plate and a UV detector as a detection method. Wakogel™C-300 or C-200 (Wako Pure Chemical Industries, Ltd.) or NH (Fuji Silysia Chemical) was used as silica gel for the column chromatography. Mass spectrum was measured by use of JMS-SX102A (JEOL Ltd.) or QUATTROII (Micromass Ltd.). Determination of NMR spectrum by use of deutero dimethyl sulfoxide was carried out with Gemini-200 spectrometer (200 MHz; Varian Inc.), Gemini-300 spectrometer (300 MHz; Varian Inc.) or VXR-300 spectrometer (300 MHz; Varian Inc.), respectively using dimethyl sulfoxide as an internal standard. All δ values were expressed in terms of ppm.

The abbreviations used in the determination of NMR spectrum are as follows:

s: singlet
d: doublet
dd: double doublet
t: triplet
dt: double triplet
q: quartet
m: multiplet
br: broad
J: coupling constant
Hz: herz
DMSO-$d_6$: deutero dimethyl sulfoxide The abbreviations used in Working Examples and Reference Examples are as follows:

TBS: t-butyldimethylsilyl
Ms: methanesulfonyl
Bz: benzoyl
TBDPS: t-butyldiphenylsilyl
Alloc: allyloxycarbonyl
Ac: acetyl
DMTrt: 4,4'-dimethoxytrityl
Boc: t-butoxycarbonyl
SEM: 2-(trimethylsilyl)ethoxymethyl
Bn: benzyl
MOM: methoxymethyl
Me: methyl
Et: ethyl Working Example 1

Synthesis of the Compound of the Following Formula [1]:

The methyl ester derivative (9.90 g, 17.2 mmol) of the following formula:

prepared by referring to the procedure of Working Example 110-2) described in WO 02/02550, and benzyl mercaptan (2.63 mL, 22.4 mmol) were dissolved in tetrahydrofuran (100 mL), and to this solution 1M tetrahydrofuran solution (22.4 mL) in which lithium hexamethyldisilazide was dissolved at room temperature, was gradually added. The reaction solution was stirred at the same temperature for 30 minutes, and then 1N aqueous sodium hydroxide (100 mL) and methanol (100 mL) were added thereto; the reaction solution was stirred at 60° C. for 150 minutes. After the reaction solution was cooled down to 0° C., it was neutralized using 1N hydrochloric acid. Saturated aqueous ammonium chloride was added to the reaction solution and it was subjected to extraction with chloroform. The organic layer was dried over anhydrous magnesium sulfate, filtered, and concentrated. The resulting residue was purified by a column chromatography on silica gel to obtain the above carboxylic acid derivative (11.4 g) as a pale yellow solid.

Triethylamine (79 μL, 561 μmol) and 5-amino-1-pentanol (29 mg, 281 μmol) were added to a chloroform solution (1 mL) containing the carboxylic acid derivative (100 mg, 151 μmol) prepared in the above (1). After that, a chloroform solution (1 mL) of 2-chloro-1,3-dimethylimidazolinium chloride (47 mg, 281 μmol) was added dropwise thereto with stirring under ice-cooling. The mixture was stirred at room temperature for 30 minutes, and then concentrated in vacuo. The residue was purified by thin layer chromatography to obtain the above amide derivative (102 mg) as a pale yellow oil.

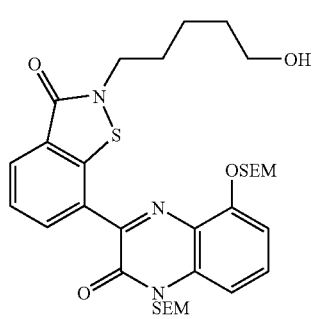

(3)

The above amide derivative (102 mg, 136 μmol) prepared in the above (2) was dissolved in chloroform (2 mL). After the solution was cooled to 0° C., 3-chloroperbenzoic acid (about 80%, 23 mg, 136 μmol) was added. The reaction solution was stirred at the same temperature for 1 hour, and triethylamine (114 μL, 816 μmol) and trichloroacetic anhydride (99 μL, 544 μmol) were added. Then, the temperature of the reaction solution was raised to room temperature, and the solution was stirred for 30 minutes, followed by addition of methanol (4 mL). After the reaction solution was stirred under heating at reflux for 1 hour, and the temperature of the reaction solution was lowered to room temperature. The reaction solution was diluted with chloroform, and washed with water and saturated brine. The organic layer was dried over anhydrous magnesium sulfate, filtered, and the filtrate was concentrated. The resulting residue was purified by a thin layer chromatography to obtain the above benzoisothiazolone derivative (80 mg) as a yellow solid.

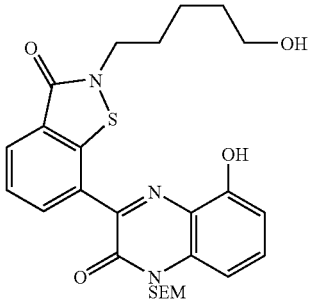

(4)

The benzoisothiazolone derivative (80 mg, 122 μmol) obtained in the above (3) was dissolved in chloroform (2 mL) and methanol (1 mL), and to this solution 4N hydrogen chloride/1,4-dioxane (3 mL) was added, and then the mixture was stirred at room temperature for 3 hours. The resulting reaction solution was neutralized with aqueous sodium hydrogencarbonate under ice-cooling, extracted with chloroform, and the organic layer was washed with saturated brine. Then, the organic layer was dried over anhydrous magnesium sulfate, filtered, and the filtrate was concentrated. The residue was purified by a thin layer chromatography to obtain the above phenol derivative (52 mg) as a yellow solid.

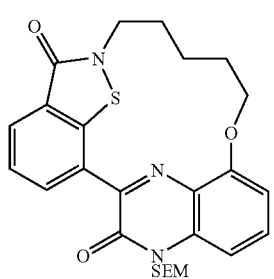

(5)

To tetrahydrofuran solution (1 nL) containing the phenol derivative (10 mg, 19 μmol) obtained in the above (4) were added triphenylphosphine (15 mg, 57 μmol) and 40% toluene solution (25 μL) containing diethyl azodicarboxylate, and the mixture was stirred at room temperature for 30 minutes. The reaction solution was concentrated, and the resulting residue was purified by a thin layer chromatography to obtain the above cyclic compound (10 mg) as a yellow solid.

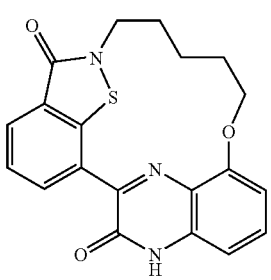

(6)

The cyclic compound obtained in the above (5) was dissolved in 4N hydrogen chloride/1,4-dioxane solution (2 mL), and the solution was stirred in a sealed tube at 100° C. for 2 hours. Diethyl ether was added to the reaction solution, and the resulting precipitated solid was filtered off to obtain the objective compound [1] (6.3 mg) as a yellow solid.

Spectral data of the compound of the above formula [1] are shown below.

$^1$H-NMR (DMSO-$d_6$) δ: 1.80-2.40 (6H, m), 3.79-3.90 (2H, m), 4.15-4.30 (2H, m), 6.81-6.97 (2H, m), 7.40-7.62 (2H, m), 7.99 (1H, d, J=7.7 Hz), 9.27 (1H, d, J=7.7 Hz), 12.8 (1H, brs). mass: 380 (M+1)$^+$ Working Example 2

Synthesis of the Compound of the Following Formula [2]:

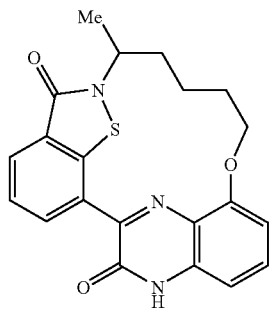

[2]

According to a method similar to the procedure described in Working Example 1, the objective compound [2] (20 mg) which is a racemate was obtained as a yellow solid from the above carboxylic acid derivative (100 mg, 154 μmol) obtained in Working Example 1-(1) and racemic 5-amino-1-hexanol synthesized by referring to the method described in J. Med. Chem., 25(8) 964 (1982).

Spectral data of the compound of the above formula [2] are shown below.

$^1$H-NMR (DMSO-$d_6$) δ: 1.24 (3H, d, J=6.6 Hz), 1.70-2.05 (3H, m), 2.20-2.65 (3H, m), 4.05-4.65 (3H, m), 6.95-6.98 (2H, m), 7.51 (1H, t, J=8.2 Hz), 7.61 (1H, t, J=7.7 Hz), 8.02 (1H, d, J=7.7 Hz), 9.42 (1H, d, J=8.0 Hz), 12.8 (1H, s). mass: 394 (M+1)$^+$ Working Example 3

Synthesis of the Compound of the Following Formula [3]:

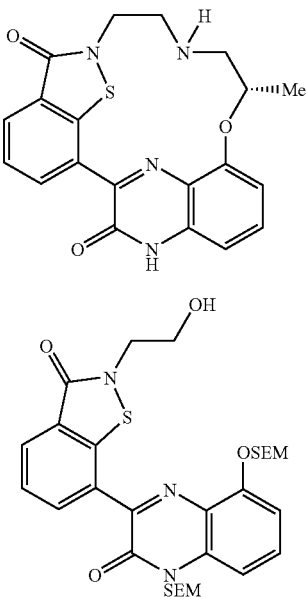

[3]

(1)

According to a method similar to the procedures described in Working Examples 1-(2) to 1-(3), the above benzoisothiazolone derivative (480 mg) was obtained as a yellow solid from the carboxylic acid derivative (1.08 g, 1.46 mmol) obtained in Working Example 1-(1) and 2-aminoethanol.

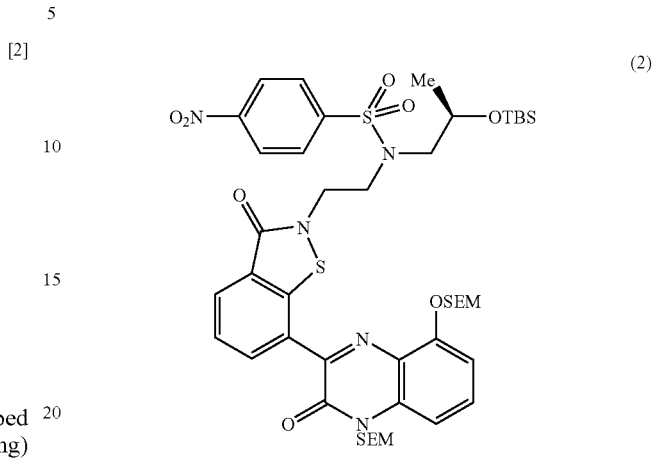

(2)

To chloroform solution (1 mL) containing the above benzoisothiazolone derivative (30 mg, 48 μmol) obtained in the above (1) were added triphenylphosphine (38 mg, 98 μmol), the sulfonamide derivative [A-3-1] (38 mg, 101 μmol) and 40% toluene solution containing diethyl azodicarboxylate (43 μL, 98 μmol), and the mixture was stirred at room temperature for 4 hours. The resulting solution was purified by thin layer chromatography to obtain the above benzoisothiazolone (41 mg) as a yellow solid.

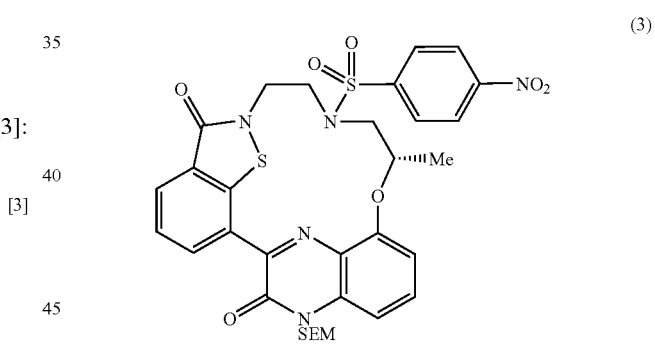

(3)

According to a method similar to the procedures described in Working Examples 1-(4) to 1-(5), the above cyclic derivative (11 mg) was obtained as a yellow solid from the above benzoisothiazolone derivative (29 mg, 30 μmol).

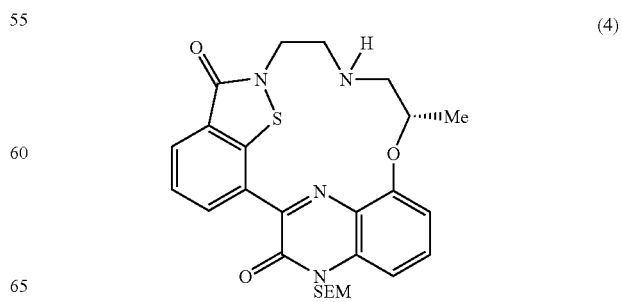

(4)

To N,N-dimethylformamide solution (1 mL) of the cyclic derivative (11 mg, 15 µmol) obtained in the above (3) were added thiophenol (19 µL, 18 µmol) and sodium carbonate (6 mg, 55 µmol), and the mixture was stirred at room temperature for 15 hours. After addition of water, the resulting reaction solution was extracted with chloroform and the organic layer was washed with saturated brine. Then, the organic layer was dried over anhydrous magnesium sulfate, filtered and the filtrate was concentrated. The resulting residue was purified by a thin layer, chromatography to obtain the amine derivative (7 mg) as a yellow solid.

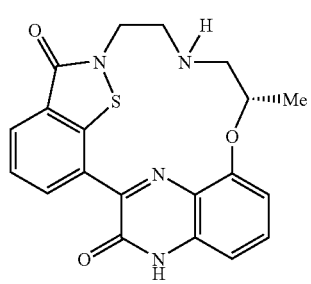

(3)

According to a method similar to the procedure described in Working Example 1-(6), the hydrochloride (2 mg) of the objective compound [3] was obtained as a yellow solid from the amine derivative (3 mg, 5.7 µmol) obtained in the above (4).

Spectral data of the compound of the above formula [3] are shown below.

$^1$H-NMR (DMSO-d$_6$) δ: 1.41 (3H, d, J=6.0 Hz) 3.20-3.90 (4H, m), 4.00-4.20 (1H, m), 4.35-4.50 (1H, m), 5.05-5.18 (1H, m), 7.00-7.15 (2H, m), 7.52-7.78 (2H, m), 8.15 (1H, d, J=7.5 Hz), 9.42 (1H, d, J=7.7 Hz), 13.0 (1H, s). mass: 395 (M+1)$^+$.

Example 4

Synthesis of the Compound of the Following Formula [4]:

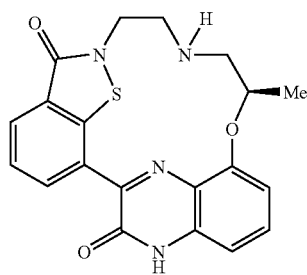

[4]

According to a method similar to the procedures described in Working Example 3-(2) to 3-(5), the hydrochloride (2 mg) of the objective compound [4] was obtained as a yellow solid from the benzoisothiazolone derivative (15 mg, 24 µmol) obtained in Working Example 3-(1) and the sulfonamide derivative [A-3-2] (19 mg, 51 µmol).

Spectral data of the compound of the above formula [4] are shown below.

$^1$H-NMR (DMSO-d$_6$) δ: 1.41 (3H, d, J=6.0 Hz), 3.20-3.90 (4H, m), 4.00-4.20 (1H, m), 4.35-4.50 (1H, m), 5.05-5.18 (1H, m), 7.00-7.15 (2H, m), 7.52-7.78 (2H, m), 8.15 (1H, d, J=7.5 Hz), 9.42 (1H, d, J=7.7 Hz), 13.0 (1H, s). mass: 395 (M+1)$^+$.

Working Example 5

Synthesis of the Compound of the Following Formula [5]:

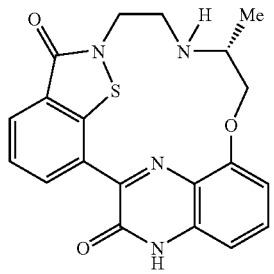

[5]

According to a method similar to the procedures described in Working Examples 3-(2) to 3-(5), the hydrochloride (2 mg) of the objective compound [5] was obtained as a yellow solid from the benzoisothiazolone derivative (15 mg, 24 µmol) obtained in Working Example 3-(1) and the sulfonamide derivative [A-3-3] (19 mg, 51 µmol).

Spectral data of the compound of the above formula [5] are shown below.

$^1$H-NMR (DMSO-d$_6$) δ: 1.44 (3H, d, J=6.2 Hz), 3.10-4.55 (7H, m), 7.04-7.13 (2H, m), 7.58-7.77 (2H, m), 8.15 (1H, d, J=7.7 Hz), 8.43 (1H, brs), 9.39 (1H, d, J=7.8 Hz), 9.98 (1H, brs), 13.0 (1H, s). mass: 395 (M+1)$^+$.

Working Example 6

Synthesis of the Compound of the Following Formula [6]:

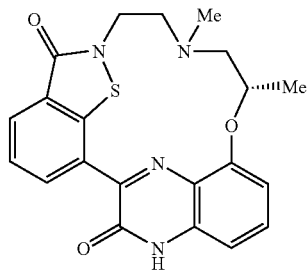

[6]

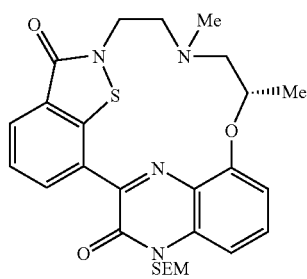

(1)

To methanol solution (500 µL) containing the amine derivative (4 mg, 7.6 µmol) obtained in Working Example 3-(4) was added 35% aqueous formalin solution (8 µL), and then methanol solution (500 μL) containing zinc chloride (10 mg, 75 μmol) and sodium cyanotrihydroborate (9.4 mg, 150 μmol) was added dropwise thereto. The mixture was stirred at room temperature for 1 hour. The reaction solution was purified by a thin layer chromatography to obtain the above N-methyl derivative (4 mg) as a yellow solid.

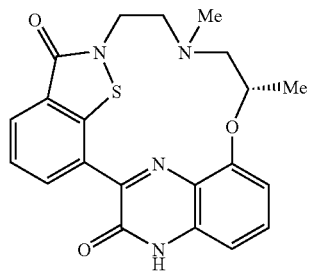

(2)

According to a method similar to the procedure of Working Example 1-(6), the hydrochloride (3 mg) of the objective compound [6] was obtained as a yellow solid from the N-methyl derivative (4 mg, 7.4 μmol) obtained in the above (1).

Spectral data of the compound of the above formula [6] are shown below.

$^1$H-NMR (DMSO-$d_6$) δ: 1.41 (3H, d, J=6.0 Hz), 2.37 (3H, s), 2.40-4.30 (6H, m), 4.85-4.98 (1H, m), 6.90-7.01 (2H, m), 7.45-7.61 (2H, m), 8.02 (1H, d, J=7.6 Hz), 9.34 (1H, d, J=8.1 Hz), 12.7 (1H, brs). mass: 409(M+1)$^+$.

Working Example 7

Synthesis of the Compound of the Following Formula [7]:

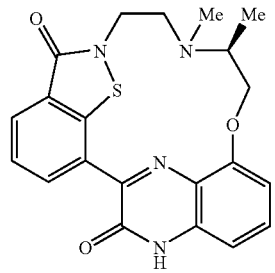

[7]

According to a method similar to the procedures of Working Examples 3-(2) to 3-(4) and 6, the hydrochloride (3 mg) of the objective compound [7] was obtained as a yellow solid from the benzoisothiazolone derivative (15 mg, 24 μmol) obtained in Working Example 3-(1) and the sulfonamide derivative [A-3-4] (19 mg, 51 μmol).

Spectral data of the compound of the above formula [7] are shown below.

$^1$H-NMR (DMSO-$d_6$) δ: 0.90-1.40 (3H, m), 2.20-4.40 (10H, m), 6.90-7.05 (2H, m), 7.50-7.70 (2H, m), 8.00-8.15 (1H, m), 9.37 (1H, d, J=7.9 Hz), 12.8 (1H, brs). mass: 409(M+1)$^+$.

Working Example 8

Synthesis of the Compound of the Following Formula [8]:

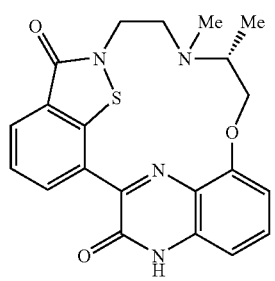

[8]

According to a method similar to the procedures described in Working Examples 3-(2) to 3-(4) and 6, the hydrochloride (2 mg) of the objective compound [8] was obtained as a yellow solid from the benzoisothiazolone derivative (15 mg, 24 μmol) obtained in Working Example 3-(1) and the sulfonamide derivative [A-3-3] (19 mg, 51 μmol).

Spectral data of the compound of the above formula [8] are shown below.

$^1$H-NMR (DMSO-$d_6$) δ: 0.90-1.40 (3H, m), 2.20-4.40 (10H, m) 6.90-7.05 (2H, m), 7.50-7.70 (2H, m), 8.00-8.15 (1H, m), 9.37 (1H, d, J=7.9 Hz),12.8 (1H, brs). mass: 409(M+1)$^+$.

Working Example 9

Synthesis of the Compound of the Following Formula [9]:

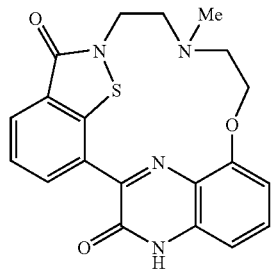

[9]

According to a method similar to the procedures described in Working Example 3-(2) to 3-(4) and 6, the hydrochloride (2 mg) of the objective compound [9] was obtained as a yellow solid from the benzoisothiazolone derivative (15 mg, 24 μmol) obtained in Working Example 3-(1) and the sulfonamide derivative [A-3-5] (19 mg, 51 μmol).

Spectral data of the compound of the above formula [9] are shown below.

$^1$H-NMR (DMSO-$d_6$) δ: 2.30-4.90 (11H, m), 6.82-7.18 (2H, m), 7.40-7.80 (2H, m), 7.95-8.20 (1H, m), 9.38 (1H, d, J=7.8 Hz), 12.7-13.1 (1H, m). mass: 395(M+1)$^+$

Working Example 10

Synthesis of the Compound of the Following Formula [10]:

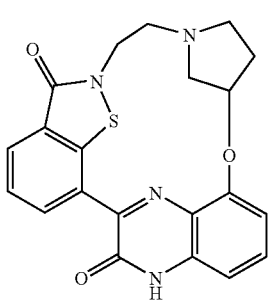

(10)

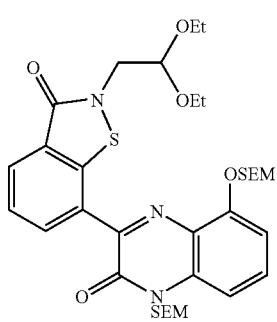

(1)

According to a method similar to the procedures described in Working Examples 1-(2) to 1-(3), the above benzoisothiazolone derivative (1.94 g) was obtained as a yellow solid from the calboxylic acid derivative (2.00 g, 3.00 mmol) obtained in Working Example 1-(1) and aminoacetaldehyde diethylacetal (873 μL, 6.02 mmol).

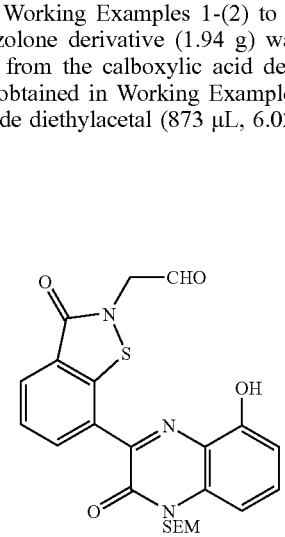

(2)

To tetrahydrofuran solution (600 mL) of the benzoisothiazolone derivative (1.94 g, 2.82 mmol) obtained in the above (1) was added water (50 mL), and then 4N hydrogen chloride/1,4-dioxane (50 mL) was added thereto. The mixture was stirred at room temperature for 15 hours. The reaction solution was concentrated to about 100 mL, and the resulting yellow solid was filtered off. After that, this solid was washed with diethylether, and dried in vacuo to obtain the above aldehyde derivative (1.01 g) as a yellow solid.

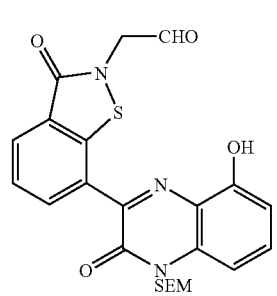

(3)

To methanol solution (5 mL) containing the aldehyde derivative (100 mg, 207 μmol) obtained in the above (2) was added racemic 3-hydroxypyrrolidine (34 μL, 414 μmol), and then methanol solution (2.8 mL) containing zinc chloride (56 mg, 414 μmol) and sodium cyanotrihydroborate (52 mg, 828 μmol) were added dropwise thereto. The mixture was stirred at room temperature for 15 hours, and the reaction solution was concentrated. The resulting residue was purified by a thin layer chromatography to obtain the above racemic amine derivative (95 mg) as a yellow solid.

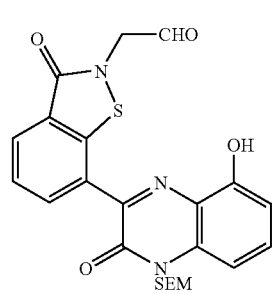

(4)

According to a method similar to the procedures described in Working Examples 1-(5) to 1-(6), the hydrochloride (31 mg) of the objective compound [10] as a racemate was obtained as, a yellow solid from the racemic amine derivative (95 mg, 171, μmol) obtained in the above (3).

Spectral data of the compound of the above formula [10] are shown below.

$^1$H-NMR (DMSO-$d_6$) δ: 1.80-4.00 (8H, m), 4.00-4.40 (2H, m), 5.38-5.42(1H, m), 6.80-7.30 (2H, m), 7.40-7.80 (2H, m), 7.95-8.18 (1H, m), 9.24-9.36 (1H, m), 12.7 (1H, s).
mass: 407(M+1)$^+$.

Working Example 11

Synthesis of the Compound of the Following Formula [11]:

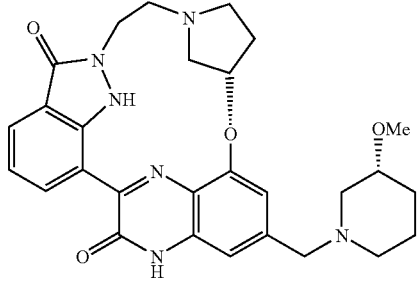

(1)

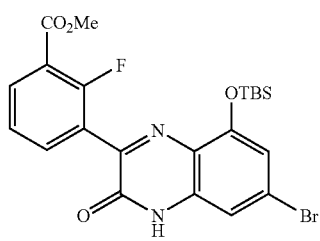

To toluene solution (4 mL) containing the keto ester derivative [A-2] (515 mg, 2.03 mmol) and the phenylenediamine derivative [A-1] (643 mg, 2.03 mmol) was added acetic acid (0.4 mL), and the mixture was stirred at room temperature for 3 days. The resulting precipitates were filtered off, washed with diethyl ether and toluene, and dried in vacuo to obtain the above quinoxalinone derivative (340 mg) as a white solid.

(2)

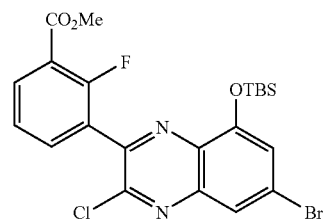

The quinoxalinone derivative (101 mg, 0.20 mmol) obtained in the above (1) was suspended in thionyl chloride (1 mL), and N,N-dimethylformamide (15.5 μL, 0.20 mmol) was added thereto. Then, the reaction solution was heated under reflux for 20 minutes. After this reaction solution was cooled to room temperature, the thionyl chloride was removed by evaporation in vacuo. The resulting residue was diluted with ethyl acetate, washed successively with water, sodium hydrogencarbonate and saturated brine. The organic layer was dried over anhydrous magnesium sulfate, filtered, and concentrated in vacuo to obtain the above chloroquinoxaline derivative (106 mg) as a pale yellow solid.

(3)

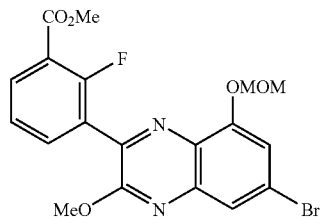

The chloroquinoxaline derivative (53 mg, 0.10 mmol) obtained in the above (2) and chloromethyl methyl ether (23 μL, 0.30 mmol) were dissolved in tetrahydrofuran (2 mL), and then 1.0M tetrahydrofuran solution (0.2 mL, 0.20 mmol) containing tetrabutyl ammonium fluoride was added dropwise at room temperature. After the dropwise addition was completed, the reaction solution was cooled in an ice-bath, methanol (1 mL) was added, and sodium hydride (14 mg, 60% dispersion in oil, 0.35 mmol) was gradually added thereto. The resulting reaction solution was stirred at room temperature for 1 hour, and saturated aqueous ammonium chloride was added to stop the reaction. The whole reaction solution was poured into water, and extracted with ethyl acetate. The organic layer was washed successively with water and saturated brine. Then, the organic layer was dried over anhydrous magnesium sulfate, filtered, and concentrated in vacuo to obtain the above methoxyquinoxaline derivative (49 mg) as a white solid.

(4)

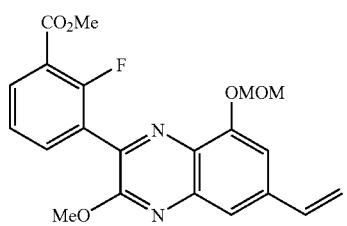

The methoxyquinoxaline derivative (45 mg, 100 μmol) obtained in the above (3) was dissolved in toluene (3 mL), and to this solution were added tributylvinyltin (36 μL, 120 μmol) and tetrakis(triphenylphosphine)palladium(0) (16 mg, 2.5 μmol). The mixture was heated at reflux for 4 hours. The resulting reaction solution was cooled down to room temperature, and filtered through a Celite pad. The filtrate was concentrated in vacuo, and the resulting residue was purified by thin layer chromatography to obtain the above vinyl derivative (30 mg) as a pale yellow solid.

(5)

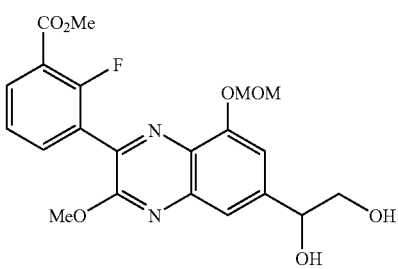

To acetonitrile solution (3 mL) containing the vinyl derivative (20 mg, 50 μmol) obtained in the above (4) were added water (1 mL), 50% aqueous solution (15 μL, 65 μmol) of N-methylmorpholine N-oxide, and 0.05M aqueous osmium tetraoxide solution (50 μL, 0.25 μmol). After the resulting solution was stirred at room temperature for 16 hours, saturated aqueous sodium thiosulfate solution was added thereto, and the mixture was stirred at room temperature for 30 minutes. After this solution was extracted with ethyl acetate, the organic layer was washed with saturated brine, dried over anhydrous magnesium sulfate, filtered, and concentrated. The resulting residue was purified by a thin layer chromatography to obtain the above diol derivative (18 mg) as a pale yellow solid.

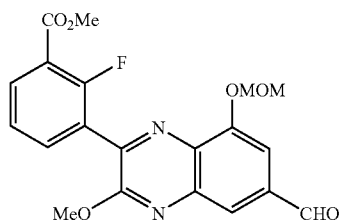

(6)

To tetrahydrofuran solution (2 mL) containing the diol derivative (18 mg) obtained in the above (5) were added water (2 mL) and potassium periodate (13 mg, 54 μmol). The resulting mixture was stirred at room temperature for 2 hours, and water was added thereto. This solution was extracted with ethyl acetate, and the organic layer was washed with saturated brine. Then, the organic layer was dried over anhydrous magnesium sulfate, filtered, and the filtrate was concentrated. The resulting residue was purified by a thin layer chromatography to obtain the above aldehyde derivative (12 mg) as a pale yellow solid.

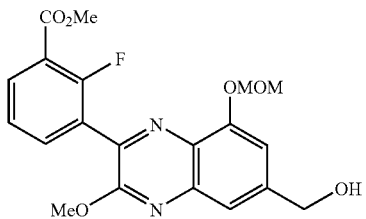

(7)

The aldehyde derivative (640 mg, 1.59 mmol) obtained in the above (6) was dissolved in chloroform (15 mL) and methanol (10 mL), and then sodium tetrahydroborate (120 mg, 3.18 mmol) was added thereto under ice-cooling. The resulting reaction solution was stirred for 15 minutes under ice-cooling. After saturated aqueous ammonium chloride was added to the reaction solution, the mixture was extracted with chloroform. The organic layer was washed successively with water and saturated brine, dried over anhydrous magnesium sulfate, filtered, and concentrated. The resulting residue was purified by a column chromatography on silica gel to obtain the above benzyl alcohol derivative (416 mg) as a pale yellow solid.

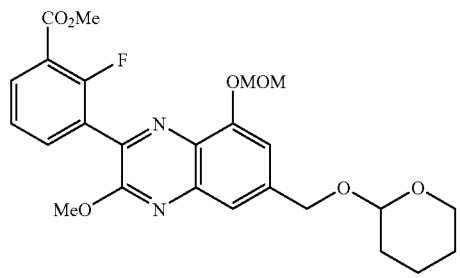

(8)

The benzyl alcohol derivative (11.0 g, 27.3 mmol) obtained in the above (7) was dissolved in chloroform (120 mL), and to this solution were added 3,4-dihydro-2H-pyran (60 mL) and pyridinium p-toluenesulfonate (1.50 g, 5.97 mmol) at room temperature. The resulting reaction solution was stirred at room temperature for 4 hours, and diluted with ethyl acetate. The organic layer was washed successively with aqueous sodium hydrogencarbonate and saturated brine, dried over anhydrous magnesium sulfate, filtered, and concentrated in vacuo to obtain the above tetrahydropyranyl ether derivative (11.1 g) as a white solid.

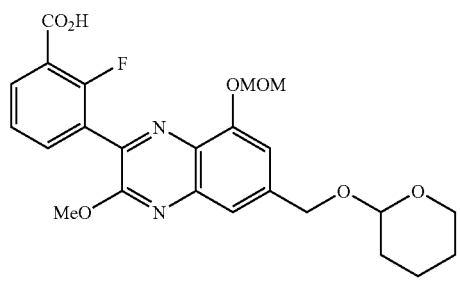

(9)

The tetrahydropyranyl ether derivative (3.00 g, 6.17 mmol) obtained in the above (8) was dissolved in tetrahydrofuran (50 mL) and methanol (50 mL), and then 1N aqueous sodium hydroxide (50 mL) was added. The mixture was stirred for 30 minutes. The resulting reaction solution was diluted with ethyl acetate, and washed successively with 1N hydrochloric acid, water, and saturated brine. The resulting organic layer was dried over anhydrous magnesium sulfate, filtered, and concentrated in vacuo to obtain the above carboxylic acid derivative (3.00 g) as a white solid.

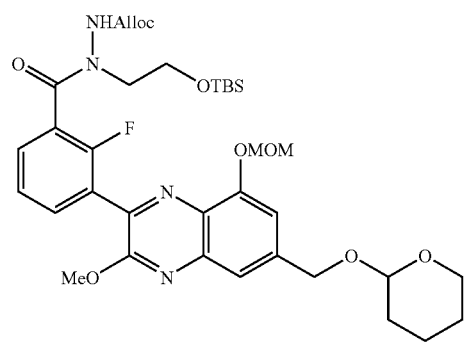

(10)

To chloroform solution (60 mL) containing the carboxylic acid derivative (1.50 g, 3.17 mmol) obtained in the above (9) was added pyridine (1.54 mL, 19.0 mmol), and then chloroform solution (10 mL) containing 2-chloro-1,3-dimethylimidazolinium chloride (1.07 g, 6.35 mmol) was added dropwise thereto with stirring under ice-cooling. The mixture was stirred at room temperature for 15 minutes. After that, chloroform solution (20 mL) containing the hydrazine derivative [A-17] (2.59 g, 9.51 mmol) was added to the solution, and the mixture was stirred at room temperature for 5 hours. Water was added to the resulting reaction solution, and the mixture was extracted with ethyl acetate. The organic layer was washed successively with 1N hydrochloric acid, water, and saturated brine, and purified by a silica gel chromatography to obtain the above hydrazide derivative (1.59 g) as a pale yellow oil.

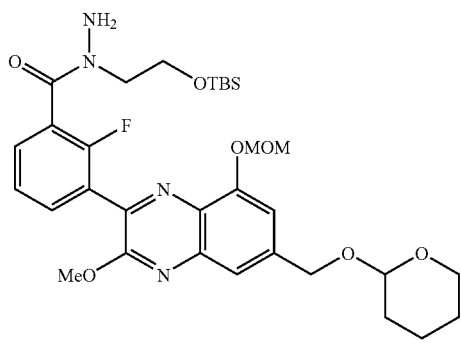

(11)

To tetrahydrofuran solution (20 mL) containing the hydrazide derivative (1.59 g, 2.18 mmol) obtained in the above (10) were added diethylamine (1.13 mL, 10.9 mmol) and formic acid (0.411 mL), and then tetrakis(triphenylphosphine)palladium(0) (252 mg, 0.218 mmol) was added thereto. After stirring the solution at room temperature for 2 hours, water was added to the reaction solution, and the mixture was extracted with ethyl acetate. The organic layer was washed successively with aqueous sodium hydrogencarbonate, water, and saturated brine, and purified by a silica gel chromatography to obtain the above de-Alloc derivative (1.10 g) as a pale yellow oil.

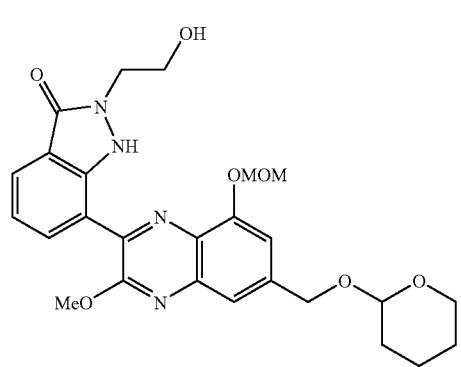

(12)

N,N-diisopropylethylamine (509 μL, 2.92 mmol) was added to N,N-dimethylformamide solution (50 mL) containing the de-Alloc derivative (628 mg, 974 μmol) obtained in the above (11), and the mixture was stirred at 120° C. for 3 hours. After that, the resulting reaction solution was cooled down to room temperature, and concentrated in vacuo. Chloroform (10 mL) was added to the resulting residue, and the resulting solid was filtered off. This solid was dried in vacuo to obtain the above 3-indazolinone derivative (251 mg) as a yellow solid.

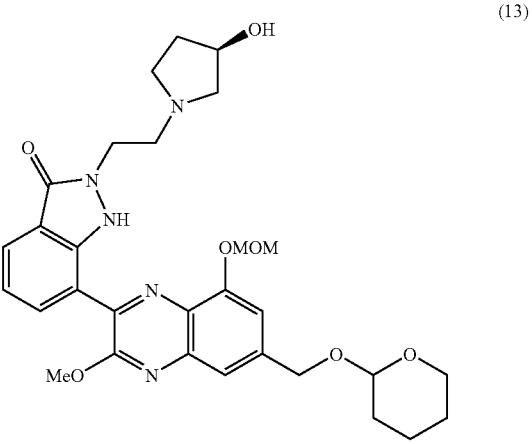

(13)

To chloroform solution (10 mL) containing the 3-indazolinone derivative (250 mg, 489 μmol) obtained in the above (12) was added N,N-diisopropylethylamine (426 μL, 2.45 mmol), and then methanesulfonyl chloride (113 μL, 1.47 mmol) was added thereto, followed by stirring for 30 minutes under ice-cooling. After addition of water to the resulting reaction solution, the organic layer was separated, and washed successively with 0.5N hydrochloric acid, water, and saturated brine. Then, the organic layer was dried over anhydrous magnesium sulfate, filtered, and concentrated. The resulting residue was dissolved in N-methylpyrrolidone (2.5 mL), and then (R)-3-hydroxypyrrolidine (250 mg, 2.87 mmol) was added. The mixture was stirred at 70° C. for 1 hour, and cooled down to room temperature. After that, aqueous sodium hydrogencarbonate was added to the solution, and the solution was extracted with ethyl acetate, and washed successively with water and saturated brine. The organic layer was dried over anhydrous magnesium sulfate, filtered, and concentrated. The resulting residue was purified by a silica gel chromatography to obtain the above amine (176 mg) as a yellow solid.

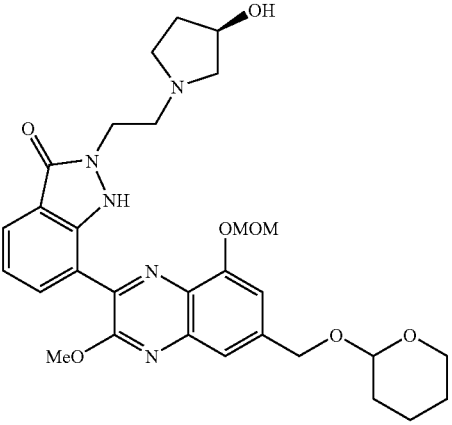

(14)

N,N-diisopropylethylamine (264 µL, 1.52 mmol) was added to tetrahydrofuran solution (3.5 mL) of the amine derivative (176 mg, 303 µmol) obtained in the above (13), and then methanesulfonyl chloride (70.5 µL, 910 µmol) was added thereto under ice-cooling. The solution was stirred for 30 minutes under ice-cooling, and 1N aqueous sodium hydroxide (3.5 mL) was added dropwise to the solution, followed by addition of methanol (3.5 mL). The solution was stirred for 15 minutes under ice-cooling, and then water was added. The solution was extracted with chloroform, and washed with saturated brine. The organic layer was dried over anhydrous magnesium sulfate, filtered, and concentrated to obtain the above mesylated derivative (170 mg) as a yellow solid.

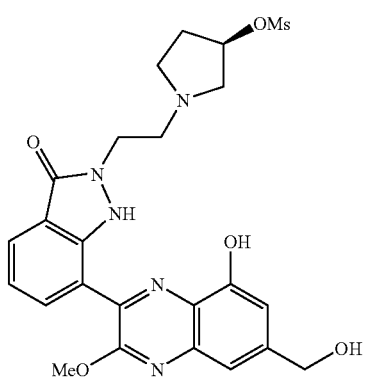

(15)

The mesylated derivative (170 mg, 258 µmol) obtained in the above (14) was dissolved in trifluoroacetic acid (15 mL) and water (1.5 mL), and the solution was stirred at room temperature for 1 hour. The resulting reaction solution was concentrated in vacuo, followed by azeotropic evaporation with ethanol and toluene to obtain the above phenol derivative (170 mg) as a yellow solid.

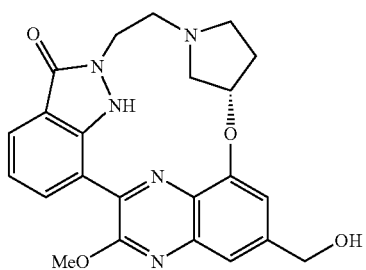

(16)

The phenol (170 mg) obtained in the above (15) was dissolved in N,N-dimethylformamide (35 mL), and then potassium carbonate (400 mg, 2.89 mmol) was added thereto. The mixture was stirred at 70° C. for 1.5 hours. The resulting reaction solution was cooled down to room temperature, filtered, and the mother liquor was concentrated in vacuo. The resulting residue was dissolved in a mixed solution of chloroform and methanol, and washed with saturated brine. The organic layer was dried over anhydrous magnesium sulfate, filtered, and concentrated. The resulting residue obtained again was purified by a silica gel chromatography to obtain the above cyclic derivative (92 mg) as a yellow solid.

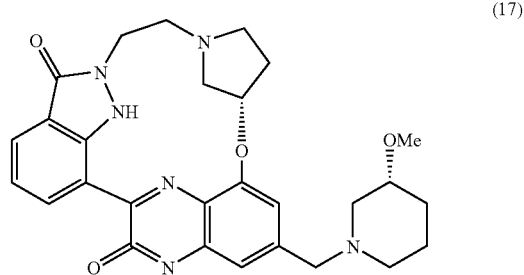

(17)

The cyclic compound (30 mg, 69 µmol) prepared in the above (16) was dissolved in chloroform (1 mL), and to this solution were added N,N-diisopropylethylamine (48 µL, 276 µmol) and methanesulfonyl chloride (13 µL, 173 µmol), then the mixture was stirred for 30 minutes. An aqueous solution (1 mL) in which sodium hydrogencarbonate (60 mg) was dissolved was added to the reaction solution. In addition, after the amine [A-23] (30 mg) was added to the solution, the mixture was stirred at 60° C. for 1 hour. The reaction solution was cooled down to room temperature, and the organic layer was separated, concentrated, and purified by a thin layer chromatography to obtain the above benzylamine derivative (30 mg) as a yellow solid.

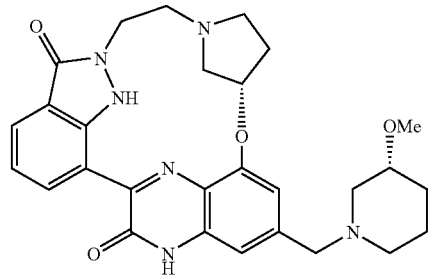

(18)

The benzylamine derivative obtained in the above (17) was dissolved in trifluoroacetic acid (5 mL) and water (500 µL), and the solution was heated at reflux for 3 days. The reaction solution was cooled down to room temperature, and concentrated in vacuo. After the resulting residue was dissolved in a mixed solution of chloroform and methanol, the solution was washed successively with water and saturated brine. The organic layer was dried over anhydrous magnesium sulfate, filtered, and concentrated. The resulting residue was purified by thin layer chromatography to give a yellow solid. To a stirred solution of the solid in chloroform (5 mL) was added dropwise 4N hydrogen chloride/1,4-dioxan solution (500 µL), and the resulting precipitates were collected by filtration, washed with diethyl ether, and dried in vacuo to obtain the hydrochloride (26 mg) of the objective compound [11] as a yellow solid.

Spectral data of the compound of the above formula [11] are shown below.

$^1$H-NMR (DMSO-$d_6$) δ: 1.50-4.50 (24H, m), 5.15-5.35 (1H, m), 7.00-7.50 (3H, m), 7.86 (1H, d, J=7.8 Hz), 9.25 (1H, bs), 9.51-9.68 (1H, brs), 1.1 (1H, brs), 12.9 (1H, brs).
mass: 517(M+1)$^+$.

Working Example 12

Synthesis of the Compound of the Following Formula [12]:

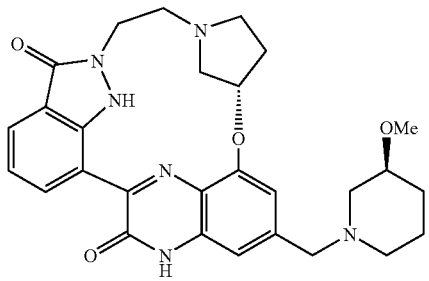

[12]

According to a method similar to the procedures described in Working Examples 11-(17) to 11-(18), the hydrochloride (26 mg) of the objective compound [12] was obtained as an orange solid from the cyclic derivative (30 mg, 69 μmol) obtained in Working Example 11-(16) and the amine derivative [A-24].

Spectral data of the compound of the above formula [12] are shown below.

$^1$H-NMR (DMSO-d$_6$) δ: 1.50-4.50 (24H, m), 5.15-5.35 (1H, m), 7.00-7.50 (3H, m), 7.86 (1H, d, J=7.8 Hz), 9.25 (1H, bs), 9.51-9.68 (1H, brs), 1.1 (1H, brs), 12.9 (1H, brs). mass: 517(M+1)$^+$.

Working Example 13

Synthesis of the Compound of the Following Formula [13]:

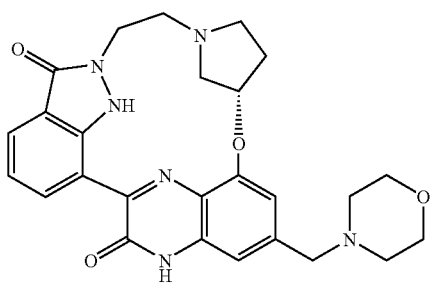

[13]

According to a method similar to the procedures described in Working Examples 11-(17) to 11-(18), the hydrochloride (25 mg) of the objective compound [13] was obtained as an orange solid from the cyclic compound derivative (30 mg, 69 μmol) obtained in Working Example 11-(16) and morpholine.

Spectral data of the compound of the above formula [13] are shown below.

$^1$H-NMR (DMSO-d$_6$) δ: 1.60-4.20 (18H, m), 4.41 (2H, s), 5.15-5.40 (1H, m), 7.00-7.96 (4H, m), 9.10-9.40 (1H, m), 10.8-12.0 (2H, m), 12.8-13.0 (1H, m). mass: 489(M+1)$^+$.

Working Example 14

Synthesis of the Compound of the Following Formula [14]:

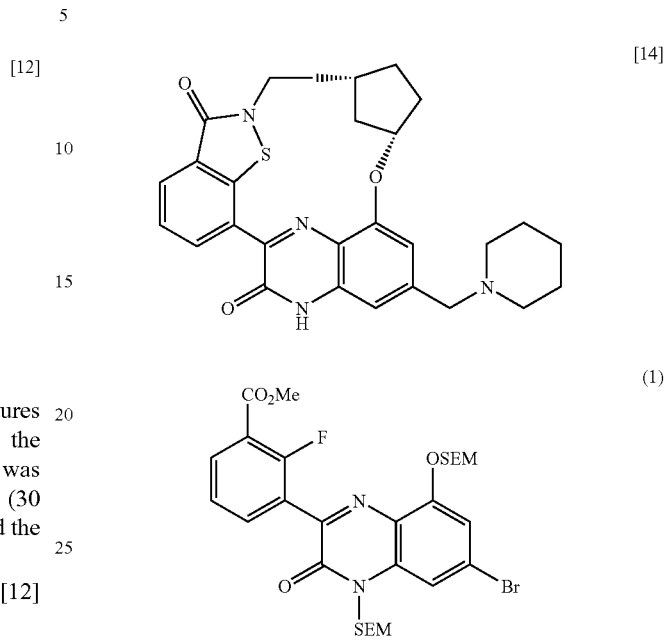

[14]

(1)

The quinoxalinone derivative (100 mg, 0.20 mmol) obtained in Working Example 11-(1) was dissolved in tetrahydrofuran (5 mL), and then chloromethyl 2-(trimethylsilyl)ethyl ether (37 μL, 0.30 mmol) was added to the solution. Then, the solution was stirred at room temperature, and to this solution was added potassium t-butoxide (29 mg, 0.26 mmol) at 0° C. The resulting reaction solution was warmed up to room temperature, and stirred for 30 minutes. After chloromethyl 2-(trimethylsilyl)ethyl ether (37 μL, 0.30 mmol) was added thereto, and then 1M tetrabutylammonium fluoride/tetrahydrofuran (260 μL, 0.26 mmol) was added thereto. The resulting reaction solution was stirred at room temperature for 40 minutes. Then chloromethyl 2-(trimethylsilyl)ethyl ether (37 μL, 0.30 mmol) was added thereto, and the mixture was stirred at room temperature for 2 hours. Water was added to the resulting reaction solution, and the solution was extracted with chloroform, and the extract was washed with saturated brine. The organic layer was dried over anhydrous magnesium sulfate, filtered in vacuo, and concentrated. The resulting residue was purified by a thin layer chromatography on silica gel to obtain the above protected derivative with SEM (83 mg) as a white solid.

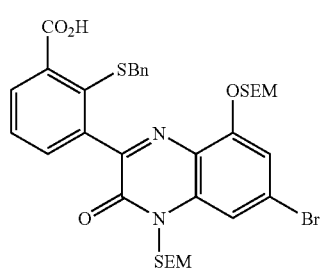

(2)

According to a method similar to the procedures described in Working Example 1-(1), the above carboxylic acid derivative (121 mg) was obtained as a pale yellow solid from the protected derivative with SEM (100 mg, 0.15 mmol) obtained in the above (1).

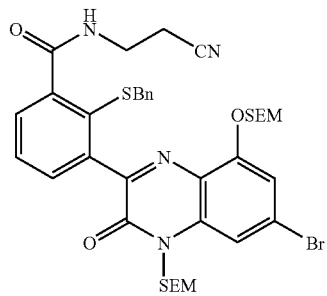

(3)

The carboxylic acid derivative (3.78 g, 5.08 mmol) obtained in the above (2) was dissolved in chloroform (30 mL), and to this solution were added 1-hydroxybenzotriazole (1.01 g, 6.60 mmol) and 1-{(3-dimethylamino)propyl}-3-ethylcarbodiimide hydrochloride (1.36 g, 6.60 mmol). After this solution was stirred at room temperature for 5 minutes, 3-aminopropionitrile (0.49 mL, 6.60 mmol) was added thereto. The resulting solution was stirred at the same temperature for 4 hours, diluted with chloroform, and washed successively with aqueous sodium hydrogencarbonate and saturated aqueous ammonium chloride. The resulting organic layer was dried over anhydrous magnesium sulfate, filtered, and concentrated. The resulting residue was purified by a column chromatography on silica gel to obtain the above amide derivative (3.28 g) as a pale yellow solid.

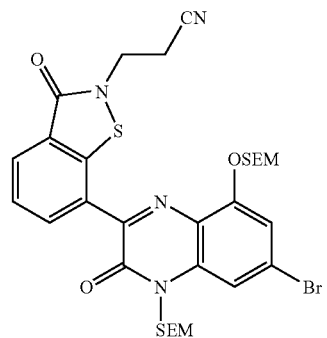

(4)

According to a method similar to the procedure described in Working Example 1-(3), the above benzisothiazolone derivative (2.93 g) was obtained as a yellow solid from the amide derivative (3.28 g, 4.12 mmol) obtained in the above (3).

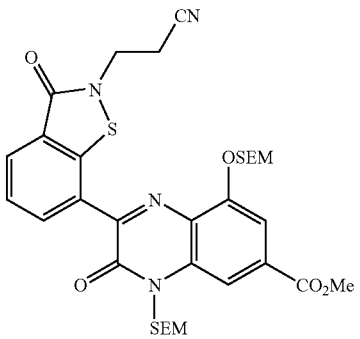

(5)

The benzoisothiazolone derivative (2.33 g, 3.31 mmol) obtained in the above (4) was dissolved in a mixed solution of N,N-dimethylformamide (25 mL) and methanol (25 mL), and then sodium hydrogencarbonate (800 mg, 9.93 mmol) was added. After substituting the reaction system with nitrogen gas, palladium(II) acetate (75 mg, 0.33 mmol) and 1,1'-bis(diphenylphosphino)ferrocene (185 mg, 0.33 mmol) were added to the reaction solution at room temperature under a nitrogen atmosphere. Then, the atmosphere in the reaction system was substituted with carbon monooxide. This reaction solution was stirred at 70° C. for 2 hours, cooled down to room temperature, diluted with chloroform, and washed successively with water and saturated aqueous ammonium chloride. The resulting organic layer was dried over anhydrous magnesium sulfate, filtered, and concentrated. The resulting residue was purified by a column chromatography on silica gel to obtain the above ester derivative (2.03 g) as a yellow solid.

(6)

The ester derivative (2.03 g, 2.97 mmol) obtained in the above (5) was dissolved in a mixed solution of tetrahydrofuran (150 mL) and methanol (50 mL), and then 1N sodium hydroxide (50 mL) was added thereto at room temperature. After the resulting reaction solution was stirred at room temperature for 1 hour, the pH of the solution was adjusted to 2 using 1N hydrochloric acid. After removal of the tetrahydrofuran and methanol from the solution by evaporation in vacuo, the resulting precipitates were filtered off. The precipitates were washed with water, and dried in vacuo to obtain the above carboxylic acid derivative (1.78 g) as a yellow solid.

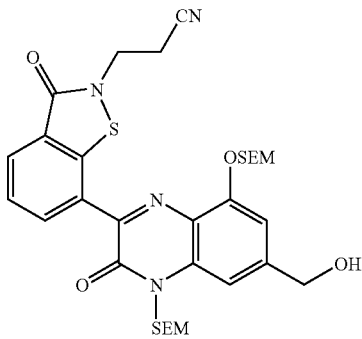

(7)

The carboxylic acid derivative (50 mg, 75 μmol) obtained in the above (6) was dissolved in tetrahydrofuran (5 mL), and to this solution were added benzotriazo-1-yloxytripyrrolidinophosphonium hexafluorophosphate (47 mg, 90 μmol) and N,N-diisopropylethylamine (17 μL, 97 μmol) at room temperature. After the resulting reaction solution was stirred at the same temperature for 5 minutes, 2M tetrahydrofuran solution (80 μL) containing lithium tetrahydroborate was added, and the solution was stirred for 20 minutes. This reaction solution was poured into aqueous ammonium chloride solution, and extracted with chloroform. The organic layer was dried over anhydrous magnesium sulfate, filtered, and concentrated. The resulting residue was purified by a thin layer chromatography to obtain the above benzyl alcohol derivative (33.5 mg) as a pale yellow oil.

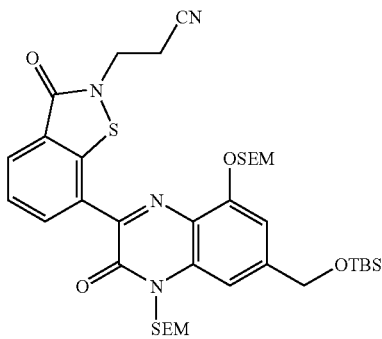

(8)

The benzyl alcohol derivative (675 mg, 1.03 mmol) obtained in the above (7) was dissolved in N,N-dimethylformamide (8 mL), and to the solution were added successively imidazole (106 mg, 1.55 mmol) and t-butyldimethylsilyl chloride (202 mg, 1.34 mmol) in an ice-bath, and then the reaction solution was stirred at room temperature overnight. The resulting reaction solution was diluted with ethyl acetate, and washed successively with water and saturated brine. The organic layer was dried over anhydrous magnesium sulfate, filtered, and concentrated in vacuo to obtain the above protected derivative with TBS (812 mg) as a yellow oil.

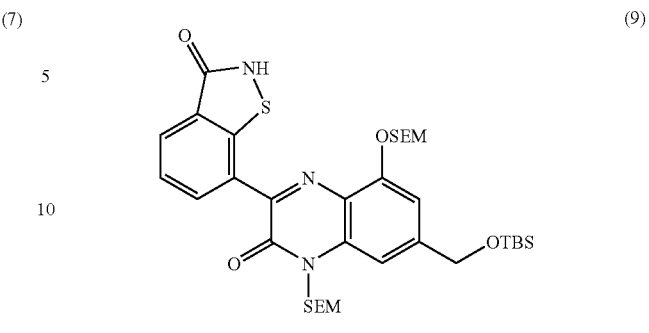

(9)

The protected derivative (78 mg) with TBS obtained in the above (8) was dissolved in tetrahydrofuran (2 mL), and to this solution was dropwise added 1M tetrahydrofuran solution (0.30 mL, 0.30 mmol) containing lithium hexamethyldisilazide in an ice-bath. After the resulting solution was stirred for 20 minutes in an ice-bath, saturated aqueous ammonium chloride was added thereto to stop the reaction. The whole solution was poured into water, extracted with ethyl acetate, and the organic layer was washed successively with water and saturated brine. The organic layer was dried over anhydrous magnesium sulfate, filtered, and concentrated in vacuo to obtain the above de-propionitrile derivative (73 mg) as an orange solid.

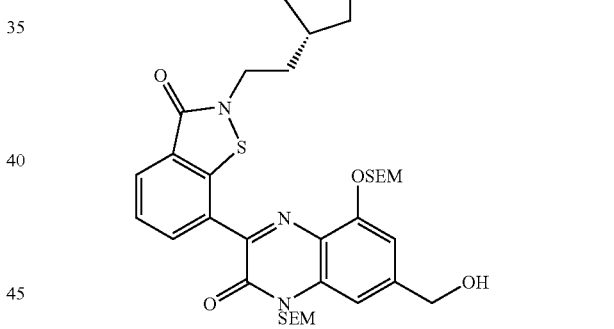

(10)

The de-propionitrile derivative (296 mg) obtained in the above (9) and the mesylated derivative [A-5] (258 mg) were dissolved in 1,4-dioxane (15 mL), and then 4N aqueous lithium hydroxide (103 μL, 413 μmol) was added to the solution. After the solution was heated at reflux for 5 hours, it was cooled down to room temperature, and 4N aqueous lithium hydroxide (824 μL, 3.30 mmol) was added thereto, whereby the reaction solution was suspended. After 1,4-dioxan and water were added to the reaction solution to dissolve the suspension, the solution was heated at reflux for 1 hour. Then, the reaction solution was cooled down to room temperature, and saturated aqueous ammonium chloride was added thereto. The solution was extracted with chloroform. The resulting organic layer was washed with saturated brine, dried over anhydrous magnesium sulfate, and filtered. The filtrate was concentrated, and the resulting residue was purified by a column chromatography on silica gel to obtain the above N-alkylbenzoisothiazolone derivative (247 mg) as a yellow solid.

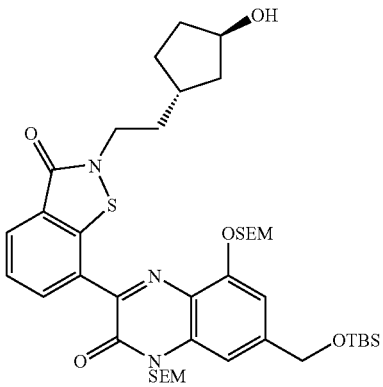

(11)

The N-alkylbenzoisothiazolone derivative (247 mg, 346 μmol) obtained in the above (10) was dissolved in chloroform (25 mL), and to the solution were added successively imidazole (28 mg, 415 μmol) and t-butyldimethylsilyl chloride (52 mg, 346 μmol) in an ice-bath. The reaction solution was stirred overnight at room temperature. The resulting reaction solution was diluted with ethyl acetate, and washed successively with water and saturated brine. The organic layer was dried over anhydrous magnesium sulfate, filtered, and concentrated in vacuo. The resulting residue was purified by a chromatography on silica gel to obtain the above protected derivative (170 mg) with TBS as a yellow solid.

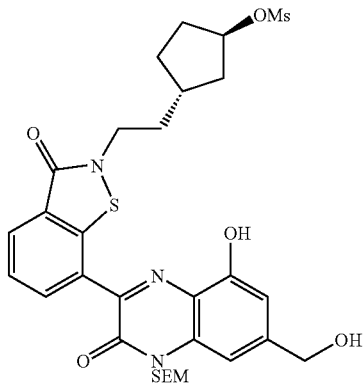

(12)

The protected derivative (170 mg, 205 μmol) with TBS obtained in the above (11) was dissolved in chloroform (5 mL), and to the solution were added triethylamine (57 μL, 410 μmol) and methanesulfonyl chloride (24 μL, 308 μmol) under ice-cooling, and the mixture was stirred for 1 hour. After aqueous sodium hydrogencarbonate was added the resulting reaction solution, the mixture was extracted with chloroform. This organic layer was washed with saturated brine, dried over anhydrous magnesium sulfate, and filtered. The filtrate was concentrated to obtain a yellow oil. The resulting yellow oil was dissolved in chloroform (4 mL) and methanol (2 mL), and then 4N hydrogen chloride in 1,4-dioxane (4 mL) was added thereto. The solution was stirred for 3 hours at room temperature. This solution was neutralized with aqueous sodium hydrogencarbonate under ice-cooling, extracted with chloroform, and the organic layer was washed with saturated brine. After the organic layer was filtered, it was concentrated. The resulting residue was purified by a column chromatography on silica gel to obtain the above mesylated derivative (82 mg) as a yellow solid.

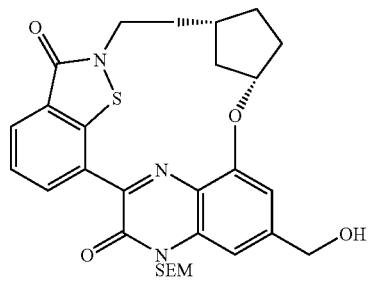

(13)

The mesylated derivative (82 mg, 154 μmol) obtained in the above (12) was dissolved in N-methylpyrrolidone (4 mL), and to the solution was added potassium carbonate (64 mg, 462 μmol). The solution was stirred at 90° C. for 5 hours. The resulting reaction was cooled down to room temperature, and ethyl acetate was added thereto. The organic layer was washed successively with water and saturated brine. After the solution was filtered and the filtrate was concentrated, and the resulting residue was purified by a thin layer chromatography to obtain the above cyclic derivative (23 mg) as a yellow solid.

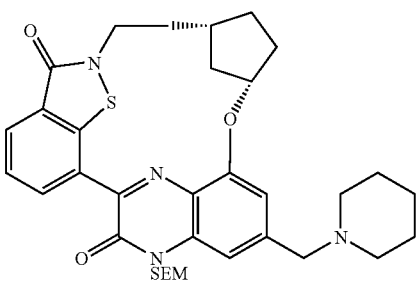

(14)

The cyclic derivative (23 mg, 40.6 μmol) obtained in the above (13) was dissolved in chloroform (1 mL), and to the solution were added triethylamine (11 μL, 81.3 μmol) and methanesulfonyl chloride (6.3 μL, 81.3 μmol) under ice-cooling. After stirring the solution for 30 minutes, piperidine (40 μL, 406 μmol) was added to the resulting reaction solution. The mixture was heated at reflux for 30 minutes. The reaction solution was cooled down to room temperature, and purified by a thin layer chromatography to obtain the above benzylamine derivative (24 mg) as a yellow solid.

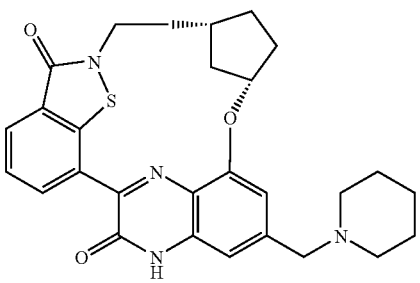

(15)

According to a method similar to the procedure described in Working Example 1-(6), the hydrochloride (21 mg) of the objective compound [14] was obtained from the benzylamine derivative (21 mg) obtained in the above (14).

Spectral data of the compound of the above formula [14] are shown below.

$^1$H-NMR (DMSO-$d_6$) δ: 1.30-1.47 (1H, m), 1.60-2.39 (14H, m), 2.80-3.00 (2H, m), 3.25-3.40 (2H, m), 3.70-4.22 (2H, m), 4.30-4.45 (2H, m), 5.39 (1H, m), 7.02 (1H, s), 7.43 (1H, s), 7.65 (1H, t, J=7.7 Hz), 8.06 (1H, d, J=7.7 Hz), 9.30 (1H, d, J=7.7 Hz), 10.2 (1H, brs), 13.0 (1H, s). mass: 503(M+1)$^+$.

Working Example 15

Synthesis of the Compound of the Following Formula [15]:

[15]

In the above formula, the stereo chemistry of the position with the symbol * is of cis-configuration (hereinafter, the same until Working Example 19).

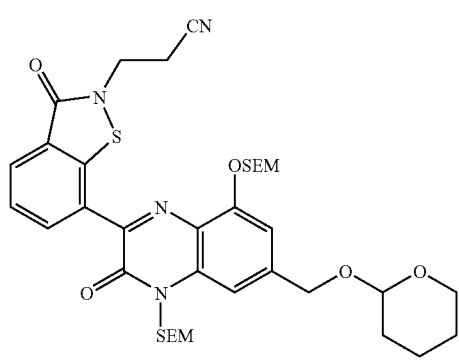
(1)

According to a method similar to the procedure described in Working Example 11-(8), the above tetrahydropyranyl ether derivative (78 mg) was obtained as a yellow solid from the benzyl alcohol derivative (65 mg, 0.10 mmol) obtained in Working Example 14-(7).

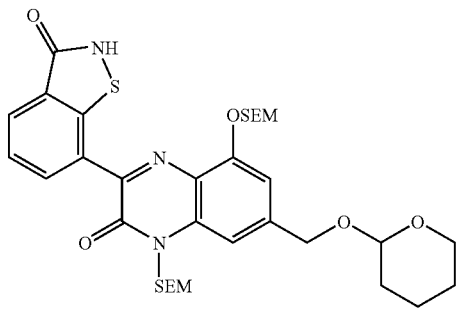
(2)

According to a method similar to the procedure described in Working Example 14-(9), the above de-propionitrile derivative (73 mg) was obtained as an orange solid from the tetrahydropyranyl ether derivative (78 mg, 0.10 mmol) obtained in the above (1).

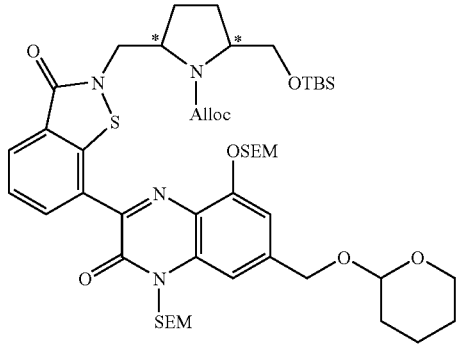
(3)

According to a method similar to the procedure described in Working Example 14-(10), the above racemic N-alkyl-benzoisothiazolone derivative (1.4 g) was obtained as a yellow solid from the de-propionitrile derivative (3.1 g, 4.6 mmol) and the racemic mesylated derivative [A-12] (3.7 g, 9.2 mmol) obtained in the above (2).

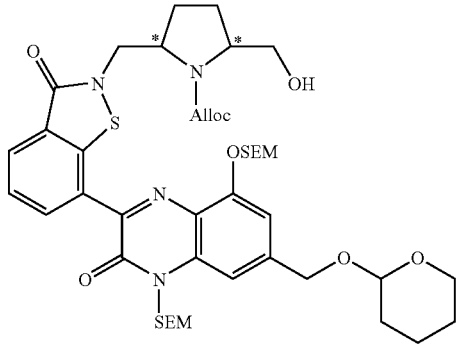
(4)

The racemic N-alkylbenzoisothiazolone derivative (2.2 g, 2.2 mmol) obtained in the above (3) was dissolved in tetrahydrofuran (30 mL), and to the solution was added 1M tetrahydrofuran solution (16 mL) containing tetrabutylammonium fluoride. The solution was stirred at room temperature for 2 hours. The resulting reaction solution was diluted with chloroform (150 mL), and washed with 0.1M phosphate buffer (pH 6.8) and saturated brine. The organic layer was dried over anhydrous magnesium sulfate, filtered, and the filtrate was concentrated. The resulting residue was purified by a column chromatography on silica gel to obtain the above racemic alcohol derivative (1.53 g) as a yellow solid.

µmol) and the racemic amine derivative [A-25] obtained in the above (5).

(7)

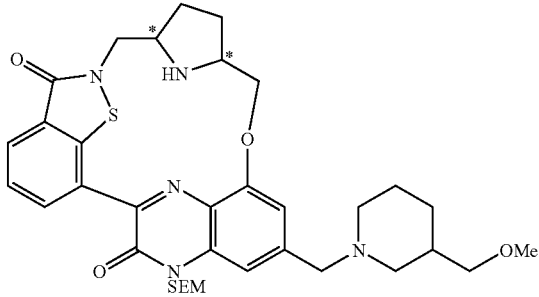

(5)

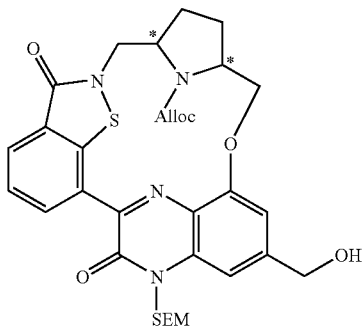

The above benzylamine derivative as a diastereomer mixture (64 mg, 80 mmol) obtained in the above (6) was dissolved in chloroform (1 mL), and to the solution were added dichlorobis(triphenylphosphine)palladium(II) (23 mg, 30 µmol), acetic acid (20 mg, 340 µmol), tributyltin hydride (73 mg, 250 µmol). The mixture was stirred at room temperature for 30 minutes. The resulting reaction solution was purified by a thin layer chromatography to obtain the above de-Alloc derivative as a diastereomer mixture (50 mg) as a yellow oil.

According to a method similar to the procedures described in Working Examples 14-(12) to 14-(13), the above racemic cyclic derivative (124 mg) was obtained as a yellow solid from the racemic alcohol derivative (1.53 g, 1.7 mmol) obtained in the above (4).

(8)

(6)

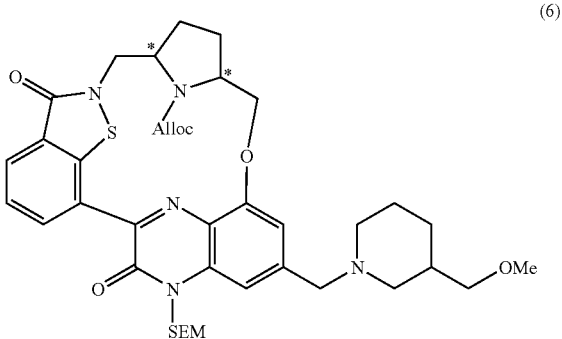

According to a method similar to the procedure described in Working Example 1-(6), the above hydrochloride (27 mg) of the objective compound [15] as a diastereomer mixture was obtained as a yellow solid from the de-Alloc derivative (50 mg, 70 µmol) as a diastereomer mixture obtained in the above (7).

Spectral data of the compound of the above formula [15] are shown below.

According to a method similar to the procedure described in Working Example 14-(14), the above benzylamine derivative as a diastereomer mixture (64 mg) was obtained as a yellow oil from the racemic cyclic derivative (100 mg, 150

$^1$H-NMR (DMSO-d$_6$) δ: 1.60-2.40 (9H, m), 2.60-3.80 (11H, m), 4.20-4.80 (6H, m), 7.15 (1H, J=4.8 Hz), 7.75 (2H, m), 8.18 (1H, d, J=7.7 Hz), 9.43(1H, d, J=7.7 Hz), 11.2 (1H, brs), 13.2 (1H, brs). mass: 548(M+1)$^+$.

Working Example 16

Synthesis of the Compound of the Following Formula [16]:

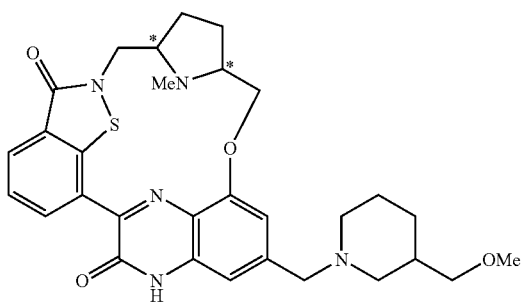

[16]

According to a method similar to the procedure described in Working Example 6-(1), the hydrochloride (6.4 mg) of the objective compound [16] as a diastereomer mixture was obtained as a yellow solid from the compound (10 mg, 20 mmol) obtained as a diastereomer mixture in Working Example 15.

Spectral data of the compound of the above formula [16] are shown below.

$^1$H-NMR (DMSO-$d_6$) δ: 1.60-2.20 (9H, m), 2.20-3.00 (4H, m), 3.00-3.80(10H, m), 4.00-4.60 (6H, m), 7.06 (1H, s), 7.60 (2H, m), 8.07 (1H, d, J=7.6 Hz), 9.37 (1H, d, J=7.6 Hz), 10.0(H, brs), 13.0 (1H, brs) mass: 562(M+1)$^+$.

Working Example 17

Synthesis of the Compound of the Following Formula [17]:

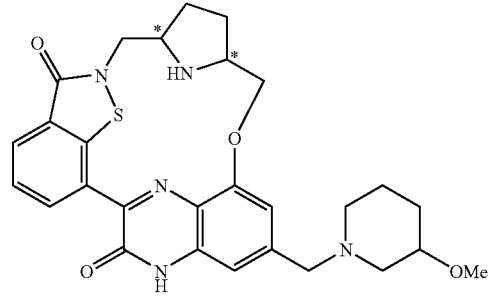

[17]

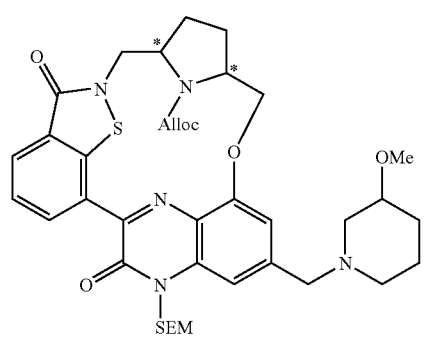

(1)

According to a method similar to the procedure described in Working Example 14-(14), the above benzylamine derivative (183 mg) as a diastereomer mixture was obtained as a yellow oil from the racemic cyclic derivative (210 mg, 320 μmol) obtained in Working Example 15-(5) and the racemic amine derivative [A-22] (147 mg, 970 μmol).

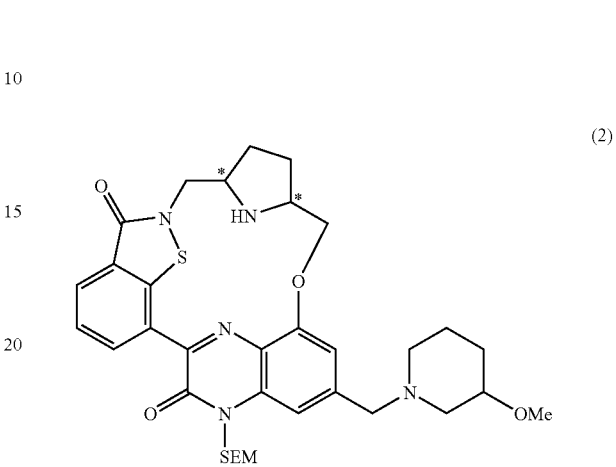

(2)

According to a method similar to the procedure described in Working Example 15-(7), the above de-Alloc derivative (131 mg) as a diastereomer mixture was obtained as a yellow oil from the benzylamine derivative as a diastereomer mixture (183 mg, 240 μmol) obtained in the above (1).

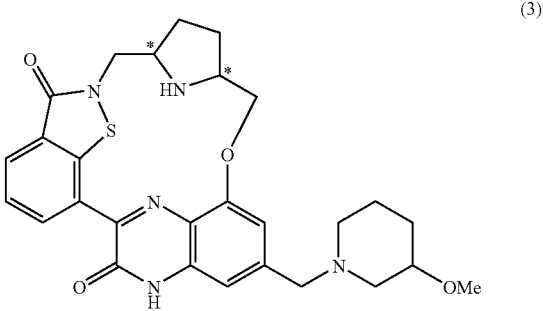

(3)

According to a method similar to the procedure described in Working Example 11-(18), the hydrochloride (51.4 mg) of the objective compound [17] was obtained as a yellow solid from the de-Alloc derivative (131 mg, 240 μmol) as a diastereomer mixture obtained in the above (2).

Spectral data of the compound of the above formula [17] are shown below.

$^1$H-NMR (DMSO-$d_6$) δ: 1.60-2.40 (12H, m), 3.20-3.80 (7H, m), 4.20-4.80 (5H, m), 7.20 (1H, m), 7.75 (2H, m), 8.18 (1H, d, J=8.0 Hz), 9.42 (1H, d, J=8.0 Hz), 9.80 (1H, brs), 11.7 (1H, brs). mass: 534(M+1)$^+$.

Working Example 18

Synthesis of the Compound of the Following Formula [18]:

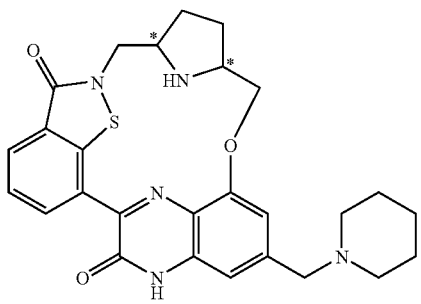

[18]

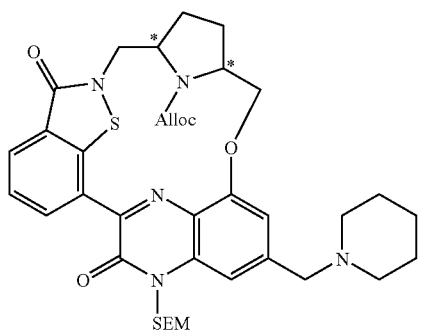

(1)

According to a method similar to the procedure described in Working Example 14-(14), the above racemic benzylamine derivative (22 mg) was obtained as a yellow solid from the racemic cyclic derivative (65 mg, 100 µmol) obtained in the Working Example 15-(5) and piperidine.

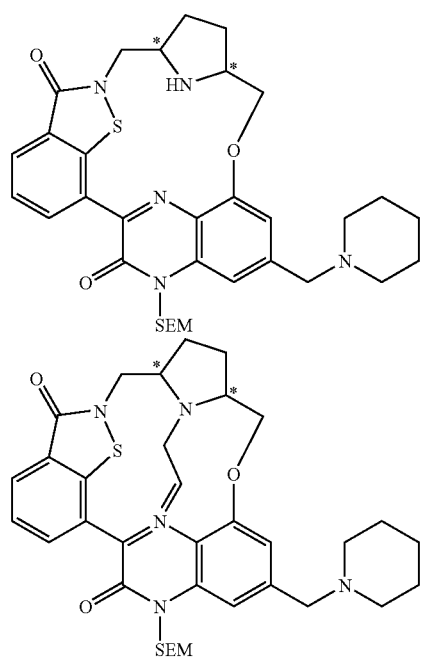

(2)

The racemic benzylamine derivative (22 mg, 30 µmol) obtained in the above (1) was dissolved in tetrahydrofuran (1 mL), and to the solution were added formic acid (7 mg, 150 µmol), diethylamine (16 µL, 830 µmol) and tetrakis(triphenylphosphine)palladium(0) (1.73 mg, 1.5 µmol) under ice-cooling. The mixture was stirred at room temperature for 3 hours. Aqueous sodium hydrogencarbonate was added to the resulting reaction solution, followed by extraction with chloroform. The organic layer was washed with saturated brine, dried over anhydrous magnesium sulfate, and filtered. The filtrate was concentrated, and purified by a thin layer chromatography to obtain the above racemic N-allyl derivative (7.1 mg, 11 µmol) as a yellow solid and the above racemic N—H derivative (6.9 mg) as a yellow solid, respectively.

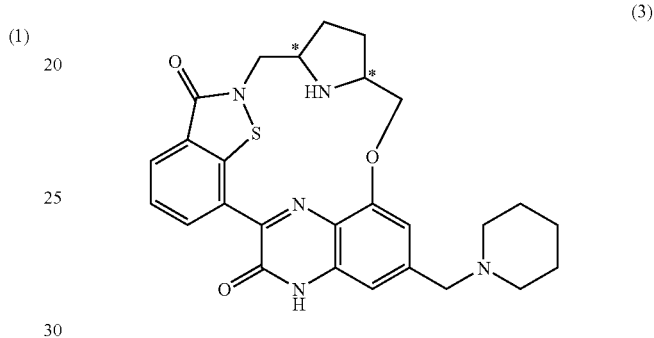

(3)

According to a method similar to the procedure described in Working Example 1-(6), the hydrochloride (5.6 mg) of the racemic objective derivative [18] was obtained as a yellow solid from the racemic N—H derivative (6.9 mg, 11 µmol) obtained in the above (2).

Spectral data of the compound of the above formula [18] are shown below.

$^1$H-NMR (DMSO-$d_6$) δ: 1.20-2.50 (10H, m), 2.60-3.80 (4H, m), 4.20-4.80 (8H, m), 7.17 (1H, s), 7.75 (1H, t, J=7.7 Hz), 7.75 (1H, s), 8.18 (1H, d, J=7.7 Hz), 9.42 (1H, d, J=7.7 Hz), 11.2 (1H, brs), 13.2 (1H, brs). mass: 506(M+1)$^+$.

Working Example 19

Synthesis of the Compound of the Following Formula:

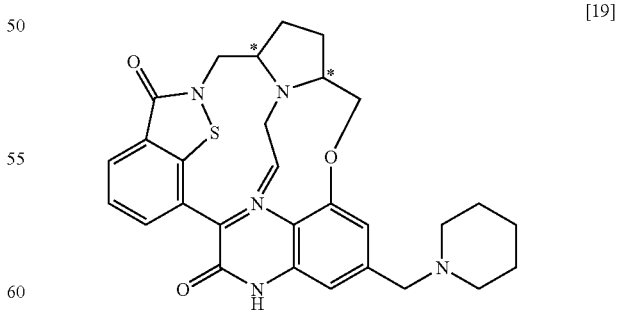

[19]

According to a method similar to the procedure described in Working Example 1-(6), the hydrochloride (4.5 mg, 11 µmol) of the racemic objective derivative [19] was obtained as a yellow solid from the racemic N-allyl derivative (7.1 mg, 11 µmol) obtained in Working Example 18-(2).

Spectral data of the compound of the above formula [19] are shown below.

¹H-NMR (DMSO-d$_6$) δ: 1.20-2.20 (10H, m), 2.20-3.10 (4H, m), 3.10-4.60 (10H, m), 5.10-5.40 (2H, m), 6.05 (1H, m), 7.06 (1H, s), 7.51 (1H, s), 7.63 (1H, t, J=7.5 Hz), 8.06 (1H, d, J=7.7 Hz), 9.37 (1H, d, J=7.7 Hz), 1.0 (1H, brs), 13.0 (1H, brs). mass: 544(M+1)$^+$.

Working Example 20

Synthesis of the Compound of the Following Formula [20]:

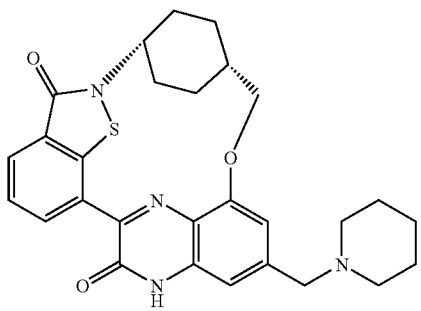

[20]

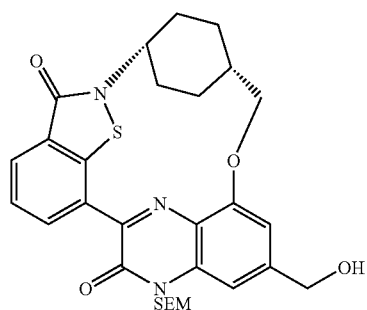

(1)

According to a method similar to the procedures described in Working Example 15-(3) to 15-(5), the above cyclic derivative (82 mg) was obtained as an orange solid from the de-propionitrile derivative (617 mg, 0.900 mmol) obtained in the Working Example 15-(2) and the mesylated derivative [A-13].

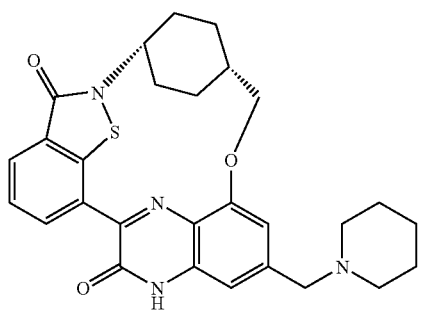

(2)

According to a method similar to the procedures described in Working Examples 14-(14) and 1-(6), the hydrochloride (36 mg) of the objective compound [20] was obtained as a yellow solid from the cyclic derivative (82 mg, 0.145 mmol) obtained in the above (1).

Spectral data of the compound of the above formula [20] are shown below.

¹H-NMR (DMSO-d$_6$) δ: 1.30-2.10 (13H, m), 2.90-3.10 (4H, m), 3.30-3.40 (2H, m), 4.20-4.40 (4H, m), 4.83 (1H, s), 7.05 (1H, s), 7.39 (1H, s), 7.63 (1H, t, J=8.0 Hz), 8.09 (1H, d, J=8.0 Hz), 9.18 (1H, d, J=8.0 Hz), 10.6(1H, brs), 13.0 (1H, s). mass: 503(M+1)$^+$.

Working Example 21

Synthesis of the Compound of the Following Formula [21]:

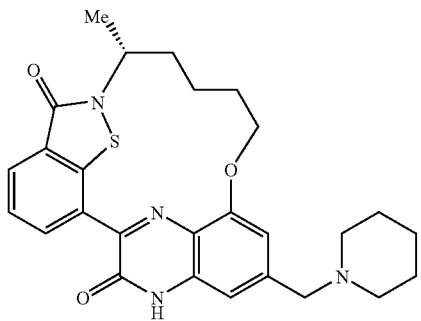

[21]

According to a method similar to the procedures described in Working Example 20, the hydrochloride (90 mg) of the objective compound [21] was obtained as a yellow solid from the de-propionitrile derivative (547 mg, 0.797 mmol) obtained in the Example 15-(2) and the mesylated derivative [A-8].

Spectral data of the compound of the above formula [21] are shown below.

¹H-NMR (DMSO-d$_6$) δ: 1.23 (3H, d, J=8.0 Hz), 1.30-2.00 (9H, m), 2.30-2.60 (3H, m), 2.80-3.00 (2H, m), 3.20-3.40 (2H, m), 4.15 (1H, t, J=10.0 Hz), 4.30-4.60 (4H, m), 7.03 (1H, s), 7.51 (1H, s), 7.62 (1H, t, J=8.0 Hz), 8.03 (1H, d, J=8.0 Hz), 9.41 (1H, d, J=8.0 Hz), 10.8 (1H, brs), 13.1 (1H, s). mass: 491(M+1)$^+$.

Working Example 22

Synthesis of the Compound of the Following Formula [22]:

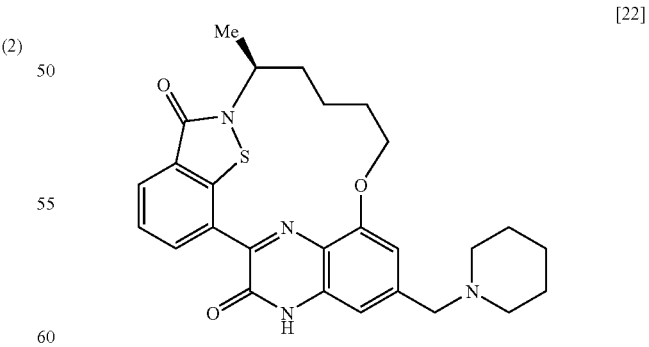

[22]

According to a method similar to the procedure described in Working Example 20, the hydrochloride (130 mg) of the objective compound [22] was obtained as a yellow solid from the de-propionitrile derivative (755 mg, 1.10 mol) obtained in the Working Example 15-(2) and the mesylated derivative [A-9].

Spectral data of the compound of the above formula [22] are shown below.

$^1$H-NMR (DMSO-d$_6$) δ: 1.22 (3H, d, J=8.0 Hz), 1.30-2.00 (9H, m), 2.30-2.60 (3H, m), 2.80-3.00 (2H, m), 3.20-3.40 (2H, m), 4.14 (1H, t, J=10.0 Hz), 4.32-4.34 (2H, m), 4.43-4.48 (1H, m), 4.55-4.60 (1H, m), 7.02 (1H, s), 7.50 (1H, s), 7.61 (1H, t, J=8.0 Hz), 8.02 (1H, d, J=8.0 Hz), 9.40 (1H, d, J=8.0 Hz), 10.8 (1H, brs), 13.0 (1H, s). mass: 491(M+1)$^+$.

Working Example 23

Synthesis of the Compound of the Following Formula [23]:

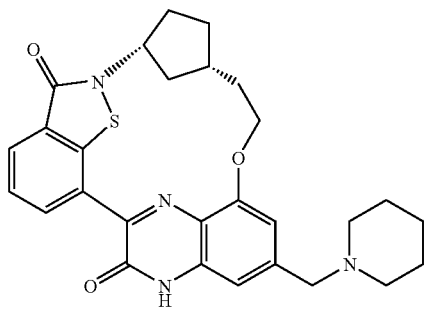

[23]

According to a method similar to the procedure described in Working Example 20, the hydrochloride (59 mg) of the objective compound [23] was obtained as a yellow solid from the de-propionitrile derivative (523 mg, 762 µmol) obtained in Working Example 15-(2) and the mesylated derivative [A-4].

Spectral data of the compound of the above formula [23] are shown below.

$^1$H-NMR (DMSO-d$_6$) δ: 1.50-1.70 (1H, m), 1.90-2.30 (8H, m), 2.40-2.58(2H, m), 2.60-3.00 (4H, m), 3.10-3.30 (2H, m), 3.50-3.80 (2H, m), 4.58-4.64 (3H, m), 4.82-5.00 (1H, m), 5.18-5.22 (1H, m), 7.36 (1H, s), 7.80 (1H, s), 7.90 (1H, t, J=7.7 Hz), 8.30 (1H, d, J=7.7 Hz)9.54 (1H, d, J=7.7 Hz), 13.2 (1H, s). mass: 503(M+1)$^+$.

Working Example 24

Synthesis of the Compound of the Following Formula [24]:

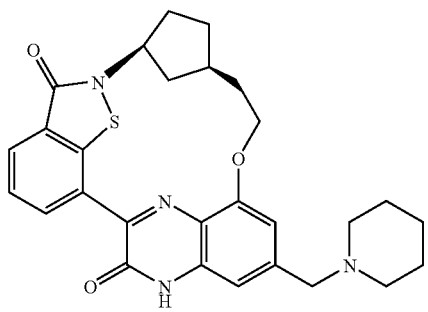

[24]

According to a method similar to the same procedure as Working Example 23, the hydrochloride (59 mg) of the objective compound [24] was obtained from the de-propi-onitrile derivative obtained in Working Example 15-(2) and the mesylated derivative [A-6].

Spectral data of the compound of the above formula [24] are shown below.

$^1$H-NMR (DMSO-d$_6$) δ: 1.50-1.70 (1H, m), 1.90-2.30 (8H, m), 2.40-2.58 (2H, m), 2.60-3.00 (4H, m), 3.10-3.30 (2H, m), 3.50-3.80 (2H, m), 4.58-4.64 (3H, m), 4.82-5.00 (1H, m), 5.18-5.22 (1H, m), 7.36 (1H, s), 7.80 (1H, s), 7.90 (1H, t, J=7.7 Hz), 8.30 (1H, d, J=7.7 Hz)9.54 (1H, d, J=7.7 Hz), 10.8 (1H, brs), 13.2 (1H, s). mass: 503(M+1)$^+$.

Working Example 25

Synthesis of the Compound of the Following Formula [25]:

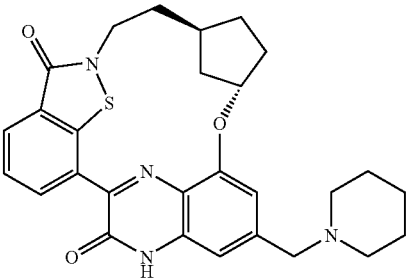

[25]

According to a method similar to the procedures described in Working Examples 14-(10) to 14-(14) and 1-(6), the hydrochloride (14 mg) of the objective compound [25] was obtained as a yellow solid from the de-propionitrile derivative (145 mg) obtained in Working Example 14-(9) and the mesylated derivative [A-7] (193 mg).

Spectral data of the compound of the above formula [25] are shown below.

$^1$HNMR (DMSO-d$_6$) δ: 1.30-1.55 (2H, m), 1.60-1.75 (4H, m), 1.75-2.05 (5H, m), 2.32 (2H, m), 2.65 (4H, m), 2.85-2.95 (2H, m), 4.00-4.15 (1H, m), 4.30-4.40 (2H, m), 4.50-4.60 (1H, m), 5.27 (1H, m), 7.00 (1H, s), 7.16(1H, s), 7.63 (1H, m), 8.08 (1H, d, J=7.6 Hz), 9.31 (1H, d, J=7.2 Hz), 9.88 (1H, brs). mass: 503(M+1)$^+$.

Working Example 26

Synthesis of the Compound of the Following Formula [26]:

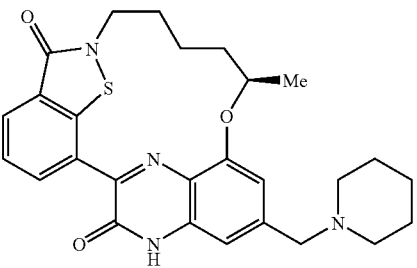

[26]

According to a method similar to the procedures described in Working Examples 14-(10) to 4-(14), and 1-(6), the hydrochloride (63.9 mg) of the objective compound [26] was obtained as a yellow solid from the de-propionitrile derivative (456 mg, 637 µmol) obtained in Working Example 14-(9) and the mesylated derivative [A-10].

Spectral data of the compound of the above formula [26] are shown below.

$^1$H-NMR (DMSO-$d_6$) δ: 1.39-1.50 (4H, m), 1.69-1.86 (7H, m), 2.08-2.11(4H, m), 2.88-2.93 (2H, m), 3.25-3.37 (2H, m), 3.55-3.70 (1H, m), 4.01-4.41 (3H, m), 4.91-4.92 (1H, m), 6.96 (1H, s), 7.44 (1H, s), 7.50-7.62 (1H, m), 7.95 (1H, d, J=7.3 Hz), 9.27 (1H, d, J=8.1 Hz), 13.0 (1H, brs). mass: 491(M+1)$^+$.

Working Example 27

Synthesis of the Compound of the Following Formula [27]:

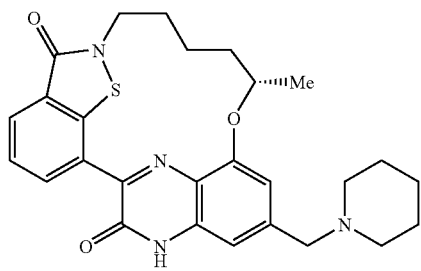

[27]

According to a method similar to the procedure as Working Example 26, the hydrochloride (63 mg) of the objective compound [27] was obtained from the mesylated derivative [A-11] and the de-propionitile derivative obtained in Working Example 14-(9).

Spectral data of the compound of the above formula [27] are shown below.

$^1$H-NMR (DMSO-$d_6$) δ: 1.39-1.50 (4H, m), 1.69-1.86 (7H, m), 2.08-2.11(4H, m), 2.88-2.93 (2H, m), 3.25-3.37 (2H, m), 3.55-3.70 (1H, m), 4.01-4.41 (3H, m), 4.91-4.92 (1H, m), 6.96 (1H, s), 7.44 (1H, s), 7.50-7.62 (1H, m), 7.95 (1H, d, J=7.3 Hz), 9.27 (1H, d, J=8.1 Hz), 13.0 (1H, brs). mass: 491(M+1)$^+$.

Working Example 28

Synthesis of the Compound of the Following Formula [28]:

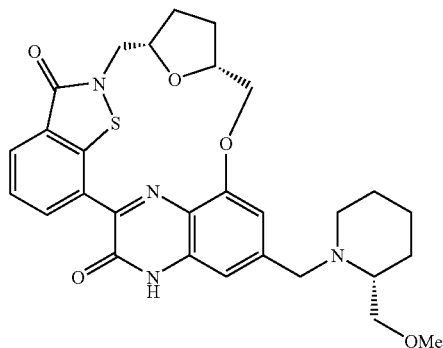

[28]

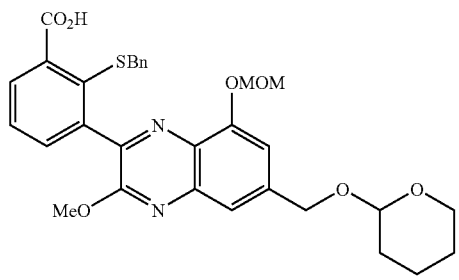

(1)

According to a method similar to the procedure described in Working Example 1-(1), the above carboxylic acid derivative (2.98 g) was obtained as a white solid from the tetrahydropyranyl ether derivative (3.00 g, 6.17 mmol) obtained in Working Example 11-(8).

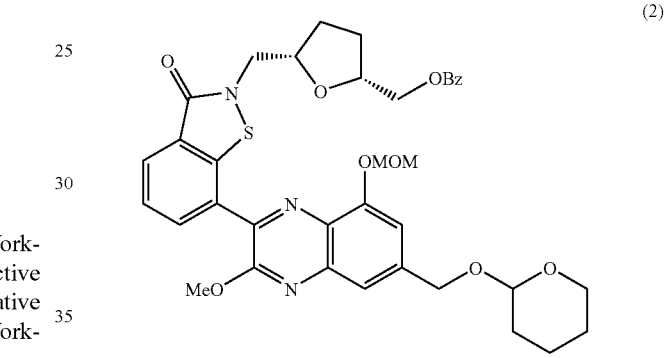

(2)

According to a method similar to the procedures described in Working Examples 1-(2) to 1-(4), the above benzoisothiazolone derivative (120 mg) was obtained as a yellow solid from the carboxylic acid derivative (426 mg, 740 µmol) obtained in the above (1) and the amine derivative [A-14].

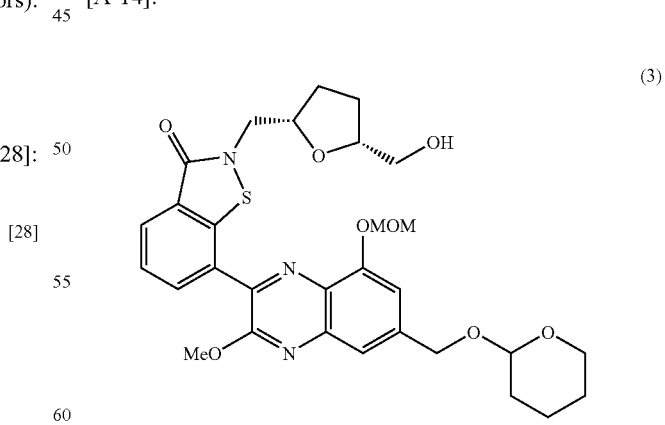

(3)

According to a method similar to the procedure described in Working Example 11-(9), the above alcohol derivative (120 mg) was obtained as a pale yellow solid from the benzoisothiazolone derivative (120 mg, 171 µmol) obtained in the above (2).

(4)

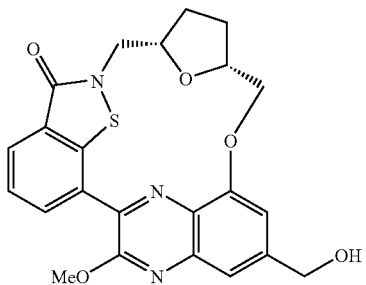

According to a method similar to the procedures described in Working Examples 14-(12) to 14-(13), the above cyclic derivative (32 mg) was obtained as a yellow solid from the alcohol derivative (120 mg) obtained in the above (3).

(5)

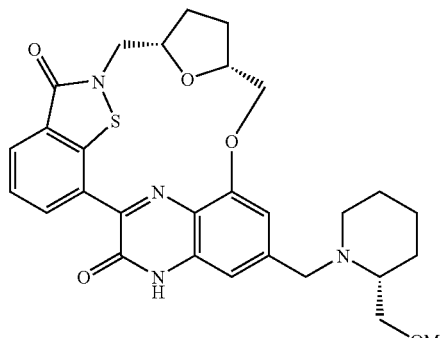

According to a method similar to the procedures described in Working Examples 14-(14) and 11-(18), the above hydrochloride (34 mg) of the objective compound [28] was obtained as a yellow solid from the cyclic derivative (32 mg, 70.9 μmol) obtained in the above (4) and the amine derivative [A-27].

Spectral data of the compound of the above formula [28] are shown below.

$^1$H-NMR (DMSO-$d_6$) δ: 1.35-2.10 (10H, m), 2.20-4.80 (16H, m), 7.07 (1H, s), 7.37 (1H, s), 7.64 (1H, t, J=7.7 Hz), 8.07 (1H, d, J=7.7 Hz), 9.33 (1H, d, J=7.7 Hz), 10.3 (1H, brs), 13.0 (1H, brs). mass: 549(M+1)$^+$.

Working Example 29

Synthesis of the Compound of the Following Formula [29]:

[29]

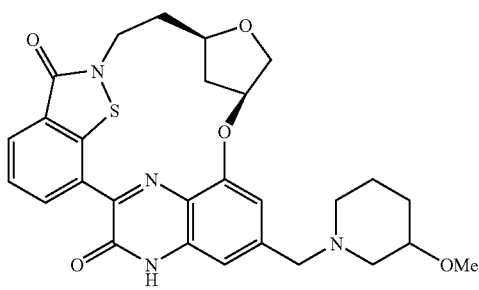

(1)

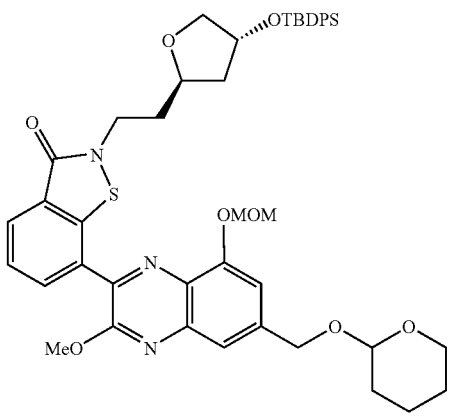

According to a method similar to the procedures described in Working Examples 1-(2) to 1-(3), the above benzoisothiazolone derivative (1.81 g) was obtained as a pale yellow solid from the carboxylic acid derivative (1.31 g, 2.26 mmol) obtained in Working Example 28-(1) and the amine derivative [A-15].

(2)

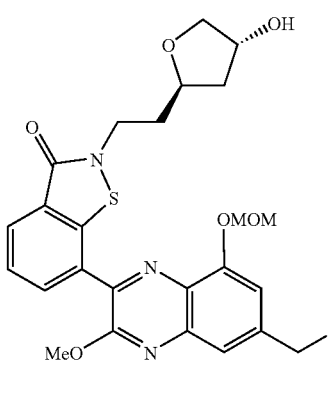

According to a method similar to the procedure described in Working Example 15-(4), the above alcohol derivative (1.08 g) was obtained as a yellow solid from the benzoisothiazolone derivative (1.81 g, 1.89 mmol) obtained in the above (1).

(3)

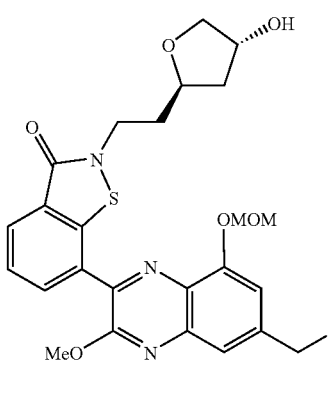

According to a method similar to the procedures described in Working Examples 14-(12) to 14-(13), the above cyclic derivative (740 mg) was obtained as a yellow solid from the alcohol derivative (1.08 g, 1.81 mmol) obtained in the above (2).

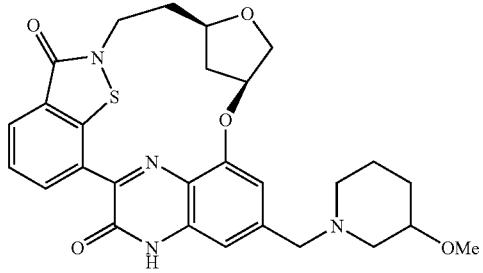

(4)

According to a method similar to the procedures described in Working Examples 14-(14) and 11-(18), the trifluoroacetate (20 mg) of the objective compound [29] as a diastereomer mixture was obtained as a yellow solid from the cyclic derivative (42 mg, 93 μmol) obtained in the above (3) and the racemic amine derivative [A-22].

Spectral data of the compound of the above formula [29] are shown below.

$^1$H-NMR (DMSO-d$_6$) δ: 1.45-1.95 (5H, m), 2.25-2.31 (2H, m), 2.80-3.15(4H, m), 3.20-3.29 (3H, m), 3.57-3.69 (2H, m), 3.82-3.95 (2H, m), 4.02-4.43 (5H, m), 5.60 (1H, m), 7.11 (1H, s), 7.43 (1H, s), 7.61 (1H, t, J=7.6 Hz), 8.05 (1H, d, J=7.6 Hz), 9.31 (1H, d, J=7.6 Hz), 9.49 (1H, brs), 1.3 (1H, brs). mass: 535(M+1)$^+$.

Working Example 30

Synthesis of the Compound of the Following Formula [30]:

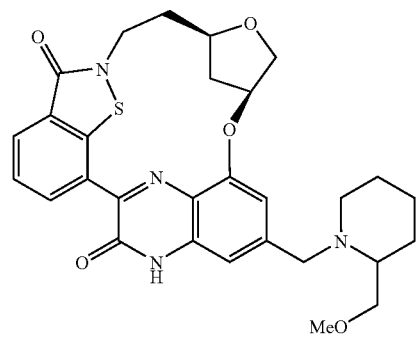

[30]

According to a method similar to the procedures described in Working Examples 14-(14) and 11-(18), the trifluoroacetate (17 mg) of the objective compound [30] as a diastereomer mixture was obtained as a yellow solid from the alcohol derivative (49 mg, 109 μmol) obtained in Working Example 29-(3) and the racemic amine derivative [A-26].

Spectral data of the compound of the above formula [30] are shown below.

$^1$H-NMR (DMSO-d$_6$) δ: 1.42-1.65 (2H, m), 1.64-1.80 (3H, m), 1.94 (1H, m), 2.80-3.15 (3H, m), 3.40 (3H, m), 3.55-3.65 (4H, m), 3.82-3.95 (4H, m), 4.05-4.30 (4H, m), 4.70 (1H, m), 5.6 (1H, m), 7.09 (1H, s), 7.39 (1H, s), 7.61 (1H, t, J=7.6 Hz), 8.05 (1H, d, J=7.6 Hz), 9.31 (1H, d, J=7.6 Hz), 9.35 (1H, brs), 13.0 (1H, brs). mass: 549(M+1)$^+$.

Working Example 31

Synthesis of the Compound of the Following Formula [31]:

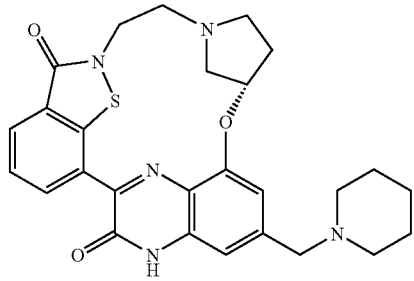

[31]

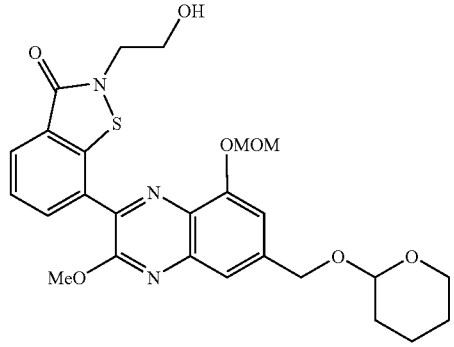

(1)

According to a method similar to the procedure described in Working Example 3-(1), the above benzoisothiazolone derivative (313 mg) was obtained as a pale yellow solid from the carboxylic acid derivative (576 mg, 1.00 mmol) obtained in Working Example 28-(1).

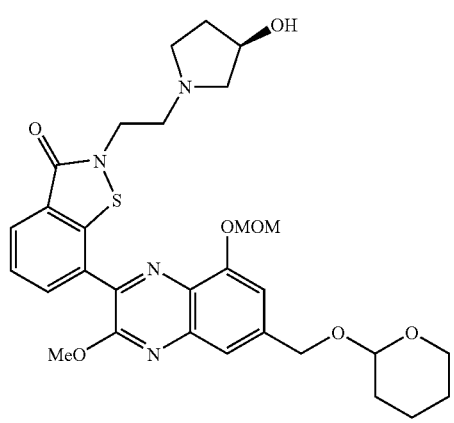

(2)

The benzoisothiazolone derivative (278 mg, 520 μmol) obtained in the above (1) was dissolved in methylene chloride (5 mL), and to the solution were added triethylamine (220 μL, 1.56 mmol) and methanesulfonyl chloride (60 μL, 780 μmol) with stirring at 0° C. The mixture was stirred at the same temperature for 1 hour. 1N aqueous potassium hydrogensulfate was added the resulting reaction solution, and the solution was stirred at room temperature for 30 minutes. Then, the reaction solution was extracted with chloroform. The organic layer was washed with saturated brine, dried with anhydrous sodium sulfate, and filtered. The filtrate was concentrated, and the resulting residue was dried with a vacumpump, and dissolved in N,N-dimethylformamide (10 mL). After potassium carbonate (222 mg, 1.56 mmol) and (R)-3-hydroxypyrrolidine hydrochloride (200 mg, 1.56 mmol) were added thereto, the mixture was heated with stirring at 70° C. for 4 hours. To this reaction solution was added 1N aqueous potassium hydrogensulfate, and the mixture was stirred at room temperature for 30 minutes, then extracted with chloroform. The organic layer was washed with saturated brine, dried over anhydrous sodium sulfate, and filtered. The filtrate was concentrated, and the resulting residue was purified by a column chromatography on silica gel to obtain the above amine derivative (114 mg) as a pale yellow solid.

(3)

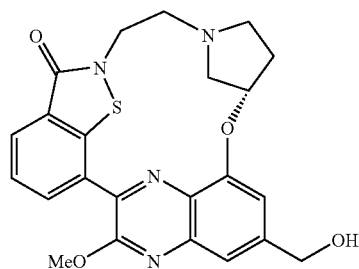

According to a method similar to the procedures described in Working Example 14-(12) to 14-(13), the above cyclic derivative (10 mg) was obtained as a yellow oil from the amine derivative (13 mg, 21 μmol) obtained in the above (2).

(4)

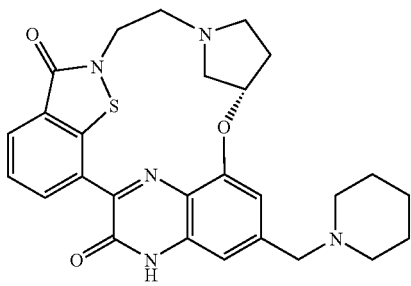

According to a method similar to the procedures described in Working Examples 14-(14) and 11-(18), the hydrochloride (13 mg) of the objective compound [31] was obtained as a yellow solid from the cyclic derivative (12 mg, 21 mmol) obtained in the above (3) and piperidine.

Spectral data of the compound of the above formula [31] are shown below.

$^1$H-NMR (DMSO-$d_6$) δ: 1.20-2.10 (8H, m), 2.20-3.50 (8H, m), 3.50-4.40(6H, m), 5.50 (1H, m), 6.98-7.10 (1H, m), 7.50-7.80 (2H, m), 7.98-8.10 (1H, m), 9.28 (1H, d, J=8.2 Hz). mass: 504(M+1)$^+$.

Working Example 32

Synthesis of the Compound of the Following Formula [32]:

[32]

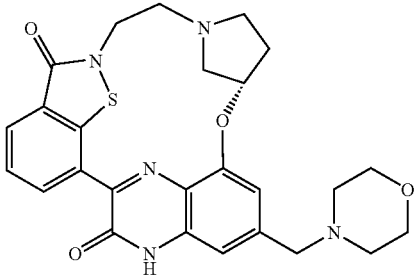

According to a method similar to the procedures described in Working Examples 14-(14) and 11-(18), the hydrochloride (88 mg) of the objective compound [32] was obtained as a yellow solid from the cyclic derivative (143 mg, 317 μmol) obtained in Working Example 31-(3) and morpholine.

Spectral data of the compound of the above formula [32] are shown below.

$^1$H-NMR (DMSO-$d_6$) δ: 1.80-2.60 (6H, m), 2.80-3.50 (3H, m), 3.50-4.30(10H, m), 4.30-4.50 (1H, m)5.50 (1H, m), 6.90-7.05 (1H, m), 7.40-7.80 (2H, m), 7.90-8.10 (1H, m), 9.20-9.30 (1H, m). mass: 506(M+1)$^+$.

Working Example 33

Synthesis of the Compound of the Following Formula [33]:

[33]

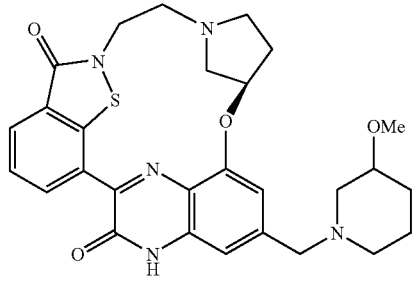

(1)

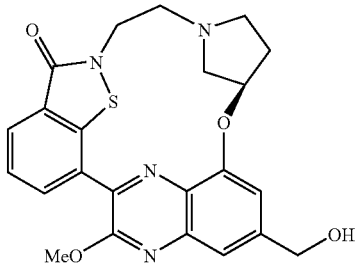

According to a method similar to the procedures as Working Examples 31-(2) and 32-(3), the above cyclic derivative was obtained from the benzoisothiazolone derivative obtained in Working Example 31-(1) and (S)-3-hydroxypyrrolidine hydrochloride.

(2)

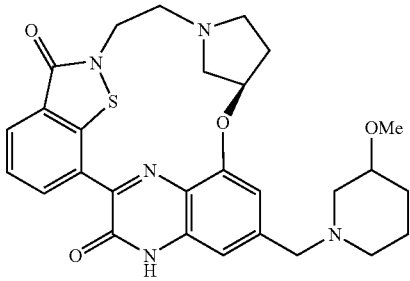

According to a method similar to the procedures described in Working Examples 14-(14) and 11-(18), the trifluoroacetate (37 mg) of the objective compound [33] as a diastereomer mixture was obtained as a yellow solid from the cyclic derivative (68 mg, 151 μmol) obtained in the above (1) and the racemic amine derivative [A-22].

Spectral data of the compound of the above formula [33] are shown below.

$^1$H-NMR (DMSO-$d_6$) δ: 0.80-1.20 (2H, m), 1.40-2.60 (8H, m), 2.60-3.80(7.10-7.20 (1H, m), 7.58 (1H, m), 8.01-8.02 (1H, m), 9.30 (1H, m), 9.48(1H, brs), 13.0 (1H, brs). mass: 534(M+1)$^+$.

Working Example 34

Synthesis of the Compound of the Following Formula [34]:

[34]

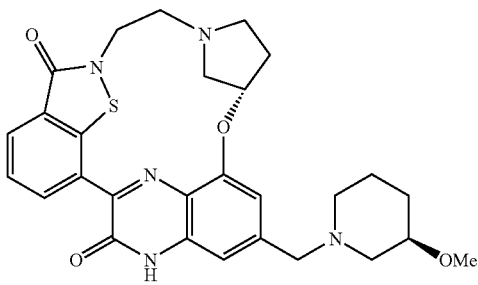

According to a method similar to the procedures described in Working Examples 14-(14) and 11-(18), the trifluoroacetate (27 mg) of the objective compound [34] was obtained as a yellow solid from the cyclic derivative (60 mg, 133 μmol) obtained in Working Example 31-(3) and the racemic amine derivative [A-23].

Spectral data of the compound of the above formula [34] are shown below.

$^1$H-NMR (DMSO-$d_6$) δ: 1.50-2.09 (5H, m), 2.25-2.33 (1H, m), 2.71-3.22(3H, m), 3.24-3.28 (3H, m), 3.31-3.43 (3H, m), 3.66-3.73 (2H, m), 3.80-4.00 (2H, m), 4.05-4.50 (5H, m), 5.31-5.43 (1H, m), 7.00-7.29 (1H, m),7.55-7.75 (2H, m), 8.03-8.15 (1H, m), 9.30-9.35 (1H, m), 9.65 (1H, brs), 12.9-13.2 (1H, m). mass: 534(M+1)$^+$.

Working Example 35

Synthesis of the Compound of the Following Formula [35]:

[35]

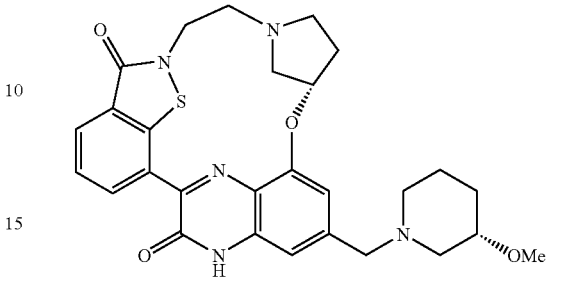

According to a method similar to the procedures described in Working Examples 14-(14) and 11-(18), the trifluoroacetate (25 mg) of the objective compound [35] was obtained as a yellow solid from the cyclic derivative (60 mg, 133 μmol) obtained in Working Example 31-(3) and the amine derivative [A-24].

Spectral data of the compound of the above formula [35] are shown below.

$^1$H-NMR (DMSO-$d_6$) δ: 1.17-1.96 (5H, m), 2.12-2.40 (1H, m), 2.72-3.23(3H, m), 3.23-3.28 (3H, m), 3.38-3.60 (5H, m), 3.60-3.74 (2H, m), 4.12-4.43 (5H, m), 5.35-5.41 (1H, m), 7.06-7.30 (1H, m), 7.50-7.80 (2H, m), 8.03-8.06 (1H, m), 9.31-9.34 (1H, m), 9.64 (1H, brs), 12.9-13.0 (1H, m). mass: 534(M+1)$^+$.

Working Example 36

Synthesis of the Compound of the Following Formula [36]:

[36]

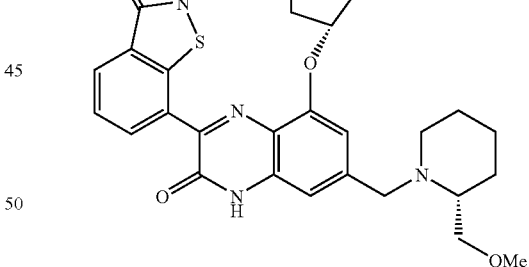

According to a method similar to the procedures described in Working Examples 14-(14) and 11-(18), the trifluoroacetate (41 mg) of the objective compound [36] was obtained as a yellow solid from the cyclic derivative (70 mg, 150 μmol) obtained in Working Example 31-(3) and the amine derivative [A-27].

Spectral data of the compound of the above formula [36] are shown below.

$^1$H-NMR (DMSO-$d_6$) δ: 1.30-1.80 (7H, m), 2.06-2.93 (7H, m), 3.06-3.87(10H, m), 4.25-4.39 (2H, m), 5.35 (1H, brs), 7.02 (1H, s), 7.19 (1H, s), 7.57 (1H, t, J=7.2 Hz), 8.03 (1H, d, J=7.2 Hz), 9.30 (1H, d, J=7.2 Hz), 1.2 (1H, s). mass: 548(M+1)$^+$.

Working Example 37

Synthesis of the Compound of the Following Formula [37]:

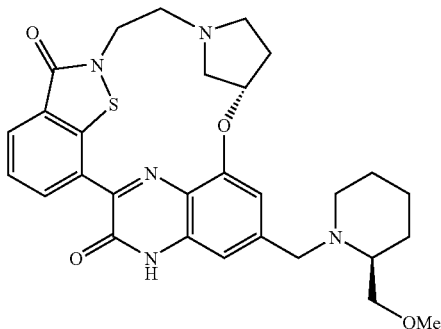

[37]

According to a method similar to the procedures described in Working Examples 14-(14) and 11-(18), the trifluoroacetate (41 mg) of the objective derivative [37] was obtained as a yellow solid from the cyclic derivative (70 mg, 150 mmol) obtained in Working Example 31-(3) and the amine derivative [A-28].

Spectral data of the compound of the above formula [37] are shown below.

$^1$H-NMR (DMSO-$d_6$) δ: 1.30-1.80 (7H, m), 2.06-2.93 (7H, m), 3.06-3.87(10H, m), 4.25-4.39 (2H, m), 5.35 (1H, brs), 7.02 (1H, s), 7.19 (1H, s), 7.57 (1H,tJ=7.2 Hz), 8.03 (1H, d, J=7.2 Hz), 9.30 (1H, d, J=7.2 Hz), 1.2 (1H, s). mass: 548(M+1)$^+$.

Working Example 38

Synthesis of the Compound of the Following Formula [38]:

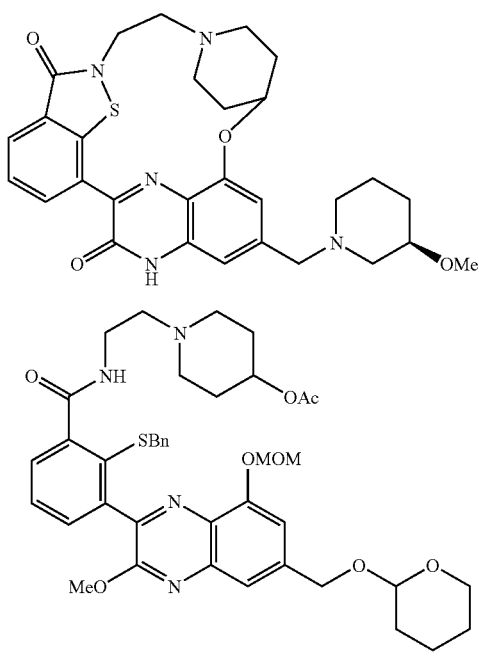

[38]

(1)

According to a method similar to the procedure described in Working Example 1-(2), the above amide derivative (250 mg) was obtained as an orange solid from the carboxylic acid derivative (200 mg, 340 μmol) obtained in Working Example 28-(1) and the amine derivative [A-16].

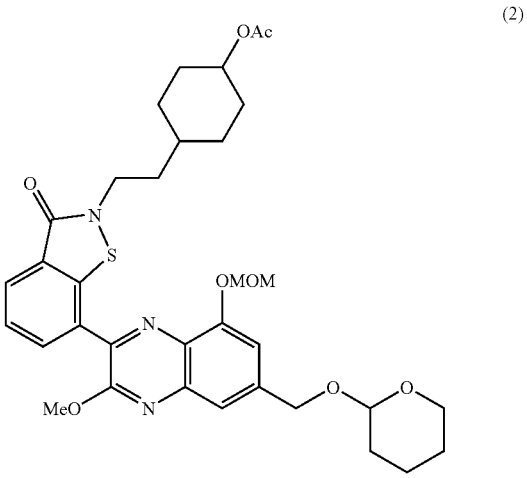

(2)

The amide derivative (190 mg, 0.26 mmol) obtained in the above (1) was dissolved in methylene chloride (5.0 mL) under a nitrogen atmosphere, and N-methylpyrrolidine (104 μL, 1.04 mmol) was added thereto. The reaction solution was cooled to –78° C., and a solution of sulfuryl chloride in methylene chloride (1.04 mL, 0.5M, 0.52 mmol) was added dropwise at –78° C. The reaction solution was stirred at the same temperature for 1 hour. The resulting reaction solution was poured into an aqueous solution of sodium sulfite and potassium carbonate, and then extracted with chloroform twice. The organic layer was dried over anhydrous sodium sulfate, filtered, and concentrated. The resulting residue was purified by a column chromatography on silica gel to obtain the above benzoisothiazolone derivative (169 mg) as a yellow solid.

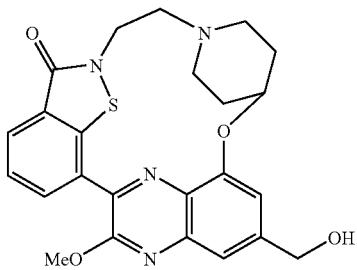

(3)

According to a method similar to the procedures described in Working Examples 11-(9), and 14-(12) to 14-(13), the above cyclic derivative (46 mg) was obtained as a yellow solid from the benzoisothiazolone derivative (225 mg, 340 μmol) obtained in the above (2).

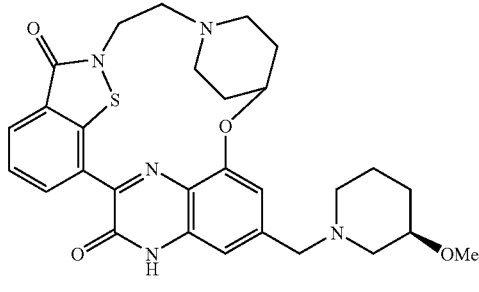

(4)

According to a method similar to the procedures described in Working Examples 14-(14) and 11-(18), the trifluoroacetate. (41 mg) of the objective compound [38] was obtained as a yellow solid from the cyclic derivative (70 mg, 150 μmol) obtained in the above (3) and the amine derivative [A-23].

Spectral data of the compound of the above formula [38] are shown below.

$^1$H-NMR (DMSO-d$_6$) δ: 1.23-2.25 (9H, m), 2.90-3.14 (2H, m), 3.25 (3H, s), 3.28-3.38 (2H, m), 3.43-3.58 (2H, m), 3.63-3.78 (2H, m), 4.10-5.10 (6H, m), 5.43 (1H, brs), 7.02-7.14 (1H, m), 7.32-7.46 (1H, m), 7.66-7.75 (1H, m), 8.08-8.18 (1H, m), 9.46-9.52 (1H, m), 12.9 (1H, s). mass: 548(M+1)$^+$.

Working Example 39

Synthesis of the Compound of the Following Formula [39]:

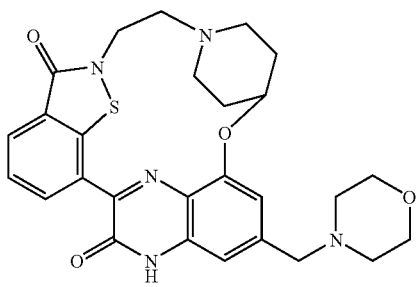

[39]

According to a method similar to the procedures described in Working Examples 14-(14) and 11-(18), the hydrochloride (14 mg) of the objective compound [39] was obtained as a yellow solid from the cyclic derivative (46 mg, 100 μmol) obtained in Working Example 38-(3) and morpholine.

Spectral data of the compound of the above formula [39] are shown below.

$^1$H-NMR (DMSO-d$_6$) δ: 2.08-2.33 (4H, m) 3.03-3.80 (12H, m), 3.84-4.03 (4H, m), 4.20-4.55 (2H, m), 5.58 (1H, brs), 7.03 (1H, s), 7.66 (1H, t, J=8.0 Hz), 7.89 (1H, s), 8.07 (1H, d, J=8.0 Hz), 9.42 (1H, d, J=8.0 Hz), 1.2 (1H, s). mass: 520(M+1)$^+$.

Working Example 40

Synthesis of the Compound of the Following Formula [40]:

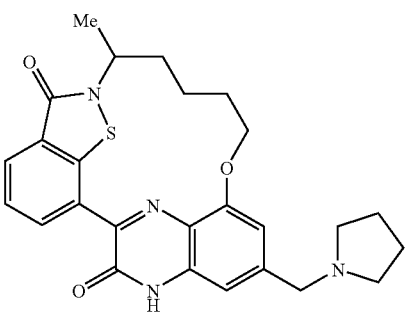

[40]

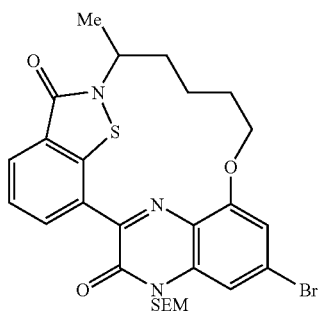

(1)

According to a method similar to the procedures of Working Examples 1-(2) to 1-(5), the above racemic cyclic derivative (2.01 g) was obtained as a yellow solid from the carboxylic acid derivative (6.61 g, 8.88 mmol) prepared in Working Example 14-(2) and a racemate of 5-amino-1-hexanol synthesized by referring to a method similar to the method described in J. Med. Chem., 25 (8) 964 (1982).

(2)

According to a method similar to the procedures described in Working Examples 14-(5) to 14-(6), the above racemic carboxylic acid derivative (464 mg) was obtained as an orange solid from the racemic cyclic derivative (529 mg, 880 μmol) obtained in the above (1).

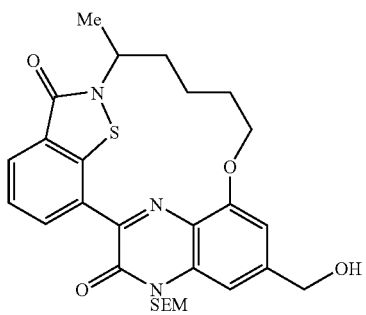

(3)

The racemic carboxylic acid derivative (464 mg, 820 µmol) obtained in the above (2) was dissolved in tetrahydrofuran (50 mL) and N,N-dimethylformamide (14 mL), and then 1,1'-carbonylbis-1H-imidazole (199 mg, 1.23 mmol) was added thereto. The reaction solution was stirred at room temperature for 11 hours, and then lithium tetrahydroborate (35.6 mg, 1.64 mmol) was added. Lithium tetrahydroborate (35.6 mg, 1.64 mmol) was added to the resulting reaction solution, and the mixture was stirred at room temperature for 30 minutes. After that, lithium tetrahydroborate (35.6 mg, 1.64 mmol) was further added thereto, and the mixture was stirred at room temperature for 30 minutes, and then chloroform (50 mL) was added to the reaction solution. After addition of saturated aqueous ammonium chloride (30 mL), the solution was extracted with chloroform. The organic layer was washed with saturated brine, and dried over anhydrous magnesium sulfate, and filtered. The filtrate was concentrated in vacuo, and the resulting residue was evaporated azeotropically using toluene. The resulting residue was dissolved in methylene chloride (30 mL) and chloroform (30 mL). After manganese dioxide (214 mg, 2.45 mmol) was added to this solution, the mixture was stirred at room temperature for 2 hours. The resulting reaction solution was filtered through a Celite pad, and then concentrated in vacuo. The residue was purified by a column chromatography on silica gel to obtain the above racemic benzyl alcohol derivative (298 mg) as a yellowish brown solid.

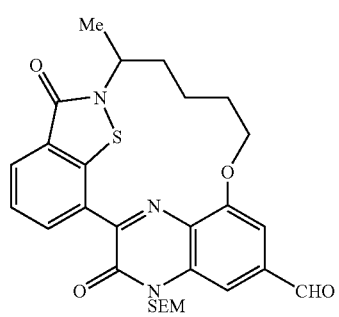

(4)

The racemic benzyl alcohol derivative (298 mg, 540 µmol) obtained in the above (3) was dissolved in chloroform (20 mL), and manganese dioxide (468 mg, 5.38 mmol) was added thereto. The mixture was stirred at room temperature for 11 hours. The resulting reaction solution was filtered through a Celite pad, and the filtrate was concentrated in vacuo. The resulting residue was purified by a thin layer chromatography to obtain the above-racemic aldehyde (175 mg) as a yellowish brown solid.

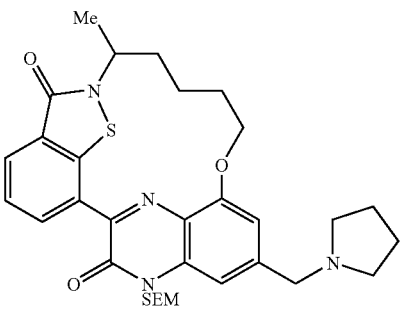

(5)

To chloroform solution (20 mL) containing the racemic aldehyde derivative (100 mg, 180 µmol) obtained in the above (4) and pyrrolidine (121 µL, 1.45 mmol) was added methanol solution (2.42 mL) containing zinc chloride (50 mg, 364 µmol) and sodium cyanotrihydroborate (47 mg, 726 µmol), and the mixture was stirred at room temperature for 12 hours. The resulting reaction solution was concentrated, and the resulting residue was diluted with chloroform, and washed with water and saturated brine. The organic layer was dried over anhydrous magnesium sulfate, and filtered. The filtrate was concentrated in vacuo, and the resulting residue was purified by a thin layer chromatography to obtain the above racemic benzylamine derivative (70 mg) as a yellowish brown solid.

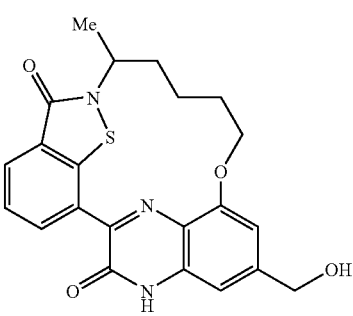

(6)

According to a method similar to the procedure described in Working Example 1-(6), the hydrochloride (49 mg) of the objective compound [40] as a racemate was obtained as a yellow solid from the racemic benzylamine derivative (70 mg, 120 µmol) obtained in the above (5).

Spectral data of the compound of the above formula [40] are shown below.

$^1$H-NMR (DMSO-d$_6$) δ: 1.24 (3H, d, J=6.6 Hz), 1.80-2.08 (10H, m), 3.05-3.12 (2H, m), 3.38-3.45 (2H, m), 4.14-4.21 (1H, m), 4.43-4.52 (3H, m), 4.58-4.63 (1H, m), 7.06 (1H, s), 7.39 (1H, s), 7.65 (1H, t, J=7.8 Hz), 8.06 (1H, d, J=7.8 Hz), 9.45 (1H, d, J=7.8 Hz), 10.8 (1H, brs), 13.0 (1H, s). mass: 477(M+1)$^+$.

Working Example 41

Synthesis of the Compound of the Following Formula [41]:

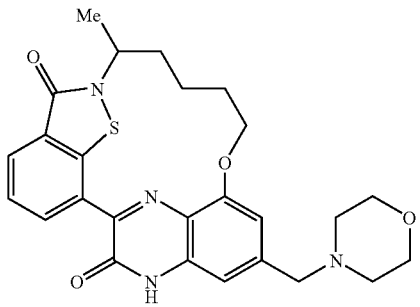

[41]

According to a method similar to the procedures described in Working Examples 40-(5) to 40-(6), the hydrochloride (12 mg) of the objective compound [41] as a racemate was obtained as a yellowish brown solid from the racemic aldehyde derivative (20 mg, 36 μmol) obtained in Working Example 40-(4) and morpholine.

Spectral data of the compound of the above formula [41] are shown below.

$^1$H-NMR (DMSO-d$_6$) δ: 1.22 (3H, d, J=6.3 Hz), 1.76-1.97 (4H, m), 2.24-2.43 (2H, m), 3.11-3.29 (4H, m), 3.81-3.95 (4H, m), 4.11-4.17 (1H, m), 4.41-4.47 (3H, m), 4.56-4.59 (1H, m), 7.02 (1H, s), 7.49 (1H, s), 7.60 (1H, t, J=7.8 Hz), 8.01 (1H, d, J=7.8 Hz), 9.44 (1H, d, J=7.8 Hz), 11.5 (1H, brs), 13.0 (1H, s). mass: 493(M+1)$^+$.

Working Example 42

Synthesis of the Compound of the Following Formula [42]:

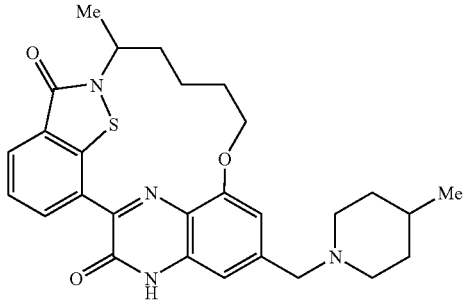

[42]

According to a method similar to the procedures described in Working Examples 14-(14) and 1-(6), the hydrochloride (40 mg) of the objective compound [42] as a racemate was obtained as a yellowish brown solid from the racemic benzyl alcohol derivative (177 mg, 140 μmol) obtained in Working Example 40-(3) and 4-methylpiperidine.

Spectral data of the compound of the above formula [42] are shown below.

$^1$H-NMR (DMSO-d$_6$) δ: 0.91 (3H, d, J=6.3 Hz), 1.24 (3H, d, J=6.9 Hz), 1.38-1.64 (4H, m), 1.74-2.01 (5H, m), 2.25-2.40 (2H, m), 2.88-3.00 (2H, m), 3.11-3.18 (1H, m), 3.25-3.45 (1H, m), 4.15-4.22 (1H, m), 4.33-4.38(2H, m), 4.45-4.51 (1H, m), 4.58-4.64 (1H, m), 7.04 (1H, s), 7.34 (1H, s), 7.66 (1H, t, J=7.8 Hz), 8.07 (1H, d, J=7.8 Hz), 9.45 (1H, d, J=7.8 Hz), 10.1 (1H, brs), 13.1 (1H, s). mass: 505(M+1)$^+$.

Working Example 43

Synthesis of the Compound of the Following Formula [43]:

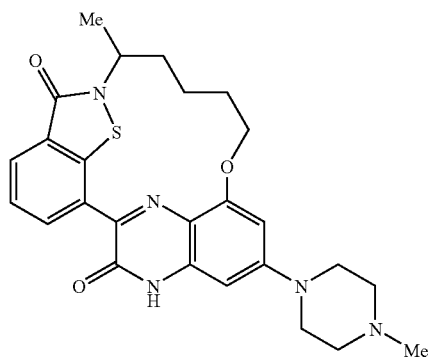

[43]

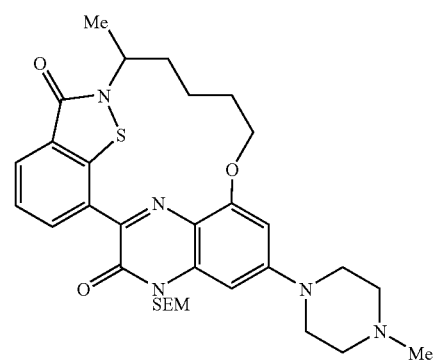

(1)

The racemic cyclic derivative (143 mg, 51 μmol) obtained in Working Example 40-(1) was dissolved in toluene (1.5 mL), and to this solution were added N-methylpiperazine (136 μL, 122 μmol), (R)-(+)-2,2'-bis(di-4-tolylphosphino)-1,1'-binaphthyl (9.5 mg, 15 μmol), tris(dibenzylideneacetone)dipalladium(0)-chloroform adduct (5.3 mg, 5 μmol) and sodium t-butoxide (9.8 mg, 102 μmol). The mixture was stirred at 80° C. for 5 hours. The resulting reaction solution was cooled down to room temperature, extracted with chloroform, and the extract was washed successively with water and saturated brine. The organic layer was dried over anhydrous magnesium sulfate, filtered, and concentrated in vacuo. The resulting residue was purified by a thin layer chromatography to obtain the above racemic 6-piperazine derivative (30 mg) as a yellowish brown liquid.

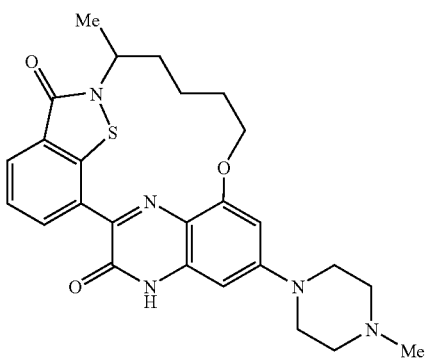

(2)

According to a method similar to the procedure described in Working Example 1-(6), the hydrochloride (11 mg) of the objective compound [43] as a racemate was obtained as a yellowish brown solid from the racemic 6-piperazine derivative (30 mg, 48 µmol) obtained in the above (1).

Spectral data of the compound of the above formula [43] are shown below.

$^{1}$H-NMR (DMSO-d$_{6}$) δ: 1.22 (3H, d, J=6.6 Hz), 1.78-1.90 (4H, m), 2.23-2.39 (2H, m), 2.83 (3H, d, J=3.9 Hz), 3.14-3.39 (6H, m), 3.96-4.11 (3H, m), 4.38-4.44 (1H, m), 4.53-4.58 (1H, m), 6.31 (1H, s), 6.68 (1H, s), 7.57 (1H, t, J=7.8 Hz), 7.94 (1H, d, J=7.8 Hz), 9.27 (1H, d, J=7.8 Hz), 10.9 (1H, brs), 12.5 (1H, s). mass: 492(M+1)$^{+}$.

Working Example 44

Synthesis of the Compound of the Following Formula [44]:

[44]

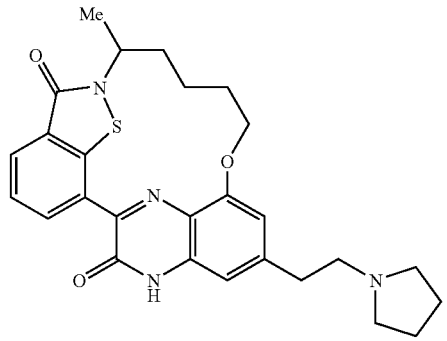

(1)

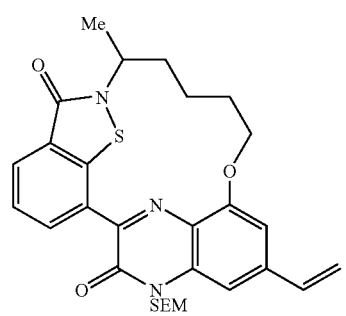

According to a method similar to the procedure described in Working Example 11-(4), the above racemic vinyl derivative (60 mg) was obtained as an orange solid from the racemic cyclic derivative (116 mg, 139 µmol) obtained in Working Example 40-(1).

(2)

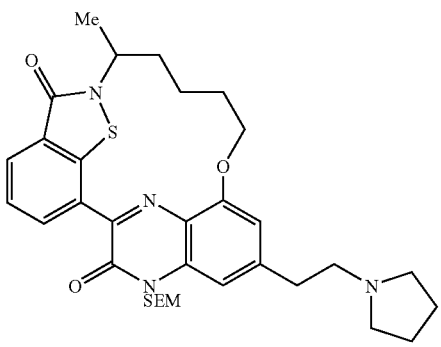

Pyrrolidine (4 mL) was added to the racemic vinyl derivative (23.5 mg, 43 µmol) obtained in the above (1), and the mixture was heated in a sealed tube at 120° C. for 15 hours. The resulting reaction solution was concentrated in vacuo, and the resulting residue was diluted with chloroform, and washed with water and saturated brine. The organic layer was dried over anhydrous magnesium sulfate, and filtered, and concentrated in vacuo. The resulting residue was purified by a thin layer chromatography to obtain the above racemic pyrrolidinylethyl derivative (6.3 mg) as a yellowish brown solid.

(3)

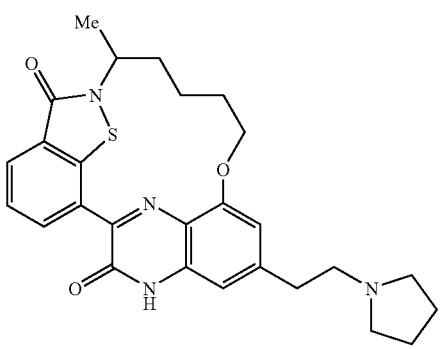

According to a method similar to the procedure described in Working Example 1-(6), the hydrochloride (2.9 mg) of the objective compound [44] as a racemate was obtained as a yellowish brown solid from the racemic pyrrolidinylethyl derivative (6.3 mg, 10 µmol) obtained in the above (2).

Spectral data of the compound of the above formula [44] are shown below.

$^{1}$H-NMR (DMSO-d$_{6}$) δ: 1.23 (3H, d, J=6.3 Hz), 1.85-2.02 (6H, m), 2.26-2.62 (4H, m), 3.05-3.12 (2H, m), 3.25-3.59 (6H, m), 4.10-4.25 (1H, m), 4.40-4.48 (1H, m), 4.54-4.68 (1H, m), 6.84 (1H, s), 6.98 (1H, s), 7.63 (1H, t, J=7.8 Hz), 8.03 (1H, d, J=7.8 Hz), 9.41 (1H, d, J=7.8 Hz), 1.0 (1H, brs), 12.9 (1H, s). mass: 491(M+1)$^{+}$.

Working Example 45

Synthesis of the Compound of the Following Formula [45]:

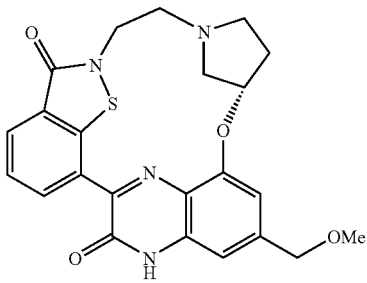

[45]

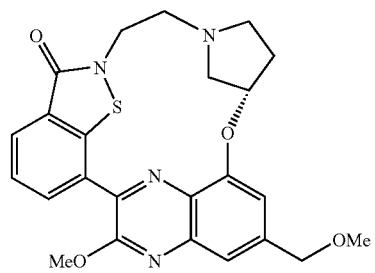

(1)

The cyclic derivative (18.9 mg, 42 μmol) obtained in Working Example 31-(3) and methyl iodide (4 μL, 63 μmol) were dissolved in N,N-dimethylformamide (10 mL). Sodium hydride (2.0 mg, 60% dispersion in oil, 50 μmol) was added to this solution in an ice-bath, and the solution was stirred at the same temperature for 2 hours. After methyl iodide (12 μL, 189 μmol) and sodium hydride (6.0 mg, 60% dispersion in oil, 150 μmol) were further added thereto in an ice-bath, the solution was stirred at room temperature for 7.5 hours. After saturated aqueous ammonium chloride was added to the resulting reaction solution, it was extracted with chloroform. The organic layer was washed with water and saturated brine, dried over anhydrous magnesium sulfate, and filtered. The filtrate was concentrated in vacuo, and the residue was evaporated azeotropically using toluene, and the resulting residue was purified by a thin layer chromatography to obtain the above methoxymethyl derivative (15.6 mg) as a yellowish brown oil.

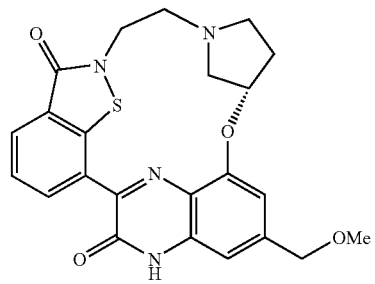

(2)

According to a method similar to the procedure described in Working Example 11-(18), the hydrochloride (6.9 mg) of the objective compound [45] was obtained as a yellowish brown solid from the methoxymethyl derivative (15.6 mg, 33 μmol) obtained in the above (1).

Spectral data of the compound of the above formula [45] are shown below.

$^1$H-NMR (DMSO-$d_6$) δ: 1.93-2.06 (1H, m), 2.21-2.30 (1H, m), 2.72-3.16(4H, m), 3.25-3.45 (4H, m), 3.59-4.10 (2H, m), 4.10-4.15 (1H, m), 4.46-4.55 (2H, m), 5.33-5.43 (1H, m), 6.78-7.04 (2H, m), 7.54-7.71 (1H, m), 8.00-8.12 (1H, m), 9.31 (1H, brs), 12.8 (1H, s). mass: 451(M+1)$^+$.

Working Example 46

Synthesis of the Compound of the Following Formula [46]:

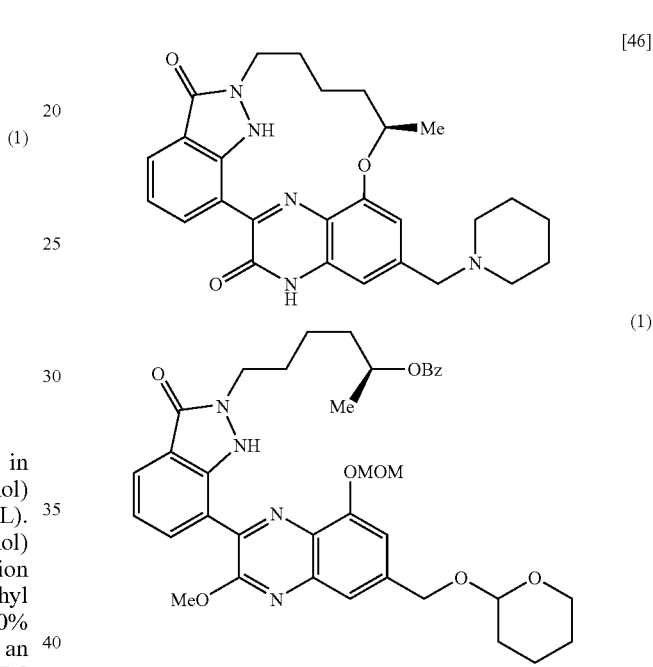

According to a method similar to the procedures described in Working Examples 11-(10) to 11-(12), the above 3-indazolinone derivative (737 mg) was obtained as an orange solid from the carboxylic acid derivative (944 mg, 2.0 mmol) obtained in Working Example 11-(9) and the hydrazine derivative [A-18].

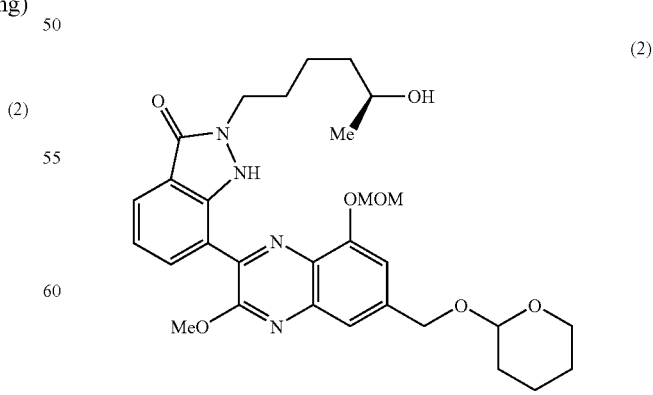

(2)

According to a method similar to the procedure described in Working Example 11-(9), the above alcohol derivative (531 mg) was obtained as an orange solid from the 3-indazolinone derivative (737 mg) obtained in the above (1).

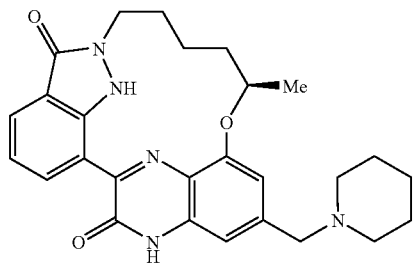

(3)

According to a method similar to the procedure described in Working Examples 11-(14) to 11-(18), the hydrochloride (95 mg) of the objective compound [46] was obtained as a purple solid from the alcohol derivative (531 mg, 940 μmol) obtained in the above (2) and piperidine.

Spectral data of the compound of the above formula [46] are shown below.

$^1$H-NMR (DMSO-d$_6$) δ: 1.30-1.44 (1H, m), 1.48 (3H, d, J=6.0 Hz), 1.65-2.00 (10H, m), 2.05-2.15 (1H, m), 2.82-2.96 (2H, m), 3.20-3.28 (1H, m), 3.30-3.38 (1H, m), 3.86-3.98 (1H, m), 4.12-4.22 (1H, m), 4.24-4.34 (1H, m), 4.36-4.44 (1H, m), 4.76-4.88 (1H, m), 6.95 (1H, s), 7.17 (1H, t, J=8.0 Hz), 7.45 (1H, s), 7.83 (1H, d, J=8.0 Hz), 9.22 (1H, d, J=8.0 Hz), 10.8-10.9 (1H, brs), 11.4 (1H, s), 12.8 (1H, s). mass: 474(M+1)$^+$.

Working Example 47

Synthesis of the Compound of the Following Formula [47]:

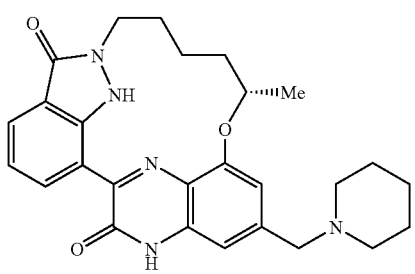

[47]

According to a method similar to the procedures as Working Example 46, the hydrochloride of the objective compound [47] was obtained from the carboxylic acid derivative obtained in Working Example 11-(9) and the hydrazine derivative [A-19].

Spectral data of the compound of the above formula [47] are shown below.

$^1$H-NMR (DMSO-d$_6$) δ: 1.30-1.44 (1H, m), 1.48 (3H, d, J=6.0 Hz), 1.65-2.00 (10H, m), 2.05-2.15 (1H, m), 2.82-2.96 (2H, m), 3.20-3.28 (1H, m), 3.30-3.38 (1H, m), 3.86-3.98 (1H, m), 4.12-4.22 (1H, m), 4.24-4.34 (1H, m), 4.36-4.44 (1H, m), 4.76-4.88 (1H, m), 6.95 (1H, s), 7.17 (1H, t, J=8.0 Hz), 7.45 (1H, s), 7.83 (1H, d, J=8.0 Hz), 9.22 (1H, d, J=8.0 Hz), 10.8-10.9 (1H, brs), 11.4 (1H, s), 12.8 (1H, s). mass: 474(M+1)$^+$.

Working Example 48

Synthesis of the Compound of the Following Formula [48]:

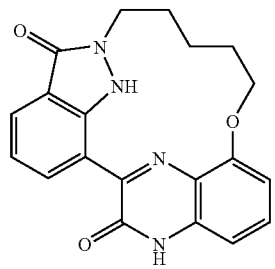

[48]

(1)

Triethylamine (167 μL, 1.20 mmol) and 2-chloro-1,3-dimethylimidazolinium chloride (102 mg, 602 μL) were added to chloroform solution (5 mL) of the carboxylic acid derivative (200 mg, 367 μmol) obtained by reference to Working Example 110-2) described in WO02/02550, and the mixture was stirred for 10 minutes. After that, to this solution was added the hydrazine derivative [A-20] (275 mg, 602 μL), and the mixture was stirred at room temperature for 2 hours. The resulting reaction solution was purified by a thin layer chromatography to obtain the above hydrazide derivative (213 mg) as a yellow oil.

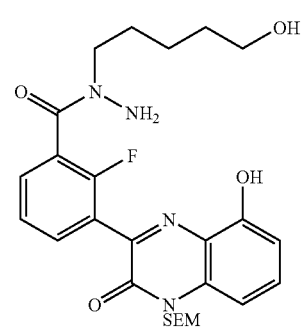

(2)

10% hydrochloric acid/methanol (2 mL) was added to the hydrazide derivative (50 mg, 50.9 μmol) obtained in the above (1), and the mixture was stirred at room temperature for 15 hours. The resulting reaction solution was concentrated, and the resulting residue was purified by a thin layer chromatography to obtain the above de-Boc derivative (28 mg) as a yellow oil.

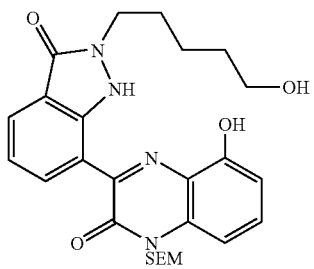

(3)

According to a method similar to the procedure described in Working Example 11-(12), the above 3-indazolinone derivative (14 mg, 27 μmol) was obtained as an orange solid from the de-Boc derivative (28 mg) obtained in the above (2).

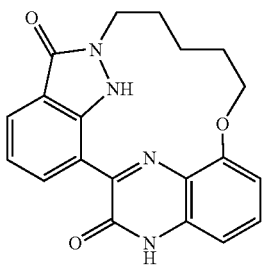

(4)

According to a method similar to the procedures described in Working Examples 1-(5) to 1-(6), the objective compound [48](8 mg) was obtained as an orange solid from the 3-indazolinone derivative (14 mg, 27 μmol) obtained in the above (3).

Spectral data of the compound of the above formula [48] are shown below.

$^1$H-NMR (DMSO-$d_6$) δ: 1.73-2.10 (6H, m), 4.00-4.11 (2H, m), 4.15-4.23(2H, m), 6.84-6.90 (2H, m), 7.17 (1H, t, J=7.7 Hz), 7.45 (1H, t, J=8.2 Hz), 7.83 (1H, d, J=7.7 Hz), 9.24 (1H, d, J=7.7 Hz), 11.6 (1H, s), 12.6(1H, brs). mass: 363(M+1)$^+$ Working Example 49

Synthesis of the Compound of the Following Formula [49]:

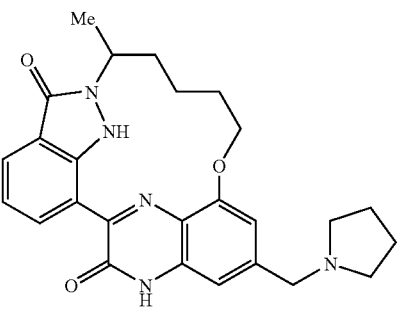

[49]

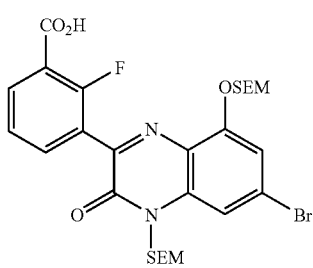

(1)

According to a method similar to the procedure described in Working Example 11-(9), the above carboxylic acid derivative (8.42 g) was obtained as a pale yellow solid from the protected derivative (10 g) with SEM obtained in Working Example 14-(1).

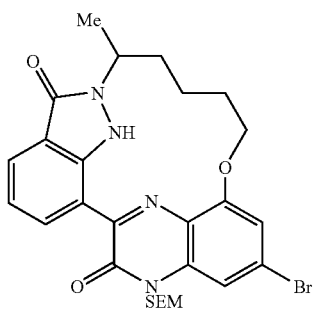

(2)

According to a method similar to the procedures including the steps of up to the macrocyclization described in Working Examples 48-(1) to 48-(4), the above racemic cyclic derivative (6.9 mg) was obtained as a yellowish brown solid from the carboxylic acid derivative (15.6 mg, 33 μmol) obtained in the above (1) and the racemic hydrazine derivative [A-21].

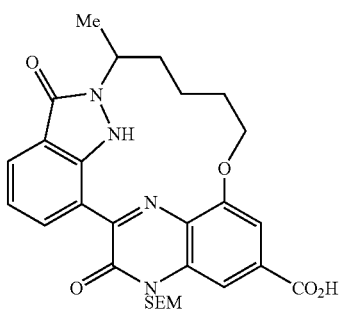

(3)

According to a method similar to the procedure described in Working Example 14-(5) to 14-(6), the above racemic carboxylic acid derivative (188 mg) was obtained as an orange solid from the racemic cyclic derivative (192 mg, 326 μmol) obtained in the above (2).

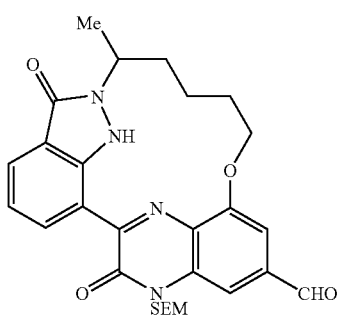

(4)

The racemic carboxylic acid derivative (188 mg, 340 μmol) obtained in the above (3) was dissolved in tetrahydrofuran (10 mL), and to the solution was added 1,1'-carbonylbis-1H-imidazole (83 mg, 510 μmol). The mixture was stirred at room temperature for 17 hours. To the resulting reaction solution were slowly added sodium tetrahydroborate (26 mg, 680 μmol) and water (10 mL), and the mixture was stirred at room temperature for 20 minutes. After saturated aqueous ammonium chloride solution was added to this reaction solution, the mixture was extracted with chloroform. The organic layer was washed with saturated brine, dried over anhydrous magnesium sulfate, filtered, and concentrated in vacuo. The resulting residue was purified by a thin layer chromatography. The resulting compound was dissolved in methylene chloride (6 mL), and manganese dioxide (133 mg, 1.53 mmol) was added thereto. The mixture was stirred at room temperature for 18 hours. The resulting reaction solution was filtered through a Celite pad and the filtrate was concentrated in vacuo. The resulting residue was purified by a thin layer chromatography to obtain the above racemic aldehyde derivative (44 mg) as an orange solid.

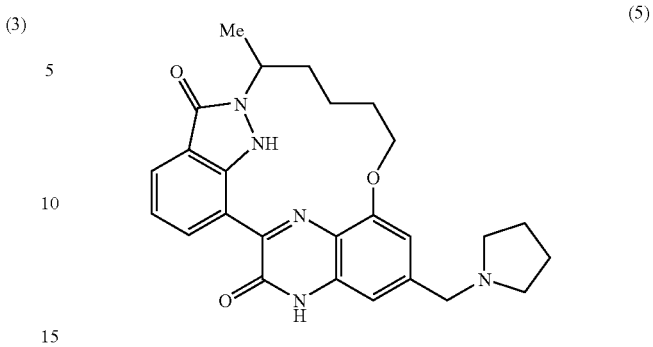

(5)

According to a method similar to the procedures described in Working Examples 40-(5) to 40-(6), the hydrochloride (12 mg) of the racemic objective compound [49] as a racemate was obtained as a deep purple solid from the racemic aldehyde derivative (22 mg, 41 μmol) obtained in the above (4) and pyrrolidine.

Spectral data of the compound of the above formula [49] are shown below.

$^1$H-NMR (DMSO-d$_6$) δ: 1.05 (3H, d, J=5.7 Hz), 1.71-1.85 (6H, m), 1.92-2.17 (4H, m), 2.96-3.05 (2H, m), 3.25-3.45 (2H, m), 4.08-4.15 (1H, m), 4.31-4.39 (3H, m), 4.48-4.54 (1H, m), 6.95 (1H, s), 7.16 (1H, t, J=7.8 Hz), 7.35 (1H, s), 7.75 (1H, d, J=7.8 Hz), 9.02 (1H, d, J=7.8 Hz), 10.5 (1H, brs), 10.9 (1H, s), 12.8 (1H, s). mass: 460(M+1)$^+$.

Working Example 50

Synthesis of the Compound of the Following Formula [50]:

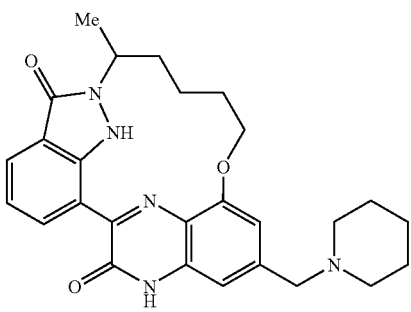

[50]

According to a method similar to the procedures described in Working Example 40-(5) to 40-(6), the hydrochloride (79 mg) of the racemic objective compound [50] as a racemate was obtained as a deep green solid from the racemic aldehyde derivative (102 mg, 169 μmol) obtained in Working Example 49-(4) and piperidine.

Spectral data of the compound of the above formula [50] are shown below.

$^1$H-NMR (DMSO-d$_6$) δ: 1.14 (3H, d, J=6.0 Hz), 1.75-1.86 (10H, m), 2.05-2.19 (2H, m), 2.88-2.95 (2H, m), 3.25-3.56 (2H, m), 4.17-4.24 (1H, m), 4.32-4.46 (3H, m), 4.56-4.73 (1H, m), 7.04 (1H, s), 7.25 (1H, t, J=7.8 Hz), 7.46 (1H, s), 7.85 (1H, d, J=7.8 Hz), 9.10 (1H, d, J=7.8 Hz), 10.2 (1H, brs), 11.0 (1H, s), 12.9 (1H, s). mass: 474(M+1)$^+$.

Working Example 51

Synthesis of the Compound of the Following Formula [51]:

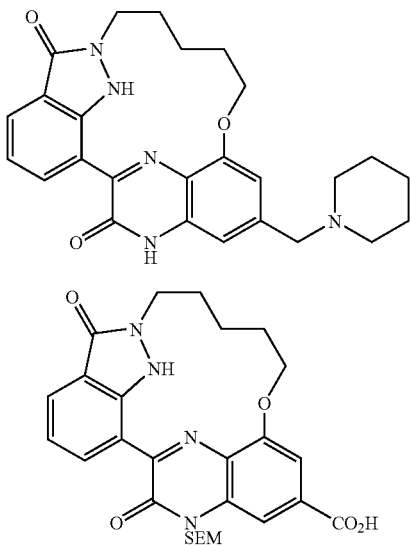

According to a method similar to the procedures up to the step of the macrocyclization described in Working Examples 48-(1) to 48-(4), and 14-(5) to 14-(6), the above carboxylic acid derivative (580 mg) was obtained as a yellowish brown solid from the carboxylic acid derivative (2.48 g, 3.87 mmol) obtained in Working Example 49-(1).

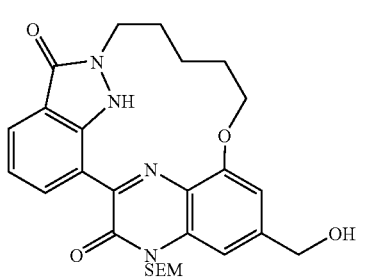

The carboxylic acid derivative (580 mg, 1.08 mmol) obtained in the above (1) was dissolved in tetrahydrofuran (60 mL) and N,N-dimethylformamide (60 mL), and to this solution was added 1,1'-carbonylbis-1H-imidazole (262 mg, 1.62 mmol). The mixture was stirred at 60° C. for 30 minutes, and further at room temperature for 11 hours. Lithium tetrahydroborate (47 mg, 2.16 mmol) was added to the resulting reaction solution, and it was stirred at room temperature for 30 minutes. After that, lithium tetrahydroborate (500 mg, 23 mmol) was further added to this solution, and the mixture was stirred at room temperature for 1 hour, followed by addition of chloroform (100 mL). Then, saturated aqueous ammonium chloride solution (50 mL) was added to this solution, and the mixture was extracted with chloroform. The organic layer was washed with saturated brine, dried over anhydrous magnesium sulfate, and filtered. The filtrate was concentrated in vacuo and evaporated azeotropically using toluene. The resulting residue was dissolved in chloroform (100 mL), and then manganese dioxide (282 mg, 3.24 mmol) was added to the solution. The mixture was stirred at room temperature for 1 hour. The resulting reaction solution was filtered through a Celite pad and concentrated in vacuo. The resulting residue was purified by a column chromatography on silica gel to obtain the above benzyl alcohol derivative (320 mg) as an orange liquid.

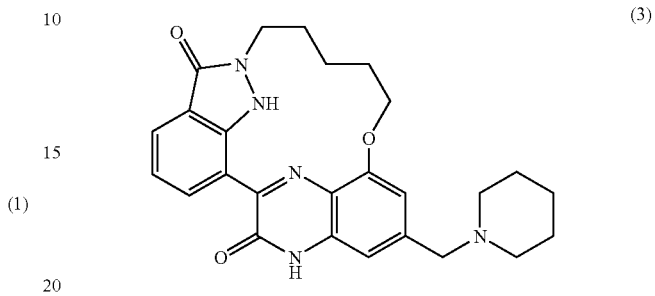

According to a method similar to the procedures described in Working Examples 11-(17) and 1-(6), the hydrochloride (55 mg) of the objective compound [51] was obtained as a deep purple solid from the benzyl alcohol derivative (88 mg, 168 µmol) obtained in the above (2) and piperidine.

Spectral data of the compound of the above formula [51] are shown below.

$^1$H-NMR (DMSO-$d_6$) δ: 1.35-1.40 (1H, m), 1.66-2.26 (11H, m), 2.88-2.94 (2H, m), 3.25-3.45 (2H, m), 4.04-4.10 (2H, m), 4.24-4.30 (2H, m), 4.31-4.37 (2H, m), 7.00 (1H, s), 7.21 (1H, t, J=7.8 Hz), 7.30 (1H, s), 7.87 (1H, d, J=7.8 Hz), 9.26 (1H, d, J=7.8 Hz), 10.3 (1H, brs), 11.6 (1H, s), 12.9 (1H, s). mass: 460(M+1)$^+$.

Working Example 52

Synthesis of the Compound of the Following Formula [52]:

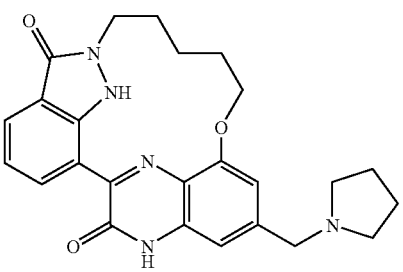

According to a method similar to the procedures described in Working Examples 11-(17) and 1-(6), the hydrochloride (28 mg) of the objective compound [52] was obtained as a deep green solid from the benzyl alcohol derivative (66 mg, 127 µmol) obtained in the above (2) and piperidine.

in Working Example 51-(2) and pyrrolidine.

Spectral data of the compound of the above formula [52] are shown below.

$^1$H-NMR (DMSO-$d_6$) δ: 1.83-1.90 (6H, m) 1.92-2.03 (4H, m), 3.03-3.10(2H, m), 3.36-3.44 (2H, m), 4.05-4.09 (2H, m), 4.22-4.26 (2H, m), 4.41-4.43 (2H, m), 7.00 (1H, s), 7.19 (1H, t, J=7.8 Hz), 7.33 (1H, s), 7.85 (1H, d, J=7.8 Hz), 9.25 (1H, d, J=7.8 Hz), 11.0 (1H, brs), 11.6 (1H, s), 12.9 (1H, s). mass: 446(M+1)$^+$.

Working Example 53

Synthesis of the Compound of the Following Formula [53]:

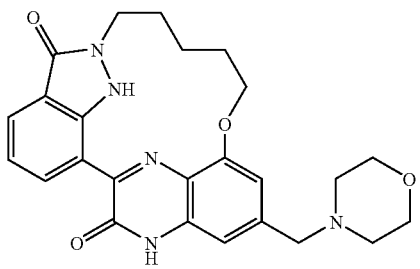

[53]

According to a method similar to the procedures described in Working Examples 11-(17) and 1-(6), the hydrochloride (7 mg) of the objective compound [53] was obtained as a yellow green solid from the benzyl alcohol derivative (10 mg, 19 μmol) obtained in Working Example 51-(2) and morpholine.

Spectral data of the compound of the above formula [53] are shown below.

$^1$H-NMR (DMSO-d$_6$) δ: 1.81-1.95 (4H, m), 2.04-2.26 (2H, m), 3.11-3.21(4H, m), 3.69-3.81 (2H, m), 3.91-3.99 (2H, m), 4.05-4.10 (2H, m), 4.26-4.31 (2H, m), 4.41-4.46 (2H, m), 7.02 (1H, s), 7.21 (1H, t, J=7.8 Hz), 7.26 (1H, s), 7.88 (1H, d, J=7.8 Hz), 9.28 (1H, d, J=7.8 Hz), 10.7 (1H, brs), 11.6 (1H, s), 12.9 (1H, s). mass: 462(M+1)$^+$.

Working Example 54

Synthesis of the Compound of the Following Formula [54]:

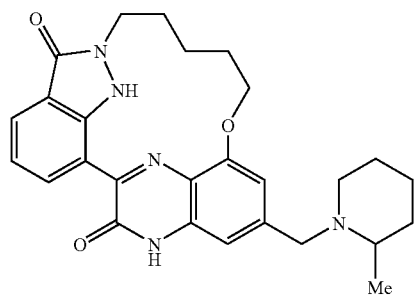

[54]

According to a method similar to the procedures described in Working Examples 11-(17) and 1-(6), the hydrochloride (6 mg) of the racemic objective compound [53] as a racemate was obtained as a deep green solid from the benzyl alcohol derivative (10 mg, 19 μmol) obtained in Working Example 51-(2) and a racemic 2-methylpiperidine.

Spectral data of the compound of the above formula [54] are shown below.

$^1$H-NMR (DMSO-d$_6$) δ: 1.36-1.50 (3H, m), 1.66-1.92 (10H, m), 1.94-2.08 (2H, m), 2.71-2.82 (1H, m), 3.01-3.11 (2H, m), 4.03-4.13 (3H, m), 4.23-4.35 (2H, m), 4.71-4.77 (1H, m), 6.99-7.18 (1H, m), 7.21 (1H, t, J=7.8 Hz), 7.31-7.40 (1H, m), 7.87 (1H, d, J=7.8 Hz), 9.26 (1H, d, J=7.8 Hz),10.2 (1H, brs), 11.6 (1H, s), 12.9 (1H, s). mass: 474 (M+1)$^+$.

Working Example 55

Synthesis of the Compound of the Following Formula [55]:

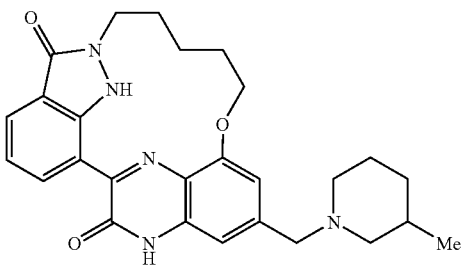

[55]

According to a method similar to the procedures described in Working Examples 11-(17) and 1-(6), the hydrochloride (7 mg) of the objective compound [55] as a racemate was obtained as a green solid from the benzyl alcohol derivative (10 mg, 19 μmol) obtained in Example 51-(2) and a racemic 3-methylpiperidine.

Spectral data of the compound of the above formula [55] are shown below.

$^1$H-NMR (DMSO-d$_6$) δ: 0.86 (3H, d, J=6.6 Hz), 1.75-2.12 (11H, m), 3.20-3.40 (4H, m), 4.04-4.10 (2H, m), 4.25-4.28 (2H, m), 4.32-4.34 (2H, m), 6.99 (1H, s), 7.20 (1H, t, J=7.8 Hz), 7.32 (1H, s), 7.87 (1H, d, J=7.8 Hz), 9.26 (1H, d, J=7.8 Hz), 10.4 (1H, brs), 11.6 (1H, s), 12.9 (1H, s). mass: 474(M+1)$^+$.

Working Example 56

Synthesis of the Compound of the Following Formula [56]:

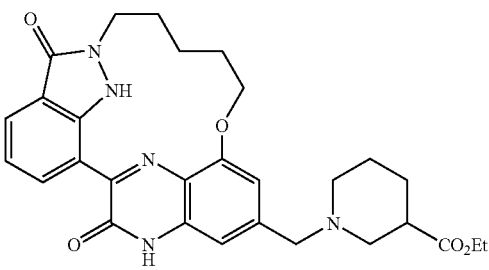

[56]

According to a method similar to the procedures described in Working Example 11-(17) and 1-(6), the hydrochloride (8 mg) of the objective compound [56] as a racemate was obtained as a yellow green solid from the benzyl alcohol derivative (10 mg, 19 μmol) obtained in Working Example 51-(2) and a racemic 3-methoxycarbonylpiperidine.

Spectral data of the compound of the above formula [56] are shown below.

$^1$H-NMR (DMSO-d$_6$) δ: 1.17 (3H, t, J=7.2 Hz), 1.44-1.49 (1H, m), 1.72-1.97 (6H, m), 2.01-2.12 (3H, m), 2.89-3.09 (4H, m), 3.50-3.58 (1H, m), 4.04-4.12 (4H, m), 4.25-4.31 (2H, m), 4.40-4.44 (2H, m), 7.01 (1H, s), 7.22 (1H, t, J=7.8

Hz), 7.24 (1H, s), 7.89 (1H, d, J=7.8 Hz), 9.29 (1H, d, J=7.8 Hz), 10.3 (1H, brs), 11.6 (1H, s), 12.9 (1H, s). mass: 532(M+1)⁺.

Working Example 57

Synthesis of the Compound of the Following Formula [57]:

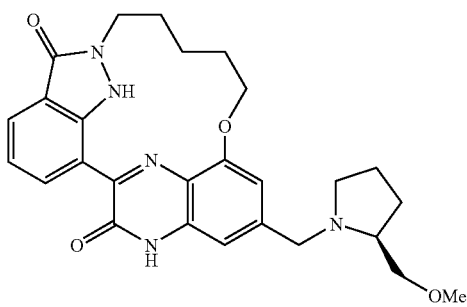

According to a method similar to the procedures described in Working Examples 11-(17) and 1-(6), the hydrochloride (6 mg) of the objective compound [57] was obtained as a deep green solid from the benzyl alcohol derivative (10 mg, 19 μmol) obtained in Working Example 51-(2) and (S)-2-methoxymethylpyrrolidine.

Spectral data of the compound of the above formula [57] are shown below.

¹H-NMR (DMSO-d₆) δ: 1.67-2.07 (9H, m), 2.12-2.25 (1H, m), 3.06-3.28(2H, m), 3.32 (3H, s), 3.66-3.92 (3H, m), 3.95-4.10 (2H, m), 4.11-4.34(3H, m), 4.57-4.63 (1H, m), 6.97 (1H, s), 7.16 (1H, t, J=7.8 Hz), 7.29-7.69 (1H, m), 7.83 (1H, d, J=7.8 Hz), 9.21 (1H, d, J=7.8 Hz), 10.8 (1H, brs), 11.5 (1H, s), 12.8 (1H, s). mass: 490(M+1)⁺.

Working Example 58

Synthesis of the Compound of the Following Formula [58]:

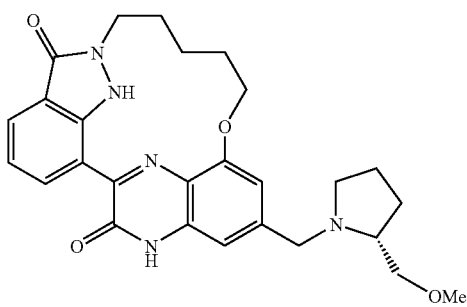

According to a method similar to the procedures described in Working Examples 11-(17) and 1-(6), the hydrochloride (9 mg) of the objective compound [58] was obtained as a deep green solid from the benzyl alcohol derivative (10 mg, 19 μmol) obtained in Working Example 51-(2) and (R)-2-methoxymethylpyrrolidine.

Spectral data of the compound of the above formula [58] are shown below.

¹H-NMR (DMSO-d₆) δ: 1.68-2.20 (10H, m), 3.12-3.19 (2H, m), 3.32 (3H, s), 3.61-3.83 (3H, m), 4.03-4.06 (2H, m), 4.22-4.34 (3H, m), 4.58-4.63 (1H, m), 7.00 (1H, s), 7.19 (1H, t, J=7.8 Hz), 7.29 (1H, m), 7.83 (1H, d, J=7.8 Hz), 9.25 (1H, d, J=7.8 Hz), 10.6 (1H, brs), 11.6 (1H, s), 12.9 (1H, s). mass: 490(M+1)⁺.

Working Example 59

Synthesis of the Compound of the Following Formula [59]:

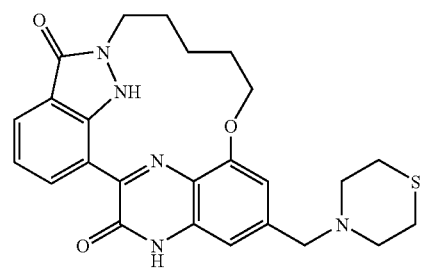

According to a method similar to the procedures described in Working Examples 11-(17) and 1-(6), the hydrochloride (8 mg) of the objective compound [59] was obtained as a deep purple solid from the benzyl alcohol derivative (10 mg, 19 μmol) obtained in Working Example 51-(2) and thiomorpholine.

Spectral data of the compound of the above formula [59] are shown below.

¹H-NMR (DMSO-d₆) δ: 1.83-1.90 (4H, m) 2.03-2.08 (2H, m), 2.71-2.87(2H, m), 3.05-3.21 (2H, m), 3.40-3.45 (2H, m), 3.56-3.75 (2H, m), 4.05-4.11 (2H, m), 4.23-4.32 (2H, m), 4.40-4.49 (2H, m), 7.02 (1H, s), 7.21(1H, t, J=7.8 Hz), 7.29 (1H, s), 7.88 (1H, d, J=7.8 Hz), 9.27 (1H, d, J=7.8 Hz), 10.7 (1H, brs), 11.6 (1H, s), 12.9 (1H, s). mass: 478(M+1)⁺.

Working Example 60

Synthesis of the Compound of the Following Formula [60]:

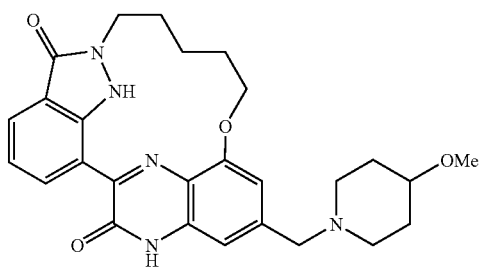

According to a method similar to the procedures described in Working Examples 11-(17) and 1-(6), the hydrochloride (6 mg) of the objective compound [60] was obtained as an ocher solid from the benzyl alcohol derivative (10 mg, 19 μmol) obtained in Working Example 51-(2) and the amine derivative [A-29].

Spectral data of the compound of the above formula [60] are shown below.

¹H-NMR (DMSO-d₆) δ: 1.55-1.65 (1H, m), 1.81-1.98 (5H, m), 2.02-2.27(4H, m), 2.95-3.22 (5H, m), 3.26 (3H, s), 4.05-4.11 (2H, m), 4.25-4.30(2H, m), 4.35-4.42 (2H, m), 7.00-7.04 (1H, m), 7.21 (1H, t, J=7.8 Hz), 7.27 (1H, s), 7.88 (1H, d, J=7.8 Hz), 9.28 (1H, d, J=7.8 Hz), 10.2 (1H, brs), 11.6 (1H, s), 12.9 (1H, s). mass: 490(M+1)⁺.

Working Example 61

Synthesis of the Compound of the Following Formula [61]:

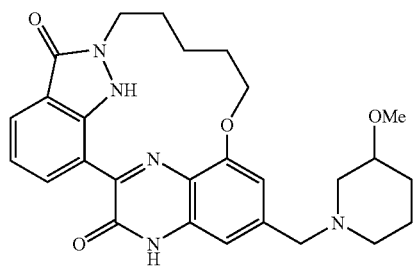

[61]

According to a method similar to the procedures described in Working Examples 11-(17) and 1-(6), the hydrochloride (8 mg) of the objective compound [61] as a racemate was obtained as a green solid from the benzyl alcohol derivative (10 mg, 19 μmol) obtained in Working Example 51-(2) and the racemic amine derivative [A-22].

Spectral data of the compound of the above formula [61] are shown below.

$^1$H-NMR (DMSO-d$_6$) δ: 1.21-1.23 (1H, m), 1.38-1.56 (1H, m), 1.61-1.95 (6H, m), 2.01-2.10 (2H, m), 2.95-3.20 (1H, m), 3.20-3.56 (5H, m), 3.56-3.80 (2H, m), 4.02-4.10 (2H, m), 4.18-4.24 (2H, m), 4.24-4.41 (2H, m), 6.97-7.04 (1H, m), 7.15-7.40 (2H, m), 7.85-7.86 (1H, m), 9.24-9.25 (1H, m), 11.2 (1H, brs), 11.6 (1H, s), 12.8-12.9 (1H, m). mass: 490(M+1)⁺.

Working Example 62

Synthesis of the Compound of the Following Formula [62]:

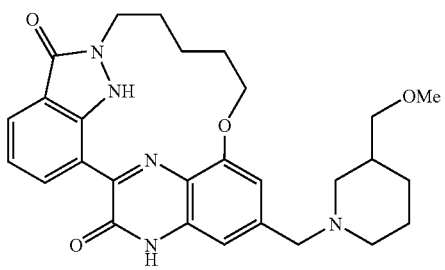

[62]

According to a method similar to the procedures described in Working Examples 11-(17) and 1-(6), the hydrochloride (7 mg) of the objective compound [62] as a racemate was obtained as a green solid from the benzyl alcohol derivative (10 mg, 19 μmol) obtained in Working Example 51-(2) and the racemic amine derivative [A-25].

Spectral data of the compound of the above formula [62] are shown below.

$^1$H-NMR (DMSO-d$_6$) δ: 1.12-1.24 (1H, m), 1.66-1.74 (1H, m), 1.78-1.96(6H, m), 2.00-2.07 (2H, m), 2.17-2.26 (1H, m), 2.67-2.87 (2H, m), 3.20(3H, s), 3.61-3.81 (4H, m), 4.06-4.09 (2H, m), 4.22-4.25 (2H, m), 4.33-4.36 (2H, m), 6.98 (1H, s), 7.19 (1H, t, J=7.8 Hz), 7.34 (1H, s), 7.86(1H, d, J=7.8 Hz), 9.26 (1H, d, J=7.8 Hz), 10.6 (1H, brs), 11.6 (1H, s), 12.9 (1H, s). mass: 504(M+1)⁺.

Working Example 63

Synthesis of the Compound of the Following Formula [63]:

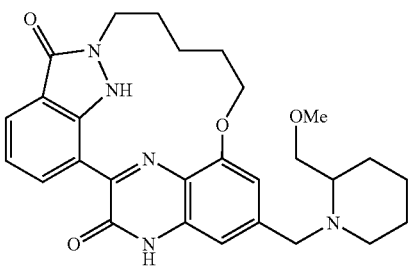

[63]

According to a method similar to the procedures described in Working Examples 11-(17) and 1-(6), the hydrochloride (6 mg) of the objective compound [63] as a racemate was obtained as a deep purple solid from the benzyl alcohol derivative (10 mg, 19 μmol) obtained in Working Example 52-(2) and the racemic amine derivative [A-26].

Spectral data of the compound of the above formula [63] are shown below.

$^1$H-NMR (DMSO-d$_6$) δ: 1.40-2.00 (10H, m), 2.00-2.12 (2H, m), 2.82-3.18 (2H, m), 3.40 (3H, s), 3.77-3.88 (2H, m), 4.02-4.10 (2H, m), 4.11-4.40 (4H, m), 4.66-4.73 (1H, m), 7.01-7.07 (1H, m), 7.18-7.24 (2H, m), 7.88 (1H, d, J=7.8 Hz), 9.28 (1H, d, J=7.8 Hz), 9.96 (1H, brs), 11.6 (1H, s), 12.9 (1H, s). mass: 504(M+1)⁺.

Working Example 64

Synthesis of the Compound of the Following Formula [64]:

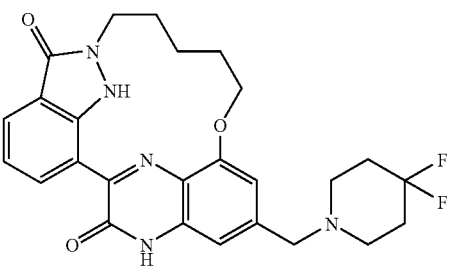

[64]

According to a method similar to the procedures described in Working Examples 11-(17) and 1-(6), the hydrochloride (8 mg) of the objective compound [64] was obtained as a deep purple solid from the benzyl alcohol derivative (10 mg, 19 μmol) obtained in Working Example 51-(2) and 4,4-difluoropiperidine.

Spectral data of the compound of the above formula [64] are shown below.

$^1$H-NMR (DMSO-d$_6$) δ: 1.81-1.96 (4H, m), 2.03-2.10 (2H, m), 2.25-2.45(2H, m), 2.45-2.56 (2H, m), 3.18-3.29 (4H, m), 4.05-4.11 (2H, m), 4.25-4.31 (2H, m), 4.44-4.73 (2H, m), 7.01 (1H, s), 7.21 (1H, t, J=7.8 Hz), 7.32(1H, s), 7.88 (1H, d, J=7.8 Hz), 9.27 (1H, d, J=7.8 Hz), 11.0 (1H, brs), 11.6 (1H, s), 12.9 (1H, s). mass: 496(M+1)+.

Working Example 65

Synthesis of the Compound of the Following Formula [65]:

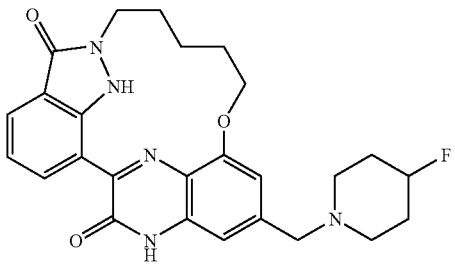

[65]

According to a method similar to the procedures described in Working Examples 11-(17) and 1-(6), the hydrochloride (5 mg) of the objective compound [65] was obtained as a brown solid from the benzyl alcohol derivative (10 mg, 19 μmol) obtained in Working Example 51-(2) and 4-fluoropiperidine.

Spectral data of the compound of the above formula [65] are shown below.

$^1$H-NMR (DMSO-d$_6$) δ: 1.80-2.00 (4H, m), 2.01-2.20 (6H, m), 3.02-3.35(4H, m), 4.05-4.09 (2H, m), 4.25-4.29 (2H, m), 4.30-4.44 (2H, m), 4.92-5.08 (1H, m), 7.03 (1H, s), 7.21 (1H, t, J=7.8 Hz);7.32 (1H, s), 7.88 (1H, d, J=7.8 Hz), 9.27 (1H, d, J=7.8 Hz), 10.6 (1H, brs), 11.6 (1H, s), 12.9 (1H, s). mass: 478(M+1)+.

Working Example 66

Synthesis of the Compound of the Following Formula [66]:

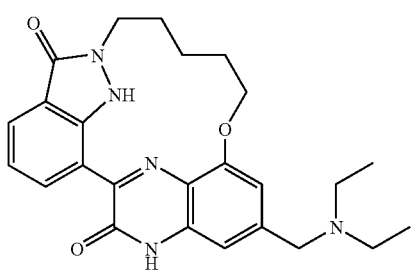

[66]

According to a method similar to the procedures described in Working Examples 11-(17) and 1-(6), the hydrochloride (5 mg) of the objective compound [66] was obtained as a brown solid from the benzyl alcohol derivative (10 mg, 19 μmol) obtained in Working Example 51-(2) and diethylamine.

Spectral data of the compound of the above formula [66] are shown below.

$^1$H-NMR (DMSO-d$_6$) δ: 1.25 (6H, t, J=7.5 Hz), 1.82-1.93 (4H, m), 2.00-2.10 (2H, m), 3.06-3.23 (4H, m), 4.05-4.11 (2H, m), 4.24-4.30 (2H, m), 4.37-4.40 (2H, m), 7.03 (1H, s), 7.22 (1H, t, J=7.8 Hz), 7.24 (1H, s), 7.88 (1H, d, J=7.8 Hz), 9.28 (1H, d, J=7.8 Hz), 9.94 (1H, brs), 11.6 (1H, s), 12.9 (1H, s). mass: 448(M+1)+.

Working Example 67

Synthesis of the Compound of the Following Formula [67]:

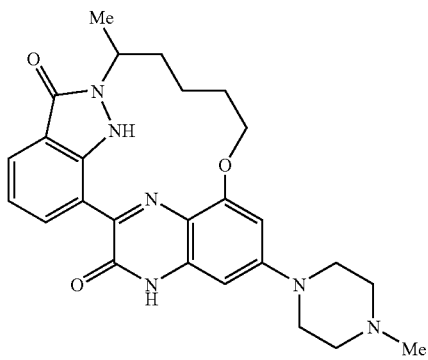

[67]

According to a method similar to the procedure described in Working Example 43, the hydrochloride (8.1 mg) of the objective compound [67] as a racemate was obtained was obtained as a deep green solid from the racemic cyclic derivative (30 mg, 51 μmol) obtained in Working Example 49-(2).

Spectral data of the compound of the above formula [67] are shown below.

$^1$H-NMR (DMSO-d$_6$) δ: 1.14 (3H, d, J=6.3 Hz), 1.76-1.86 (4H, m), 2.08-2.28 (2H, m), 2.84 (3H, d, J=4.8 Hz), 3.13-3.29 (4H, m), 3.40-3.60 (2H, m), 3.99-4.10 (2H, m), 4.10-4.17 (1H, m), 4.38-4.45 (1H, m), 4.60-4.66(1H, m), 6.33 (1H, s), 6.88 (1H, s), 7.21 (1H, t, J=7.8 Hz), 7.75 (1H, d, J=7.8 Hz), 8.98 (1H, d, J=7.8 Hz), 10.6 (1H, brs), 11.0 (1H, s), 12.5 (1H, s). mass: 475(M+1)+.

Working Example 68

Synthesis of the Compound of the Following Formula [68]:

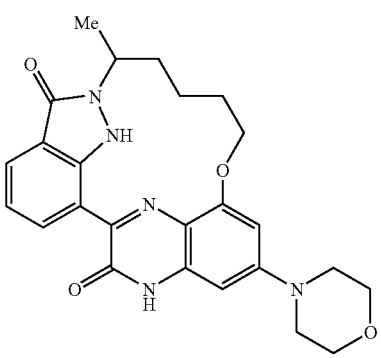

[68]

According to a method similar to the procedure described in Working Example 43, the hydrochloride (11 mg) of the objective compound [68] as a racemate was obtained as a deep green solid from the racemic cyclic derivative (20 mg, 34 μmol) obtained in Working Example 49-(2) and morpholine.

Spectral data of the compound of the above formula [68] are shown below.

$^1$H-NMR (DMSO-d$_6$) δ: 1.14 (3H, d, J=6.0 Hz) 1.71-1.86 (4H, m), 2.06-2.27 (2H, m), 3.17-3.31 (4H, m), 3.75-3.80 (4H, m), 4.01-4.17 (1H, m), 4.37-4.43 (1H, m), 4.58-4.64 (1H, m), 6.28 (1H, s), 6.80 (1H, s), 7.19 (1H, t, J=7.8 Hz), 7.73 (1H, d, J=7.8 Hz), 8.96 (1H, d, J=7.8 Hz), 11.0 (1H, s), 12.4 (1H, s). mass: 462(M+1)$^+$.

Working Example 69

Synthesis of the Compound of the Following Formula [69]:

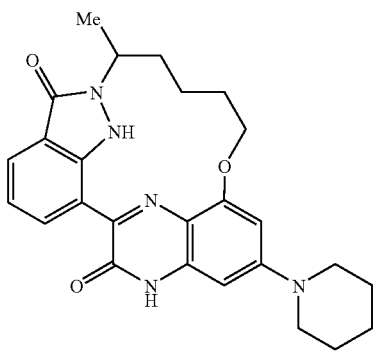

[69]

According to a method similar to the procedure described in Working Example 43, the hydrochloride (11 mg) of the objective compound [69] as a racemate was obtained as a deep green solid from the racemic cyclic derivative (20 mg, 34 μmol) obtained in Working Example 49-(2) and piperidine.

Spectral data of the compound of the above formula [69] are shown below.

$^1$H-NMR (DMSO-d$_6$) δ: 1.14 (3H, d, J=6.3 Hz), 1.73-1.87 (6H, m), 2.06-2.28 (4H, m), 2.72-2.85 (2H, m), 3.12-3.36 (2H, m), 4.01-4.18 (3H, m), 4.38-4.45 (1H, m), 4.53-4.65 (1H, m), 6.32 (1H, s), 6.88 (1H, s), 7.21 (1H, t, J=7.8 Hz), 7.75 (1H, d, J=7.8 Hz), 8.98 (1H, d, J=7.8 Hz), 10.6(1H, brs), 11.0 (1H, s), 12.5 (1H, s). mass: 460(M+1)$^+$.

Working Example 70

Synthesis of the Compound of the Following Formula [70]:

[70]

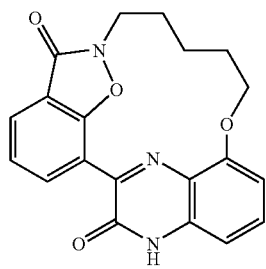

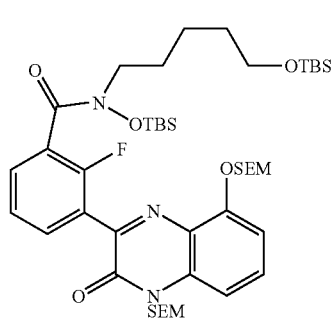

(1)

According to a method similar to the procedure described in Working Example 1-(2), the above hydroxylamide (71 mg) was obtained as a pale yellow oil from the carboxylic acid derivative (82 mg, 190 μmol) which is a starting material in Working Example 48-(1) and the above hydroxylamine derivative [A-30] (98 mg, 282 μmol).

(2)

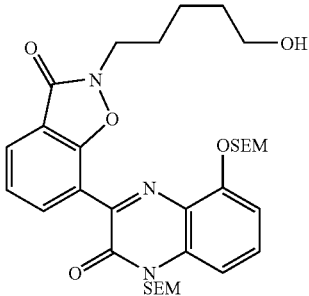

(2)

According to a method similar to the procedure described in Working Example 15-(4), the above 3-benzoisoxazolone derivative (40 mg) was obtained as a yellow solid from the hydroxylamide derivative (71 mg, 80 μmol) obtained in the above (1).

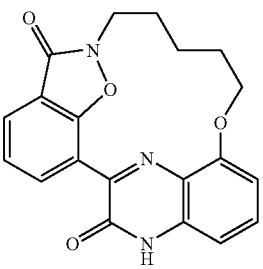

(3)

According to a method similar to the procedures described in Working Examples 1-(4) to 1-(6), the objective compound [70] (9 mg) was obtained as a yellow solid from the 3-benzoisoxazolone derivative (40 mg) obtained in the above (2).

Spectral data of the compound of the above formula [70] are shown below.

$^{1}$H-NMR (DMSO-$d_6$) δ: 1.82 (4H, m), 2.05 (2H, m), 4.05 (2H, m), 4.20 (2H, m), 6.91 (2H, m), 7.44 (2H, m), 7.87 (1H, d, J=7.6 Hz), 9.05 (1H, d=7.6 Hz), 12.6 (1H, s). mass: 364 (M+1)$^+$.

Working Example 71

Synthesis of the Compound of the Following Formula [71]:

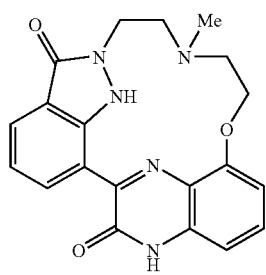

[71]

According to a method similar to the procedure described in Working Example 48, the hydrochloride (84 mg) of the objective compound [71] was obtained as a yellow solid from the carboxylic acid derivative (711 mg, 1.27 mmol) which is a starting material in Working Example 48-(1) and the hydrazine derivative [A-31] (576 mg, 1.65 mmol).

Spectral data of the compound of the above formula [71] are shown below.

$^{1}$H-NMR (DMSO-$d_6$) δ: 3.00 (3H, brs), 3.55-3.75 (2H, m), 4.20-4.65 (6H, m), 6.93 (1H, d, J=7.5 Hz), 6.98 (1H, d, J=7.5 Hz), 7.26 (1H, d, J=7.5 Hz), 7.53 (1H, t, J=7.5 Hz), 7.87 (1H, d, J=7.5 Hz), 9.24 (1H, d, J=7.5 Hz), 9.78 (1H, brs), 11.5 (1H, brs), 12.8 (1H, s). mass: 378(M+1)$^+$.

Working Example 72

Synthesis of the Compound of the Following Formula [72]:

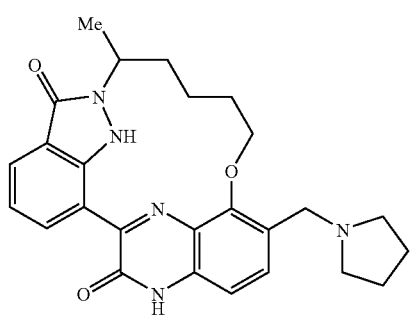

[72]

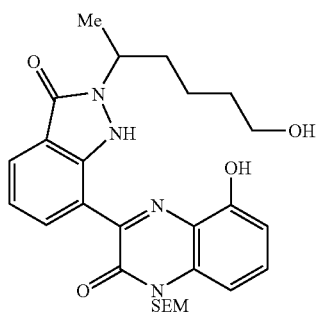

(1)

According to a method similar to the procedures described in Working Examples 48-(1) to 48-(3), the above racemic diol derivative (121 mg) was obtained as a yellow oil from the carboxylic acid (287 mg, 0.50 mmol) which is a starting material in Working Example 48-(1) and the racemic hydrazine derivative [A-21].

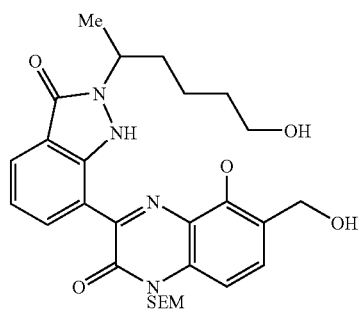

(2)

The racemic diol derivative (370 mg, 0.705 mmol) obtained in the above (1) was dissolved in tetrahydrfuran (10 mL), and to this solution were added 1N sodium hydroxide (1 mL) and 35% aqueous formalin solution (2.5 mL) at room temperature. The mixture was stirred at room temperature overnight, and the resulting reaction solution was stirred at 50° C. for 2 hours. This reaction solution was cooled down to room temperature, diluted with ethyl acetate, and washed successively with water and saturated brine. The organic layer was dried over anhydrous magnesium sulfate, filtered and concentrated in vacuo to obtain the racemic triol derivative (366 mg) as an orange oil.

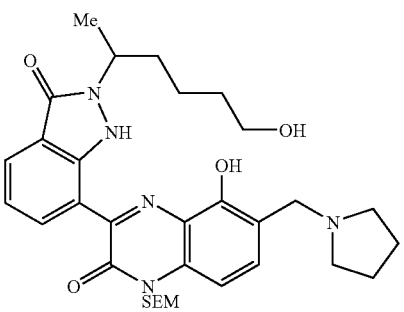

(3)

The racemic triol derivative (55 mg, 0.10 mmol) obtained in the above (2) was dissolved in toluene (3 mL), and to the solution were added acetic acid (0.3 mL) and pyrrolidine (0.3 mL). The solution was stirred under heating at 50° C. for 2 days. The resulting reaction solution was cooled down to room temperature, poured into water, and extracted twice with ethyl acetate. The organic layer was washed with saturated brine, dried over anhydrous magnesium sulfate, filtered and then concentrated in vacuo. The resulting residue was purified by a thin layer chromatography to obtain the racemic benzylamine derivative (46 mg) as an orange oil.

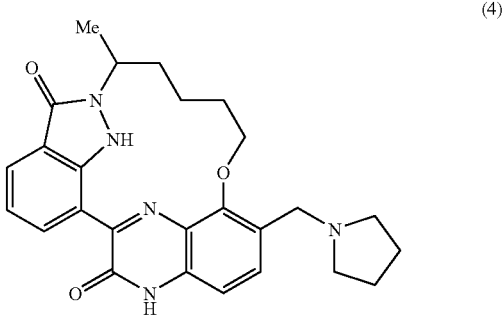
(4)

According to a method similar to the procedures described in Working Examples 1-(5) to 1-(6), the hydrochloride (5 mg) of the objective compound [72] as a racemate was obtained as a yellow solid from the racemic benzylamine derivative (10 mg, 17 μmol) obtained in the above (3).

Spectral data of the compound of the above formula [72] are shown below.

$^1$H-NMR (DMSO-d$_6$) δ: 1.20 (3H, d, J=6.5 Hz), 1.30-1.50 (2H, m), 1.80-2.10 (7H, m), 2.20-2.40 (1H, m), 3.02-3.25 (2H, m), 3.30-3.42 (1H, m), 3.42-3.55 (1H, m), 4.00-4.10 (2H, m), 4.30-4.50 (3H, m), 7.23 (1H, d, J=8.0 Hz), 7.25 (1H, t, J=8.0 Hz), 7.87 (1H, d, J=8.0 Hz), 7.88 (1H, d, J=8.0 Hz), 9.20 (1H, d, J=8.0 Hz), 10.50-10.60 (1H, m), 10.84 (1H, s), 12.94 (1H, s). mass: 460(M+1)$^+$.

Working Example 73

Synthesis of the Compound of the Following Formula [73]:

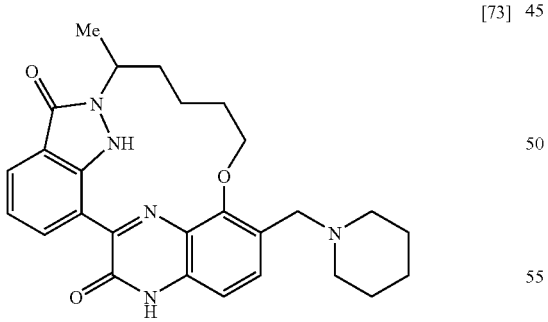
[73]

According to a method similar to the procedures described in Working Examples 72-(3), and 1-(5) to 1-(6), the hydrochloride (28 mg) of the objective compound [73] as a racemate was obtained as a yellow solid from the racemic triol derivative (55 mg, 0.10 mmol) obtained in Working Example 72-(2) and piperidine.

Spectral data of the compound of the above formula [73] are shown below.

$^1$H-NMR (DMSO-d$_6$) δ: 1.19 (3H, d, J=6.5 Hz), 1.30-1.50 (2H, m), 1.60-2.05 (9H, m), 2.20-2.38 (1H, m), 2.80-2.95 (1H, m), 2.95-3.10 (1H, m), 3.22-3.32 (1H, m), 3.36-3.46 (1H, m), 4.00-4.05 (2H, m), 4.30-4.50 (3H, m), 7.24 (1H, d, J=8.0 Hz), 7.26 (1H, t, J=8.0 Hz), 7.87 (1H, d, J=8.0 Hz), 7.93 (1H, d, J=8.0 Hz), 9.20 (1H, d, J=8.0 Hz), 10.15-10.25 (1H, m), 10.84 (1H, s), 12.95 (1H, s). mass: 474(M+1)$^+$.

Working Example 74

Synthesis of the Compound of the Following Formula [74]:

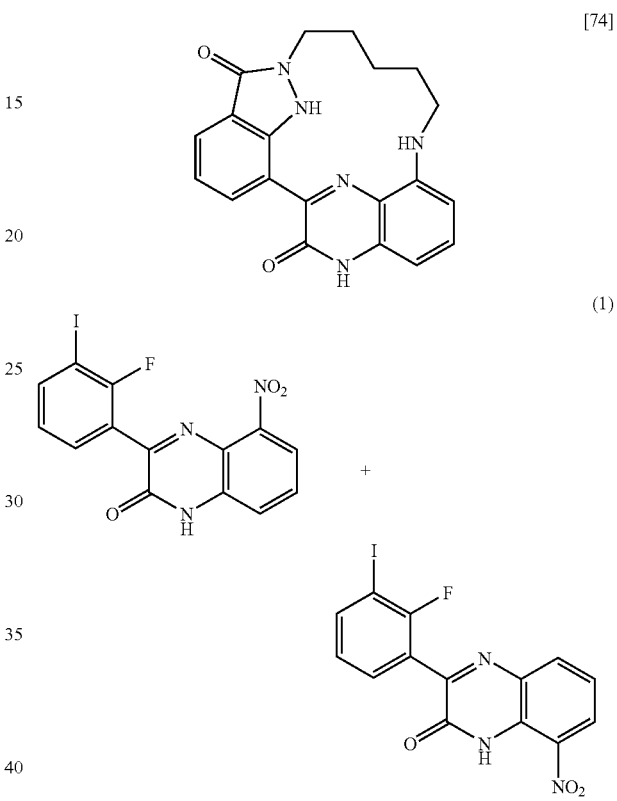

According to a method similar to the procedure of Example 11-(1), a mixture (21.6 g) of the above 5-nitroquinoxalin-2-one derivative and the above 8-nitroquinoxalin-2-one derivative was obtained as a yellow solid from ethyl (2-fluoro-3-iodophenyl)oxoacetate (21.5 g, 66.8 mmol) obtained according to a method similar to the method of the general formula (II-d) described in WO 02/02550 and 3-nitrophenylenediamine (10.2 g, 66.6 mmol).

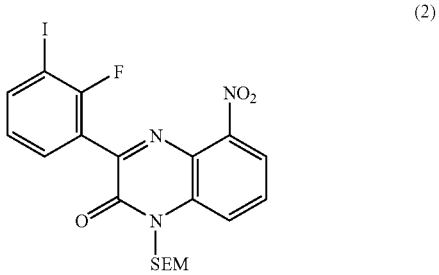
(2)

Chloromethyl 2-(trimethylsilyl)ethyl ether (10.0 mL, 56.3 mmol) was added to tetrahydrofuran solution (500 mL) containing a mixture (21.6 g) of the 5-nitroquinoxalin-2-one derivative and the 8-nitroquinoxalin-2-one derivative obtained in the above (1), and then sodium hydride (2.30 g, 60% dispersion in oil, 57.3 mmol) was added thereto under ice-cooling. After the resulting reaction solution was stirred at room temperature for 1.5 hours, aqueous ammonium chloride solution was added thereto, and the mixture was extracted with chloroform. After the organic layer was washed with saturated brine, it was dried over anhydrous magnesium sulfate, filtered, and concentrated in vacuo. To the resulting residue was added 4N hydrogen chloride/1,4-dioxane solution (100 mL), and the solution was stirred at room temperature for 1 hour. After removal of the insolubles by filtration, the filtrate was concentrated in vacuo. The resulting residue was purified by a column chromatography on silica gel to obtain the above 5-nitroquinoxaline-2-one derivative (11.6 g) protected with SEM, as a yellow solid.

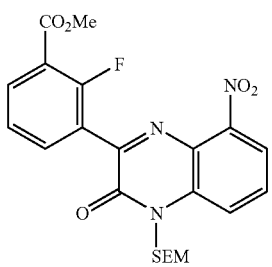
(3)

According to a method similar to the procedure described in Working Example 14-(5), the above ester derivative (8.06 g) was obtained as a yellow solid from the protected derivative with SEM (11.6 g, 21.4 mmol) obtained in the above (2).

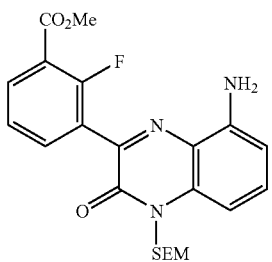
(4)

The ester derivative (191 mg, 0.40 mmol) obtained in the above (3) was dissolved in ethanol (10 mL), and to this solution were added saturated aqueous ammonium chloride solution (2 mL) and iron powder (110 mg). After the resulting reaction solution was heated under reflux for 20 minutes, saturated aqueous ammonium chloride solution (2 mL) and iron powder (300 mg) were added thereto. Further, after this reaction solution was heated under reflux for 20 minutes, iron powder (500 mg) was added thereto. Then, the resulting reaction solution was heated under reflux for 20 minutes, cooled down to room temperature, and water and chloroform were added. After the reaction solution was filtered, the filtrate was extracted with chloroform, and dried over anhydrous magnesium sulfate. After removal of the insolubles by filtration, the filtrate was concentrated in vacuo to obtain the aniline derivative (168 mg) as a yellow solid.

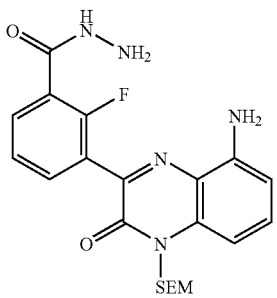
(5)

Hydrazine monohydrate (5 mL) was added to ethanol solution (20 mL) containing the aniline derivative (1.60 g, 3.61 mmol) obtained in the above (4), and the mixture was stirred at room temperature for 2 hours. The resulting reaction solution was concentrated in vacuo to obtain the above hydrazide derivative (1.60 g) as a yellow solid.

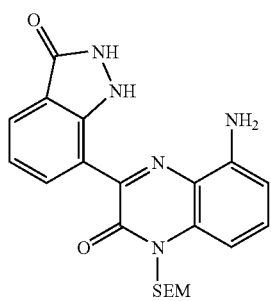
(6)

According to a method similar to the procedure described in Working Example 11-(12), the above 3-indazolinone derivative (684 mg) was obtained as a yellow solid from the hydrazide derivative (1.60 g, 3.61 mmol) obtained in the above (5).

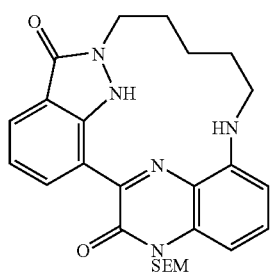
(7)

The 3-indazolinone derivative (10 mg, 24 μmol) obtained in the above (6) was dissolved in N,N-dimethylformamide (1 mL), and then 1,5-diiodopentane (50 μL, 340 μmol) was added thereto. The mixture was stirred at 100° C. for 3.5 hours. After the resulting reaction solution was cooled down to room temperature, it was concentrated in vacuo. The resulting residue was purified by a thin layer chromatography to obtain the cyclic derivative (2.5 mg) as a yellow solid.

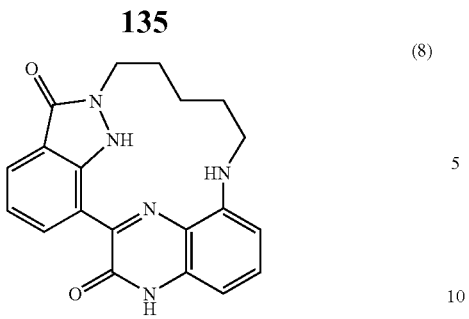

According to a method similar to the procedure described in Working Example 1-(6), the objective compound [74] (1.8 mg) was obtained as a yellow solid from the cyclic derivative (2.5 mg, 5.1 µmol) obtained in the above (7).

Spectral data of the compound of the above formula [74] are shown below.

$^1$H-NMR (DMSO-d$_6$) δ: 1.62 (2H, m), 1.95 (4H, m), 3.20 (4H, m), 7.19(1H, t, J=7.8 Hz), 7.20-7.70 (4H, m), 7.86 (1H, d, J=7.8 Hz), 9.18 (1H, br), 12.18(1H, br), 12.78 (1H, br). mass: 362(M+1)$^+$.

Working Example 75

Synthesis of the Compound of the Following Formula [75]:

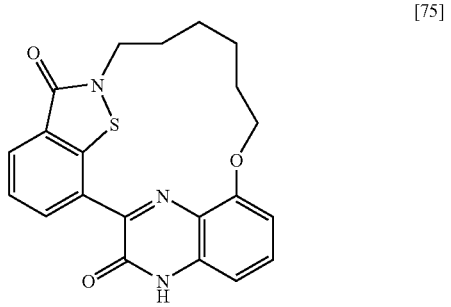

According to a method similar to the procedures described in Working Examples 1-(2) to 1-(6), the objective compound [75] (10 mg) was obtained as a yellow solid from the carboxylic acid derivative (30 mg, 45 µmol) obtained in Working Example 1-(1) and 6-amino-1-hexanol.

Spectral data of the compound of the above formula [75] are shown below.

$^1$H-NMR (DMSO) δ: 1.60-2.00 (8H, m), 3.80-3.90 (2H, m), 4.15-4.30 (2H, m), 6.90-6.98 (2H, m), 7.43-7.65 (2H, m), 8.01 (1H, d, J=7.6 Hz), 9.51 (1H, d, J=7.8 Hz), 12.8 (1H, brs). mass: 394(M+1)$^+$.

Working Example 76

Synthesis of the Compound of the Following Formula [76]:

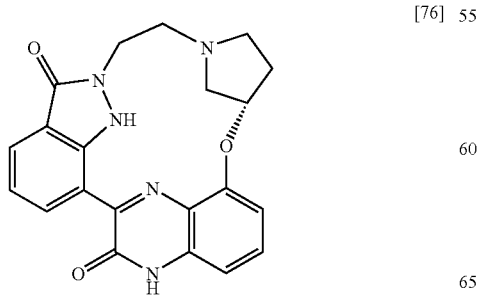

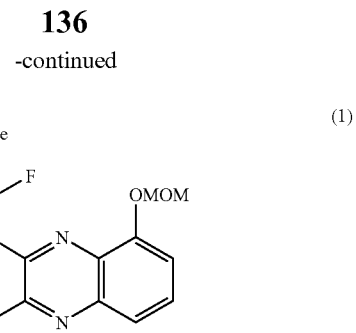

Diisoproylethylamine (2.90 mL, 16.7 mmol), trioctylsilane (5.98 mL, 13.3 mmol) and dichloro-bistriphenylphosphine palladium (777 mg, 1.11 mmol) were successively added to a mixed solution of N,N-dimethylformamide (75 mL) and 1,4-dioxane (75 mL) containing the methoxyquinoxaline derivative (5.00 g, 11.1 mmol) obtained in Working Example 11-(3). The resulting reaction solution was stirred at 90° C. for 30 minutes, and then cooled down to room temperature. After hexane and water were added to this reaction solution, it was filtered through a Celite pad and the filtrate was extracted with ethyl acetate. The resulting organic layer was washed with saturated brine, dried over anhydrous magnesium sulfate, filtered, and concentrated in vacuo. The resulting residue was purified by a column chromatography on silica gel to obtain the reduced derivative (4.10 g) as a gray solid.

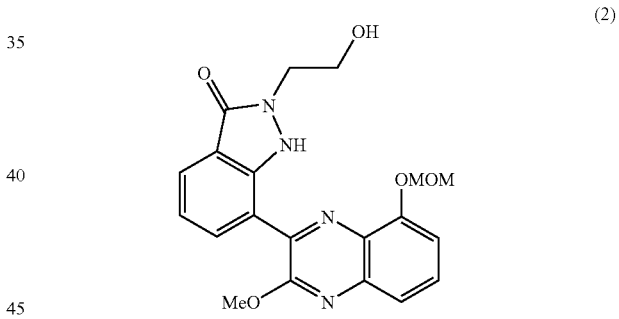

According to a method similar to the procedures described in Working Examples 11-(9) to 11-(12), the above alcohol derivative (2.13 g) was obtained as a yellow solid from the reduced derivative (4.10 g) obtained in the above (1).

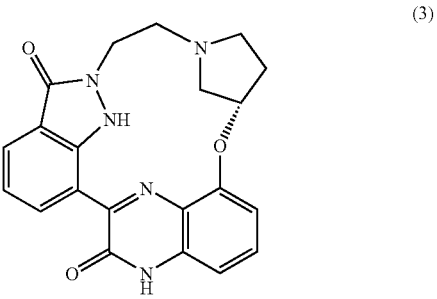

According to a method similar to the procedures described in Working Examples 11-(13) to 11-(16), and 11-(18), the hydrochloride (510 mg) of the objective compound [76] was obtained as a yellow solid from the reduced derivative (2.13 g) obtained in the above (2).

Spectral data of the compound of the above formula [76] are shown below.

$^1$H-NMR (DMSO) δ: 1.75-2.40 (3H, m), 2.40-2.55 (1H, m), 3.00-3.35 (2H, m), 3.50-3.80 (1H, m), 3.82-4.35 (3H, m), 5.34-5.42 (1H, m), 6.96-7.27 (3H, m), 7.49-7.56 (1H, m), 7.84 (1H, d, J=7.8 Hz), 9.20-9.30 (1H, m), 11.8-12.0 (1H, m), 12.7-12.8 (1H, m). mass: 390(M+1)$^+$.

Working Example 77

Synthesis of the Compound of the Following Formula [77]:

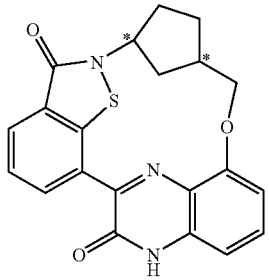

[77]

In the formula, the stereo chemistry of the position with the symbol * is of cis-configuration.

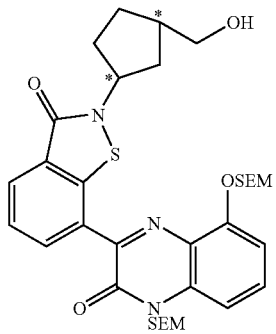

(1)

According to a method similar to the procedures described in Working Examples 1-(2) to 1-(3), the racemic benzoisothiazolone derivative (177 mg) was obtained as a yellow oil from the carboxylic acid derivative (665 mg, 1.00 mmol) obtained in Working Example 1-(1) and the racemate derivative [A-32].

(2)

According to a method similar to the procedures described in Working Examples 14-(12) to 14-(13), and 1-(6), the objective compound [77] (6 mg) as a racemate was obtained as a yellow solid from the racemic benzoisothiazolone derivative (177 mg, 264 mmol) obtained in the above (1).

Spectral data of the compound of the above formula [77] are shown below.

$^1$H-NMR (DMSO-d$_6$) δ: 1.78-1.90 (1H, m), 1.95-2.04 (2H, m), 2.61-2.70(2H, m), 2.85-2.92 (2H, m), 4.50-4.58 (1H, m), 4.70-4.82 (2H, m), 7.00-7.02 (2H, m), 7.50-7.65 (2H, m), 8.05 (1H, d, J=7.3 Hz), 9.01 (1H, d, J=6.6 Hz), 12.8 (1H, brs). mass: 392(M+1)$^+$.

Example 78

Synthesis of the Compound of the Following Formula [78]:

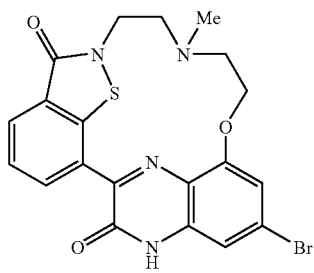

[78]

According to a method similar to the procedures described in Working Examples 3-(1) to 3-(4) and 6, the hydrochloride (6 mg) of the objective compound [78] was obtained as a yellow solid from the carboxylic acid derivative (475 mg, 0.64 mmol) obtained in Working Example 14-(2) and the sulfonamide derivative [A-3-5].

Spectral data of the compound of the above formula [78] are shown below.

$^1$H-NMR (DMSO-d$_6$) δ: 2.30-4.80 (11H, m), 7.10 (1H, s), 7.45-7.70 (2H, m), 7.97-8.05 (1H, m), 9.25-9.32 (1H, m), 12.9 (1H, brs). mass: 473(M+1)$^+$.

Working Example 79

Synthesis of the Compound of the Following Formula [79]:

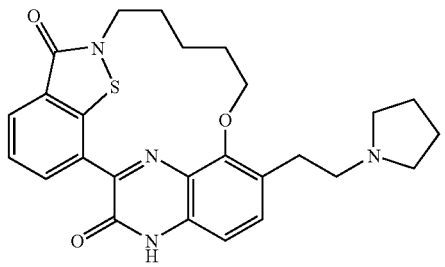

According to a method similar to the procedure described in Working Example 1-(4), the above phenol derivative (774 mg) was obtained as a white solid from the methyl ester derivative (1.00 g, 1.74 mmol) which is a starting material of Example 1-(1).

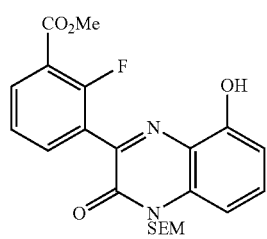

To tetrahydrofuran solution (20 mL) of the phenol derivative (774 mg, 1.74 mmol) obtained in the above (1) was added 40% toluene solution (1.52 mL) containing triphenylphosphine (912 mg, 3.48 mmol), allyl alcohol (202 mg, 3.48 mmol) and diethyl azodicarboxylate, and the mixture was stirred at room temperature for 30 minutes. After addition of water (100 µL), the reaction solution was concentrated in vacuo, and the resulting residue was purified by a column chromatography on silica gel to obtain the allyl ether derivative (725 mg) as a white solid.

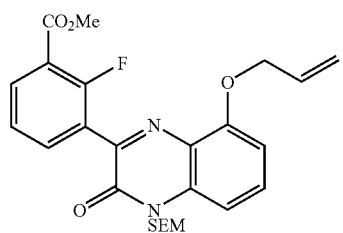

Xylene solution (100 mL) containing the allyl ether derivative (725 mg, 1.50 mmol) obtained in the above (2) was stirred at 180° C. for 3 days. The reaction solution was concentrated, and the resulting residue was purified by a column chromatography on silica gel to obtain the above allyl rearrangement derivative (543 mg) as a white solid.

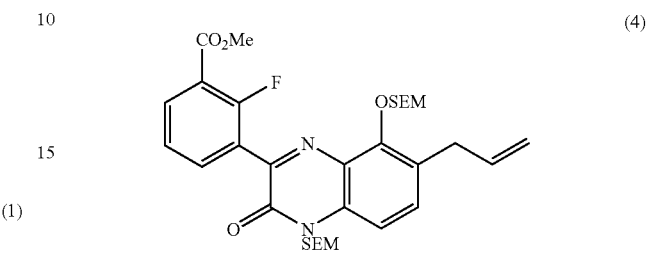

Chloromethyl 2-(trimethylsilyl)ethyl ether (400 µL, 2.26 mmol) was added to tetrahydrofuran solution (20 mL) of the allyl rearrangement derivative (543 mg, 1.13 mmol) obtained in the above (3), under ice-cooling, and sodium hydride (90 mg, 60% dispersion in oil, 2.26 mmol) was added thereto. The mixture was stirred at room temperature for 2 hours. After saturated aqueous ammonium chloride solution was added to the reaction solution, it was extracted with ethyl acetate. The organic layer was washed with water and saturated brine, dried over anhydrous magnesium sulfate, and filtered. The filtrate was concentrated and the resulting residue was purified by a column chromatography on silica gel to obtain the protected derivative (695 mg) with SEM as a white solid.

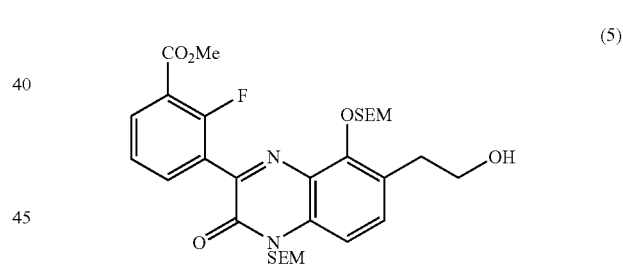

Ozone was bubbled at −78° C. through a mixed solution of dichloromethane (14 mL) and methanol (6 mL) containing the derivative (1.00 g, 1.63 mmol) protected with SEM obtained in the above (4), and the mixture was stirred at the same temperature for 30 minutes. Nitrogen gas was bubbled through the solution, and dimethyl sulfide (5 ml) was added dropwise thereto. The reaction solution was warmed up to room temperature. After sodium tetrahydroborate (100 mg) was added thereto under ice-cooling, the mixture was stirred for 1 hour. After saturated aqueous ammonium chloride solution was added to the reaction solution, it was extracted with ethyl acetate. The organic layer was washed with water and saturated brine, dried over anhydrous magnesium sulfate, and filtered. The filtrate was concentrated, and the resulting residue was purified by silica gel chromatography on to obtain the hydroxyethyl derivative (800 mg) as a pale yellow solid.

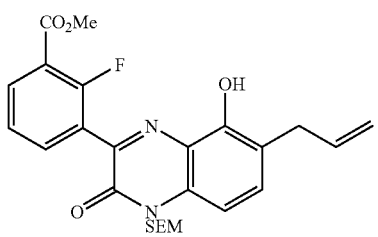

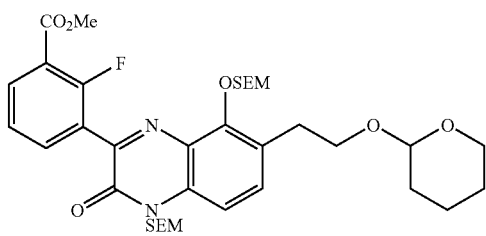

(6)

According to a method similar to the procedure described in Working Example 11-(8), the above derivative (820 mg) protected with THP was obtained as a pale yellow solid from the hydroxyethyl derivative (800 mg, 1.29 mmol) obtained in the above (5).

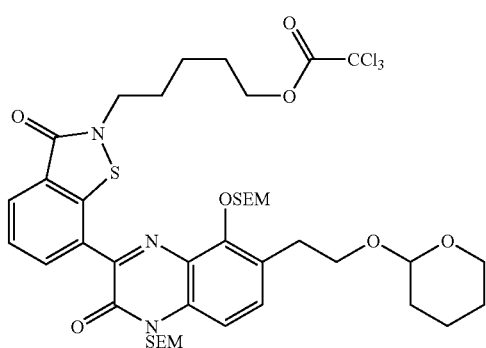

(7)

According to a method similar to the procedures described in Working Examples 1-(1) to 1-(3), the above benzoisothiazolone derivative (129 mg) was obtained as a yellow solid from the derivative protected with THP (820 mg, 1.16 mmol) obtained in the above (6).

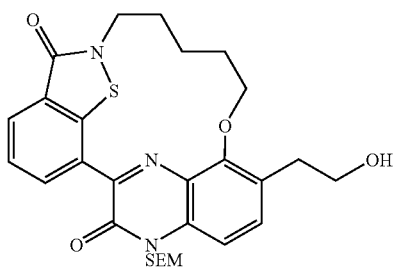

(8)

According to a method similar to the procedures described in Working Examples 11-(19), and 14-(12) to 14-(13), the above cyclic derivative (42 mg) was obtained as a yellow solid from the benzoisothiazolone derivative (110 mg, 118 μmol) obtained in the above (7).

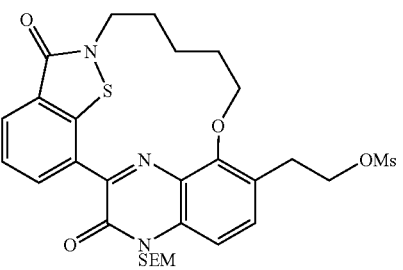

(9)

According to a method similar to the procedure described in Working Example 11-(14), the above mesylated derivative (3.0 mg) was obtained as a yellow solid from the cyclic derivative (3.0 mg, 5.42 μmol) obtained in the above (8).

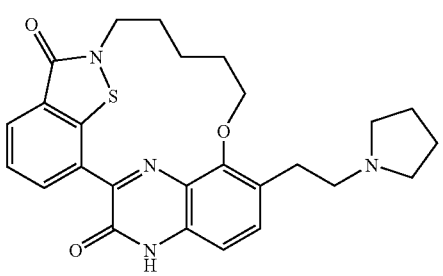

(10)

The mesylated derivative (3.0 mg, 4.75 μmol) obtained in the above (9) was dissolved in toluene (450 μL), and to this solution were added pyrrolidine (45 μL) and aqueous sodium hydrogencarbonate solution (45 mg, 450 μL)) at room temperature. The mixture was stirred in a sealed tube at 130° C. for 12 hours. After this reaction solution was cooled down to room temperature. it was extracted with ethyl acetate. The organic layer was washed with saturated brine, dried over anhydrous magnesium sulfate, and filtered. The filtrate was concentrated, and the resulting residue was purified by a column chromatography on silica gel to obtain the pyrrolidinoethyl derivative (3.0 mg) as a pale yellow solid.

(11)

According to a method similar to the procedure described in Working Example 1-(6), the above hydrochloride (2 mg) of the objective compound [79] was obtained as a yellow solid from the pyrrolidinoethyl derivative (2.5 mg, 4.12 μmol) obtained in the above (10).

Spectral data of the compound of the above formula [79] are shown below.
¹H-NMR (DMSO-d₆) δ: 1.80-2.12 (9H, m), 2.18-2.33 (3H, m), 3.01-3.20(4H, m), 3.53-3.70 (2H, m), 3.71-3.85 (2H, m), 4.30-4.41 (2H, m), 7.20(1H, d, J=8.7 Hz), 7.59 (1H, d, J=8.7 Hz), 7.66 (1H, dd, J=7.6 Hz, 8.0 Hz), 8.08 (1H, d, J=7.6 Hz), 9.53 (1H, d, J=8.0 Hz), 10.15-10.32 (1H, m), 12.94 (1H, s). mass: 477(M+1)⁺.

Working Example 80

Synthesis of the Compound of the Following Formula [80]:

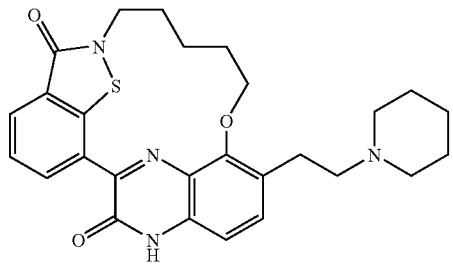

[80]

According to a method similar to the procedures described in Working Examples 79-(10) and 1-(6), the hydrochloride (2.0 mg) of the objective compound [80] was obtained as a yellow solid from the mesylated derivative (3 mg, 19 μmol) obtained in Working Example 79-(9) and piperidine (45 μL).

Spectral data of the compound of the above formula [80] are shown below.
¹H-NMR (DMSO-d₆) δ: 1.30-2.18 (11H, m), 2.19-2.36 (3H, m), 2.90-3.06 (2H, m), 3.10-3.21 (2H, m), 3.50-3.65 (2H, m), 3.72-3.88 (2H, m), 4.28-4.42 (2H, m), 7.21 (1H, d, J=8.7 Hz), 7.57 (1H, d, J=8.7 Hz), 7.66(1H, dd, J=7.4 Hz, 7.9 Hz), 8.08 (1H, d, J=7.4 Hz), 9.53 (1H, d, J=7.9 Hz), 9.70-9.90 (1H, m), 12.93 (1H, s). mass: 491(M+1)⁺.

Working Example 81

Synthesis of the Compound of the Following Formula [81]:

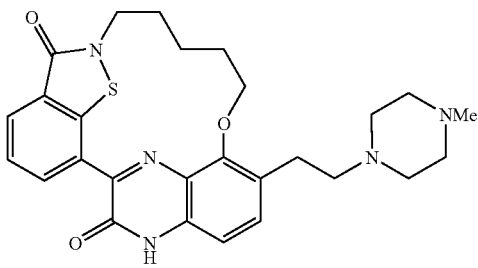

[81]

According to a method similar to the procedure described in Working Examples 79-(10) and 1-(6), the hydrochloride (1.2 mg) of the objective compound [81] was obtained as a yellow solid from the mesylated derivative (3 mg, 19 μmol) obtained in Working Example 79-(9) and N-methylpiperazine (45 μL).

Spectral data of the compound of the above formula [81] are shown below.
¹H-NMR (DMSO-d₆) δ: 1.90-4.00 (23H, m), 4.28-4.42 (2H, m), 7.20 (1H, d, J=8.7 Hz), 7.55-7.75 (2H, m), 8.08 (1H, d, J=7.5 Hz), 9.30-9.48 (1H, m), 9.53 (1H, d, J=8.0 Hz), 12.94 (1H, s). mass: 506(M+1)⁺.

Working Example 82

Synthesis of the Compound of the Following Formula [82]:

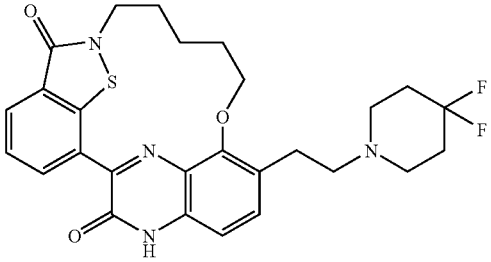

[82]

According to a method similar to the procedures described in Working Examples 79-(10) and 1-(6), the hydrochloride (14.5 mg) of the objective compound [82] was obtained as a yellow solid from the mesylated derivative (20 mg, 19 μmol) obtained in Working Example 79-(9) and 4,4-difluoropiperidine (300 μL).

Spectral data of the compound of the above formula [82] are shown below.
¹H-NMR (DMSO-d₆) δ: 1.92-2.18 (4H, m), 2.20-2.78 (6H, m), 3.12-3.38(5H, m), 3.70-3.88 (5H, m), 4.28-4.42 (2H, m), 7.21 (1H, d, J=8.5 Hz), 7.57 (1H, d, J=8.9 Hz), 7.66 (1H, dd, J=7.4 Hz, 8.2 Hz), 8.08 (1H, d, J=7.4 Hz), 9.53 (1H, d, J=8.2 Hz), 10.70-10.88 (1H, m), 12.93 (1H, s). mass: 527(M+1)⁺.

Working Example 83

Synthesis of the Compound of the Following Formula [83]:

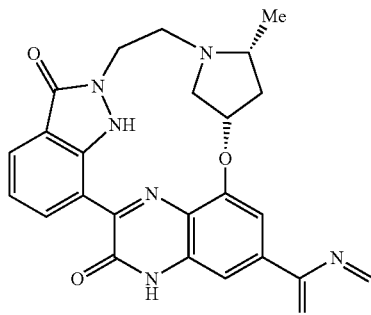

[83]

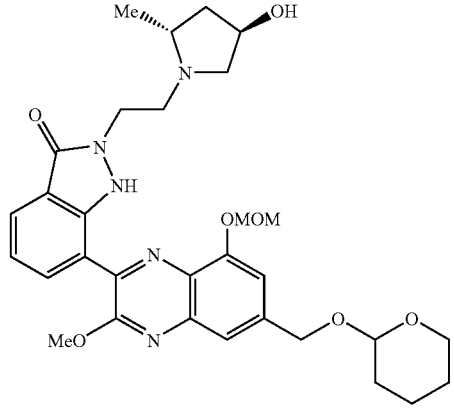

(1)

N,N-Diisopropylethylamine (12.8 mL, 73.5 mmol) was added to chloroform solution (300 mL) containing the 3-indazolidinone derivative (10.0 g, 19.6 mmol) obtained in Working Example 11-(12), and methanesulfonyl chloride (5.00 mL, 64.6 mmol) was added dropwise thereto under ice-cooling. The mixture was stirred for 30 minutes. Water was added to the resulting reaction solution, and the organic layer was separated, washed successively with saturated aqueous sodium hydrogencarbonate, water and saturated brine, dried over anhydrous magnesium sulfate and filtered. The filtrate was concentrated. The resulting residue was dissolved in ethyl acetate, and the solution was washed with water. The resulting organic layer was dried over anhydrous magnesium sulfate, filtered, and concentrated. The resulting residue was dissolved in 1,4-dioxane (30 mL), and the pyrrolidine derivative [A-33] (11.9 g, 118 mmol) was added thereto. The mixture was stirred at 85° C. for 2 hours and then cooled down to room temperature. The reaction solution was concentrated and the resulting residue was purified by a column chromatography on silica gel to produce the above amine derivative (9.61 g) as a yellow solid.

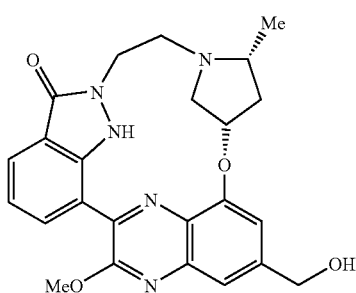

(2)

According to a method similar to the procedures described in Working Examples 11-(14) to 11-(16), the above cyclic derivative (4.68 g) was obtained as a yellow solid from the amine derivative (9.61 g, 16.2 mmol) obtained in the above (1).

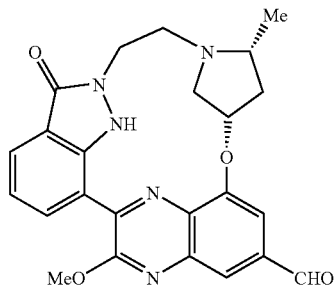

(3)

According to a method similar to the procedure described in Working Example 40-(4), the above aldehyde derivative (1.62 g) was obtained as an orange solid from the cyclic derivative (2.34 g, 5.23 mmol) obtained in the above (2).

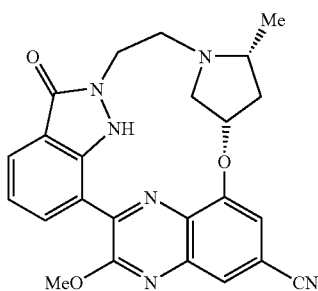

(4)

To tetrahydrofuran solution (3 mL) containing the aldehyde derivative (171 mg, 384 µmol) obtained in the above (3) were added 2 M isopropanol solution (6.2 mL) containing ammonia and anhydrous magnesium sulfate (1.49 g). After the reaction solution was stirred for 1 hour, manganese dioxide (1.27 g) was added thereto, and the mixture was stirred for 15 hours. The resulting reaction solution was filtered through a Celite pad, and the mother liquor was concentrated. The residue was purified by a silica gel chromatography to obtain the above nitrile derivative (106 mg) as an orange solid.

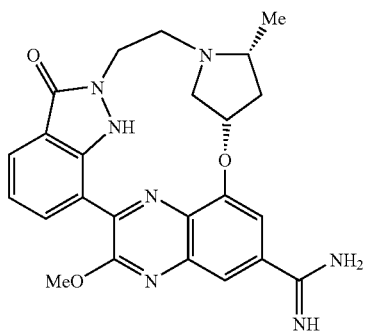

(5)

To tetrahydrofuran solution (1 mL) containing the nitrile derivative (11 mg, 24.8 µmol) obtained in the above (4) was added 1 M tetrahydrofuran solution (1 mL) containing lithium bis (trimethylsilyl)amide at room temperature, and the solution was stirred for 15 minutes. The reaction solution was subjected to ice-cooling, and 6N hydrogen chloride/ethanol (1 mL) was added dropwise. The solution was stirred at room temperature for 30 minutes. After the reaction solution was diluted in diethyl ether, the resulting precipitates were filtered off, and washed with diethyl ether. The resulting precipitates were dissolved in methanol, and the solution was diluted with ethyl acetate and water. After N,N-diisopropylethylamine (3 mL) and sodium chloride were added to the mixed solution until the aqueous layer was saturated with them, the organic layer was separated. The resulting organic layer was washed with saturated brine, dried over anhydrous magnesium sulfate, and filtered. The filtrate was concentrated, and chloroform (2 mL) was added to the resulting residue. The mixture was stirred for 15 minutes to give a suspension. After 4N hydrogen chloride/1,4-dioxane (100

μL) was added dropwise to the suspension, diethyl ether (3 mL) was added thereto. The resulting precipitates were filtered off, washed with diethyl ether, and dried in vacuo to obtain the above amidine derivative (9.7 mg) as a purple solid.

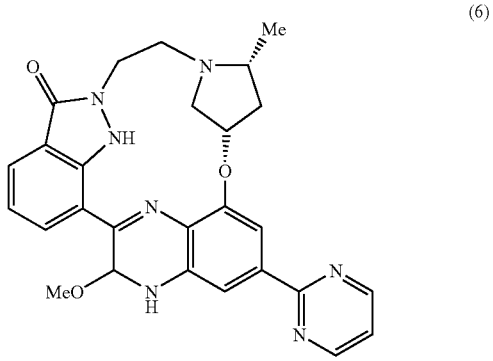

(6)

The amidine derivative (4.6 mg, 8.63 μmol) obtained in the above (5) was suspended in 1,1,3,3-tetramethoxypropane (500 μL). The suspension was stirred in a sealed tube at 180° C. for 2 hours. The reaction solution was cooled down to room temperature, and diluted with methanol. After triethylamine (1 mL) was added to the suspension, it was concentrated in vacuo. The resulting residue was purified by a silica gel chromatography to obtain the hydrochloride (0.90 mg) of the objective compound [83] as an orange solid.

Spectral data of the compound of the above formula [83] are shown below.

$^1$H-NMR (DMSO-$d_6$) δ: 0.60-0.80 (3H, m), 1.00-4.00 (8H, m), 4.40-4.55(1H, m), 5.32-5.42 (1H, m), 7.12-7.23 (1H, m), 7.48-7.57 (1H, m), 7.84-7.95 (2H, m), 8.09 (1H, s), 8.95-9.03 (2H, m), 9.42-9.53 (1H, m), 12.29-12.40 (1H, m), 12.81 (1H, brs). mass: 482(M+1)$^+$.

Working Example 84

Synthesis of the Compound of the Following Formula [84]:

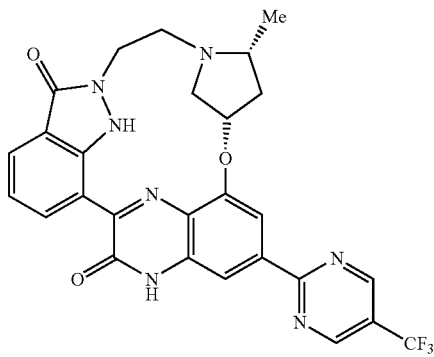

[84]

The amidine derivative (5.0 mg, 9.4 μmol) obtained in Working Example 83-(5) was suspended in acetonitrile (2 mL). To the suspension were added β-trifluoromethyl vinamidinium chloride (4.4 mg, 18.8 μmol) synthesized according to a method similar to the method described in Tetrahedron Lett., 37 (11) 1829 (1996) and 1.0 M methanol solution (22.5 μL, 22.5 μmol) containing sodium methoxide. The mixture was stirred at room temperature for 2.5 hours. Water was added to the reaction solution, and it was extracted with a mixed solvent of chloroform:methanol=9:1. The organic layer was washed with saturated brine, dried over anhydrous sodium sulfate, and filtered. The filtrate was concentrated, and the resulting residue was purified by a thin layer chromatography, followed by treatment according to a method similar to the procedure described in Working Example 1-(6), thereby to obtain the hydrochloride (2.5 mg) of the objective compound [84] as a brown solid Spectral data of the compound of the above formula [84] are shown below.

$^1$H-NMR (DMSO-$d_6$) δ: 0.64-0.78 (3H, m), 1.35-1.45 (1H, m), 2.23-2.40(2H, m), 2.52-2.63 (1H, m), 2.71-2.85 (1H, m), 2.94-3.08 (1H, m), 3.77-3.91 (2H, m), 4.44-4.51 (1H, m), 5.35-5.39 (1H, m), 7.13-7.20 (1H, m), 7.84-7.91 (2H, m), 8.12 (1H, s), 9.39 (2H, s), 9.45 (1H, d, J=7.8 Hz), 12.28-12.30 (1H, m), 12.9 (1H, s). mass: 550(M+1)$^+$.

Working Example 85

Synthesis of the Compound of the Following Formula [85]:

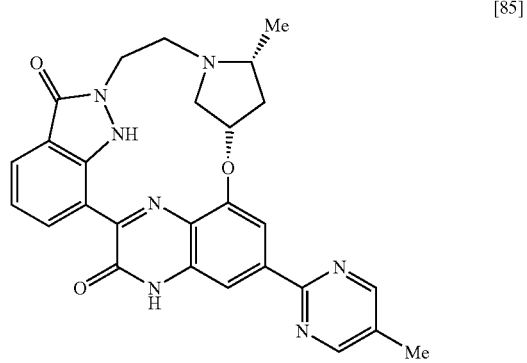

[85]

3-(Dimethylamino)-2-methyl-2-propenal (4.5 mg, 39.4 μmol) and 1.0 M methanol solution (47.3 μL, 47.3 μmol) containing sodium methoxide were added to methanol solution (3.0 mL) containing the amidine derivative (10.5 mg, 19.7 μmol) obtained in Working Example 83-(5). The solution was heated at reflux with stirring for 6.5 hours. Further, 3-(dimethylamino)-2-methyl-2-propenal (27.0 mg, 238 μmol) and 1.0 M methanol solution (284 μL, 284 μmol) containing sodium methoxide were added thereto. The mixture was heated at reflux with stirring for 18 hours. After the resulting reaction solution was cooled down to room temperature, water was added to the solution, which was then extracted with a mixed solvent of chloroform:methanol=9:1. The organic layer was washed with saturated brine, dried over anhydrous sodium sulfate, filtered. The filtrate was concentrated, and the resulting residue was purified by a thin layer chromatography, followed by treatment according to a method similar to the procedure described in Working Example 1-(6), thereby to obtain the hydrochloride (4.8 mg) of the objective compound [85] as a deep purple solid.

Spectral data of the compound of the above formula (85) are shown below.

$^1$H-NMR (DMSO-$d_6$) δ: 0.66-0.90 (3H, m), 1.38-1.47 (1H, m), 2.31 (3H, s), 2.25-2.41 (2H, m), 2.75-3.20 (2H, m), 3.82-3.93 (2H, m), 4.25-4.56(2H, m), 5.36-5.42 (1H, m), 7.15-7.23 (1H, m), 7.87 (1H, d, J=7.8 Hz), 7.89 (1H, s), 8.06 (1H, s), 8.81 (2H, s), 9.40-9.47 (1H, m), 12.2-12.4 (1H, m), 12.8 (1H, s). mass: 496(M+1)$^+$.

Working Example 86

Synthesis of the Compound of the Following Formula [86]:

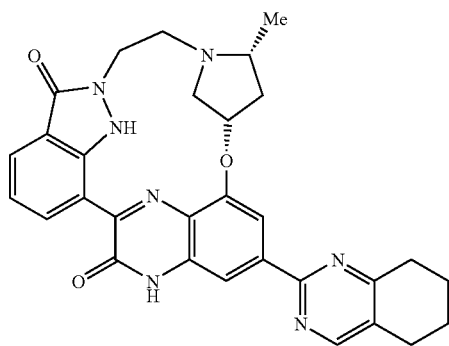

[86]

The amidine derivative (9.9 mg, 18.6 μmol) obtained in Working Example 83-(5) was suspended in ethanol (3 mL), and to the suspension were added 2-methoxymethylene cyclohexanone (5.2 mg, 37.2 μmol) synthesized according to a method similar to the method described in J. Heterocycl. Chem., 27, 1537 (1990) and sodium acetate (3.7 mg, 44.6 μmol). The mixture was stirred under heating at reflux for 6.5 hours. Then, after further addition of 2-methoxymethylene cyclohexanone (10.4 mg, 74.3 μmol) and sodium acetate (37.3 mg, 89.3 μmol), the mixture was stirred under heating at reflux for 10 hours. The resulting reaction solution was cooled down to room temperature, and 10% aqueous sodium carbonate solution (2 mL) was added thereto. The mixture was stirred at room temperature for 5 minutes and then extracted with a mixed solvent of chloroform:methanol=9:1. The organic layer was washed with water and saturated brine, dried over anhydrous sodium sulfate, and filtered. The filtrate was concentrated, and the resulting residue was purified by thin layer chromatography, followed by treatment according to a method similar to the procedure described in Working Example 1-(6), thereby to obtain the hydrochloride (0.4 mg) of the objective compound [86] as a brown solid.

Spectral datum of the compound of the above formula [86] is shown below. mass: 536(M+1)$^+$.

Working Example 87

Synthesis of the Compound of the Following Formula [87]:

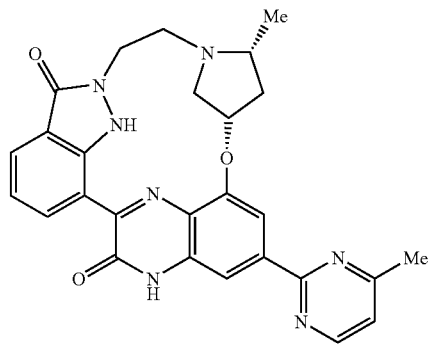

[87]

To methanol solution (3.0 mL) containing the amidine derivative (10.0 mg, 18.8 μmol) obtained in Working Example 83-(5) were added acetylacetaldehyde dimetyhlacetal (5.0 μL, 37.6 μmol) and 1.0 M methanol solution (45.1 μL, 45.1 μmol) containing sodium methoxide. The mixture was stirred at 50° C. for 4.5 hours. Then, acetylacetaldehyde dimetyhlacetal (10.0 μL, 75.2 μmol) and 1.0 M methanol solution (90.2 μL, 90.2 μmol) containing sodium methoxide were added thereto. The mixture was stirred at 50° C. for 13 hours. After the resulting reaction solution was cooled down to room temperature, water was added thereto, and the reaction solution was extracted with a mixed solvent of chloroform:methanol=9:1. The organic layer was washed with saturated brine, dried over anhydrous sodium sulfate, and filtered. The filtrate was concentrated and the resulting residue was purified by a thin layer chromatography, followed by treatment according to a method similar to the procedure described in Working Example 1-(6), thereby to obtain the hydrochloride (7.2 mg) of the objective compound [87] as a deep purple solid.

Spectral data of the compound of the above formula [87] are shown below.

$^1$H-NMR (DMSO-d$_6$) δ: 0.67-0.82 (3H, m), 1.40-1.45 (1H, m), 2.25-2.42(2H, m), 2.58 (3H, s), 2.56-3.07 (3H, m), 3.83-3.98 (2H, m), 4.50-4.65(1H, m), 5.34-5.41 (1H, m), 7.15-7.24 (1H, m), 7.40 (1H, d, J=5.1 Hz), 7.88 (1H, d, J=8.1 Hz), 7.92 (1H, s), 8.10 (1H, s), 8.80 (1H, d, J=5.1 Hz), 9.38-9.45 (1H, m), 12.2-12.3 (1H, m), 12.8 (1H, s). mass: 496(M+1)$^+$.

Working Example 88

Synthesis of the Compound of the Following Formula [88]:

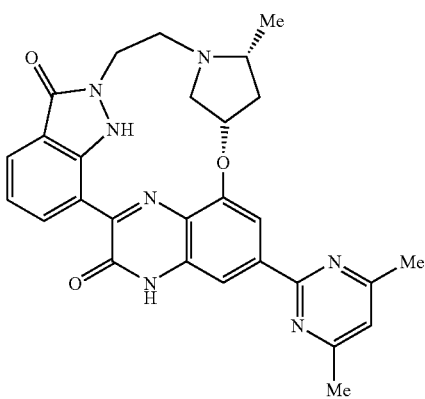

[88]

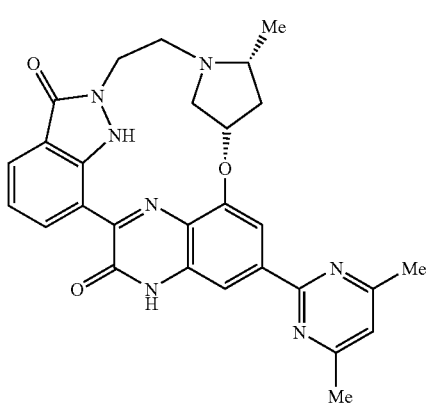

[88]

Acetylacetone (7.7 µL, 75.1 µmol) and acetic acid (8.6 µL, 150 µmol) were added to 1-pentanol solution (4.0 mL) containing the amidine derivative (10.0 mg, 18.8 µmol) obtained in Working Example 83-(5). The mixture was stirred at 135° C. for 1.5 hours. Acetylacetone (77.2 µL, 751 µmol) and acetic acid (86.0 µL, 1.50 mmol) were further added thereto. The mixture was stirred at 135° C. for 27 hours. The resulting reaction solution was cooled down to room temperature, and saturated aqueous sodium hydrogencarbonate was added to the reaction solution. The solution was extracted with a mixed solvent of chloroform:methanol=9:1. The organic layer was washed with water and saturated brine, dried over anhydrous sodium sulfate, and filtered. The filtrate was concentrated and the resulting residue was purified by a thin layer chromatography, followed by treatment according to a method similar to the procedure described in Working Example 1-(6), thereby to obtain the hydrochloride (1.3 mg) of the objective compound [88] as a deep purple solid.

Spectral data of the compound of the above formula [88] are shown below.

$^1$H-NMR (DMSO-$d_6$) δ: 0.65-0.79 (3H, m), 1.38-1.59 (1H, m), 2.08-2.50(3H, m), 2.55 (6H, s), 2.78-3.08 (2H, m), 3.71-3.90 (2H, m), 4.44-4.49(1H, m), 5.32-5.38 (1H, m), 7.13-7.26 (1H, m), 7.27 (1H, s), 7.90 (1H, d, J=8.1 Hz), 7.90 (1H, s), 8.10 (1H, s), 9.40-9.47 (1H, m), 12.2-12.4 (1H, m), 12.7 (1H, s). mass: 510(M+1)$^+$.

Working Example 89

Synthesis of the Compound of the Following Formula [89]:

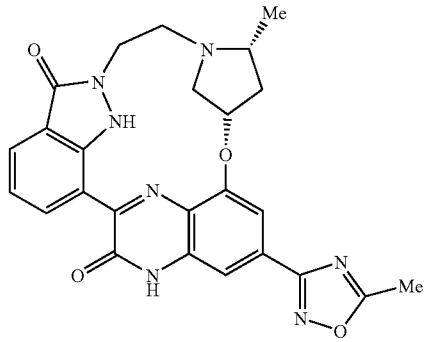

[89]

Hydroxylamine (12.6 mg, 181 µmol) andtriethylamine (25.2 µg, 181 µmol) were added to methanol solution (4.0 mL) containing the nitrile derivative (20 mg, 45.2 µmol) obtained in Working Example 83-(4). The mixture was stirred at room temperature for 10 hours. Hydroxylamine (12.6 mg, 181 µmol) and triethylamine (25.2 µg, 181 µmol) were further added thereto. The mixture was stirred at room temperature for 3 days. The resulting reaction solution was concentrated in vacuo. Acetic anhydride (15 mL) was added to the resulting residue, and the mixture was stirred at 100° C. for 24 hours. After the resulting reaction solution was concentrated in vacuo, it was evaporated azeotropically using toluene. The resulting residue was dissolved in tetrahydrofuran (10 mL) and methanol (10 mL), and 1N sodium hydroxide (10 mL) was added to the solution. The solution was stirred at room temperature for 30 minutes. After the resulting reaction solution was neutralized using 1N hydrochloric acid, it was extracted with a mixed solvent of chloroform:methanol=9:1. The organic layer was washed with water and saturated brine, dried over anhydrous sodium sulfate, and filtered. The filtrate was concentrated and the resulting residue was purified by a thin layer chromatography, followed by treatment according to a method similar to the procedure described in Working Example 1-(6), thereby to obtain the hydrochloride (8.4 mg) of the objective compound [89] as an ocher solid.

Spectral data of the compound of the above formula [89] are shown below.

$^1$H-NMR (DMSO-$d_6$) δ: 0.65-0.76 (3H, m), 1.35-1.41 (1H, m), 2.25-2.45(2H, m), 2.69 (3H, s), 2.55-2.80 (2H, m), 2.91-3.05 (1H, m), 3.77-3.94(2H, m), 4.42-4.51 (1H, m), 5.36-5.41 (1H, m), 7.14-7.21 (1H, m), 7.48(1H, s), 7.62 (1H, s), 7.85 (1H, d, J=7.8 Hz), 9.44 (1H, d, J=7.8 Hz), 12.25-12.29 (1H, m), 12.8 (1H, s). mass: 486(M+1)$^+$.

Working Example 90

Synthesis of the Compound of the Following Formula [90]:

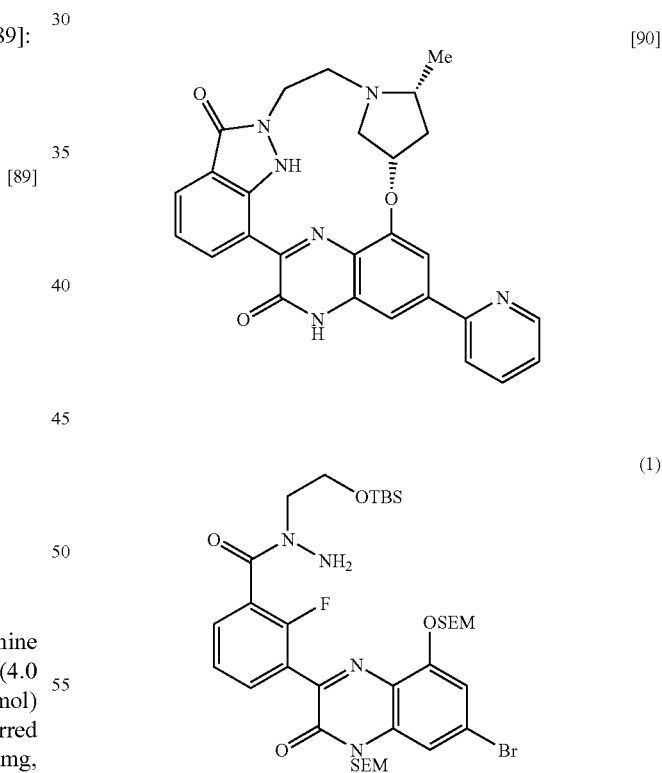

According to a method similar to the procedures described in Working Examples 11-(10) to 11-(11), the above hydrazide derivative (24.3 g) was obtained as an orange solid from the carboxylic acid derivative (24.4 g, 36.9 mmol) obtained in Working Example 49-(1).

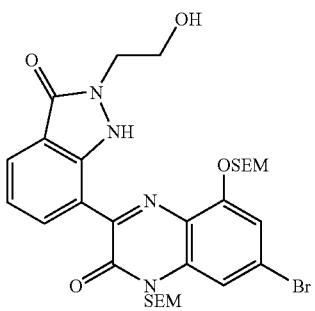

(2)

N,N-Diisopropylethylamine (13.3 mL, 76.3 mmol) was added to n-butanol solution (200 mL) containing the hydrazide derivative (22.2 g, 27.3 mmol) obtained in the above (1). The mixture was stirred at 120° C. for 5 hours. After that, the resulting reaction solution was cooled down to room temperature, and concentrated in vacuo to give a residue, to which was added ether (200 mL). The resulting solid was filtered off and dried in vacuo, followed by treatment according to a method similar to the procedure described in Working Example 15-(4), thereby to obtain the above alcohol derivative (17.5 g, 25.8 mmol) as a yellow solid

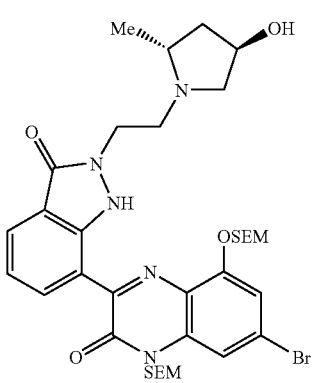

(3)

According to a method similar to the procedure described in Working Example 83-(1), the above amine derivative (10.6 g) was obtained as a yellow solid from the alcohol derivative (12.5 g, 18.4 mmol) obtained in the above (2).

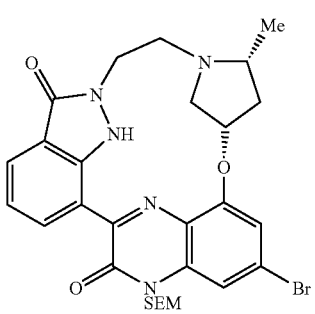

(4)

According to a method similar to the procedures described in Working Examples 1-(4) to 1-(5), the above cyclic derivative (7.06 g) was obtained as a yellow solid from the amine derivative (9.78 g, 12.8 mmol) obtained in the above (3).

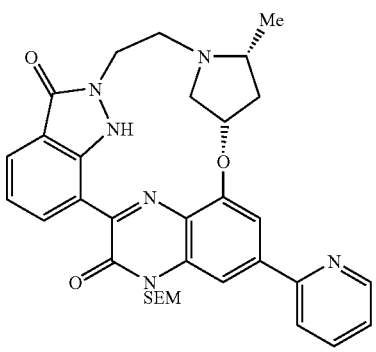

(5)

The cyclic derivative (15 mg, 24.5 μmol) obtained in the above (4) was dissolved in a mixture of 1,2-dimethoxyethane and water (9:1) (1 mL). To the solution were added tetrakis (triphenylphospine)palladium (10 mg), potassium carbonate (10 mg) and dimethyl 2-pyridylboronate (10 mg), and the mixture was stirred at 85° C. for 12 hours. Water and ethyl acetate were added to the resulting reaction solution, and the organic layer was separated, then washed successively with water and saturated brine. This organic layer was dried over anhydrous magnesium sulfate, filtered, and concentrated. The resulting residue was purified by a silica gel chromatography to obtain the above pyridine derivative (5 mg) as a yellow solid.

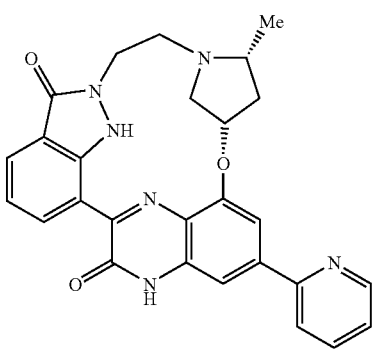

(6)

According to a method similar to the procedure described in Working Example 11-(18), the trifluoroacetate (2.4 mg) of the objective compound [90] was obtained as a dark yellow solid from the pyridine derivative (5 mg, 8.19 μmol) obtained in the above (5).

Spectral data of the compound of the above formula [90] are shown below.

$^1$H-NMR (DMSO-$d_6$) δ: 0.68-0.70 (3H, m), 1.38-1.44 (1H, m), 2.24-2.38 (1H, m), 2.40-2.60 (2H, m), 2.70-2.79 (1H, m), 2.90-3.02 (1H, m), 3.76-3.86 (2H, m), 4.41-4.48 (1H, m), 5.38-5.40 (1H, m), 7.12-7.18 (1H, m), 7.40-7.42 (1H, m), 7.66 (1H, s), 7.70 (1H, s), 7.81-7.84 (1H, m), 7.90-8.00 (1H, m), 8.01-8.02 (1H, m), 8.70-8.72 (1H, m), 9.42-9.44 (1H, m), 12.3 (1H, bs), 12.7 (1H, bs). mass: 481(M+1)$^+$.

Working Example 91

Synthesis of the Compound of the Following Formula [91]:

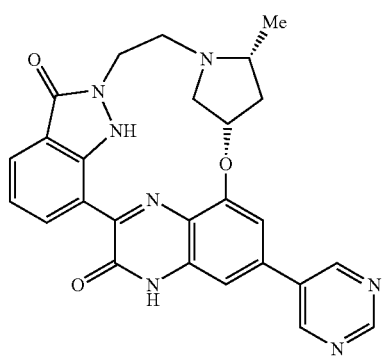

[91]

According to a method similar to the procedures described in Working Examples 90-(5) and 11-(18), the trifluoroacetate (1.9 mg) of the objective compound [91] was obtained as a dark yellow solid from the cyclic derivative (15 mg, 24.5 μmol) obtained in Working Example 90-(4) and pyrimidine-5-boronic acid.

Spectral datum of the compound of the above formula [91] is shown below. mass: $482(M+1)^+$.

Working Example 92

Synthesis of the Compound of the Following Formula [92]:

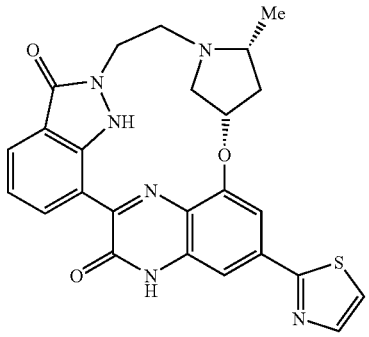

[92]

According to a method similar to the procedures described in Working Examples 90-(5) and 11-(18), the hydrochloride (7.7 mg) of the objective compound [92] was obtained as a dark yellow solid from the cyclic derivative (50 mg, 81.6 μmol) obtained in Working Example 90-(4) and thiazole-2-boronic acid.

Spectral datum of the compound of the above formula [92] is shown below. mass: $487(M+1)^+$.

Working Example 93

Synthesis of the Compound of the Following Formula [93]:

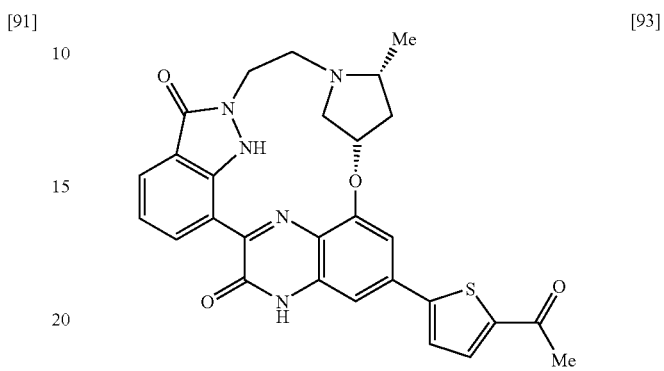

[93]

According to a method similar to the procedures described in Working Examples 90-(5) and 11-(18), the trifluoroacetate (2.6 mg) of the objective compound [93] was obtained as a dark yellow solid from the cyclic derivative (10 mg, 16.3 μmol) obtained in Working Example 90-(4) and 5-acetyl-2-thiopheneboronic acid.

Spectral datum of the compound of the above formula [93] is shown below. mass: $528(M+1)^+$.

Working Example 94

Synthesis of the Compound of the Following Formula [94]:

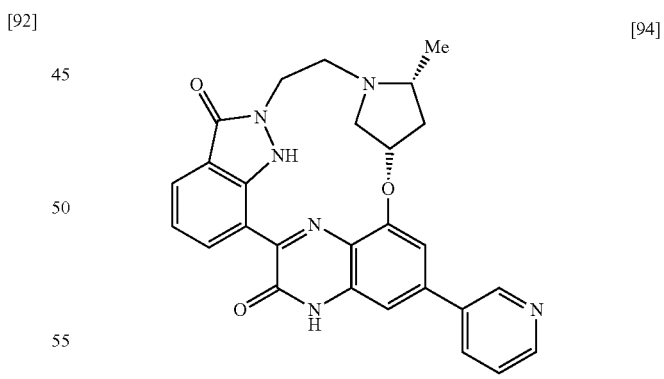

[94]

According to a method similar to the procedures described in Example 90-(5) and 11-(18), the trifluoroacetate (7.3 mg) of the objective compound [94] was obtained as a dark purple solid from the cyclic derivative (10 mg, 16.3 μmol) obtained in Working Example 90-(4) and pyridine-3-boronic acid.

Spectral datum of the compound of the above formula [94] is shown below. mass: $481(M+1)^+$.

Working Example 95

Synthesis of the Compound of the Following Formula [95]:

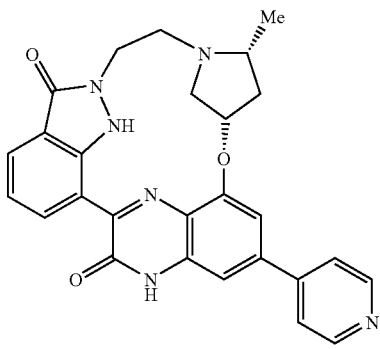

[95]

According to a method similar to the procedures described in Example 90-(5) and 11-(18), the trifluoroacetate (5.9 mg) of the objective compound [95] was obtained as a dark yellow solid from the cyclic derivative (10 mg, 16.3 μmol) obtained in Working Example 90-(4) and pyridine-4-boronic acid.

Spectral datum of the compound of the above formula [95] is shown below. mass: 481(M+1)$^+$.

Working Example 96

Synthesis of the Compound of the Following Formula [96]:

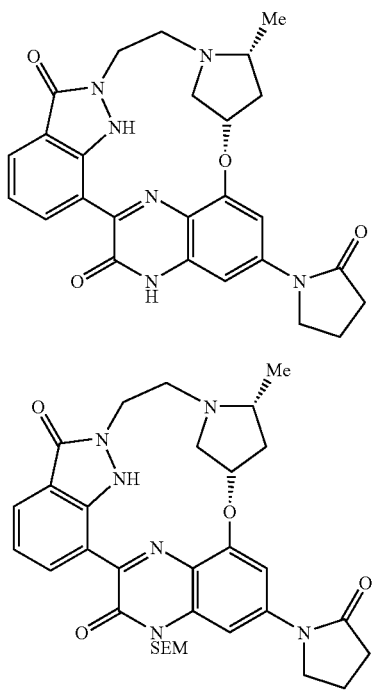

[96]

The cyclic derivative (20 mg, 32.7 μmol) obtained in Working Example 90-(4) was dissolved in 1,4-dioxane (1 mL). To this solution were added 2-pyrrolidinone (4.97 μL, 65.4 μmol), 4,5-bis(diphenylphosphino)-9,9-dimethylxanthene (5.68 mg, 9.81 μmol), tris(dibenzylideneacetone)dipalladium (0)-chloroform adduct (3.38 mg, 3.27 μmol) and cesium carbonate (23.4 mg, 71.9 μmol). The mixture was stirred at 110° C. for 1 hour under an argon atmosphere. The resulting reaction solution was cooled down to room temperature and concentrated in vacuo. The resulting residue was purified by a thin layer chromatography to obtain the above amide derivative (18 mg) as a yellow solid.

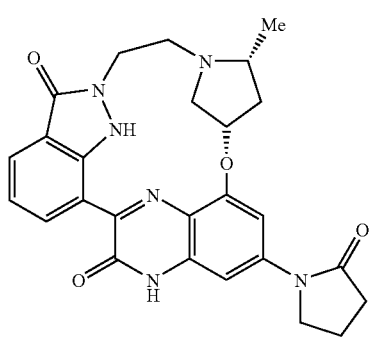

(2)

According to a method similar to the procedure described in Working Example 1-(6), the hydrochloride (14 mg) of the objective compound [96] was obtained as a dark purple solid from the amide derivative (18 mg, 29.2 μmol) obtained in the above (1).

Spectral data of the compound of the above formula [96] are shown below.

$^1$H-NMR (DMSO-d$_6$) δ: 0.58-0.75 (3H, m) 1.22-1.45 (1H, m), 2.00-4.00(13H, m), 4.35-4.53 (1H, m), 5.18-5.28 (1H, m), 7.07-7.20 (1H, m), 7.29-7.42 (2H, m), 7.78-7.86 (1H, m), 9.37-9.43 (1H, m), 12.25 (1H, brs), 12.56 (1H, s). mass: 487(M+1)$^+$.

Working Example 97

Synthesis of the Compound of the Following Formula [97]:

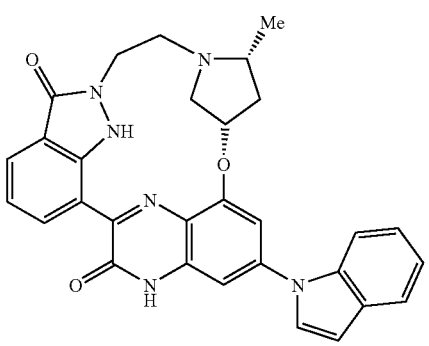

[97]

According to a method similar to the procedures described in Working Examples 96-(1) and 1-(6), the hydrochloride (3.3 mg) of the objective compound [97] was obtained as a dark purple solid from the cyclic derivative (10 mg, 16.3 μmol) obtained in Working Example 90-(4) and indole.

Spectral datum of the compound of the above formula [97] is shown below. mass: 519(M+1)$^+$.

Working Example 98

Synthesis of the Compound of the Following Formula [98]:

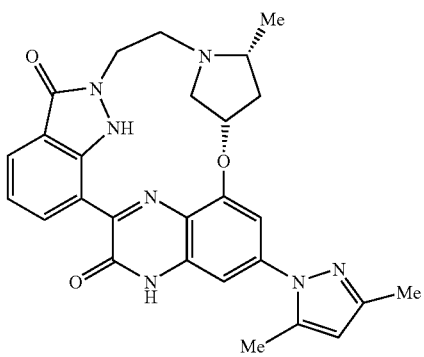

[98]

According to a method similar to the procedures described in Working Examples 96-(1) and 1-(6), the trifluoroacetate (5.9 mg) of the objective compound [98] was obtained as a dark purple solid from the cyclic derivative (10 mg, 16.3 µmol) obtained in Working Example 90-(4) and 3,5-dimethylpyrazole.

Spectral datum of the compound of the above formula [98] is shown below. mass: 498(M+1)$^+$.

Working Example 99

Synthesis of the Compound of the Following Formula [99]:

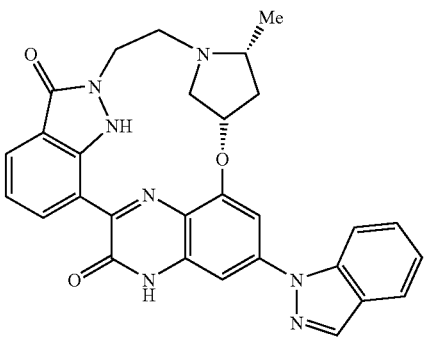

[99]

According to a method similar to the procedures described in Working Examples 96-(1) and 1-(6), the trifluoroacetate (4.6 mg) of the objective compound [99] was obtained as a dark purple solid from the cyclic derivative (10 mg, 16.3 mmol) obtained in Working Example 90-(4) and indazole.

Spectral datum of the compound of the above formula [99] is shown below. mass: 520(M+1)$^+$.

Working Example 100

Synthesis of the Compound of the Following Formula [100]:

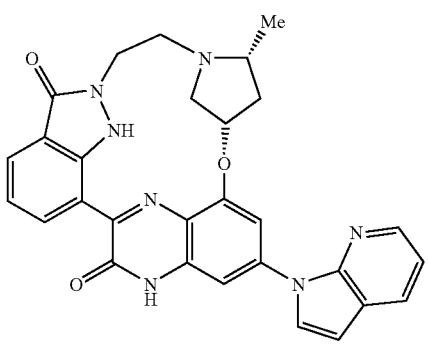

[100]

According to a method similar to the procedures described in Working Examples 96-(1) and 1-(6), the trifluoroacetate (6.3 mg) of the objective compound [100] was obtained as a dark purple solid from the cyclic derivative (10 mg, 16.3 µmol) obtained in Working Example 90-(4) and 7-azaindole.

Spectral datum of the compound of the above formula [100] is shown below. mass: 520(M+1)$^+$.

Working Example 101

Synthesis of the Compound of the Following Formula [101]:

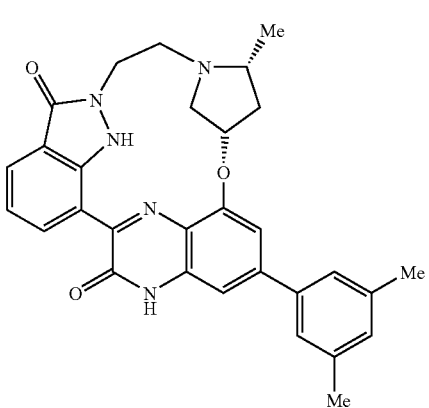

[101]

According to a method similar to the procedures described in Working Examples 90-(5) and 11-(18), the hydrochloride (14.5 mg) of the objective compound [101] was obtained as a dark purple solid from the cyclic derivative (30 mg, 49.0 µmol) obtained in Working Example 90-(4) and 3,5-dimethylphenylboronic acid.

Spectral datum of the compound of the above formula [101] is shown below. mass: 508(M+1)$^+$.

Working Example 102

Synthesis of the Compound of the Following Formula [102]:

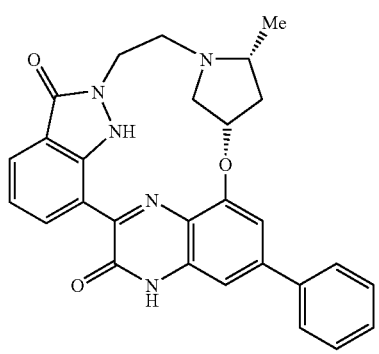

[102]

According to a method similar to the procedures described in Working Examples 90-(5) and 11-(18), the hydrochloride (7.0 mg) of the objective compound [102] was obtained as a dark purple solid from the cyclic derivative (10 mg, 16.3 μmol) obtained in Working Example 90-(4) and phenylboronic acid.

Spectral datum of the compound of the above formula [102] is shown below. mass: 480(M+1)$^+$.

Working Example 103

Synthesis of the Compound of the Following formula [103]:

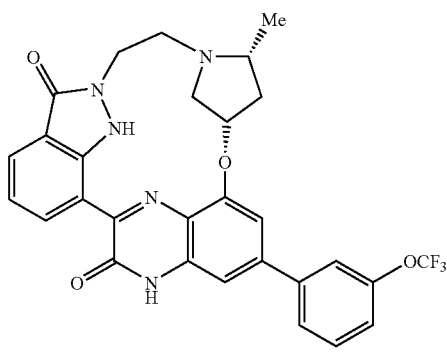

[103]

According to a method similar to the procedures described in Working Examples 90-(5) and 11-(18), the trifluoroacetate (5.1 mg) of the objective compound [103] was obtained as a dark purple solid from the cyclic derivative (10 mg, 16.3 μmol) obtained in Working Example 90-(4) and 3-(trifluoromethoxy)phenylboronic acid.

Spectral datum of the compound of the above formula [103] is shown below. mass: 564(M+1)$^+$.

Working Example 104

Synthesis of the Compound of the Following Formula [104]:

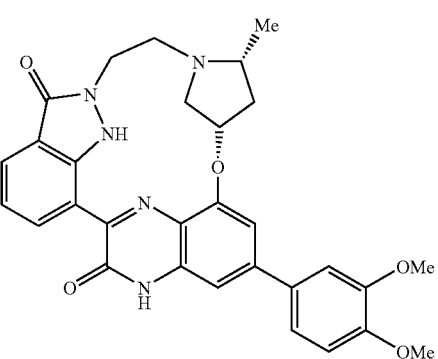

[104]

According to a method similar to the procedures described in Working Examples 90-(5) and 11-(18), the trifluoroacetate (9.0 mg) of the objective compound [104] was obtained as a dark purple solid from the cyclic derivative (10 mg, 16.3 μmol) obtained in Working Example 90-(4) and 3,4-dimethoxyphenylboronic acid.

Spectral datum of the compound of the above formula [104] is shown below. mass: 540(M+1)$^+$.

Working Example 105

Synthesis of the Compound of the Following Formula [105]:

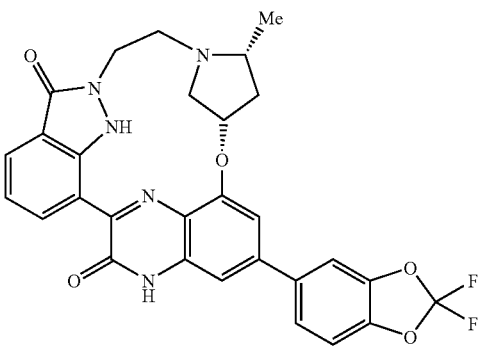

[105]

According to a method similar to the procedures described in Working Examples 90-(5) and 11-(18), the hydrochloride (5.2 mg) of the objective compound [105] was obtained as a dark purple solid from the cyclic derivative (10 mg, 16.3 μmol) obtained in Working Example 90-(4) and 2,2-difluorobenzodioxole-5-boronic acid.

Spectral datum of the compound of the above formula [105] is shown below. mass: 560(M+1)$^+$.

Working Example 106

Synthesis of the Compound of the Following Formula [106]:

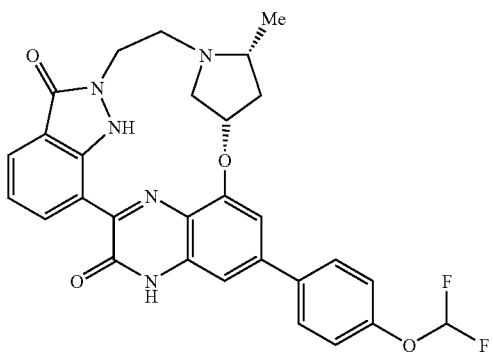

[106]

According to a method similar to the procedures described in Working Examples 90-(5) and 11-(18), the hydrochloride (1.1 mg) of the objective compound [106] was obtained as a dark purple solid from the cyclic derivative (10 mg, 16.3 μmol) obtained in Working Example 90-(4) and 4-(difluoromethoxy)phenylboronic acid.

Spectral datum of the compound of the above formula [106] is shown below. mass: 546(M+1)$^+$.

Working Example 107

Synthesis of the Compound of the Following Formula [107]:

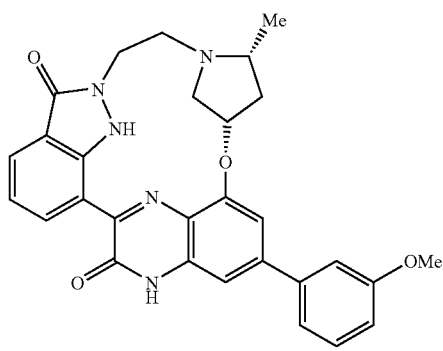

[107]

According to a method similar to the procedures described in Working Examples 90-(5) and 11-(18), the trifluoroacetate (20.9 mg) of the objective compound [107] was obtained as a dark purple solid from the cyclic derivative (20 mg, 32.6 μmol) obtained in Working Example 90-(4) and 3-methoxyphenylboronic acid.

Spectral datum of the compound of the above formula [107] is shown below. mass: 510(M+1)$^+$.

Working Example 108

Synthesis of the Compound of the Following Formula [108]:

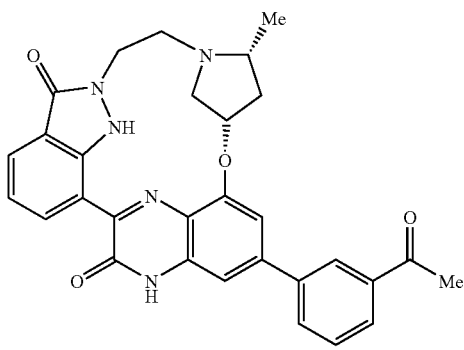

[108]

According to a method similar to the procedures described in Working Examples 90-(5) and 11-(18), the trifluoroacetate (14.3 mg) of the objective compound [108] was obtained as a dark purple solid from the cyclic derivative (20 mg, 32.6 mmol) obtained in Working Example 90-(4) and 3-acetylphenylboronic acid.

Spectral datum of the compound of the above formula [108] is shown below. mass: 522(M+1)$^+$.

Working Example 109

Synthesis of the Compound of the Following Formula [109]:

[109]

According to a method similar to the procedures described in Working Examples 90-(5) and 11-(18), the trifluoroacetate (13.2 mg) of the objective compound [109] was obtained as a dark purple solid from the cyclic derivative (20 mg, 32.6 μmol) obtained in working Example 90-(4) and 3-acetamidophenylboronic acid.

Spectral datum of the compound of the above formula [109] is shown below. mass: 537(M+1)$^+$.

Working Example 110

Synthesis of the Compound of the Following Formula [110]:

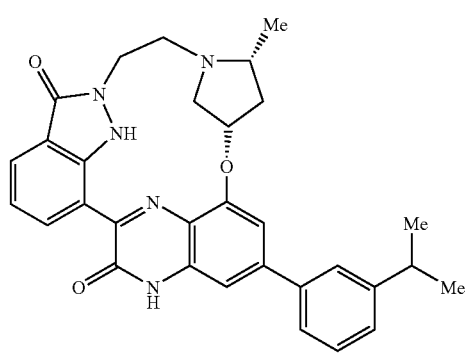

[110]

According to a method similar to the procedures described in Working Examples 90-(5) and 11-(18), the trifluoroacetate (8.8 mg) of the objective compound [110] was obtained as a dark purple solid from the cyclic derivative (20 mg, 32.6 µmol) obtained in Working Example 90-(4) and 3-isopropylphenylboronic acid.

Spectral datum of the compound of the above formula [110] is shown below. mass: 522(M+1)$^+$.

Working Example 111

Synthesis of the Compound of the Following Formula [111]:

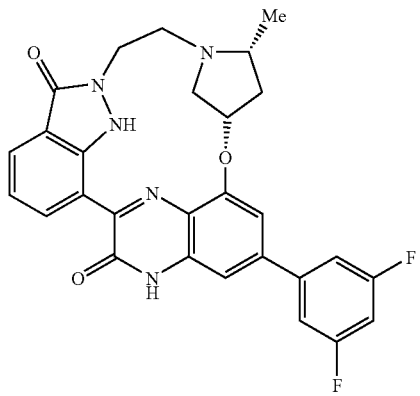

[111]

According to a method similar to the procedures described in Working Examples 90-(5) and 11-(18), the trifluoroacetate (10.7 mg) of the objective compound [111] was obtained as a dark purple solid from the cyclic derivative (20 mg, 32.6 µmol) obtained in Working Example 90-(4) and 3,5-difluorophenylboronic acid.

Spectral datum of the compound of the above formula [111] is shown below. mass: 516(M+1)$^+$.

Working Example 112

Synthesis of the Compound of the Following Formula [112]:

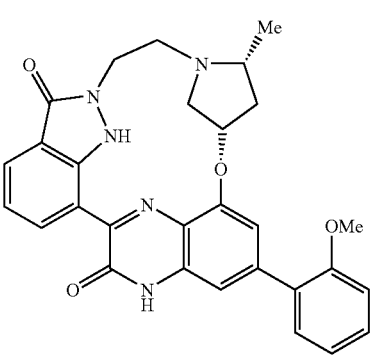

[112]

According to a method similar to the procedures described in Working Examples 90-(5) and 11-(18), the trifluoroacetate (8.6 mg) of the objective compound [112] was obtained as a dark purple solid from the cyclic derivative (10 mg, 16.3 µmol) obtained in Working Example 90-(4) and 2-methoxyphenylboronic acid.

Spectral datum of the compound of the above formula [112] is shown below. mass: 510(M+1)$^+$.

Working Example 113

Synthesis of the Compound of the Following Formula [113]:

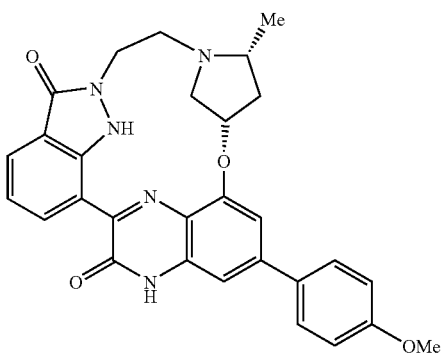

[113]

According to a method similar to the procedures described in Working Examples 90-(5) and 11-(18), the trifluoroacetate (5.3 mg) of the objective compound [113] was obtained as a dark purple solid from the cyclic c derivative (10 mg, 16.3 µmol) obtained in Working Example 90-(4) and 4-methoxyphenylboronic acid.

Spectral datum of the compound of the above formula [113] is shown below. mass: 510(M+1)$^+$.

Working Example 114

Synthesis of the Compound of the Following Formula [114]:

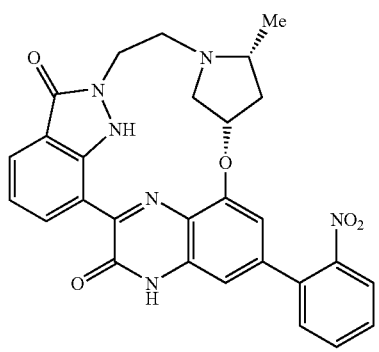

[114]

According to a method similar to the procedures described in Working Examples 90-(5) and 11-(18), the trifluoroacetate (6.8 mg) of the objective compound [114] was obtained as a dark purple solid from the cyclic derivative (10 mg, 16.3 μmol) obtained in Working Example 90-(4) and 2-nitrophenylboronic acid.

Spectral datum of the compound of the above formula [114] is shown below. mass: 525(M+1)$^+$.

Working Example 115

Synthesis of the Compound of the Following Formula [115]:

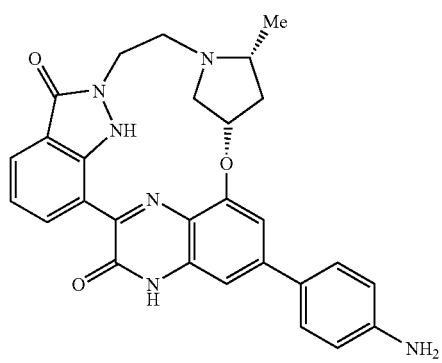

[115]

According to a method similar to the procedures described in Working Examples 90-(5) and 11-(18), the trifluoroacetate (8.5 mg) of the objective compound [115] was obtained as a dark purple solid from the cyclic derivative (10 mg, 16.3 μmol) obtained in Working Example 90-(4) and 4-aminophenylboronic acid.

Spectral datum of the compound of the above formula [115] is shown below. mass: 495(M+1)$^+$.

Working Example 116

Synthesis of the Compound of the Following Formula [116]:

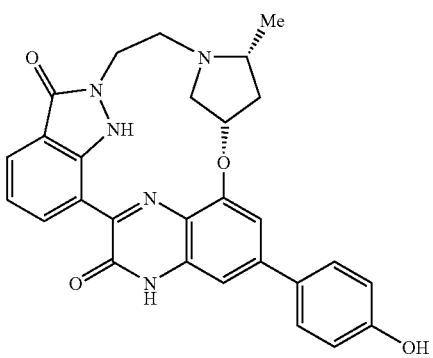

[116]

According to a method similar to the procedures described in Working Examples 90-(5) and 11-(18), the trifluoroacetate (1.3 mg) of the objective compound [116] was obtained as a dark purple solid from the cyclic derivative (10 mg, 16.3 μmol) obtained in Working Example 90-(4) and 4-hydroxyphenylboronic acid.

Spectral datum of the compound of the above formula [116] is shown below. mass: 496(M+1)$^+$.

Working Example 117

Synthesis of the Compound of the Following Formula [117]:

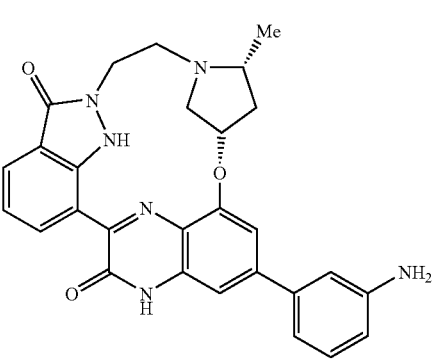

[117]

According to a method similar to the procedures described in Working Examples 90-(5) and 11-(18), the trifluoroacetate (10.8 mg) of the objective compound [117] was obtained as a dark purple solid from the cyclic derivative (10 mg, 16.3 μmol) obtained in Working Example 90-(4) and 3-aminophenylboronic acid.

Spectral datum of the compound of the above formula [117] is shown below. mass: 495(M+1)$^+$.

Working Example 118

Synthesis of the Compound of the Following Formula [118]:

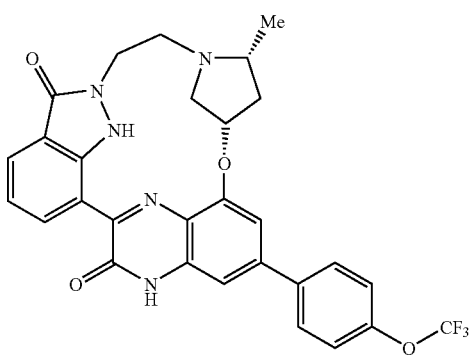

[118]

According to a method similar to the procedures described in Working Examples 90-(5) and 11-(18), the trifluoroacetate (5.6 mg) of the objective compound [118] was obtained as a dark purple solid from the cyclic derivative (10 mg, 16.3 μmol) obtained in Working Example 90-(4) and 4-(trifluoromethoxy)phenylboronic acid.

Spectral datum of the compound of the above formula [118] is shown below. mass: 564(M+1)$^+$.

Working Example 119

Synthesis of the Compound of the Following Formula [119]:

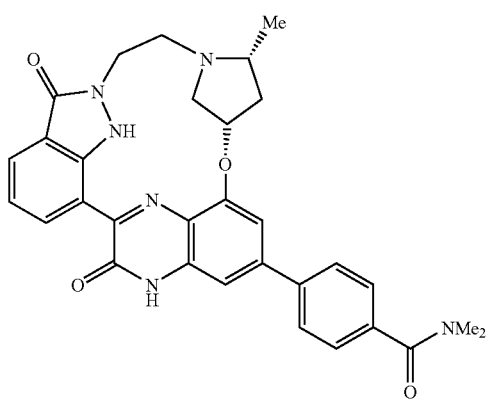

[119]

According to a method similar to the procedures described in Working Examples 90-(5) and 11-(18), the trifluoroacetate (5.5 mg) of the objective compound [119] was obtained as a dark purple solid from the cyclic derivative (10 mg, 16.3 μmol) obtained in Working Example 90-(4) and 4-(N,N-dimethylaminocarbonyl)phenylboronic acid.

Spectral datum of the compound of the above formula [119] is shown below. mass: 551(M+1)$^+$.

Working Example 120

Synthesis of the Compound of the Following Formula [120]:

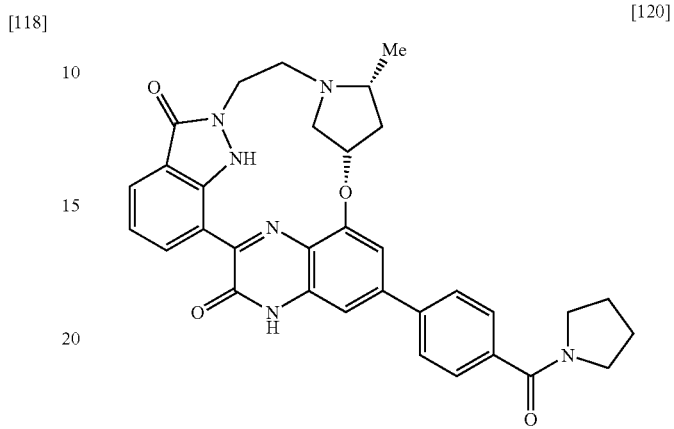

[120]

According to a method similar to the procedures described in Working Examples 90-(5) and 11-(18), the trifluoroacetate (4.8 mg) of the objective compound [120] was obtained as a dark purple solid from the cyclic derivative (10 mg, 16.3 μmol) obtained in Working Example 90-(4) and 4-(pyrrolidine-1-carbonyl)phenylboronic acid.

Spectral datum of the compound of the above formula [120] is shown below. mass: 577(M+1)$^+$.

Working Example 121

Synthesis of the Compound of the Following Formula [121]:

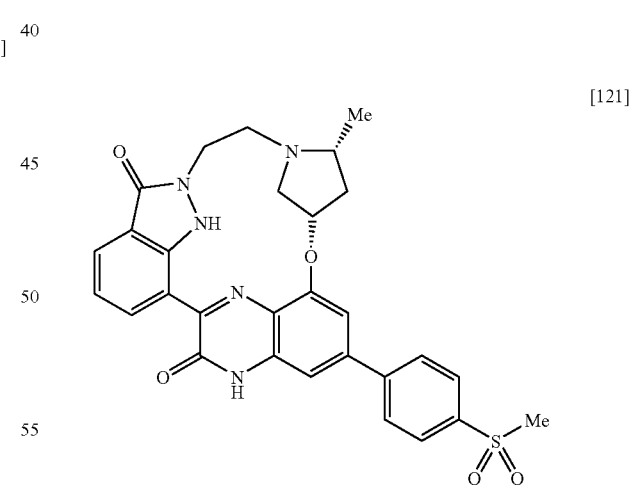

[121]

According to a method similar to the procedures described in Working Examples 90-(5) and 11-(18), the trifluoroacetate (7.3 mg) of the objective compound [121] was obtained as a dark purple solid from the cyclic derivative (10 mg, 16.3 μmol) obtained in Working Example 90-(4) and 4-methylsulfonylphenylboronic acid.

Spectral datum of the compound of the above formula [121] is shown below. mass: 558(M+1)$^+$.

Working Example 122

Synthesis of the Compound of the Following Formula [122]:

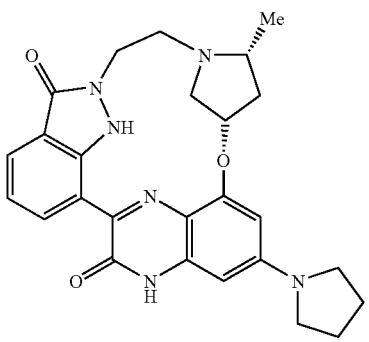

[122]

According to a method similar to the procedures described in Working Examples 43-(1) and 1-(6), the trifluoroacetate (1.5 mg) of the objective compound [122] was obtained as a dark purple solid from the cyclic derivative (10 mg, 16.3 μmol) obtained in Working Example 90-(4) and pyrrolidine.

Spectral data of the compound of the above formula [122] are shown below.

$^1$H-NMR (DMSO-d$_6$) δ: 0.60-0.80 (3H, m), 1.30-1.50 (1H, m), 1.95-4.38(15H, m), 4.38-4.50 (1H, m), 5.18-5.28 (1H, m), 5.93 (1H, s), 6.30 (1H, s), 7.02-7.18 (1H, m), 7.65-7.75 (1H, m), 9.22-9.30 (1H, m), 12.02-12.23 (2H, m). mass: 473(M+1)$^+$.

Working Example 123

Synthesis of the Compound of the Following Formula [123]:

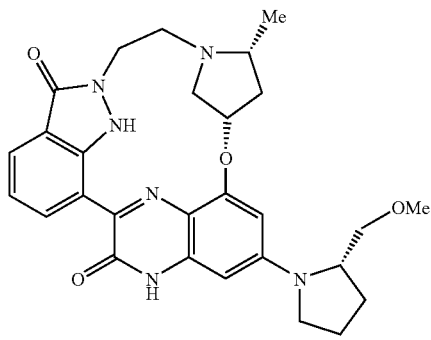

[123]

According to a method similar to the procedures described in Working Examples 43-(1) and 1-(6), the trifluoroacetate (1.7 mg) of the objective compound [123] was obtained as a dark purple solid from the cyclic derivative (10 mg, 16.3 μmol) obtained in Working Example 90-(4) and (S)-2-methoxymethylpyrrolidine.

Spectral datum of the compound of the above formula [123] is shown below. mass: 517(M+1)$^+$.

Working Example 124

Synthesis of the Compound of the Following Formula [124]:

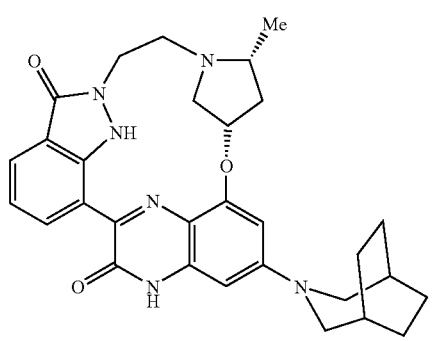

[124]

According to a method similar to the procedures described in Working Examples 43-(1) and 1-(6), the trifluoroacetate (1.5 mg) of the objective compound [124] was obtained as a dark purple solid from the cyclic derivative (10 mg, 16.3 μmol) obtained in Working Example 90-(4) and 3-azabicyclo[3,2,2]nonane.

Spectral datum of the compound of the above formula [124] is shown below. mass: 527(M+1)$^+$.

Working Example 125

Synthesis of the Compound of the Following Formula [125]:

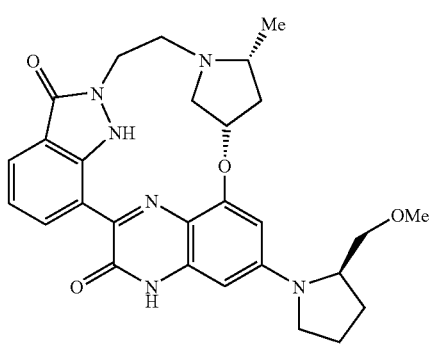

[125]

According to a method similar to the procedures described in Working Examples 43-(1) and 1-(6), the trifluoroacetate (1.9 mg) of the objective compound [125] was obtained as a dark purple solid from the cyclic derivative (10 mg, 16.3 μmol) obtained in Working Example 90-(4) and (R)-2-methoxymethylpyrrolidine.

Spectral datum of the compound of the above formula [125] is shown below. mass: 517(M+1)$^+$.

Working Example 126

Synthesis of the Compound of the Following Formula [126]:

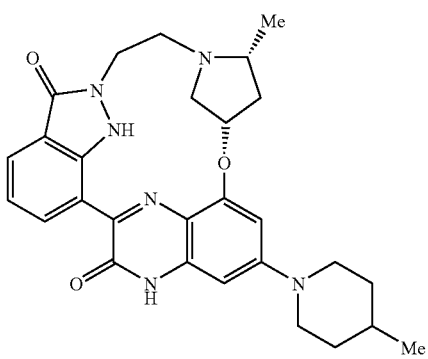

[126]

According to a method similar to the procedures described in Working Examples 43-(1) and 1-(6), the trifluoroacetate (1.4 mg) of the objective compound [126] was obtained as a dark purple solid from the cyclic derivative (10 mg, 16.3 µmol) obtained in Working Example 90-(4) and 4-methylpiperidine.

Spectral datum of the compound of the above formula [126] is shown below. mass: 501(M+1)$^+$.

Working Example 127

Synthesis of the Compound of the Following Formula [127]:

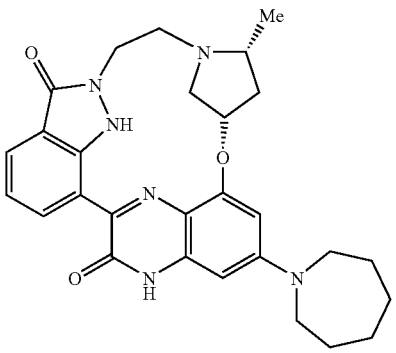

[127]

According to a method similar to the procedures described in Working Examples 43-(1) and 1-(6), the trifluoroacetate (1.7 mg) of the objective compound [127] was obtained as a dark purple solid from the cyclic derivative (10 mg, 16.3 µmol) obtained in Working Example 90-(4) and hexamethyleneimine.

Spectral datum of the compound of the above formula [127] is shown below. mass: 501(M+1)$^+$.

Working Example 128

Synthesis of the Compound of the Following Formula [128]:

[128]

According to a method similar to the procedures described in Working Examples 43-(1) and 1-(6), the trifluoroacetate (1.1 mg) of the objective compound [128] was obtained as a dark purple solid from the cyclic derivative (10 mg, 16.3 µmol) obtained in Working Example 90-(4) and 1-(2-fluorophenyl)-piperazine.

Spectral datum of the compound of the above formula [128] is shown below. mass: 582(M+1)$^+$.

Working Example 129

Synthesis of the Compound of the Following Formula [129]:

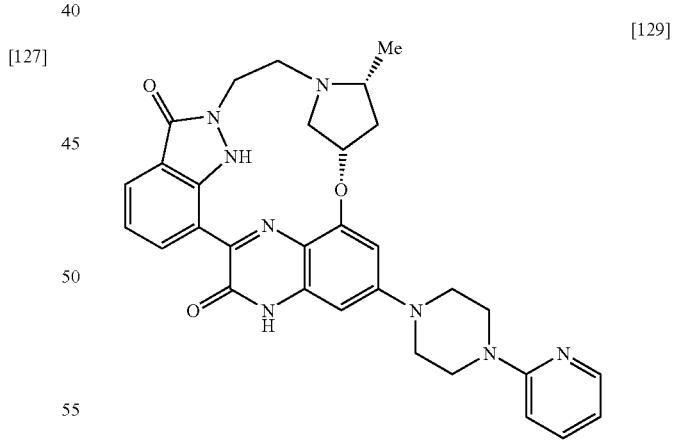

[129]

According to a method similar to the procedures described in Working Examples 43-(1) and 1-(6), the trifluoroacetate (1.1 mg) of the objective compound [129] was obtained as a dark purple solid from the cyclic derivative (10 mg, 16.3 µmol) obtained in Working Example 90-(4) and 1-(2-pyridyl)piperazine.

Spectral datum of the compound of the above formula [129] is shown below. mass: 565(M+1)$^+$.

Working Example 130

Synthesis of the Compound of the Following Formula [130]:

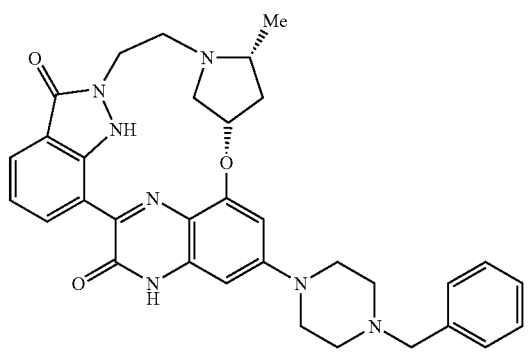

[130]

According to a method similar to the procedures described in Working Examples 43-(1) and 1-(6), the trifluoroacetate (1.0 mg) of the objective compound [130] was obtained as a dark purple solid from the cyclic derivative (10 mg, 16.3 μmol) obtained in Working Example 90-(4) and 1-benzylpiperazine. Spectral datum of the compound of the above formula [130] is shown below. mass: 578(M+1)$^+$.

Working Example 131

Synthesis of the Compound of the Following Formula [131]:

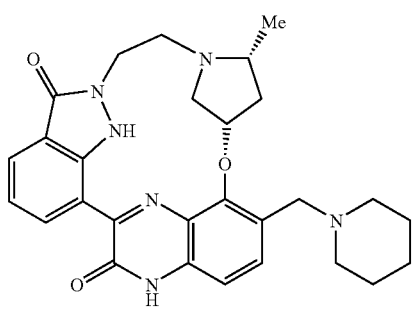

[131]

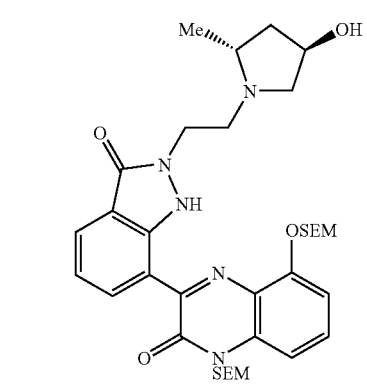

(1)

The amine derivative (320 mg, 421 μmol) obtained in Working Example 90-(3) was dissolved in tetrahydrofuran (18 mL) and methanol (6 mL), and 10% palladium-carbon catalyst (64 mg) was added thereto under a nitrogen atmosphere. The reaction system was substituted by hydrogen gas, and the mixture was stirred at room temperature for 1 hour. The resulting reaction solution was filtered through a Celite pad to remove the catalyst. The filtrate was concentrated in vacuo and the resulting residue was purified by a silica gel chromatography to obtain the reduced derivative (290 mg) as a yellowish brown solid.

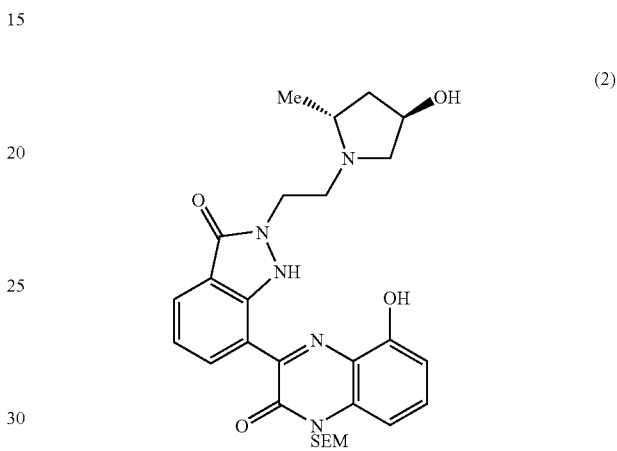

(2)

According to a method similar to the procedure described in Working Example 1-(4), the above phenol derivative (200 mg) was obtained as a yellowish brown solid from the reduced derivative (290 mg, 421 μmol) obtained in the above (1).

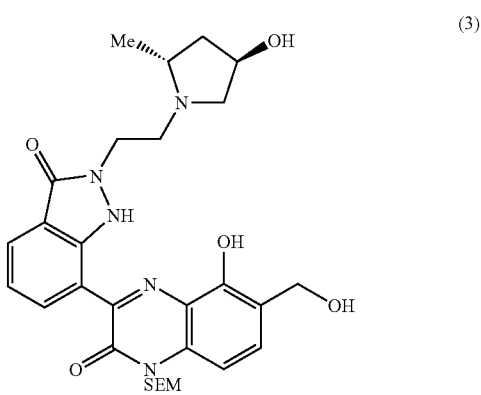

(3)

According to the procedure described in Working Example 72-(2), the above hydroxymethyl derivative (210 mg) was obtained as a ocher solid from the phenol derivative (200 mg, 363 μmol) obtained in the above (2).

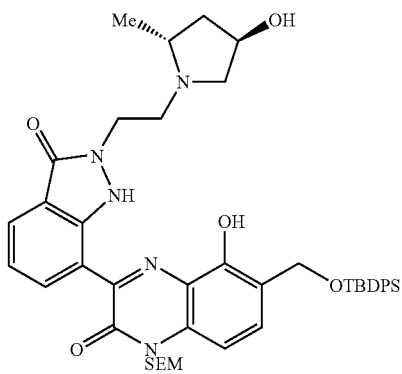

(4)

To a stirred chloroform suspension (10 mL) of the hydroxymethyl derivative (210 mg, 363 μmol) obtained in the above (3) were added triethylamine (202 μL, 725 μmol), 4-dimethylaminopyridine (8.9 mg, 72.5 μmol) and t-butyldiphenylsilyl chloride (141 μL, 544 μmol) at 0° C., and the mixture was stirred at room temperature for 30 minutes. After further addition of triethylamine (606 μL, 2.17 mmol), 4-dimethylaminopyridine (16.7 mg, 217 μmol) and t-butyldiphenylsilyl chloride (324 μL, 1.63 mmol) with stirring at 0° C., the reaction solution was stirred at room temperature for 1.5 hours. After addition of water, the resulting reaction solution was extracted with chloroform. The organic layer was washed with saturated brine, dried over anhydrous sodium sulfate and filtered. The filtrate was concentrated, and the resulting residue was purified by a column chromatography on silica gel to obtain the protected derivative with TBDPS (257 mg) as a yellowish brown solid.

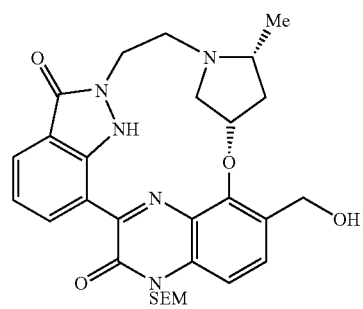

(5)

According to a method similar to the procedures described in Working Examples 1-(5) and 15-(4), the above alcohol derivative (130 mg) was obtained as a yellowish brown solid from the derivative protected with TBDPS (257 mg, 313 μmol) obtained in the above (4).

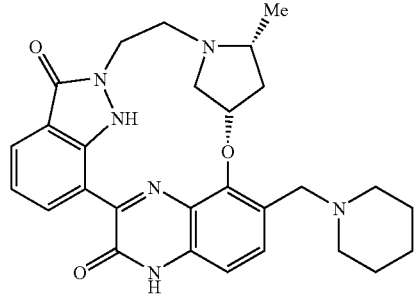

(6)

According to a method similar to the procedures described in Working Examples 11-(17) and 1-(6), the hydrochloride (4.6 mg) of the objective compound [131] was obtained as a yellow green solid from the alcohol derivative (11.3 mg, 20.1 μmol) obtained in the above (5) and piperidine.

Spectral data of the compound of the above formula [131] are shown below.

$^1$H-NMR (DMSO-$d_6$) δ: 0.60-0.68 (3H, m), 1.24-1.43 (1H, m), 1.63-1.85(6H, m), 2.00-2.26 (1H, m), 2.71-3.46 (8H, m), 3.54-3.77 (1H, m), 3.78-3.97 (1H, m), 4.30-4.52 (3H, m), 5.33-5.43 (1H, m), 7.18-7.24 (1H, m), 7.21 (1H, d, J=8.4 Hz), 7.75-7.90 (1H, m), 7.88 (1H, d, J=7.5 Hz), 9.43-9.59 (1H, m), 9.98-10.0 (1H, m), 12.7-12.9 (1H, m), 12.9 (1H, s). mass: 501(M+1)$^+$.

Working Example 132

Synthesis of the Compound of the Following Formula [132]:

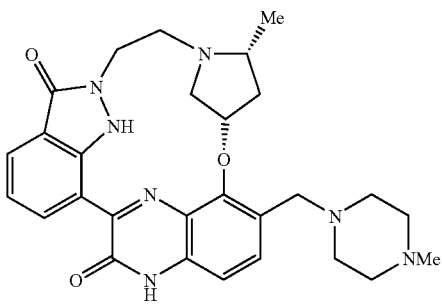

[132]

According to a method similar to the procedures described in Working Examples 11-(17) and 1-(6), the hydrochloride (6.9 mg) of the objective compound [132] was obtained as a dark green solid from the alcohol derivative (18.4 mg, 32.7 μmol) obtained in Working Example 131-(5) and N-methylpiperazine.

Spectral datum of the compound of the above formula [132] is shown below. mass: 516(M+1)$^+$.

Working Example 133

Synthesis of the Compound of the Following Formula [133]:

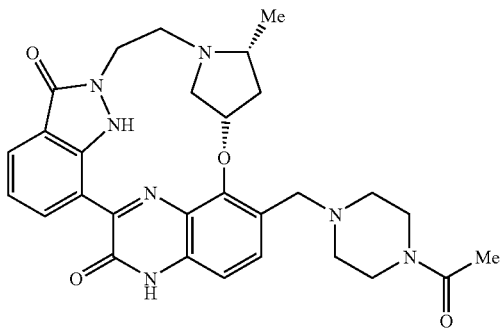

[133]

According to a method similar to the procedures described in Working Examples 11-(17) and 1-(6), the hydrochloride (11.7 mg) of the objective compound [133] was obtained as a dark green solid from the alcohol derivative (20.7 mg, 36.8 μmol) obtained in Working Example 131-(5) and N-acetylpiperazine.

Spectral datum of the compound of the above formula [133] is shown below. mass: 544(M+1)$^+$.

Working Example 134

Synthesis of the Compound of the Following Formula [134]:

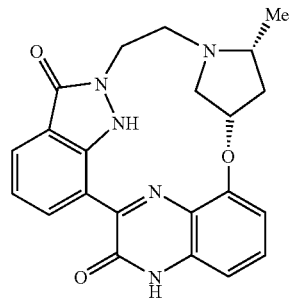

[134]

According to a method similar to the procedures described in Working Examples 83-(1), 11-(14) to 11-(16) and 11-(18), the hydrochloride (9.6 mg) of the objective compound [134] was obtained as a dark green solid from the alcohol derivative (140 mg, 351 μmol) obtained in Working Example 76-(2).

Spectral data of the compound of the above formula [134] are shown below.

$^1$H-NMR (DMSO-d$_6$) δ: 0.68 (3H, m), 1.34 (1H, m), 2.00-3.10 (5H, m), 3.40-4.00 (2H, m), 4.46 (1H, m), 5.24 (1H, brs), 6.94 (2H, m), 7.14 (1H, m), 7.48 (1H, m), 7.83 (1H, d, J=8.4 Hz), 9.43 (1H, m), 12.2 (1H, brs), 12.6 (1H, brs). mass: 404(M+1)$^+$.

Working Example 135

Synthesis of the Compound of the Following Formula [135]:

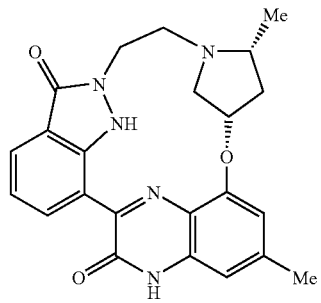

[135]

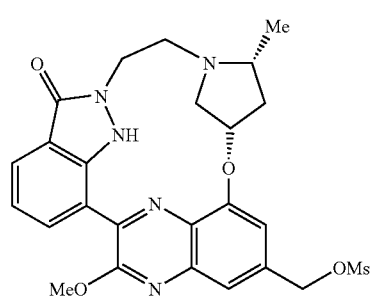

(1)

According to a method similar to the procedure described in Working Example 11-(14), the above mesylated derivative (270 mg) was obtained as a yellow solid from the cyclic derivative (240 mg, 536 μmol) obtained in Working Example 83-(2).

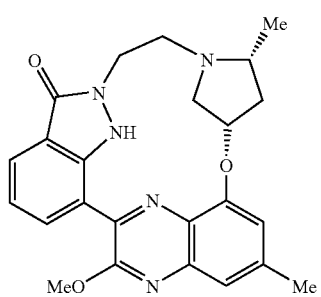

(2)

According to a method similar to the procedure described in Working Example 131-(1), the above methyl derivative (24 mg) was obtained as a yellow solid from the mesylated derivative (90 mg, 171 μmol) obtained in the above (1).

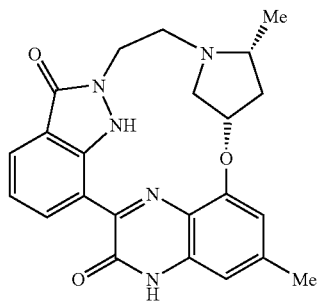

(3)

According to a method similar to the procedure described in Working Example 1-(6), the hydrochloride (15 mg) of the objective compound [135] was obtained as a dark purple solid from the methyl derivative (24 mg, 55.6 μmol) obtained in the above (2).

Spectral data of the compound of the above formula [135] are shown below.

$^1$H-NMR (DMSO-d$_6$) δ: 0.60-0.75 (3H, m), 1.25-1.41 (1H, m), 2.20-2.61(6H, m), 2.63-2.82 (1H, m), 2.85-3.10 (1H, m), 3.55-3.90 (2H, m), 4.38-4.50 (1H, m), 5.18-5.25 (1H, m), 6.72-6.79 (1H, m), 6.82-6.90 (1H, m), 7.02-7.22 (1H, m), 7.80-7.86 (1H, m), 9.35-9.45 (1H, m), 12.20-12.31 (1H, m), 12.55-12.65 (1H, m). mass: 418(M+1)$^+$.

Working Example 136

Synthesis of the Compound of the Following Formula [136]:

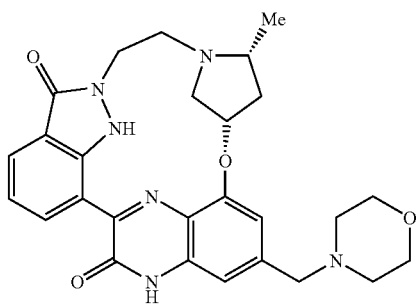

[136]

According to a method similar to the procedure described in Working Examples 11-(17) and 1-(6), the hydrochloride (49 mg) of the objective compound [136] was obtained as a yellow solid from the mesylated derivative (80 mg, 179 μmol) obtained in Working Example 135-(1) and morpholine.

Spectral data of the compound of the above formula [136] are shown below.

$^1$H-NMR (DMSO-d$_6$) δ: 0.62-0.78 (3H, m), 1.30-1.42 (1H, m), 2.22-3.40(9H, m), 3.60-4.00 (6H, m), 4.35-4.52 (3H, m), 5.12-5.23 (1H, m), 7.05(1H, d, J=0.9 Hz), 7.17 (1H, dd, J=7.9 Hz, 8.3 Hz), 7.37 (1H, d, J=0.9 Hz), 7.88 (1H, d, J=7.9 Hz), 9.44 (1H, d, J=8.3 Hz), 10.82-11.01 (1H, m), 12.24 (1H, s), 12.89 (1H, s). mass: 503(M+1)$^+$.

Working Example 137

Synthesis of the Compound of the Following Formula [137]:

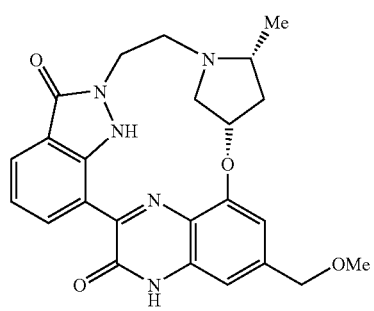

[137]

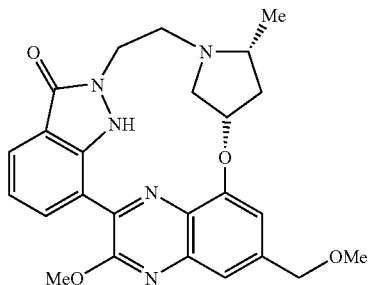

(1)

To tetrahydrofuran solution (5 mL) containing the mesylated derivative (80 mg, 179 μmol) obtained in Example 135-(1) was added 1M methanol solution containing sodium methoxide at room temperature. The mixture was stirred at 60° C. for 3 hours. The reaction solution was cooled down to room temperature, diluted with chloroform, and washed successively with water and saturated brine. The organic layer was dried over anhydrous magnesium sulfate and filtered. The filtrate was concentrated in vacuo and the resulting residue was purified by a silica gel chromatography to produce the methoxymethyl derivative (56 mg) as a yellow solid.

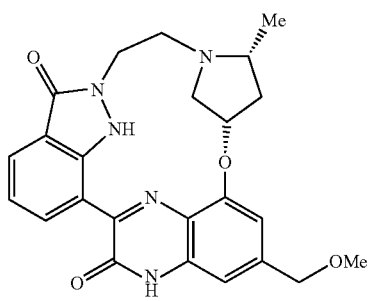

(2)

According to a method similar to the procedure described in Working Example 11-(18), the hydrochloride (40 mg) of the objective compound [137] was obtained as a purple solid from the methoxymethyl derivative (56 mg, 121 μmol) obtained in the above (1).

Spectral data of the compound of the above formula [137] are shown below.

$^1$H-NMR (DMSO-d$_6$) δ: 0.60-0.80 (3H, m), 1.20-1.50 (1H, m), 2.20-3.10(5H, m), 3.56 (3H, s), 3.72-4.60 (5H, m), 5.20-5.31 (1H, m), 6.89-7.00(2H, m), 7.10-7.22 (1H, m), 7.80-7.88 (1H, m), 9.38-9.48 (1H, m), 12.20-12.38 (1H, m), 12.62-12.70 (1H, m). mass: 448(M+1)$^+$.

Working Example 138

Synthesis of the Compound of the Following Formula [138]:

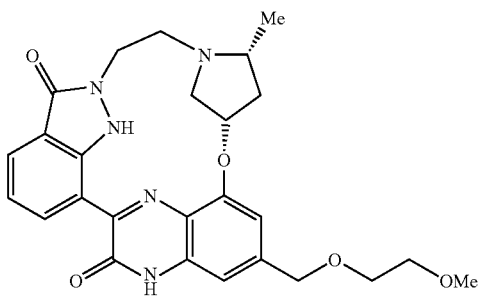
(1)

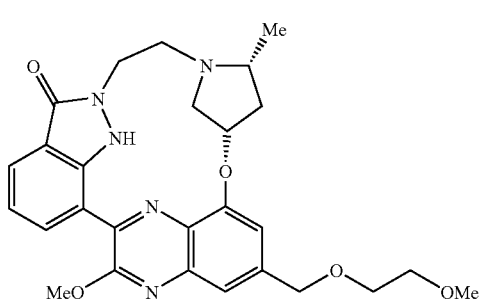
(2)

To tetrahydrofuran solution (5 mL) containing the mesylated derivative (50 mg, 95 μmol) obtained in Example 135-(1) was added 1M tetrahydrofuran solution (5 mL) containing sodium 2-methoxyethoxide at room temperature, and the mixture was stirred at 60° C. for 3 hours. The reaction solution was cooled down to room temperature, diluted with chloroform, and washed successively with water and saturated brine. The organic layer was dried over anhydrous magnesium sulfate, and filtered. The filtrate was concentrated in vacuo, and the resulting residue was purified by a silica gel chromatography to obtain the methoxyethoxymethyl derivative (12 mg) as a yellow solid.

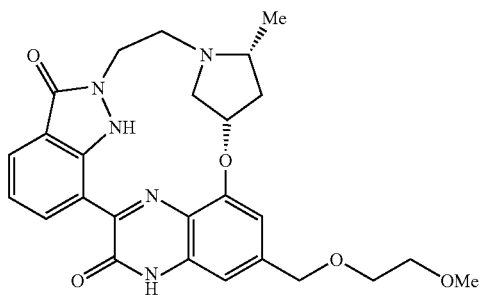

According to a method similar to the procedure described in Working Example 11-(18), the hydrochloride (6.2 mg) of the objective compound [138] was obtained as a dark purple solid from the methoxyethoxymethyl derivative (12 mg, 23.7 μmol) obtained in the above (1).

Spectral data of the compound of the above formula [138] are shown below.

$^1$H-NMR (DMSO-$d_6$) δ: 0.60-0.78 (3H, m), 1.20-1.50 (1H, m), 2.20-4.20(14H, m), 4.38-4.52 (1H, m), 4.59 (2H, s), 5.19-5.27 (1H, m), 6.90-6.98 (2H, m), 7.08-7.12 (1H, m), 7.81-7.87 (1H, m), 9.35-9.45 (1H, m), 12.18-12.32 (1H, m), 12.55-12.70 (1H, m). mass: 492(M+1)$^+$.

Working Example 139

Synthesis of the Compound of the Following Formula [139]:

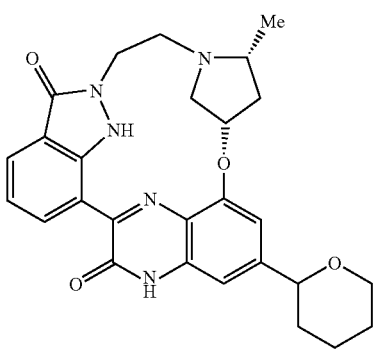
[139]

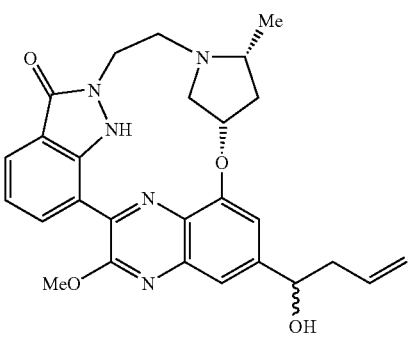
(1)

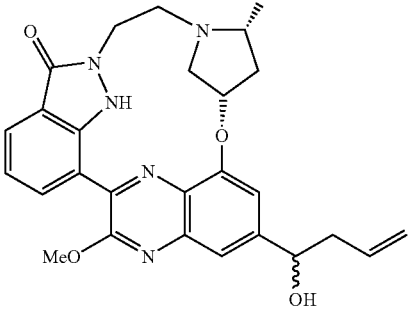

To tetrahydrofuran solution (100 mL) containing the aldehyde derivative (197 mg, 442 pool) obtained in Working Example 83-(3) was dropwise added 1M diethyl ether solution (2.64 mL) containing allyl magnesium bromide at −78° C., and the mixture was stirred at the same temperature for 15 minutes. After acetic acid (500 μL) was added dropwise to the reaction solution, it was warmed up to room temperature. This reaction solution was concentrated in vacuo, and the resulting residue was purified by a silica gel chromatography to obtain the diol derivative (127 mg), which was a diastereomer mixture, as a yellow solid.

(2)

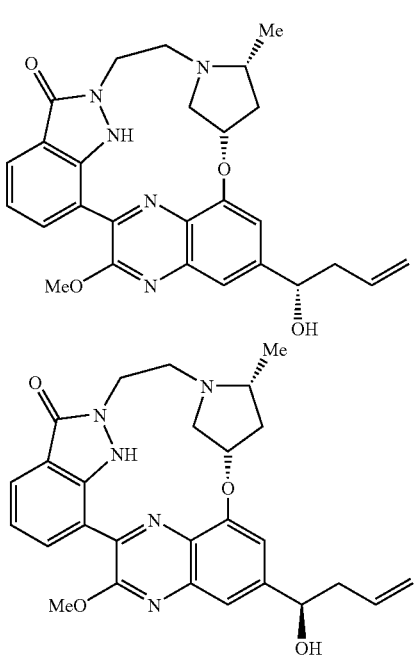

The alcohol derivative (74 mg) which was a diastereomer mixture obtained in the above (1) was resolved by Chiralpack AD to produce the chiral alcohol derivative A (430 mg) with a shorter retention time as a yellow solid and the chiral alcohol derivative B (38 mg) with a longer retention time as a yellow solid.

(3)

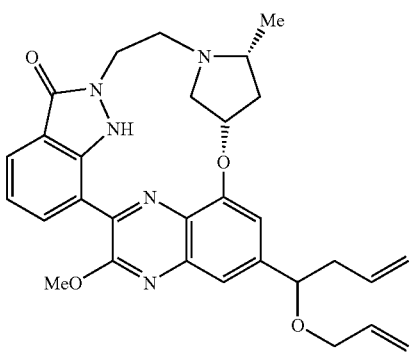

To N,N-dimethylformamide solution (15 mL) containing the chiral alcohol derivative A (30 mg, 61.5 µmol) obtained in the above (2) was added sodium hydride (16 mg, 60% dispersion in oil) at 70° C., and the mixture was stirred at the same temperature for 10 minutes. The resulting reaction solution was kept at 0° C., and allyl bromide (34 µL) was added thereto, and then the mixture was further stirred for 30 minutes. After acetic acid (100 µL) was added dropwise, pyrrolidine (55 µL) was added dropwise thereto. This reaction solution was diluted with ethyl acetate, and the organic layer was washed with saturated brine, dried over anhydrous magnesium sulfate and filtered. The filtrate was concentrated in vacuo, and the resulting residue was purified by a column chromatography on silica gel to obtain the allyl ether derivative (5.1 mg) as a yellow solid.

(4)

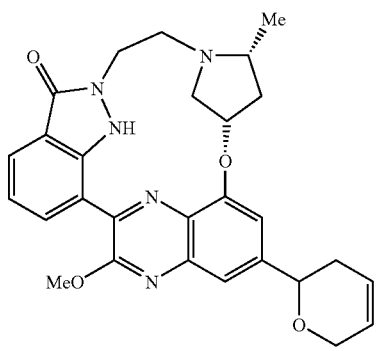

To dichloromethane solution (3 mL) containing the allyl ether derivative (5.1 mg, 9.77 µmol) obtained in the above (3) was added benzylidene-bis(tricyclohexylphosphine)dichlorolutenium (795 µg) at room temperature under an argon atmosphere, and the mixture was stirred for 15 hours. The resulting reaction solution was purified by a column chromatography on silica gel to obtain the cyclic derivative (5.0 mg) as a yellow solid.

(5)

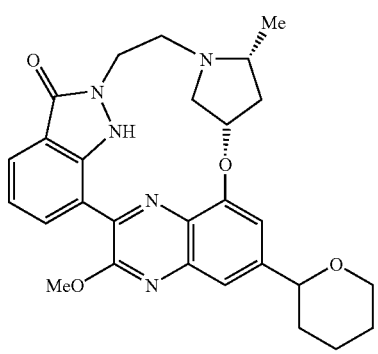

According to a method similar to the procedure described in Working Example 131-(1), the above tetrahydropyran derivative (5.0 mg) was obtained as a yellow solid from the cyclic derivative (5.0 mg, 10.0 µmol) obtained in the above (4).

(6)

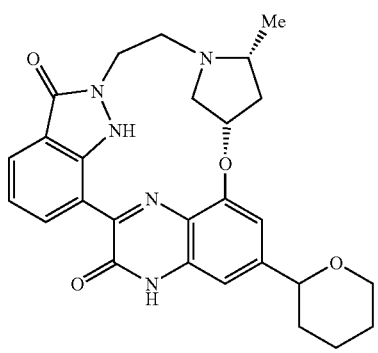

According to a method similar to the procedure described in Working Example 1-(6), the hydrochloride (2.0 mg) of the objective compound [139] was obtained as a dark purple solid from the tetrahydropyran derivative (2.0 mg, 3.98 μmol) obtained in the above (5).

Spectral data of the compound of the above formula [139] are shown below.

$^1$H-NMR (DMSO-d$_6$) δ: 0.52-0.78 (3H, m), 1.22-1.98 (8H, m), 2.88-3.08(1H, m), 3.50-4.11 (6H, m), 4.35-4.53 (3H, m), 5.18-5.35 (1H, m), 6.90-7.00 (2H, m), 7.10-7.22 (1H, m), 7.81-7.88 (1H, m), 9.38-9.48 (1H, m), 12.20-12.35 (1H, m), 12.61 (1H, brs). mass: 488(M+1)$^+$.

Working Example 140

Synthesis of the Compound of the Following Formula [140]:

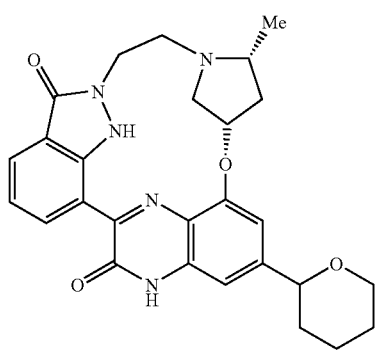

[140]

According to a method similar to the procedures described in Working Examples 139-(3) to 139-(4), 131-(1) and 1-(6), the hydrochloride (3.2 mg) of the objective compound [140] was obtained as a dark purple solid from the chiral alcohol derivative (38 mg, 77.9 μmol) obtained in Working Example 139-(2).

Spectral datum of the compound of the above formula [140] is shown below. mass: 488(M+1)$^+$.

Working Example 141

Synthesis of the Compound of the Following Formula [141]:

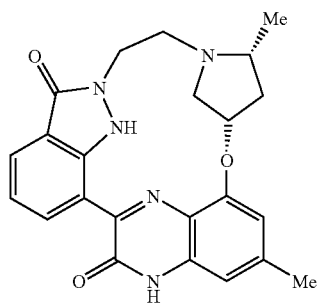

[141]

According to a method similar to the procedures described in working Examples 11-(14), 131-(1) and 1-(6), the hydrochloride (1.8 mg) of the objective compound [141] was obtained as a dark purple solid from the cyclic derivative (8.5 mg) obtained in Working Example 11-(16).

Spectral data of the compound of the above formula [141] are shown below.

$^1$H-NMR (DMSO-d$_6$) δ: 2.00-2.70 (7H, m), 2.80-4.40 (6H, m), 5.32 (1H, m), 6.80-7.40 (3H, m), 7.80 (1H, m), 9.18 (1H, m), 11.8 (1H, m), 12.6 (1H, m). mass: 404(M+1)$^+$.

Working Example 142

Synthesis of the Compound of the Following Formula [142]:

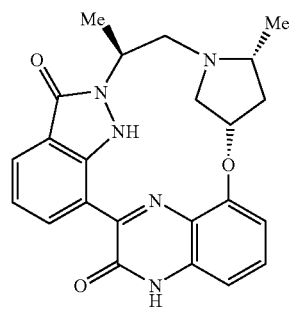

[142]

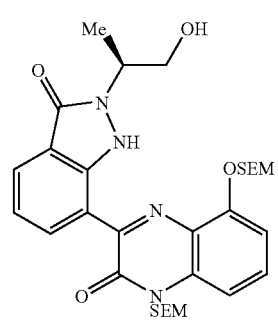

(1)

According to a method similar to the procedures described in Working Examples 11-(10) to 11-(11), 90-(2) and 15-(4), the indazolinone derivative (250 mg) was obtained as a yellowish brown viscous liquid from the carboxylic acid (382 mg, 696 μmol) which is a starting material of Example 48-(1), and the hydrazine derivative [A-34] (304 mg, 1.05 mmol).

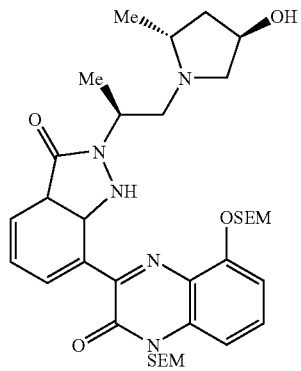

(2)

According to a method similar to the procedure described in Working. Example 83-(1), the above amine derivative (6.8 mg) was obtained as a yellowish brown viscous liquid from the indazolinone derivative (38.0 mg, 62.0 μmol) obtained in the above (1).

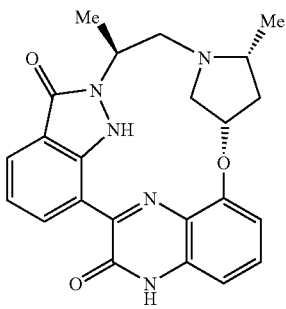

(3)

According to a method similar to the procedures described in Working Examples 1-(4) to 1-(6), the hydrochloride (1.4 mg) of the objective compound [142] was obtained as a dark purple solid from the amine derivative (6.8 mg, 9.77 μmol) obtained in the above (2).

Spectral data of the compound of the above formula [142] are shown below.

$^1$H-NMR (DMSO-d$_6$) δ: 0.60-0.72 (3H, m), 1.25-1.49 (1H, m), 1.51 (3H, d, J=6.9 Hz), 2.20-2.30 (1H, m), 2.68-3.23 (4H, m), 3.66-3.82 (1H, m), 4.79-4.91 (1H, m), 5.21-5.25 (1H, m), 7.00 (1H, d, J=8.1 Hz), 7.09-7.19(2H, m), 7.51 (1H, d, J=8.1 Hz), 7.85 (1H, d, J=7.2 Hz), 9.33-9.42 (1H, m), 12.15-12.24 (1H, m), 12.7 (1H, s). mass: 418(M+1)$^+$.

Working Example 143

Synthesis of the Compound of the Following Formula [143]:

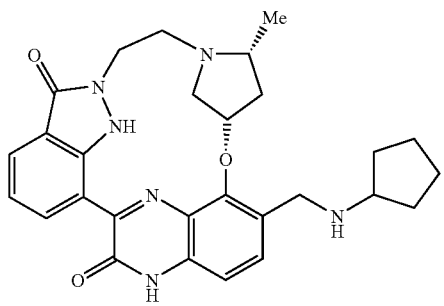

[143]

According to a method similar to the procedures described in Working Examples 11-(17) and 1-(6), the hydrochloride (6.4 mg) of the objective compound [143] was obtained as a yellowish green solid from the alcohol derivative (10.0 mg, 17.7 μmol) obtained in Working Example 131-(5) and cyclopentylamine.

Spectral data of the compound of the above formula [143] are shown below.

$^1$H-NMR (DMSO-d$_6$) δ: 0.52-0.74 (3H, m), 1.06-1.29 (1H, m), 1.46-1.59(2H, m), 1.59-1.80 (4H, m), 1.97-2.07 (2H, m), 2.09-2.27 (1H, m), 2.82-3.16 (2H, m), 3.46-3.59 (2H, m), 3.60-3.95 (3H, m), 4.09-4.39 (2H, m), 4.39-4.46 (1H, m), 5.21-5.42 (1H, m), 7.15-7.22 (1H, m), 7.19 (1H, d, J=8.4 Hz), 7.77-7.84 (1H, m), 7.87 (1H, d, J=7.5 Hz), 9.05-9.15 (1H, m), 9.23-9.34 (1H, m), 9.42-9.55 (1H, m), 12.66-12.70 (1H, m), 12.8 (1H, s). mass: 501(M+1)$^+$.

Example 144

Synthesis of the Compound of the Following Formula [144]:

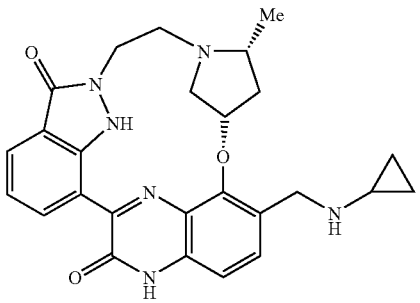

[144]

According to a method similar to the procedures described in Working Examples 11-(17) and 1-(6), the hydrochloride (4.7 mg) of the objective compound [144] was obtained as a yellowish green solid from the alcohol derivative (10.0 mg, 17.7 μmol) obtained in Working Example 131-(5) and cyclopropylamine.

Spectral data of the compound of the above formula [144] are shown below.

$^1$H-NMR (DMSO-d$_6$) δ: 0.60-0.90 (5H, m), 0.90-0.96 (2H, m) 1.10-1.30(1H, m), 2.05-2.25 (1H, m), 2.61-2.80 (2H, m), 2.93-3.15 (2H, m), 3.55-3.80 (1H, m), 3.82-4.02 (2H, m), 4.27-4.51 (3H, m), 5.24-5.42 (1H, m), 7.14-7.23 (1H, m), 7.17 (1H, d, J=8.7 Hz), 7.73-7.80 (1H, m), 7.87(1H, d, J=7.8 Hz), 9.35-9.60 (3H, m), 12.7-12.8 (1H, m), 12.9 (1H, s). mass: 473(M+1)$^+$.

Working Example 145

Synthesis of the Compound of the Following Formula [145]:

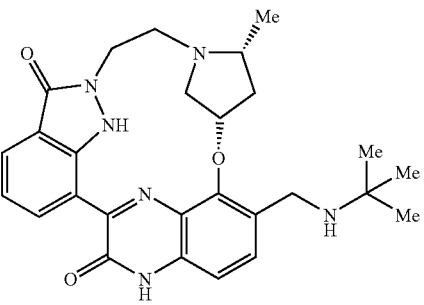

[145]

According to a method similar to the procedures described in Working Examples 11-(17) and 1-(6), the hydrochloride (4.7 mg) of the objective compound [145] was obtained as a yellowish green solid from the alcohol derivative (10.0 mg, 17.7 μmol) obtained in Working Example 131-(5) and t-butylamine.

Spectral data of the compound of the above formula [145] are shown below.

$^1$H-NMR (DMSO-d$_6$) δ: 0.55-0.77 (3H, m), 1.05-1.39 (1H, m), 1.40 (9H, s), 2.03-2.31 (1H, m), 2.80-3.05 (2H, m), 3.35-3.79 (2H, m), 3.80-4.03(2H, m), 4.09-4.38 (2H, m), 4.39-4.51 (1H, m), 5.27-5.38 (1H, m), 7.14-7.23 (1H, m), 7.19 (1H, d, J=8.7 Hz), 7.81-7.89 (1H, m), 7.86 (1H, d, J=7.8 Hz), 8.60-8.85 (1H, m), 9.05-9.25 (1H, m), 9.35-9.65 (1H, m), 12.7-12.9 (1H, m), 12.9 (1H, s). mass: 489(M+1)$^+$.

Working Example 146

Synthesis of the Compound of the Following Formula [146]:

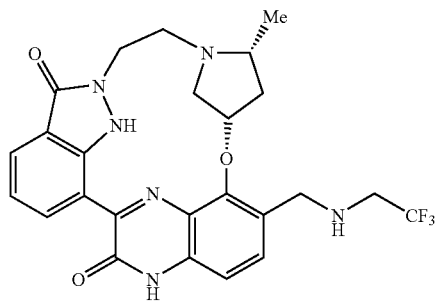

[146]

According to a method similar to the procedures described in Working Examples 11-(17) and 1-(6), the hydrochloride (5.0 mg) of the objective compound [146] was obtained as a yellowish green solid from the alcohol derivative (10.0 mg, 17.7 μmol) obtained in Working Example 131-(5) and trifluoroethylamine.

Spectral data of the compound of the above formula [146] are shown below.

$^1$H-NMR (DMSO-d$_6$) δ: 0.59-0.92 (3H, m), 1.05-1.54 (1H, m), 1.90-2.15(1H, m), 2.85-3.20 (2H, m), 3.45-4.10 (6H, m), 4.10-4.39 (2H, m), 4.40-4.46 (1H, m), 5.21-5.42 (1H, m), 7.13-7.23 (1H, m), 7.16 (1H, d, J=8.7 Hz), 7.70-7.85 (1H, m), 7.87 (1H, d, J=7.5 Hz), 9.40-9.65 (1H, m), 12.6-12.8 (1H, m), 12.8 (1H, s). mass: 515(M+1)$^+$.

Reference Example 1

Synthesis of the Compound of the Following Formula [A-1]:

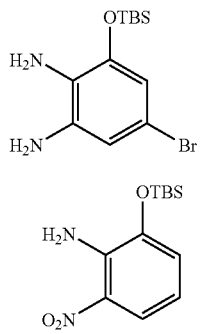

[A-1]

(1)

2-Amino-3-nitrophenol (77 mg, 0.50 mmol) was dissolved in N,N-dimethylformamide (2 mL), and to this solution were added successively imidazole (68 mg, 1.00 mmol) and t-butyldimethylsilyl chloride (90 mg, 0.60 mmol) under ice-cooling. The mixture was stirred at room temperature overnight. The resulting reaction solution was diluted with ethyl acetate, and washed successively with water and saturated brine. The organic layer was dried over anhydrous magnesium sulfate, filtered, and concentrated in vacuo to obtain the above protected derivative with TBS (140 mg) as a deep orange oil.

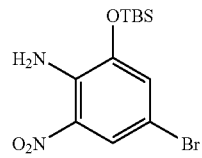

(2)

The protected derivative with TBS (140 mg, 0.50 mmol) obtained in the above (1) was dissolved in ethyl acetate (2 mL), and to the solution was added gradually N-bromosuccinimide (98 mg, 0.55 mmol) in a water-bath. The reaction solution was stirred at room temperature for 10 minutes. The resulting reaction solution was diluted with ethyl acetate, and washed successively with saturated aqueous sodium sulfite, aqueous sodium hydrogencarbonate and saturated brine. The organic layer was dried over anhydrous magnesium sulfate, filtered, and concentrated in vacuo to obtain the above brominated derivative (169 mg) as a deep yellow solid.

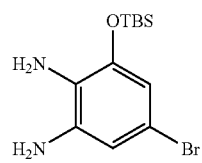

(3)

The brominated derivative (165 mg, 0.48 mmol) obtained in the above (2) was dissolved in tetrahydrofuran (2 mL), and 5% platinum carbon catalyst (33 mg) was added thereto under a nitrogen atmosphere. After substitution of the atmosphere of the reaction system with hydrogen, the solution was stirred at room temperature for 8 hours. The resulting reaction solution was filtered through a Celite pad to remove the catalyst, and the filtrate was concentrated in vacuo to obtain the objective compound [A-1] (151 mg) as a deep brown oil.

Reference Example 2

Synthesis of the Compound of the Following Formula [A-2]:

[A-2]

Ethyl (2-fluoro-3-iodophenyl)oxoacetate (10.0 g, 31.1 mmol) according to a method similar to the method of general formula (II-d) described in WO 02/02550 pamphlet was dissolved in N,N-dimethylformamide (100 mL) and methanol (100 mL), and to this solution was added sodium hydrogencarbonate (7.84 g, 93.3 mmol). The atmosphere in the reaction system was substituted with nitrogen gas. Palladium acetate(II) (75 mg, 3.11 mmol) and 1,1'-bis(diphenylphosphino)ferrocene (185 mg, 3.11 mmol) were added thereto at room temperature under a nitrogen atmosphere, and then the atmosphere in the reaction system was substituted by carbon monooxide gas. This solution was stirred at 70° C. for 2 hours, cooled down to room temperature, diluted with chloroform, and washed successively with water and saturated aqueous ammonium chloride. The organic layer was dried over anhydrous magnesium sulfate, filtered, and concentrated. The resulting residue was purified by a column chromatography on silica gel to obtain the objective compound [A-2] (2.90 g) as a yellow solid.

Reference Example 3

Synthesis of the Compounds of the Following Formulae [A-3-1] to [A-3-5]:

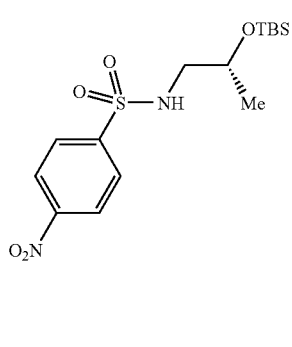
[A-3-1]

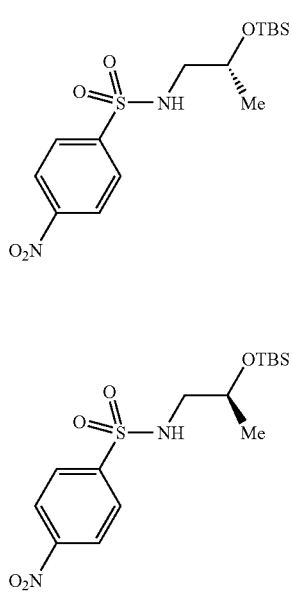
[A-3-2]

[A-3-3]

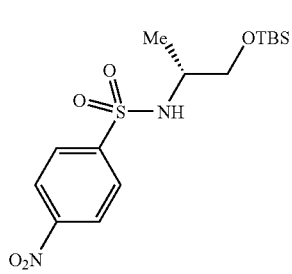

[A-3-4]

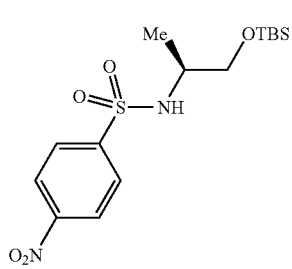

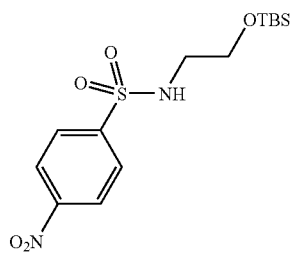
[A-3-5]

According to a method similar to the method described in Journal of Synthetic Organic Chemistry, Japan, 59 (8) 779 (2001) and the procedure of Reference Example 1-(1), (R)-1-amino-2-propanol, (S)-1-amino-2-propanol, (R)-2-amino-1-propanol, (S)-2-amino-1-propanol, and 2-aminoethanol were respectively sulfonated and silylated to obtain the corresponding O-silyl-sulfonamide derivatives [A-3-1] to [A-3-5].

Reference Example 4

Synthesis of the Compound of the Following Formula [A-4]:

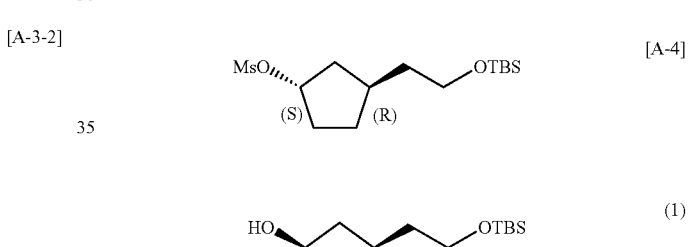

According to a method similar to the method described in Bull. Chem. Soc. Jpn., 57 (7) 2019 (1984), the above TBS derivative was obtained from (1R,3R)-3-(2'-hydroxyethyl)cyclopentanol synthesized by the method described in J. Am. Chem. Soc., 99 (5) 1625 (1977).

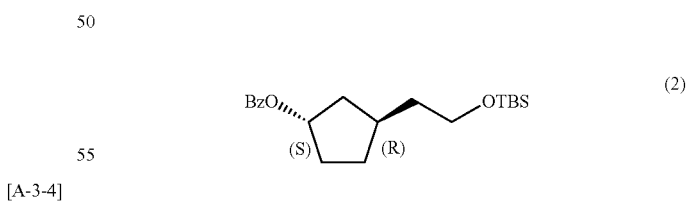

The TBS derivative (9.8 g, 40 mmol) obtained in the above (1) was dissolved in toluene (150 mL), and to the solution was added 40% toluene solution (35 mL, 80 mmol) containing benzoic acid (9.8 g, 80 mmol), triphenylphosphine (21 g, 80 mmol) and diethyl azodicarboxylate under ice-cooling. The solution was stirred for 1 hour under ice-cooling, and water was added thereto. The solution was stirred at room temperature for 30 minutes, and the resulting solid was filtered off, and the filtrate was washed with saturated brine. The organic layer was dried over anhydrous magnesium sulfate, filtered, and concentrated. The resulting residue was purified by a column chromatography on silica gel to obtain the above benzoyl derivative (9.8 g) as a colorless oil.

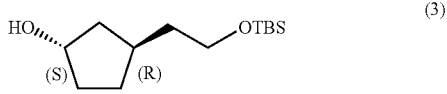
(3)

The benzoyl derivative (4.5 g, 12.9 mmol) obtained in the above (2) was dissolved in methanol (20 mL), and then 0.05 M methanol solution (150 mL) containing sodium hydroxide was added thereto under ice-cooling. The solution was stirred at room temperature for 12 hours. The resulting reaction solution was diluted with t-butyl methyl ether, and the organic layer was washed successively with water and saturated brine, dried over anhydrous magnesium sulfate, filtered, and concentrated. The resulting residue was purified by a column chromatography on silica gel to obtain the above alcohol derivative (2.6 g) as a colorless oil.

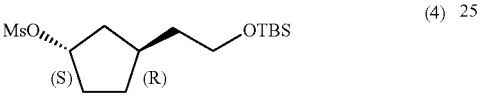
(4)

The alcohol derivative (566 mg, 2.31 mmol) obtained in the above (3) was dissolved in chloroform (10 mL), and to the solution were added triethylamine (414 μL, 2.97 mmol) and methanesulfonylchloride (231 μL, 2.97 mmol) under ice-cooling. The mixture was stirred for 1 hour. After aqueous sodium hydrogencarbonate was added to the reaction solution, it was extracted with chloroform. The organic layer was washed with saturated brine, dried over anhydrous magnesium sulfate, filtered, and concentrated to obtain the objective derivative [A-4] (746 mg) as a pale yellow oil.

Reference Example 5

Synthesis of the Compound of the Following Formula [A-5]:

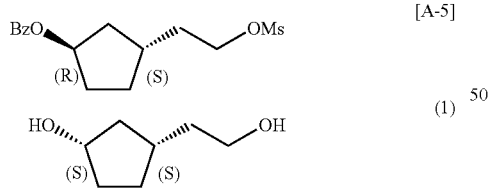
[A-5]

(1)

The above diol derivative was obtained from norcamphor according to the method described in J. Am. Chem. Soc., 99 (5) 1625 (1977).

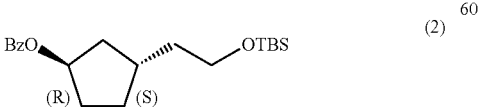
(2)

The above benzoyl compound was obtained from the diol derivative obtained in the above (1) according to a method similar to the procedures of Reference Examples 4-(1) to 4-(2).

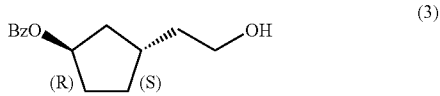
(3)

The benzoyl derivative (4.5 g, 12.9 mmol) obtained in the above (2) was dissolved in chloroform (80 mL), and hydrochloric acid/methanol (20 mL) was added thereto under ice-cooling. The resulting reaction solution was stirred for 15 minutes under ice-cooling, and chloroform was added thereto. The organic layer was washed successively with water, saturated aqueous sodium hydrogencarbonate and saturated brine. Then, the organic layer was dried over anhydrous magnesium sulfate, filtered, and concentrated. The resulting residue was purified by a column chromatography on silica gel to obtain the above alcohol derivative (2.7 g) as a colorless oil.

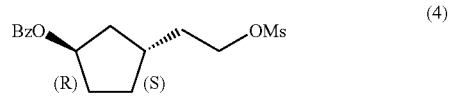
(4)

The objective compound [A-5] (258 mg) was obtained as a pale yellow oil from the alcohol derivative (194 mg, 826 μmol) obtained according to the procedure of Reference Example 4-(4).

Reference Example 6

Synthesis of the Compound of the Following Formula [A-6]:

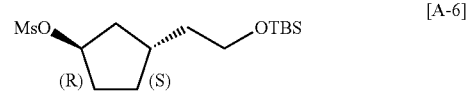
[A-6]

According to a method similar to the procedures as Reference Examples 4-(3) to 4-(4), the objective compound [A-6] was obtained from the benzoyl derivative obtained in Reference Example 5-(2).

Reference Example 7

Synthesis of the Compound of the Following Formula [A-7]:

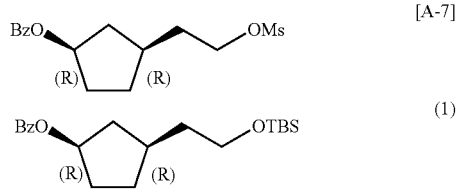
[A-7]

(1)

The TBS-derivative (4 g, 16 mmol) obtained in Reference Example 4-(1) was dissolved in chloroform (80 mL), and to the solution were added triethylamine (3.4 mL, 21 mmol), 4-dimethylaminopyridine (600 mg, 4.3 mmol), and benzoyl chloride (2.2 mL, 17 mmol). The mixture was stirred at room temperature for 3 hours. Aqueous sodium hydrogencarbonate solution was added to the resulting reaction solution, and it was extracted with chloroform. The organic layer was washed with saturated brine, dried over anhydrous magnesium sulfate, filtered, and the filtrate was concentrated. The resulting residue was purified by a column chromatography on silica gel to obtain the above benzoyl derivative (5.6 g) as a colorless oil.

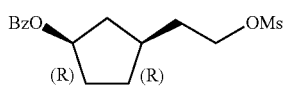

(2)

According to a method similar to the procedures of Reference Examples 5-(3) to 5-(4), the objective compound [A-7] (670 mg) was obtained as a colorless oil from the benzoyl derivative (583 mg, 1.68 mmol) obtained in the above (1)

Reference Example 8

Synthesis of the Compound of the Following Formula [A-8]:

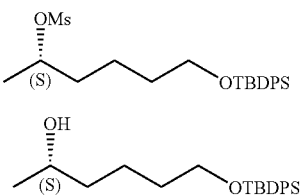

[A-8]

(1)

According to a method similar to the procedure of Reference Example 1-(1), the above TBDPS-derivative (88.2 g) was obtained as a colorless oil from (S)-hexane-1,5-diol (29.9 g, 253 mmol) synthesized by referring to the method described in J. Chem. Soc. Perkin Trans. I, 20 2467 (1996) and t-butyldiphenylsilyl chloride.

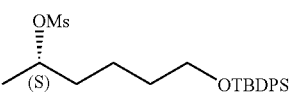

(2)

According to a method similar to the procedure of Reference Example 4-(4), the objective compound [A-8] (652 mg) was obtained as a colorless oil from the TBDPS-derivative (535 mg, 1.5 mmol) prepared in the above (1)

Reference Example 9

Synthesis of the Compound of the Following Formula [A-9]:

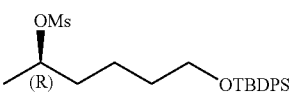

[A-9]

According to a method similar to the method as Reference Example 8, the objective compound [A-9] was obtained from (R)-hexane-1,5-diol.

Reference Example 10

Synthesis of the Compound of the Following Formula [A-10]:

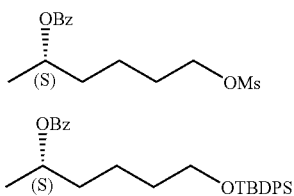

[A-10]

(1)

According to a method similar to the procedure of Reference Example 7-(1), the above benzoyl compound (2.6 g) was obtained as a colorless oil from TBDPS-derivative (2 g, 5.6 mmol) obtained in Reference Example 8-(1)

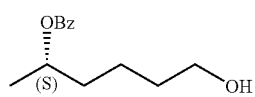

(2)

The benzoyl derivative (2.5 g, 5.4 mmol) obtained in the above (1) was dissolved in tetrahydrofuran (16 mL), and to this solution was added 1 M tetrahydrofuran solution (16 mL) containing tetrabutylammonium fluoride. The solution was stirred at room temperature for 2 hours. The resulting reaction solution was diluted with diethyl ether (100 mL), and washed successively with 0.1M phosphate buffer (pH 6.8) and saturated brine. The organic layer was dried over anhydrous magnesium sulfate, filtered, and the filtrate was concentrated. The resulting residue was purified by a column chromatography on silica gel to obtain the above alcohol derivative (1.2 g) as a colorless oil.

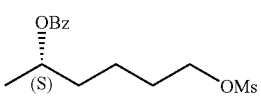

(3)

According to a method similar to the procedure of Reference Example 4-(4), the objective compound [A-10] was obtained as a colorless oil from the alcohol derivative (378 mg, 1.70 mmol) prepared in the above (2). The product was used without separation and purification.

Reference Example 11

Synthesis of the Compound of the Following Formula [A-11]:

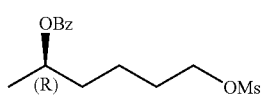

[A-11]

According to a method similar to the procedures of Reference Examples 8-(1) and 10, the objective compound [A-11]

was obtained from (R)-hexane-1,5-diol synthesized by referring to the method described in J. Chem. Soc. Perkin Trans. I, 20 2467 (1996).

Reference Example 12

Synthesis of the Compound of the Following Formula [A-12]:

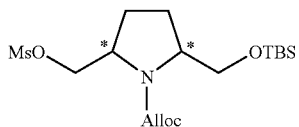
[A-12]

In the above formula, the stereo chemistry of the position with the asterisk * is of cis configuration.

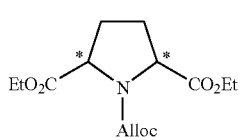
(1)

Cis-2,5-di(ethoxycarbonyl)pyrrolidine (10.5 g, 49.1 mmol) synthesized by referring to the method described in J. Org. Chem., 26 (5) 1500 (1961) was dissolved in pyridine (30 mL), and to the solution was added allyl chloroformate (8.9 g, 73.6 mmol) under ice-cooling. The solution was stirred for 30 minutes, and aqueous sodium hydrogencarbonate was added to the resulting reaction solution. The reaction solution was extracted with diethylether. The organic layer was washed with saturated brine, dried over anhydrous magnesium sulfate, filtered, and concentrated. The resulting residue was purified by a column chromatography on silica gel to obtain the above protected derivative with Alloc (10.6 g) as a colorless oil.

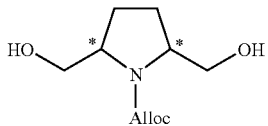
(2)

The above protected derivative with Alloc (10.6 g, 35.4 mmol) obtained in the above (1) was dissolved in tetrahydrofuran (170 mL), and then lithium tetrahydroborate (3.9 g, 177 mmol) was added thereto. The mixture was stirred at room temperature for 2 hours. Methanol was gradually added dropwise to the resulting reaction solution, and the reaction solution was diluted with aqueous sodium hydrogencarbonate solution. This solution was extracted with ethyl acetate, and the organic layer was washed with saturated brine, dried over anhydrous magnesium sulfate, and filtered. The filtrate was and concentrated, and the resulting residue was purified by a column chromatography on silica gel to obtain the above diol derivative (5.5 g) as a colorless oil.

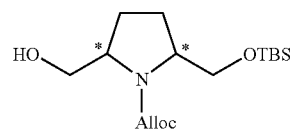
(3)

The diol derivative (5.5 g, 25.5 mmol) obtained in the above (2) was dissolved in chloroform (250 mL), and to the solution were added triethylamine (4.1 mL, 30 mmol), t-butyldimethylsilyl chloride (4.0 g, 25.5 mmol), and 4-dimethylaminopyridine (940 mg, 7.7 mmol). The mixture was stirred at room temperature for 2 hours. After aqueous sodium hydrogencarbonate solution was added to the resulting reaction solution, it was extracted with chloroform. The organic layer was washed with saturated brine, dried over anhydrous magnesium sulfate, and filtered. The filtrate was concentrated, and the resulting residue was purified by a column chromatography on silica gel to obtain the above racemic TBS-derivative (3.5 g) as a colorless oil.

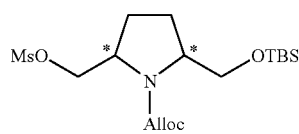
(4)

According to a method similar to the procedure of Reference Example 4-(4), the objective compound (A-12) (4.6 g) was obtained as a colorless oil from the compound (3.5 g, 11.5 mmol) obtained in the above (3)

Reference Example 13

Synthesis of the Compound of the Following Formula [A-13]:

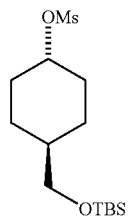
[A-13]

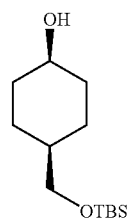
(1)

According to a method similar to the procedure of Reference Example 12-(3), the above TBS-derivative (995 mg) was obtained as a colorless oil from cis-4-hydroxymethylcyclohexanol (601 mg, 4.62 mmol) prepared by reference to the method described in J. Org. Chem., 35 (7) 2368 (1970)

(2)

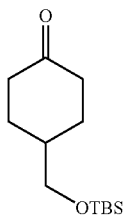

The TBS-derivative (489 mg, 2.00 mmol) obtained in the above (1) and triethylamine (1.11 mL, 8.00 mmol) were dissolved in dimethyl sulfoxide (5 mL), and then sulfur trioxide-pyridine complex (637 mg, 4.00 mmol) was added thereto in a water-bath. The resulting reaction solution was stirred at room temperature for 10 minutes, diluted with ethyl acetate, and washed successively with water (twice) and saturated brine. The organic layer was dried over anhydrous magnesium sulfate, filtered, and concentrated in vacuo to obtain the above ketone derivative (444 mg) as a colorless oil.

(3)

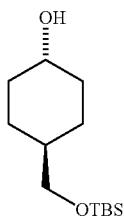

The ketone derivative (121 mg, 160 μmol) obtained in the above (2) was dissolved in tetrahydrofuran (3 mL), and to the solution was added dropwise 1M tetrahydrofuran solution (750 μL, 750 μmol) containing lithium tri-t-buthoxy-aluminium hydride at −65° C. The resulting reaction solution was warmed up to 0° C., and saturated aqueous Rochelle salt and ethyl acetate were added thereto. The mixture was stirred at room temperature for 1 hour. This reaction solution was extracted with ethyl acetate, and the extract was washed successively with water and saturated brine, dried over anhydrous magnesium sulfate, filtered, and concentrated in vacuo to obtain the above trans-alcohol derivative (122 mg) as a pale yellow oil.

(4)

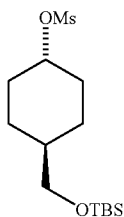

According to a method similar to the procedure of Reference Example 4-(4), the objective compound [A-13] (659 mg) was obtained as a colorless oil from the trans-alcohol derivative (518 mg, 2.12 mmol) obtained in the above (3).

Reference Example 14

Synthesis of the Compound of the Following Formula [A-14]:

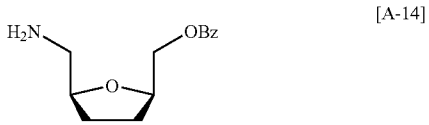
[A-14]

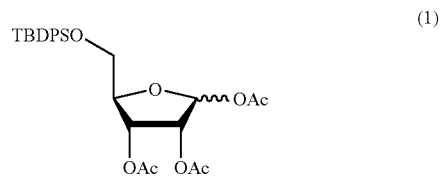
(1)

To a stirred solution of (R)-(−)-ribose (5.00 g, 33.3 mmol) in N,N-dimethylformamide (10 mL) were added imidazole (4.50 g, 66.6 mmol) and t-butyldiphenylsilyl chloride (9.07 mL, 34.8 mmol) at 0° C. The reaction solution was stirred at room temperature overnight. 1N aqueous potassium hydrogensulfate was added to the resulting reaction solution, and the solution was stirred at room temperature for 30 minutes, and then extracted with ethyl acetate. The organic layer was washed with saturated brine, dried over anhydrous magnesium sulfate, filtered, and the filtrate was concentrated. Pyridine (30 mL) and acetic anhydide (10 mL) were added to the resulting residue, and the mixture was stirred at room temperature for 2 hours. To this reaction solution was added 1N aqueous potassium hydrogensulfate, and the reaction solution was extracted with ethyl acetate. The organic layer was washed with saturated brine, dried over anhydrous magnesium sulfate, filtered, and the filtrate was concentrated. The resulting residue was purified by a column chromatography on silica gel to obtain the above protected derivative with TBDPS (12.3 g) as a pale yellow solid.

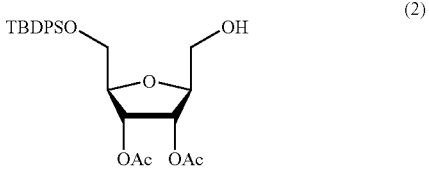
(2)

The protected derivative with TBDPS (11 g, 21.4 mmol) obtained in the above (1) was dissolved in methylene chloride (60 mL), and the reaction system was substituted with carbon monooxide. To this solution were added diethylmethylsilane (22 mL, 215 mmol) and dicobalt octacarbonyl (1.0 g, 2.92 mmol), and the mixture was stirred at room temperature overnight, after which time water was added thereto. The reaction solution was extracted with ethyl acetate, and the organic layer was washed with saturated brine, dried over anhydrous sodium sulfate, filtered, and concentrated in vacuo. The resulting residue was purified by a column chromatography on silica gel to obtain the above alcohol derivative (5.37 g) as a pale yellow solid.

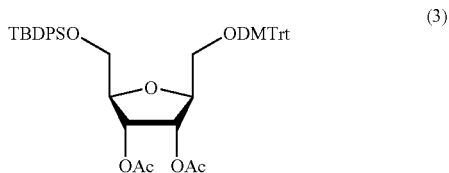

(3)

To a stirred solution of the alcohol derivative (1.00 g, 2.05 mmol) obtained in the above (2) in methylene chloride (10 mL) were added triethylamine (860 μL, 6.15 mmol), 4,4'-dimethoxytrityl (692 mg, 780 μmol) and 4-dimethylaminopyridine (251 mg, 2.05 mmol) at 0° C. The reaction solution was stirred at room temperature for 2 hours. Water was added to the resulting reaction solution, and the solution was stirred at room temperature for 30 minutes, and then extracted with ethyl acetate. The organic layer was washed with saturated brine, dried over anhydrous sodium sulfate, filtered, and the filtrate was concentrated. The resulting residue was purified by a column chromatography on silica gel to obtain the above tritylated derivative (765 mg) as a pale yellow solid.

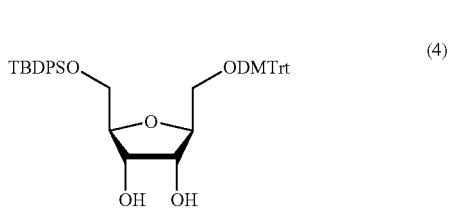

(4)

According to a method similar to the procedure of Reference Example 4-(3), the above diol derivative (511 mg) was obtained as a pale yellow solid from the tritylated derivative (711 mg, 2.05 mmol) obtained in the above (3)

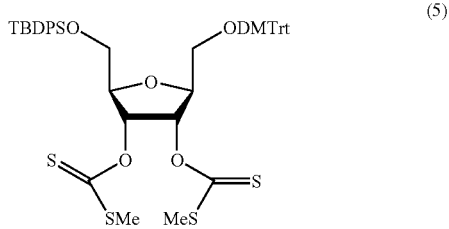

(5)

To a stirred tetrahydrofuran solution (10 mL) containing the diol derivative (511 mg, 720 μmol) obtained in the above (4) was added 60% sodium hydride dispersion in oil (116 mg, 2.90 mmol) at 0° C., and the mixture was stirred at room temperature for 30 minutes. After addition of carbon disulfide (230 μL, 3.02 mmol), the reaction solution was stirred at room temperature for 5 minutes, and methyl iodide (170 μL, 2.73 mmol) was added thereto. The mixture was stirred at room temperature for 1 hour, and 1N aqueous potassium hydrogensulfate was added. The reaction solution was extracted with ethyl acetate. The organic layer was washed with saturated brine, dried over anhydrous sodium sulfate, filtered, and the filtrate was concentrated. The resulting residue was purified by a column chromatography on silica gel to obtain the above dithiocarbonate derivative (585 mg) as a pale yellow solid.

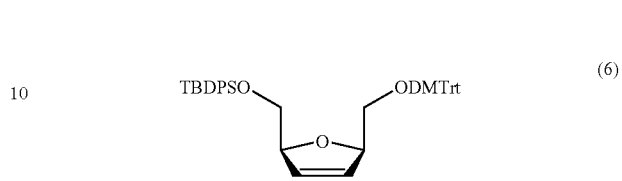

(6)

To a stirred toluene solution (10 mL) containing the dithiocarbonate derivative (585 mg, 660 μmol) obtained in the above (5) were added tributyltin hydride (360 μL, 1.23 mmol) and 2,2'-azobisisobutyronitrile (24 mg, 140 μmol) under a nitrogen atmosphere, and the mixture was stirred overnight under heating at reflux. Water was added to the reaction solution, and it was extracted with ethyl acetate. The organic layer was washed with saturated brine, dried over anhydrous sodium sulfate, filtered, and the filtrate was concentrated. The resulting residue was purified by a column chromatography on silica gel to obtain the above intra-olefin derivative (367 mg) as a pale yellow solid.

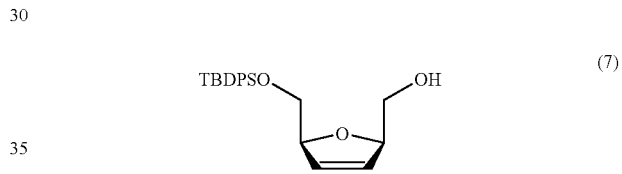

(7)

To methylene chloride solution, (30 mL) containing the above intra-olefin derivative (665 mg, 990 μmol) obtained in the above (6) was added gradually trichloroacetic acid (160 mg, 979 μmol). The reaction solution was stirred at room temperature for 2 hours. Aqueous sodium hydrogencarbonate solution was added to the resulting reaction solution, and the solution was extracted with chloroform. The organic layer was washed with saturated brine, dried over anhydrous sodium sulfate, filtered, and the filtrate was concentrated. The resulting residue was purified by a column chromatography on silica gel to obtain the above alcohol derivative (213 mg) as a pale yellow solid.

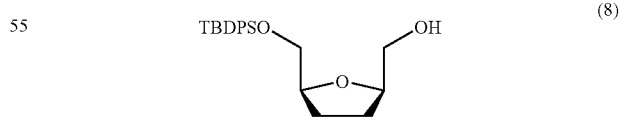

(8)

The alcohol derivative (1.40 g, 3.77 mmol) obtained in the above (7) was dissolved in tetrahydrofuran (30 mL) and methanol (30 mL), and to the solution was added platinum oxide catalyst (700 mg) under a nitrogen atmosphere. After substitution of the reaction system with hydrogen gas, the mixture was stirred at room temperature for 15 hours. The resulting reaction solution was filtered through a Celite pad to remove the catalyst, and the filtrate was concentrated in vacuo. The resulting residue was purified by a column chromatography on silica gel to obtain the above tetrahydrofuran derivative (1.28 g) as a colorless oil.

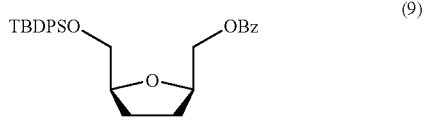

(9)

According to a method similar to the procedure of Reference Example 7-(1), the above benzoyl derivative (421 mg) was obtained as a colorless oil from the tetrahydrofuran derivative (402 mg, 1.08 mmol) obtained in the above (8).

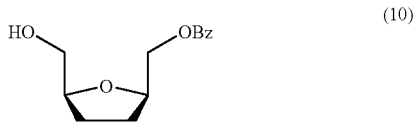

(10)

According to a method similar to the procedure of Reference Example 10-(2), the above alcohol derivative (402 mg) was obtained as a pale yellow oil from the benzoyl derivative (421 mg, 887 μmol) obtained in the above (9)

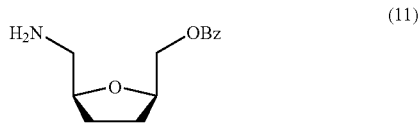

(11)

The alcohol derivative (402 mg) obtained in the above (10) was dissolved in diethyl ether (5 mL), and then N,N-diisopropylethylamine (223 μL, 1.28 mmol) and methanesulfonyl chloride (82 μL, 1.06 mmol) were added thereto under ice-cooling. The mixture was stirred for 2 hours. After diethyl ether was added to the resulting reaction solution, the organic layer was washed successively with 1N hydrochloric acid, water, and saturated brine, dried over anhydrous magnesium sulfate, and filtered. The filtrate was concentrated, and the resulting residue was dissolved in N,N-dimethylformamide (5 mL), and then sodium azide (115 mg, 1.77 mmol) was added thereto. The reaction solution was stirred at 80° C. for 12 hours, and cooled down to room temperature. After addition of ethyl acetate to this reaction solution, the organic layer was washed successively with water and saturated brine, dried over anhydrous magnesium sulfate, and filtered. The filtrate was concentrated, and the resulting residue was dissolved in tetrahydrofuran (5 mL) and methanol (5 mL), and 10% palladium carbon catalyst (700 mg) was added thereto under a nitrogen atmosphere. The atmosphere in the reaction system was substituted with hydrogen gas, and the solution was stirred at room temperature for 3 hours. The resulting solution was filtered through a Celite pad to remove the catalyst, and the filtrate was concentrated in vacuo. The resulting residue was purified by a silica gel chromatography to obtain the objective compound [A-14] (81 mg) as a colorless oil.

Reference Example 15

Synthesis of the Compound of the Following Formula [A-15]:

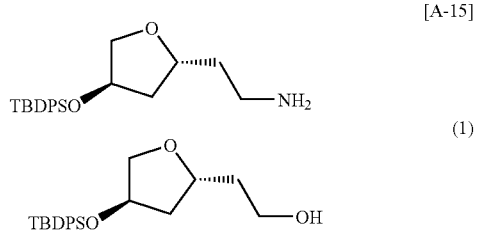

Ethyl (3R,5S)-3-(t-butyldiphenylsilyloxy)tetrahydro-5-furanylacetate (11.9 g, 29 mmol) prepared according to a method similar to the method described in Tetrahedron Lett., 26 (9) 1185 (1985) was dissolved in ether (100 mL), and lithium aluminium hydride (660 mg, 1.7 mmol) was added thereto in an ice-bath. The reaction solution was stirred at room temperature for 1 hour. Anhydrous sodium sulfate decahydrate (3 g) was added thereto in an ice-bath, and the mixture was stirred at room temperature for 2 hours. The reaction solution was dried over anhydrous magnesium sulfate, and filtered through a Celite pad to remove the insolubles. The filtrate was concentrated in vacuo to obtain the above primary alcohol derivative (9.52 g) as a colorless oil.

According to a method similar to the procedure of Reference Example 14-(11), the objective compound [A-15] (2.27 g) was obtained as a colorless oil from the primary alcohol derivative (2.50 g, 6.75 mmol) obtained in the above (1)

Reference Example 16

Synthesis of the Compound of the Following Formula [A-16]:

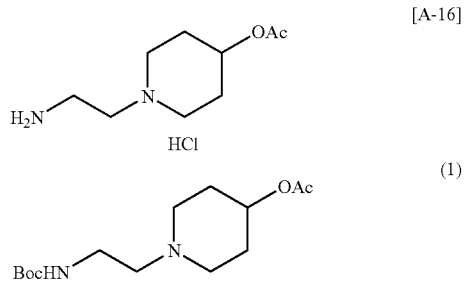

4-Acetoxypiperidine hydrochloride (1.5 g, 8.6 mmol) prepared by referring to EP122855 and t-butyl-N-(2-oxoethyl) carbamate (1.1 g, 6.9 mmol) were dissolved in methanol (20 mL). To the solution was portionwise added sodium cyanotrihydroborate (641 mg, 10 mmol) in an ice-water bath, and the mixture was stirred at room temperature for 2 hours. The resulting reaction solution was concentrated in vacuo, poured into aqueous sodium hydrogencarbonate solution, and extracted with chloroform three times. The resulting extract was dried over anhydrous sodium sulfate, and filtered. The filtrate was concentrated in vacuo and the resulting residue was purified by a column chromatography to obtain the above N-alkylpiperidin derivative (850 mg) as a colorless oil.

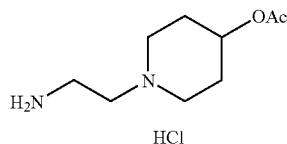
(2)

4N hydrogen chloride/1,4-dioxane solution (5 mL) was added to the N-alkylpiperidine derivative (850 mg, 3.0 mmol) obtained in the above (1) at room temperature, and the mixture was stirred at room temperature for 2 hours. The resulting reaction solution was concentrated in vacuo to obtain the objective compound [A-16] (666 mg) as a white solid.

Reference Example 17

Synthesis of the Compound of the Following Formula [A-17]:

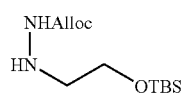
[A-17]

To a solution of (t-butyldimethylsilyloxy)acetaldehyde (5.00 g, 28.6 mmol) in chloroform (50 mL) was added the allyl carbazinate derivative (5.00 g, 43.1 mmol) prepared by referring to JP 04117361, and the mixture was stirred at room temperature for 15 hours. After addition of saturated brine to the resulting reaction solution, the organic layer was separated. The resulting organic layer was dried over anhydrous magnesium sulfate, filtered, and the filtrate was concentrated. To the resulting residue were added zinc chloride (1.02 g, 75.0 mmol) and methanol solution (500 mL) containing sodium cyanotrihydroborate (1.41 g, 150 mmol), and the mixture was stirred at room temperature for 2 days. After hexane and ethyl acetate were added to the resulting reaction solution, it was filtered through a Celite pad, and the filtrate was washed with water and saturated brine. The organic layer was dried over anhydrous magnesium sulfate, filtered, and the filtrate was concentrated. The resulting residue was purified by a chromatography on silica gel to obtain the objective compound [A-17] (5.03 g) as a colorless oil.

Reference Example 18

Synthesis of the Compound of the Following Formula [A-18]:

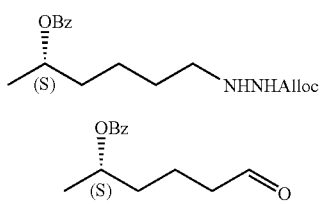
[A-18]

(1)

According to a method similar to the procedure of Reference Example 13-(2), the above aldehyde derivative (1.51 g) was obtained as a colorless oil from the de-TBDPS derivative (1.56 g, 7.0 mmol) obtained in Reference Example 10-(2).

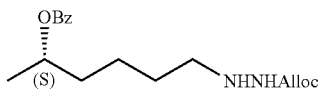
(2)

According to a method similar to the procedure of Reference Example 17, the objective compound [A-18] (1.33 g) was obtained as a colorless oil from the aldehyde derivative (1.51 g, 6.9 mmol) obtained in the above (1).

Reference Example 19

Synthesis of the Compound of the Following Formula [A-19]:

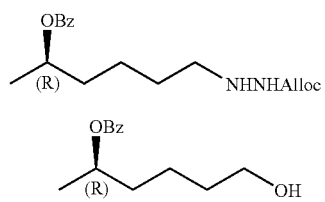
[A-19]

(1)

According to a method similar to the method as Reference Examples 8-(1) and 10-(1) to 10-(2), the above primary alcohol derivative was obtained from (R)-hexane-1,5-diol which is a starting material of Reference Example 11

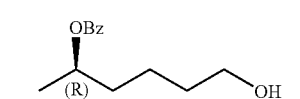
(2)

According to a method similar to the procedure as Reference Example 18, the objective compound [A-19] was obtained from the primary alcohol derivative obtained in the above (1)

Reference Example 20

Synthesis of the Compound of the Following Formula [A-20]:

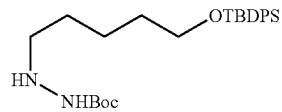
[A-20]

According to a method similar to the procedure of Reference Example 17, the objective compound [A-20] (335 mg) was obtained as a colorless oil from 5-t-butyldiphenylsilyloxy-1-pentanal (500 mg, 1.47 mmol) synthesized by referring to the method described in J. Org. Chem., 59 (2), 324 (1994) and t-butyl carbazinate (194 mg, 1.47 mmol)

Reference Example 21

Synthesis of the Compound of the Following Formula [A-21]:

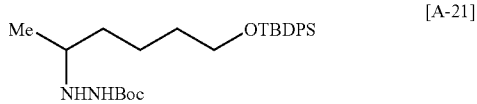

According to a method similar to the procedure of Reference Example 17, the objective compound [A-21] (7.40 g) was obtained as a colorless oil from the ketone derivative (10.8 g, 30.4 mmol) synthesized by referring to the method described in Tetrahedron Lett., 56 (8) 1065 (2000).

Reference Example 22

Synthesis of the Compound of the Following Formula [A-22]:

Racemic 3-hydroxypiperidine hydrochloride (662 mg, 4.81 mmol) was dissolved in a mixed solution of water (2 mL) and 1,4-dioxane (4 mL), and to this solution was added 4N aqueous sodium hydroxide (3 mL). To this solution was added di-t-butyl dicarbonate (1.11 mL, 4.81 mmol). After the solution was stirred at room temperature for 7 hours, ethyl acetate was added to the resulting reaction solution for extraction. The organic layer was washed successively with water and saturated brine, dried over anhydrous magnesium sulfate, filtered, and concentrated in vacuo to obtain the above protected derivative with Boc (968 mg) as a colorless oil.

The resulting protected derivative with Boc (968 mg, 4.81 mmol) was dissolved in N,N-dimethylformamide (5 mL), and then methyl iodide (449 μL, 7.22 mmol) was added thereto. After addition of sodium hydride (231 mg, 60% dispersion in oil, 5.77 mmol) under ice-cooling, the mixture was stirred for 5 minutes at the same temperature. The resulting reaction solution was warmed up to room temperature, and stirred for further 10 hours. After saturated aqueous ammonium chloride solution was added to this solution, it was extracted with a mixed solvent of hexane and ethyl acetate. The organic layer was washed with water and saturated brine, dried over anhydrous magnesium sulfate, and filtered. The filtrate was concentrated in vacuo, and azeotropic evaporation was carried out using toluene. The residue was purified by a column chromatography on silica gel to obtain the above methyl ether derivative (885 mg) as a colorless liquid.

The resulting methyl ether derivative (885 mg) was dissolved in chloroform (5 mL), and to this solution was added 4N hydrogen chloride/1,4-dioxane solution (5 mL). The solution was stirred at room temperature for 2 hours, and the resulting reaction solution was concentrated in vacuo to obtain the racemic objective compound [A-22] (596 mg) as a white solid.

Reference Example 23

Synthesis of the Compound of the Following Formula [A-23]:

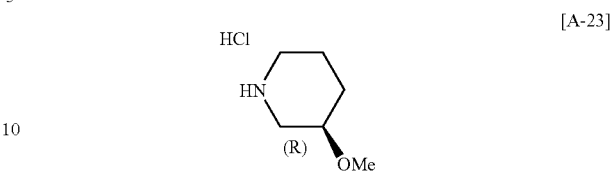

According to a method similar to the procedure of Reference Example 22, the objective compound [A-23] was obtained from (R)-3-hydroxypiperidine hydrochloride.

Reference Example 24

Synthesis of the Compound of the Following Formula [A-24]:

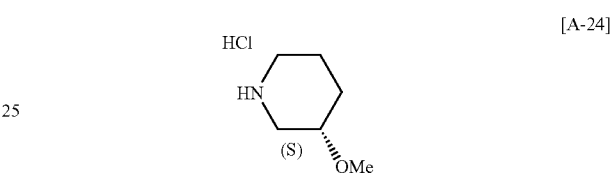

According to a method similar to the procedure as Reference Example 22, the objective compound [A-24] was obtained from (S)-3-hydroxypiperidine synthesized according to the method described in Tetrahedron Lett., 51 (21) 5935 (1995).

Reference Example 25

Synthesis of the Compound of the Following Formula [A-25]:

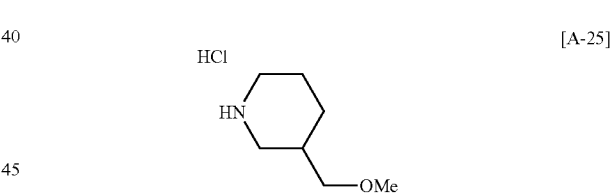

According to a method similar to the procedure of Reference Example 22, the racemic objective compound [A-25] (352 mg) was obtained as a white solid from racemic 3-hydroxymethylpiperidine (569 mg, 4.94 mmol).

Reference Example 26

Synthesis of the Compound of the Following Formula [A-26]:

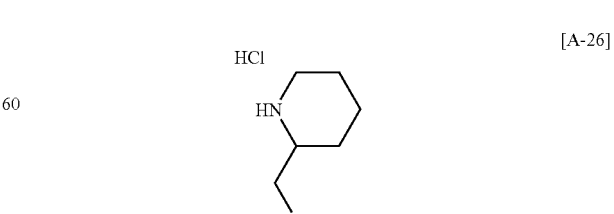

According to a method similar to the procedure of Reference Example 22, the racemic objective compound [A-26]

(899 mg) was obtained as a white solid from racemic 2-hydroxymethylpiperidine (857 mg, 7.44 mmol).

Reference Example 27

Synthesis of the Compound of the Following Formula [A-27]:

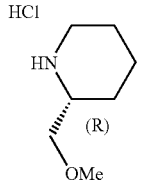

[A-27]

According to a method similar to the procedure as Reference Example 22, the objective compound [A-27] was obtained from (R)-2-hydroxymethylpiperidine synthesized according to the method described in Heterocycles, 41 (9) 1931 (1995).

Reference Example 28

Synthesis of the Compound of the Following Formula [A-28]:

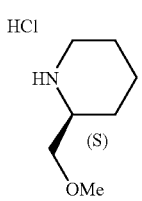

[A-28]

According to a method similar to the procedure as Reference Example 22, the objective compound [A-28] was obtained from (S)-2-hydroxymethylpiperidine synthesized according to the method described in Heterocycles, 41 (9) 1931 (1995), Reference Example 29

Synthesis of the Compound of the Following Formula [A-29]:

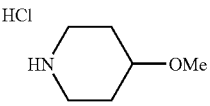

[A-29]

According to a method similar to the procedure of Reference Example 22, the objective compound [A-29] (222 mg) was obtained as a milky yellow solid from 4-hydroxypiperidine (251 mg, 2.48 mmol).

Reference Example 30

Synthesis of the Compound of the Following Formula [A-30]:

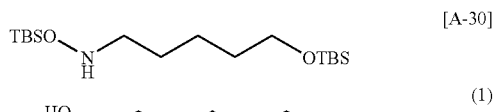

[A-30]

(1)

To a solution of 5-hydroxypentanal oxime (300 mg, 2.56 mmol) in methanol (10 mL) was added sodium cyanotrihydroborate (193 mg, 3.07 mmol), and then a mixture of conc. hydrochloric acid and methanol was added dropwise so as to adjust the pH to 3. The mixture was stirred for 30 minutes. After this solution was neutralized using aqueous sodium hydroxide, it was concentrated. The resulting residue was purified by a column chromatography on silica gel to obtain the above hydroxylamine derivative (299 mg) as a colorless oil.

(2)

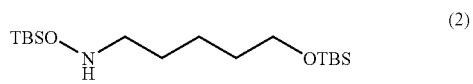

(2)

According to a method similar to the procedure of Reference Example 1-(1), the objective compound [A-30] (481 mg) was obtained as a pale yellow oil from the hydroxylamine derivative (235 mg, 1.97 mmol) obtained in the above (1).

Reference Example 31

Synthesis of the Compound of the Following Formula [A-31]:

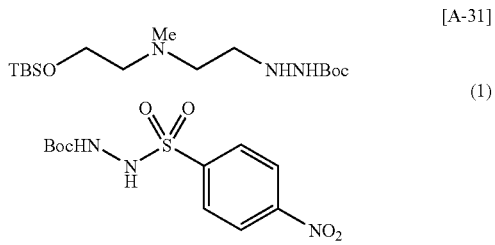

[A-31]

(1)

To a solution of t-butyl carbazinate (350 mg, 2.65 mmol) in pyridine (5 mL) was added 4-nitrobenzenesulfonyl chloride (590 mg, 2.65 mmol) in an ice-bath, and the mixture was stirred at room temperature for 1 hour. After the resulting reaction solution was diluted with chloroform, it was washed successively with 1N hydrochloric acid and saturated brine. The organic layer was dried over anhydrous magnesium sulfate, filtered, and concentrated in vacuo to obtain the above sulfone hydrazide derivative (910 mg) as a white solid.

(2)

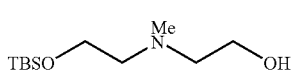

According to a method similar to the procedure of Reference Example 17, the above amine derivative (599 mg) was obtained from (t-butyldimethylsilyloxy)acetaldehyde (500 μL) and N-methyl-2-aminoethanol (200 μL)

(3)

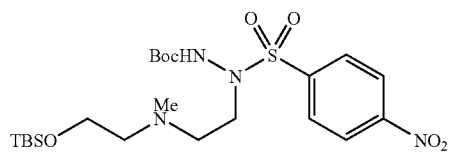

According to a method similar to the procedure of Reference Example 4-(2), the above N-alkylsulfone hydrazide derivative (1.35 g) was obtained as a pale yellow solid from the sulfone hydrazide derivative (815 mg, 2.57 mmol) obtained in the above (1) and the amine derivative (599 mg, 2.57 mmol) obtained in the above (2)

(4)

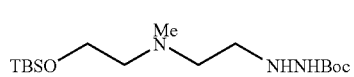

According to a method similar to the method described in Journal of Synthetic Organic Chemistry, Japan 59 (8) 779 (2001), deprotection of the 4-nitrobenzenesulfonyl group was carried out to obtain the objective compound [A-31] (576 mg) as a colorless oil from the N-alkylsulfone hydrazide derivative (1.35 g) obtained in the above (3)

Reference Example 32

Synthesis of the Compound of the Following Formula [A-32]:

[A-32]

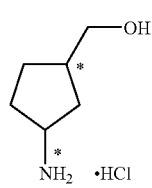

In the structure, the stereo chemistry of the position with the symbol * is of cis-configuration.

(1)

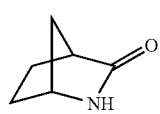

To a solution of racemic 2-azabicyclo[2,2,1]hept-5-ene-3-one (1.12 g, 10.2 mmol) in ethanol (20 mL) was added 10% palladium carbon (250 mg), and atmosphere in the reaction system was substituted with hydrogen gas. The mixture was stirred at room temperature for 3 hours under normal pressure. The resulting reaction solution was filtered through a Celite pad, and the filtrate was concentrated to obtain the above racemic reduced derivative (1.14 g) as a colorless oil.

(2)

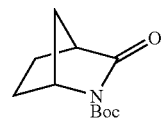

The racemic reduced derivative (1.85 g, 16.6 mmol) obtained in the above (1) was dissolved in methylene chloride (30 mL), and then di-t-butyl dicarbonate (3.63 g, 16.6 mmol), triethylamine (6.00 mL, 43.1 mmol) and 4-dimethylaminopyridine (3.23 g, 26.4 mmol) were added to the solution at 0° C. with stirring, and the mixture was stirred overnight at room temperature. 1N potassium hydrogensulfate solution was added to the resulting reaction solution, and it was extracted with ethyl acetate. The organic layer was washed with saturated brine, dried over anhydrous sodium sulfate, and filtered. The filtrate was concentrated in vacuo to obtain the above racemic protected derivative with Boc (2.24 g) as a colorless solid.

(3)

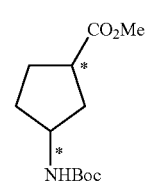

The racemic protected derivative with Boc (1.00 g, 4.73 mmol) obtained in the above (2) was dissolved in methanol (20 mL), and to this solution was added potassium carbonate (654 mg, 4.73 mmol) at 0° C. with stirring. The solution was stirred at room temperature for 1 hour. Water was added the resulting reaction solution, and it was extracted with ethyl acetate. The organic layer was washed with saturated brine, dried over anhydrous sodium sulfate, filtered, and the filtrate was concentrated in vacuo to obtain the above racemic ester derivative (1.00 g) as a colorless solid.

(4)

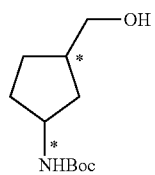

According to a method similar to the procedure of Reference Example 12-(2), the racemic alcohol derivative (884 mg) was obtained as a colorless solid from the racemic ester derivative (1.00 g, 4.11 mmol) prepared in the above (3)

(5)

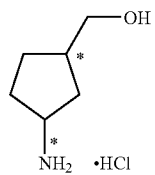

According to a method similar to the procedure of Reference Example 16-(2), the racemic objective derivative [A-32] (151 mg) was obtained as a yellow oil from the racemic alcohol derivative (215 mg, 1.00 mmol) obtained in the above (4).

Reference Example 33

Synthesis of the Compound of the Following Formula [A-33]:

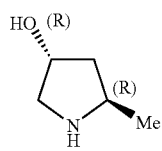

[A-33]

(2R,4R)-1-(buthoxycarbonyl)-4-hydroxy-2-methylpyrrolidine (861 mg) prepared by referring to the method described in Tetrahedron Lett., 54,10029 (1988) was dissolved in 4N hydrogen chloride/1,4-dioxane solution (3 mL), and the solution was stirred at room temperature for 19 hours. The reaction solution was concentrated, filtered, washed with diethyl ether, and dried to obtain a white solid (338 mg). 0.5M methanol solution (5.4 mL) containing sodium methoxide was added to this white solid, and the mixture was stirred for 1 hour. The resulting reaction solution was filtered, and the mother liquor was concentrated to give a residue, to which was added chloroform (2 mL). The mixture was stirred for 30 minutes, and the resulting suspension was filtered. The mother liquor was concentrated, and distilled to obtain the objective compound [A-33] (205 mg) as a colorless clear oil.

Reference Example 34

Synthesis of the Compound of the Following Formula [A-34]:

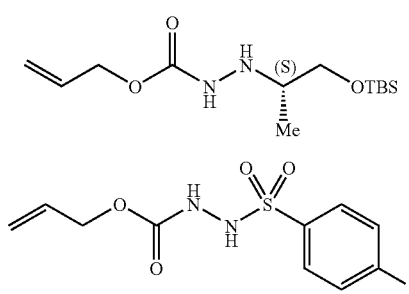

[A-34]

(1)

According to a method similar to the procedure of Reference Example 31-(1), the above sulfone hydrazide derivative (3.22 g) was obtained as a white solid from the allyl carbazinate derivative (2.00 g, 17.2 mmol) synthesized by referring to the method described in JP 04117361.

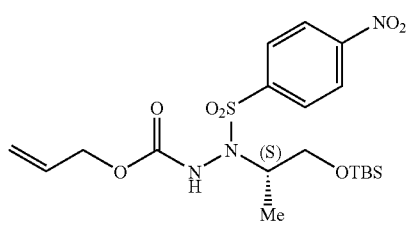

(2)

According to a method similar to the procedure of Reference Example 4-(1), the above N-alkylsulfone hydrazide derivative (1.08 g) was obtained as a colorless oil from (S)-1-(t-butyldimethylsiloxy)-2-propanol (678 mg, 3.56 mmol) synthesized by referring to the method described in J. Org. Chem., 53 (10) 2300 (1988).

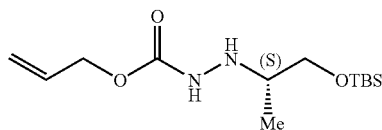

(3)

Deprotection of the 4-nitrobenzenesulfonyl group of the N-alkylsulfone hydrazide derivative (1.08 g) obtained in the above (2) was carried out according to a method similar to the method described in Journal of Synthetic Organic Chemistry, Japan 59 (8) 779 (2001), to obtain the objective compound [A-34] (304 mg) as a colorless oil.

INDUSTRIAL APPLICABILITY

As described above, the compounds of the present invention have strong Cdk inhibitory activity. Since the compounds of the present invention also show strong inhibitory activity of BrdU uptake, they have clearly inhibitory activity of cell growth. Therefore, the compounds of the present invention are useful as an anti-cancer agent (agent for the treatment of cancers). That is, it is considered that anti-cancer agents containing a new quinoxalinone derivative or a salt or ester thereof of the present invention are useful for the treatment of cancer patients.

The invention claimed is:

1. A quinoxalinone derivative of the formula (I):

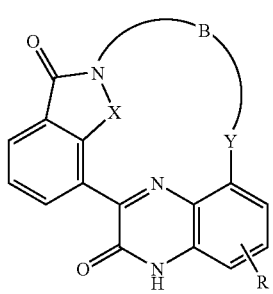

(I)

or a pharmaceutically acceptable salt thereof, wherein
X is NH;
Y is O or NR', wherein R' is hydrogen or lower alkyl;
the partial structure

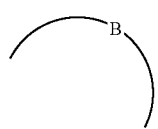

is the following formula:

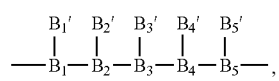

wherein
$B_1$, $B_2$, $B_3$, $B_4$ and $B_5$ are each independently CH, $CR_0$, N or O, wherein
when $B_1$, $B_2$, $B_3$, $B_4$ and $B_5$ are each independently O, then $B'_1$, $B'_2$, $B'_3$, $B'_4$ and $B'_5$ are each taken together with $B_1$, $B_2$, $B_3$, $B_4$ and $B_5$, respectively, to form O, with the proviso that two or more members of $B_1$, $B_2$, $B_3$, $B_4$ and $B_5$, at the same time, are not taken together with $B'_1$, $B'_2$, $B'_3$, $B'_4$ and $B'_5$, respectively, to form O; and $R_0$ is lower alkyl, and $B'_1$, $B'_2$, $B'_3$, $B'_4$ and $B'_5$ are each independently hydrogen, halogen, hydroxy, oxo, lower alkoxy, amino, lower alkylamino, di-lower alkylamino, lower alkyl or lower alkenyl, wherein said lower alkyl and said lower alkenyl may be substituted with one or more, same or different substituents selected from the group consisting of hydroxy, lower alkoxy, amino and lower alkylamino, and among $B'_1$, $B'_2$, $B'_3$, $B'_4$ and $B'_5$, $B'_1$ and $B'_3$ taken together with $B_1$, $B_2$ and $B_3$, $B'_2$ and $B'_4$ taken together with $B_2$, $B_3$ and $B_4$, $B'_3$ and $B'_5$ taken together with $B_3$, $B_4$ and $B_5$, $B'_1$ and $B'_4$ taken together with $B_1$, $B_2$, $B_3$ and $B_4$, or $B'_2$ and $B'_5$ taken together with $B_2$, $B_3$, $B_4$ and $B_5$ may form a $C_5$-$C_6$ cycloalkyl or an aliphatic heterocyclic group selected from the substituent group $\beta_1$ mentioned below, and said cycloalkyl and said aliphatic heterocyclic group may be substituted with one or more, same or different substituents selected from lower alkyl and the substituent group a mentioned below;

R is hydrogen, lower alkyl, lower alkenyl, amino in which the nitrogen atom is di-substituted with $R_a$ and $R_b$, amino-lower alkyl in which the nitrogen atom is di-substituted with $R_a$ and $R_b$, or L, wherein $R_a$ and $R_b$ are each independently hydrogen, lower alkyl, lower alkoxyalkyl or halogenated lower alkyl, and L is $L_1$-$L_2$-$L_3$, wherein $L_1$ is a single bond, —(CH$_2$)$_{k1}$—, —(CH$_2$)$_{k1}$—O— or —(CH$_2$)$_{k1}$—NH—, in which k1 is an integer of 1 to 3; $L_2$ is a single bond or —(CH$_2$)$_{k2}$—, in which k2 is an integer of 1 to 3; and $L_3$ is lower alkyl, lower alkoxy, $C_3$-$C_6$ cycloalkyl, phenyl, pyridyl, pyrrolidinyl or piperidinyl, said lower alkyl, lower alkoxy, $C_3$-$C_6$ cycloalkyl, phenyl, pyridyl, pyrrolidinyl or piperidinyl being optionally substituted with one or more fluorine atoms; or alternatively R is a substituent selected from the substituent group α mentioned below, which may be substituted with one or more, same or different substituents selected from the substituent group γ mentioned below, or R is lower alkyl substituted with said substituent; or alternatively R is a cyclic group selected from the substituent group $\beta_2$ mentioned below, which may be substituted with one or more, same or different substituents selected from a lower alkyl, the substituent group a mentioned below and the substituent group γ mentioned below and also which may be substituted with J, wherein J is $J_1$-$J_2$-$J_3$; $J_1$ is a single bond, —C(=O)—, —O—, —NH—, —NHCO—, —(CH$_2$)$_{k3}$— or —(CH$_2$)$_{k3}$—O—, in which k3 is an integer of 1 to 3; $J_2$ is a single bond or —(CH$_2$)$_{k4}$—, in which k4 is an integer of 1 to 3; and $J_3$ is lower alkyl, lower alkoxy, —CONR$_a$R$_b$, wherein $R_a$ and $R_b$ each have the same meaning as defined above, phenyl, pyridyl, pyrrolidinyl or piperidinyl, said lower alkyl, lower alkoxy, phenyl, pyridyl, pyrrolidinyl or piperidinyl being optionally substituted with one or more fluorine atoms, or R is lower alkyl substituted with said cyclic group, and in the above, the substituent group α, the substituent group $\beta_1$, the substituent group $\beta_2$ and the substituent group γ each have the meanings shown below:

the substituent group α is a member selected from the group consisting of hydroxy, hydroxy-lower alkyl, cyano, halogen, carboxyl, lower alkanoyl, lower alkoxy-carbonyl, lower alkoxy, lower alkoxyalkyl, amino, lower alkylamino, lower alkylsulfonyl, halogenated lower alkyl, halogenated lower alkoxy, halogenated lower alkylamino, nitro and lower alkanoylamino, the substituent group $\beta_1$ is a member selected from the group consisting of

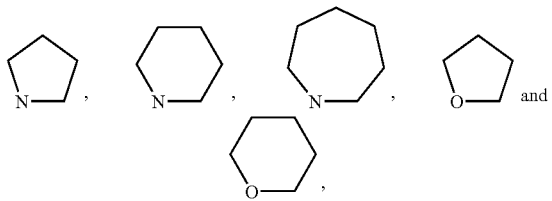

the substituent group $\beta_2$ is a member selected from the group consisting of

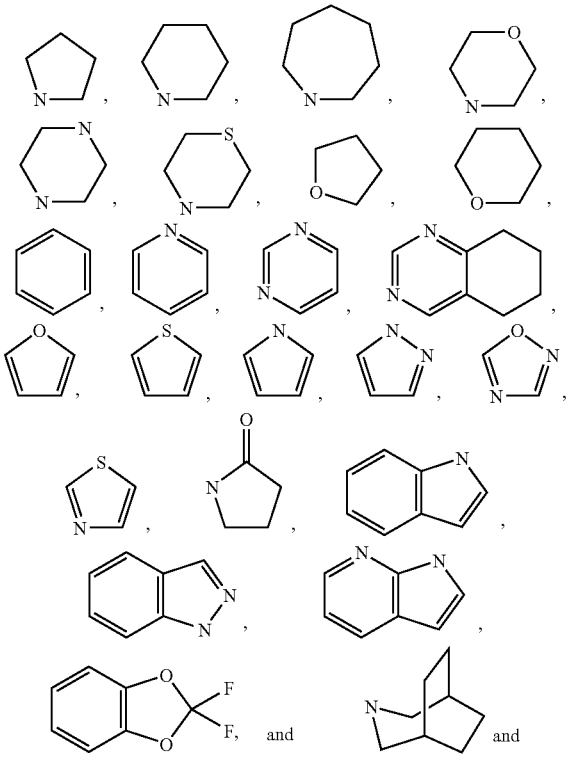

the substituent group γ is a member selected from the group consisting of $C_3$-$C_6$ cycloalkyl, lower alkyl substituted with $C_3$-$C_6$ cycloalkyl, phenyl, lower alkyl substituted with phenyl, pyridyl, pyrrolidinyl and piperidinyl, said $C_3$-$C_6$ cycloalkyl, phenyl, pyridyl, pyrrolidinyl and piperidinyl being optionally substituted with one or more fluorine atoms.

2. The compound according to claim 1 or a pharmaceutically acceptable salt thereof, wherein X is NH; and Y is O.

3. The compound according to claim 2 or a pharmaceutically acceptable salt thereof, wherein $B_1$, $B_2$, $B_3$, $B_4$ and $B_5$ are each independently CH; or $B_1$, $B_2$, $B_4$ and $B_5$ are each independently CH, and $B_3$ is N or O.

4. The compound according to claim 3 or a pharmaceutically acceptable salt thereof, wherein
the substituent group α is selected from hydroxy, hydroxy-lower alkyl, halogen, lower alkoxycarbonyl, lower alkoxy, lower alkoxyalkyl, lower alkylamino, methyl substituted with one to three fluorine atoms, methoxy substituted with one to three fluorine atoms and lower alkylamino substituted with one to three fluorine atoms; and the substituent group β$_1$ is

5. The compound according to claim 4 or a pharmaceutically acceptable salt thereof, wherein
B$_1$, B$_2$, B$_4$ and B$_5$ are each independently CH, B$_3$ is N, and
(a) all of B'$_1$, B'$_2$, B'$_3$, B'$_4$ and B'$_5$ are hydrogen; or
(b) one of B'$_1$, B'$_2$, B'$_3$, B'$_4$ and B'$_5$ is lower alkyl or lower alkenyl, and all the others are hydrogen; or
(c) at least two of B'$_1$, B'$_2$, B'$_3$, B'$_4$ and B'$_5$ are each independently lower alkyl or lower alkenyl, and all the others are hydrogen; or
(d) among B'$_1$, B'$_2$, B'$_3$, B'$_4$ and B'$_5$,
B'$_1$ and B'$_3$ taken together with B$_1$, B$_2$ and B$_3$,
B'$_2$ and B'$_4$ taken together with B$_2$, B$_3$ and B$_4$, or
B'$_3$ and B'$_5$ taken together with B$_3$, B$_4$ and B$_5$,
form an aliphatic heterocyclic group selected from the substituent group β$_1$, wherein said aliphatic heterocyclic group may be substituted with one or more, same or different substituents selected from lower alkyl and the substituent group α, and the others are hydrogen, lower alkyl or lower alkenyl.

6. The compound according to claim 5 or a pharmaceutically acceptable salt thereof, wherein
X is NH;
B$_1$, B$_2$, B$_4$ and B$_5$ are each independently CH, and B$_3$ is N;
among B'$_1$, B'$_2$, b'$_3$, B'$_4$ and B'$_5$,
B'$_1$ and B'$_3$ taken together with B$_1$, B$_2$ and B$_3$ form an aliphatic heterocyclic group selected from the substituent group β$_1$, wherein said aliphatic heterocyclic group may be substituted with lower alkyl, and the others are hydrogen.

7. The compound according to claim 5 or a pharmaceutically acceptable salt thereof, wherein
the R binds to quinoxalinone as described in the following formula:

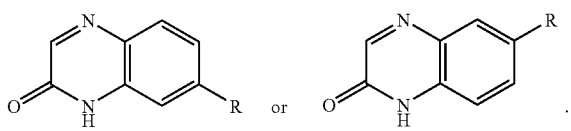

8. The compound according to claim 7 or a pharmaceutically acceptable salt thereof, wherein
R is hydrogen, amino-lower alkyl in which the nitrogen atom is di-substituted with R$_a$ and R$_b$, or L, wherein R$_a$ and R$_b$ are each independently lower alkyl, and L is L$_1$-L$_2$-L$_3$, wherein L$_1$ is a single bond, —(CH$_2$)$_{k1}$—, —(CH$_2$)$_{k1}$—O— or —(CH$_2$)$_{k1}$—NH—, in which k1 is an integer of 1 or 2; L$_2$ is a single bond or —(CH$_2$)$_{k2}$—, in which k2 is an integer of 1 or 2; and L$_3$ is lower alkoxy or C$_3$-C$_6$ cycloalkyl; or
R is a cyclic group selected from the substituent group β$_2$, which may be substituted with one or more, same or different substituents selected from lower alkyl and the substituent group α, or R is lower alkyl substituted with said cyclic group, wherein the substituent group β$_2$ is selected from

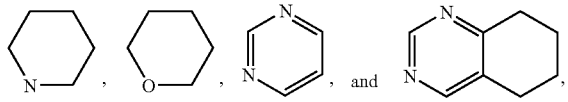

and the substituent group α is selected from halogen, lower alkoxy, lower alkoxyalkyl, methyl substituted with one to three fluorine atoms, and methoxy substituted with one to three fluorine atoms; or lower alkyl substituted with a substituent selected from the group consisting of lower alkylamino and lower alkylamino substituted with one to three fluorine atoms.

9. The compound according to claim 2 or a pharmaceutically acceptable salt thereof, wherein
the partial structure

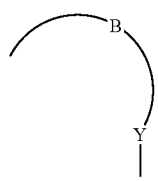

is selected from the group consisting of

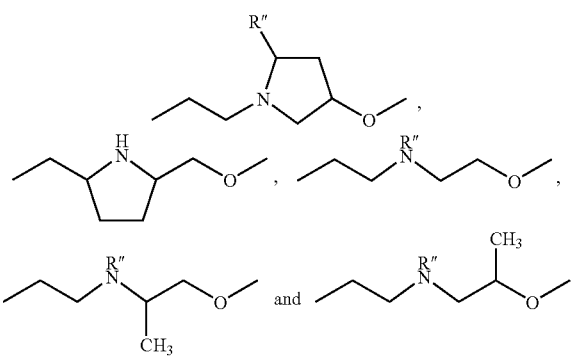

wherein R" is hydrogen or methyl; and
R is selected from the group consisting of

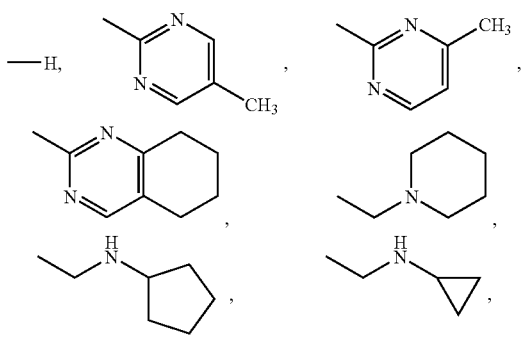

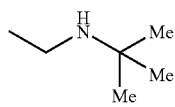 and 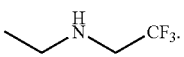
10. The compound according to claim 9 or a pharmaceutically acceptable salt thereof, wherein
X is NH; and the partial structure
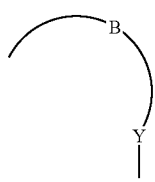
is the formula:
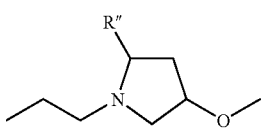
wherein R″ is methyl.
11. The compound according to claim 1 or a pharmaceutically acceptable salt thereof, wherein
the quinoxalinone derivative is
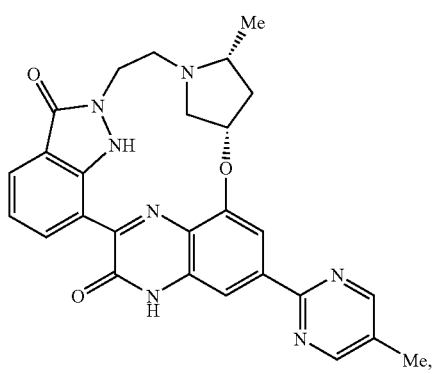
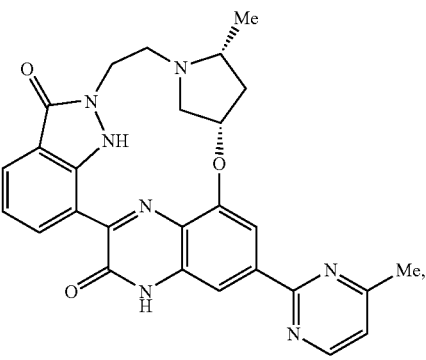
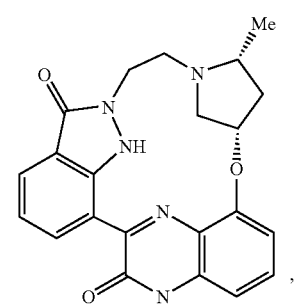,
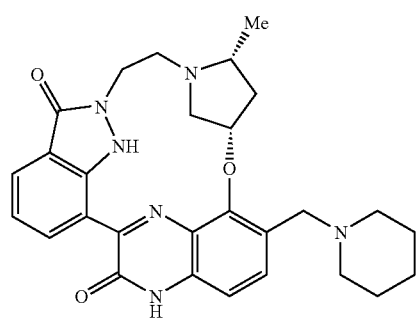
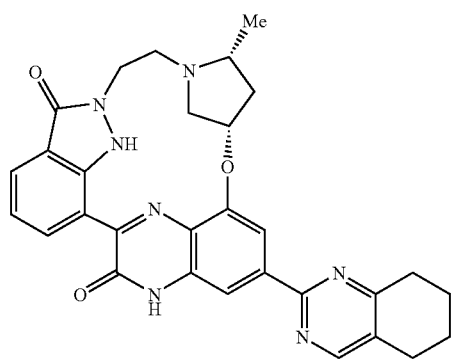
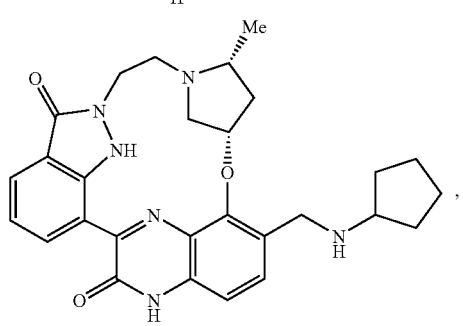,
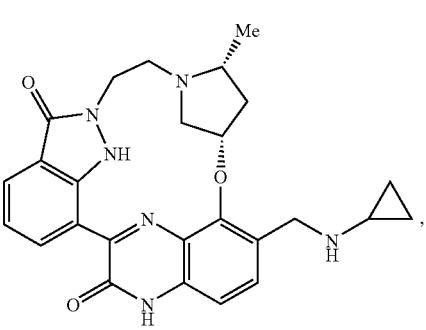, -continued

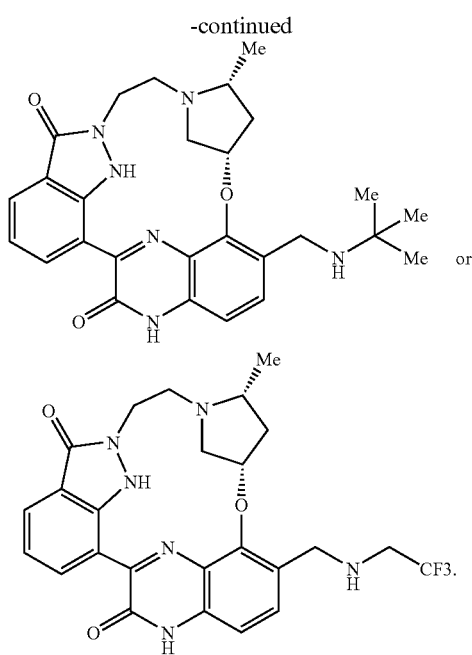

12. A pharmaceutical composition comprising a quinoxalinone derivative according to claim 1 as an active ingredient, together with a pharmaceutically acceptable carrier or diluent.

13. A method for treatment of cancer selected from the group consisting of glioma (blastoma), breast, lung, gastrointestinal, endometrial, leukemia, head and neck, liver, ovary or testicular, and mesothelima, which comprises administering to a patient in need thereof a therapeutically effective amount of a quinoxalinone derivative according to claim 1 as an active ingredient, together with a pharmaceutically acceptable carrier or diluent.

14. The compound according to claim 6 or a pharmaceutically acceptable salt thereof, wherein
the R binds to quinoxalinone as described in the following formula:

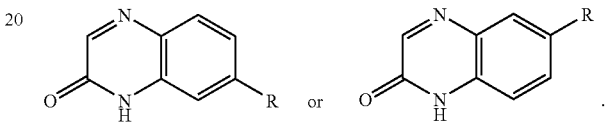

* * * * *